US011279733B2

(12) United States Patent
Cooper et al.

(10) Patent No.: US 11,279,733 B2
(45) Date of Patent: Mar. 22, 2022

(54) PEPTIDE ANTIBIOTICS

(71) Applicant: THE UNIVERSITY OF QUEENSLAND, St Lucia (AU)

(72) Inventors: Matthew Cooper, St Lucia (AU); Mark Blaskovich, St Lucia (AU); Alejandra Gallardo-Godoy, St Lucia (AU); Karl Hansford, St Lucia (AU); Alysha Elliott, St Lucia (AU); Craig Muldoon, Springwood (AU); Bernd Becker, New Farm (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 0 days.

(21) Appl. No.: 16/761,067

(22) PCT Filed: Nov. 2, 2018

(86) PCT No.: PCT/AU2018/051194
§ 371 (c)(1),
(2) Date: May 1, 2020

(87) PCT Pub. No.: WO2019/084628
PCT Pub. Date: May 9, 2019

(65) Prior Publication Data
US 2020/0361994 A1  Nov. 19, 2020

(30) Foreign Application Priority Data

Nov. 2, 2017 (AU) .................................. 201704465

(51) Int. Cl.
| | |
|---|---|
| *A61K 38/12* | (2006.01) |
| *C07K 7/56* | (2006.01) |
| *C07K 7/62* | (2006.01) |
| *A61P 31/04* | (2006.01) |
| *A61K 38/00* | (2006.01) |
| *A61K 45/06* | (2006.01) |

(52) U.S. Cl.
CPC ............... *C07K 7/62* (2013.01); *A61K 38/12* (2013.01); *A61P 31/04* (2018.01); *C07K 7/56* (2013.01); *A61K 38/00* (2013.01); *A61K 45/06* (2013.01)

(58) Field of Classification Search
CPC . A61K 38/12; C07K 7/50; C07K 7/54; C07K 7/56; C07K 7/60; C07K 7/62
See application file for complete search history.

(56) References Cited

U.S. PATENT DOCUMENTS

| 3,880,994 A | 4/1975 | Kawaguchi et al. | |
| 9,234,006 B2 * | 1/2016 | Saadi | C07K 7/62 |
| 2013/0053305 A1 | 2/2013 | Barcelona | |
| 2014/0162937 A1 * | 6/2014 | Vaara | A61K 38/12 |
| | | | 514/2.8 |

FOREIGN PATENT DOCUMENTS

| EP | 0471453 | 2/1992 |
| JP | S50-25795 | 3/1975 |
| WO | WO 2002/055543 | 7/2002 |
| WO | WO 2010130007 | 11/2010 |
| WO | WO 2012168820 | 12/2012 |
| WO | WO 2014188178 | 11/2014 |
| WO | WO 2015135976 | 9/2015 |
| WO | WO 2015149131 | 10/2015 |
| WO | WO 2016083531 | 6/2016 |
| WO | WO 2016100578 | 6/2016 |
| WO | WO 2016150576 | 9/2016 |
| WO | WO 2017054047 | 4/2017 |
| WO | WO 2017189868 | 11/2017 |

OTHER PUBLICATIONS

Shoji et al. The Structure of Polymyxin T1 (Studies On Antibiotics From The Genus Bacillus. XXII). The Journal Of Antibiotics. Dec. 1977, vol. XXX, No. 12, pp. 1042-1048. (Year: 1977).*
Tamaki et al. Biomimetic formation of gramicidin S by dimerization-cyclization of pentapeptide precursor on solid support. Tetrahedron Letters. 2006, vol. 47, pp. 8475-8478. (Year: 2006).*
Vaara et al. Structure-activity studies on polymyxin derivatives carrying three positive charges only reveal a new class of compounds with strong antibacterial activity. Peptides. Mar. 11, 2017, vol. 91, pp. 8-12. (Year: 2017).*
Becker et al. "Synthesis of octapeptin C4 and biological profiling against NDM-1 and polymyxinresistant bacteria" 2017 Bioorg Med Chem Lett. 27(11), 2407-2409.
Bruch et al. "Higher-Order Structure of Polymyxin B: The Functional Significance of Topological Flexibility" 1999 *J Am Chem Soc*, 121 11993-12004.
Chitty et al. "Antimicrobial Octapeptin C4 Analogues Active against *Cryptococcus* Species" 2018 *Antimicrobial Agents and Chemotherapy* 62, e00986-17, accepted manuscript published online Nov. 20, 2017.
Chong ZS et al. "Osmoporin OmpC forms a complex with MlaA to maintain outer membrane lipid asymmetry in *Escherichia coli*" 2015. *Mol. Microbiol.* 98: 1133-1146.
Cummings "Expression of Glutathione-Dependent Enzymes and Cytochrome P450s in Freshly Isolated and Primary Cultures of Proximal Tubular Cells from Human Kidney" 2000 *Pharmacol. Exp. Ther.* 293, 677-85.
Cummings et al. "Metabolism and Toxicity of Trichloroethylene and S-(1,2-Dichlorovinyl)-L-Cysteine in Freshly Isolated Human Proximal Tubular Cells" 2000 *Toxicological Sciences* 53, 458-466.
De Zoysa et al. "Antimicrobial Peptides with Potential for Biofilm Eradication: Synthesis and Structure Activity Relationship Studies of Battacin Peptides" 2015, *J. Med. Chem.* 58, 625-639.

(Continued)

*Primary Examiner* — Jeffrey E. Russel
(74) *Attorney, Agent, or Firm* — Nixon & Vanderhye P.C.

(57) ABSTRACT

There is provided a range of novel compounds. These novel compounds may demonstrate abroad spectrum antibacterial and antifungal activity. These compounds may be active against the emerging polymyxin resistant bacteria. These compounds may also be useful when used in conjunction with other pharmaceutically active agents.

20 Claims, 7 Drawing Sheets

(56) References Cited

OTHER PUBLICATIONS

Deng et al. "Isolation and characterization of peptide antibiotics LI-F04 and polymyxin B6 produced by Paenibacillus polymyxa strain JSa-9" *Peptides*, 2011, 32, 1917-1923.
Huang et al. "Cell- and biomarker-based assays for predicting Nephrotoxicity" *Expert Opinion on Drug Metabolism & Toxicology*. 2014, 10 (12) 1621-1635.
Huang et al. "Evaluation of biomarkers for in vitro prediction of drug-induced nephrotoxicity: comparison of HK-2, immortalized human proximal tubule epithelial, and primary cultures of human proximal tubular cells" *Pharmacology Research & Perspectives*, 2015, 3 (3), 14.
Galea et al. "Characterization of the Polymyxin D Synthetase Biosynthetic Cluster and Product Profile of Paenibacillus polymyxa ATCC 10401" *Journal of Natural Products* (2017), 80(5), 1264-1274.
Gallardo-Godoy et al. "Activity and Predicted Nephrotoxicity of Synthetic Antibiotics Based on Polymyxin B" Journal of Medicinal Chemistry (2016), 59(3), 1068-1077.
Gottlieb et al. "NMR Chemical Shifts of Common Laboratory Solvents as Trace Impurities" *J. Org. Chem.*, 1997, 62, 7512.
Govaerts et al., "Mass spectrometric fragmentation of cyclic peptides belonging to the polymyxin and colistin antibiotics studied by ion trap and quadrupole/orthogonal-acceleration time-of-flight technology" *Rapid Commun. Mass Spectrom*. 2002, 16, 823-833.
Gucinski et al. "Influence of N-terminal Residue Composition on the Structure of Proline-Containing $b_2$+Ions" *J. Phys. Chem. A*, 2013, 117, 1291-1298.
Kadar et al.; The Renaissance of Polymyxins; Curr Med Chem 2013 (20), 3759.
Kanazawa et al. "Contribution of each amino acid residue in polymyxin B3 to antimicrobial and liposaccharide binding activity" *Chem. Pharma Bull* 2009, 57(3) 240-244.
Kato et al. "The amino acid sequence of octapeptin C1 (333-25). (Studies On Antibiotics From the Genus *Bacillus*. XIX)." The Journal of Antibiotics. Vol. 29 (1976) No. 12, p. 1339-1340.
Kato et al. "The Structure of Octapeptin D Studies on Antibiotics from the Genus Bacillus. XXVIII". The Journal of Antibiotics. vol. 33 (1980) No. 2, p. 186-191.
Knight, et al. "Inhibitory Cyclic Analogues and Chlorambucil Derivatives of Bombesin-Like Peptides", Peptides, 1995, vol. 16, No. 6, pp. 1109-1115.
Kohanski et al. "A Common Mechanism of Cellular Death Induced by Bactericidal Antibiotics" 2007 *Cell* 130, 797-810.
Konishi et al. "Bu-2470, A New Peptide Antibiotic Complex I. Production, Isolation and Properties of Bu-2470 A, $B_1$ and $B_2$" 1983 *The Journal of Antibiotics* 625.
Lash et al. "Susceptibility of primary cultures of proximal tubular and distal tubular cells from rat kidney to chemically induced toxicity" 1995 *Toxicology* 103, 85-103.
Li et al. "Syntheses of Dap-3 Polymyxin Analogues via a Tris-Boc-Protected Polymyxin B Heptapeptide" *Synthesis* (2015), 47(14), 2088-2092.
Lim et al. "Resurgence of Colistin: A Review of Resistance, Toxicity, Pharmacodynamics, and Dosing" 2010 *Pharmacotherapy* 30(12) 1279-1291.
Liu et al. "Nuclear Magnetic Resonance Structure Elucidation of Peptide b2 Ions" *Angew. Chem. Int. Ed*, 2015, 54, 1547-1550.
Magee et al. "Discovery of Dap-3 Polymyxin Analogues for the Treatment of Multidrug-Resistant Gram-Negative Nosocomial Infections" *Journal of Medicinal Chemistry* (2013), 56(12), 5079-5093.
Magiorakos et al. "Multidrug-resistant, extensively drug-resistant and pandrug-resistant bacteria: an international expert proposal for interim standard definitions for acquired resistance" *Clin Microbiol Infect* 2012, 18, 268-281.
Malinverni JC and Silhavy TJ. "An ABC transport system that maintains lipid asymmetry in the Gram-negative outer membrane" 2009. *PNAS*. 106: 8009-8014.

McMillian et al. "An improved resazurin-based cytotoxicity assay for hepatic cells" *Cell Biol. Toxicol*. 2002, 18, 157-173.
Meyers "A Nomenclature proposal for the octapeptin antibiotics" *The Journal of Antibiotics* 1976, 29, 1241.
Meyers et al. "EM49: A New Polypeptide Antibiotic Active Against Cell Membranes" Annals of the New York Academy of Sciences, May 1974, vol. 235(1), pp. 493-501.
Meyers et al. "EM49, A new peptide antibiotic: III. biological characterization in vitro and in vivo" *The Journal of Antibiotics*, 1973, vol. 26(8), pp. 457-462.
O'Brien et al. "Investigation of the Alamar Blue (resazurin) fluorescent dye for the assessment of mammalian cell cytotoxicity" *Eur. J. Biochem*. 2000, 267, 5421-5426.
Oddo et al. "The effect of glycine replacement with flexible w-amino acids on the antimicrobial and hemolytic activity of an amphipathic cyclic heptapeptide" *European Journal of Medicinal Chemistry* (2015), 102, 574-581.
Olaitan et al. "Mechanisms of polymyxin resistance: acquired and intrinsic resistance in bacteria" Front Microbiol. 2014 26, 643.
Orlowski et al. "Gamma-glutamyl-p-nitroanilide: A new convenient substrate for determination and study of L- and D-gamma-glutamyltranspeptidase activities" 1963, Biochim. Biophys. Acta 73, 679-681.
Parker, et al. "EM49, A New Peptide Antibiotic II. Chemical Characterization", The Journal of Antibiotics, 1973, vol. 26, No. 8, pp. 449-456.
Parker et al. "EM49, A New Peptide Antibiotic IV. The Structure of EM49" *The Journal of antibiotics*, May 1975, vol. 28(5), pp. 379-389.
Paur "Carbon-13 NMR Studies of EM49 and related octapeptins" *The Journal of Antibiotics* 1980, 33(7), 760.
Plusec et al. "N-Substituted Derivatives of EM49 Structure-Activity Relationships" *The Journal of Antibiotics* 1977 vol. 30 Issue 9 756-759.
Pristovsek et al. "Solution Structure of Polymyxins B and E and Effect of Binding to Lipopolysaccharide: An NMR and Molecular Modeling Study" 1999 *J. Med. Chem*. 42, 4604-4613.
Qian et al. "Battacin (Octapeptin B5), a New Cyclic Lipopeptide Antibiotic from Paenibacillus tianmuensis Active against Multidrug-Resistant Gram-Negative Bacteria" 2012 *Antimicrob Agents Chemother*. 56(3): 1458-1465.
Rosenthal et al. "Disruption of *Escherichia coli* Outer Membranes by EM49. A New Membrane Active Peptide Antibiotic" Biochemistry, Dec. 1, 1976, vol. 15(26), pp. 5783-5792.
Sampson et al. "Rapid Killing of Acinetobacter baumannii by Polymyxins Is Mediated by a Hydroxyl Radical Death Pathway" 2012 *Antimicrobial Agents and Chemotherapy* 56, 5642-5649.
Sato, et al. "Novel Des-Fatty Acyl-Polymyxin B Derivatives with *Pseudomonas aeruginosa*—Specific Antimicrobial Activity", *Chem. Pharm. Bull*. 2011, vol. 59, No. 5, pp. 597-602.
Shoji et al. "The constituent amino acids and fatty acid of antibiotic 333-25. (Studies On Antibiotics From the Genus *Bacillus*. XII)." The Journal of Antibiotics. vol. 29 (1976), No. 5, p. 521-525.
Storm et al.; "Polymyxin and Related Peptide Antibiotics" Ann Rev Biochem 1977 (46), 723-63.
Sugawara "Bu-2470, a new peptide antibiotic complex. II. Structure determination of Bu-2470 A, B1, B2a and B2b." The Journal of Antibiotics. 1983; vol. 36, No. 6, p. 634.
Swanson, et al. "Characterization of Octapeptin-Membrane Interactions Using Spin-Labeled Octapeptin", Biochemistry, 1980, vol. 19, pp. 3307-3314.
Terabe et al. "Separation of polymyxins and octapeptins by high-performance liquid chromatography." *Journal of Chromatography* 173 (1979): 313-320.
Todd et al. "Enzymatic isolation and serum-free culture of human renal cells" 1995, In Methods in Molecular Medicine: Human Cell Culture Protocols. (G.E. Jones, Ed.), Chapter 32. Humana Press Inc., Totowa, NJ.
Tsubery et al. "Structure-Function Studies of Polymyxin B Nonapeptide: Implications to Sensitization of Gram-Negative Bacteria" *Journal of Medicinal Chemistry* (2000), 43(16), 3085-3092.
Tsubery et al. Advances in Experimental Medicine and Biology (2000), 479(Biology and Pathology of Innate Immunity Mechanisms), 219-222.

(56) References Cited

OTHER PUBLICATIONS

Urakawa et al. "Structure-activity relationships of bacterial outer-membrane permeabilizers based on polymyxin B heptapeptides" *Bioorganic & Medicinal Chemistry Letters* (2010), 20(5), 1771-1775.

Tsubery et al. "Peptides for the New Millennium", Proceedings of the American Peptide Symposium, 16th, Minneapolis, MN, United States, Jun. 26-Jul. 1, 1999 (2000), 742-743.

Vaara, M; Novel derivatives of polymyxins; J Antimicr Chemother 2013, 1213-1219.

Velkov, et al. "A Novel Chemical Biology Approach for Mapping of Polymyxin Lipopeptide Antibody Binding Epitopes", ACS Infec. Dis., 2016, vol. 2, pp. 341-351.

Velkov et al. "Molecular basis for the increased polymyxin susceptibility of Klebsiella pneumoniae strains with under-acylated lipid A" *Innate Immun.* 2013 19, 265-277.

Velkov et al. "Pharmacology of Polymyxins: new insights into an 'old' class of antibiotics" *Future Microbiol* 2013 (8), 711.

Velkov et al. "Structure, function and biosynthetic origin of octapeptin antibiotics active against extensively drug-resistant Gram-negative bacteria" Cell Chern Biol, Apr. 19, 2018, 25(4), 380-391.

Velkov et al. Structure-Activity Relationships of Polymyxin Antibiotics; *J Med Chem* 2010, 53, 1898-1916.

Velkov et al. "Teaching 'Old' Polymyxins New Tricks: New-Generation Lipopeptides Targeting Gram-Negative 'Superbugs'" 2014 *ACS Chemical Biology* 9(5), 1172-1177.

Weinstein, et al. "Selective Reductive Cleavage of a Threonine Peptide Bond in Polymyxin Antibiotics", Annals New York Academy of Science, 1986, vol. 471, pp. 321-323.

Weinstein et al. "Selective chemical modifications of polymyxin B" *Bioorganic & Medicinal Chemistry Letters* (1998), 8(23), 3391-3396.

Wu et al. "Syntheses and studies of amamistatin B analogs reveals that anticancer activity is relatively independent of stereochemistry, ester or amide linkage and select replacement of one of the metal chelating groups" *Bioorg. Med. Chem. Lett.* 2011, 21, 2611-2615.

Sakura et al. "Synthesis of Cyclic Peptide Antibiotic Polymyxin B Derivatives" Peptide Science 1999: N. Fujii (Ed). The Japanese Peptide Society (2000), 413-416.

Urakawa et al. "Structure-Activity Relationship of Polymyxin B Heptapeptide and Analogs", Peptide science 2007: S. Aimoto and S. Ono (eds), The Japanese Peptide Society (2008), 293-296.

Han, M.-L., et al., "Investigating the Interaction of Octapeptin A3 with Model Bacterial Membranes," ACS Infectious Diseases, 3:606-619 (2017).

Vaara, M., "Polymyxins and their novel derivatives," Current Opinion in Microbiology, 13:574-581 (2010).

* cited by examiner

PEPTIDE ANTIBIOTICS

FEDERALLY SPONSORED RESEARCH OR DEVELOPMENT

This invention was made with U.S. government support under contract R33 AI098731 awarded by the National Institute of Allergy and Infectious Diseases (NIAID) of the National Institutes of Health. The U.S. government has certain rights in the invention.

RELATED APPLICATIONS

This application is the U.S. national phase of International Application No. PCT/AU2018/051194 filed 2 Nov. 2018, which designated the U.S. and claims priority to AU Patent Application No. 2017904465 filed 2 Nov. 2017. The entire contents of International Application No. PCT/AU2018/051194 are hereby incorporated by reference.

FIELD OF THE INVENTION

The invention relates to the field of medical treatment. More particularly, the invention relates to antimicrobial compounds and their use. Most particularly, this invention relates to novel peptide antimicrobials to treat bacterial or fungal infections.

BACKGROUND TO THE INVENTION

Any reference to background art herein is not to be construed as an admission that such art constitutes common general knowledge in Australia or elsewhere.

The emergence of multi-drug resistant bacteria and fungi represents a serious and growing threat to human lives. Bacterial sepsis kills millions of people annually, and multi-drug resistant bacteria are a cause of a significant number of these deaths. Sepsis is most commonly caused by Gram-positive *Staphylococcus aureus* and *Streptococcus pyogenes*, and Gram-negative *Klebsiella* spp., *Escherichia coli*, and *Pseudomonas aeruginosa*. Unfortunately, there has been an ominous rise in highly multi-drug resistant Gram-negative bacteria. The emergence of multi-drug resistant Gram-negative bacteria has led to a return to the clinical use of 'last resort' antibiotics such as polymyxin B and polymyxin E (colistin) However, the emergency of polymyxin resistant bacteria is a worrying issue as there is currently no adequate treatment for these strains.

One limitation on the wider use of polymyxins is their nephrotoxicity. This complicates treatment and may result in treatment with sub-optimal dosages and/or treatment being discontinued. Octapeptins have a somewhat similar structure to polymyxins. However, octapeptins have not been explored extensively as antibiotics against polymyxin resistant bacteria.

There are few effective treatments for fungal infections, and resistance to antibiotics used to treat fungal infections is increasing. Naturally occurring octapeptins have been shown to be active against fungi, but have not been explored extensively. It would be further advantageous if these new antimicrobials could demonstrate increased efficacy against fungi and/or reduced nephrotoxicity in humans and veterinary animals.

It should be clear that there is a need for the development of new antibiotics that are effective against infective microorganisms, particularly against polymyxin-resistant bacteria. It would be further advantageous if these new antibiotics could demonstrate one or more of reduced nephrotoxicity, improved stability and increased efficacy. Alternatively, it would be desirable to have a larger selection of antibiotics which can be chosen from to address specific patient infections.

SUMMARY OF THE INVENTION

In a first aspect, although it need not be the only or indeed the broadest aspect, the invention resides in a compound of formula (I), or a salt or stereoisomer thereof:

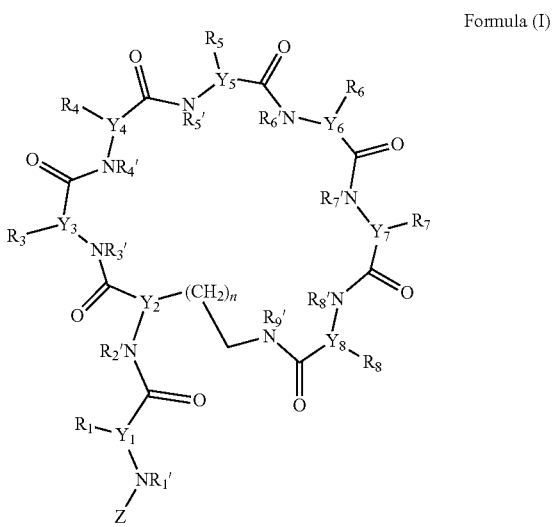

Formula (I)

wherein, $Y_1$, $Y_2$, $Y_3$, $Y_4$, $Y_5$, $Y_6$, $Y_7$ and $Y_8$ are independently selected from the group consisting of C and N;

$R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

$R_1'$, $R_2'$, $R_3'$, $R_4'$, $R_5'$, $R_6'$, $R_7'$, $R_8'$ and $R_9'$ are independently selected from the group consisting of hydrogen and substituted or unsubstituted alkyl, or each pair of $R_1'$ and $R_1$, $R_3'$ and $R_3$, $R_4'$ and $R_4$, $R_5'$ and $R_5$, $R_6'$ and $R_6$, $R_7'$ and $R_7$, and $R_8'$ and $R_8$ may together form a cycloalkyl;

n is an integer selected from 0, 1, 2, or 3; and

Z is selected from

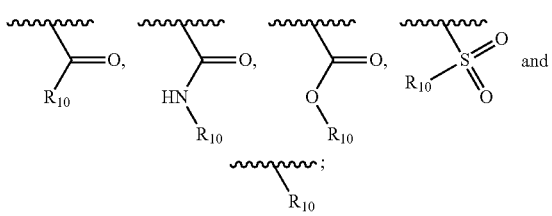

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In one embodiment, the compound of formula (I) may be selected from a compound of formula (Ia), or a salt or stereoisomer thereof:

Formula (Ia)

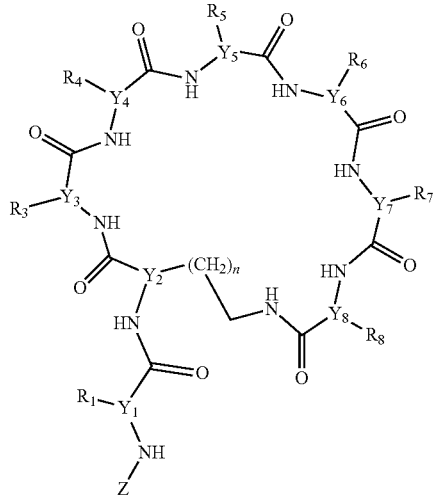

wherein, $Y_1$, $Y_2$, $Y_3$, $Y_4$, $Y_5$, $Y_6$, $Y_7$ and $Y_8$ are independently selected from the group consisting of C and N;

$R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

n is an integer selected from 0, 1, 2, or 3; and

Z is selected from

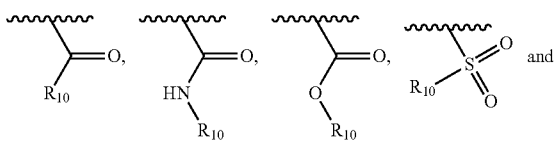

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In an embodiment, the compound of formula (I) or (Ia) may be selected from a compound of formula (Ib), or a salt or stereoisomer thereof:

Formula (Ib)

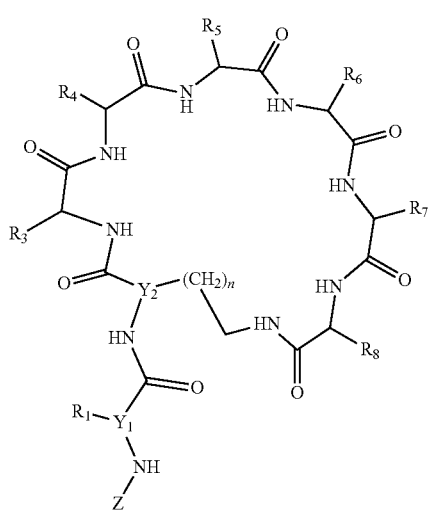

wherein, $Y_1$ and $Y_2$ are independently selected from the group consisting of C and N;

$R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

n is an integer selected from 0, 1, 2, or 3; and

Z is selected from

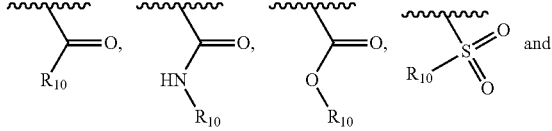

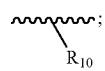

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In a preferred embodiment, the compound of formula (I), (Ia) or (Ib) may be selected from a compound of formula (Ic), or a salt or stereoisomer thereof:

In another preferred embodiment, the compound of formula (I), (Ia), (Ib) or (Ic) may be selected from a compound of formula (Id), or a salt or stereoisomer thereof:

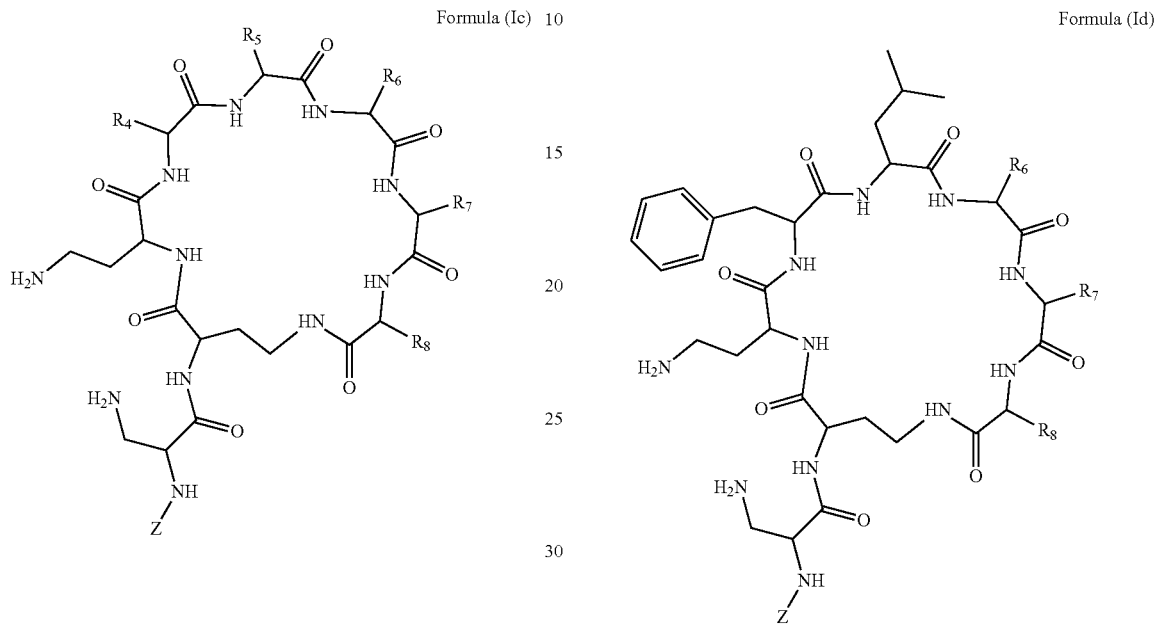

Formula (Ic)

Formula (Id)

wherein, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and Z is selected from wherein $R_6$, $R_7$, and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and Z is selected from

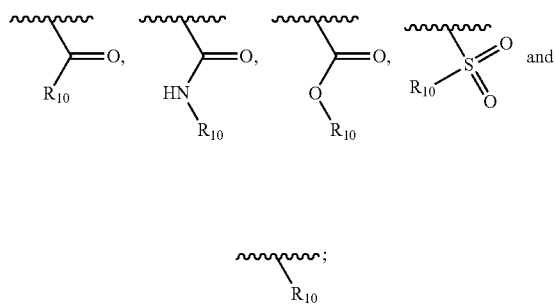

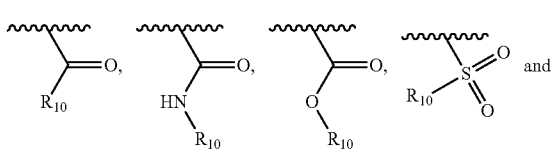

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted;

In another embodiment, the compound of formula (I) may be selected from a compound of formula (Ie), or a salt or stereoisomer thereof:

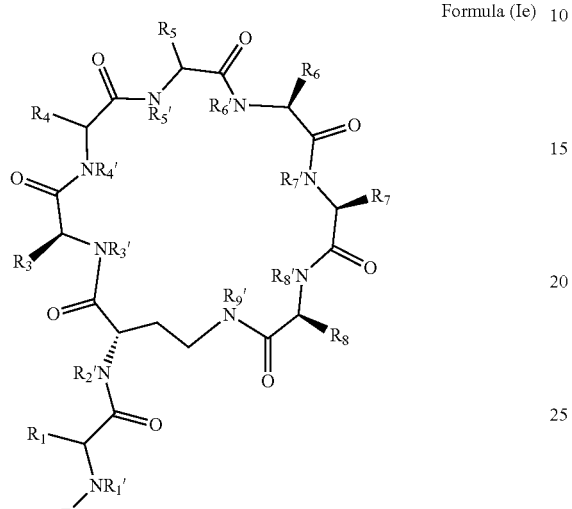

Formula (Ie)

wherein, $R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

$R_1'$, $R_2'$, $R_3'$, $R_4'$, $R_5'$, $R_6'$, $R_7'$, $R_8'$ and $R_9'$ are independently selected from the group consisting of hydrogen and substituted or unsubstituted alkyl, or wherein each or of $R_1'$ and $R_1$, $R_3'$ and $R_3$, $R_4'$ and $R_4$, $R_5'$ and $R_5$, $R_6'$ and $R_6$, $R_7'$ and $R_7$, and $R_8'$ and $R_8$ may together form a cycloalkyl; and Z is selected from

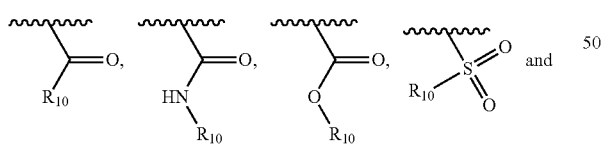

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In an embodiment, the compound of formula (I), (Ia), (Ib), (Ic), or (Id) may be selected from a compound of formula (If), or a salt or stereoisomer thereof

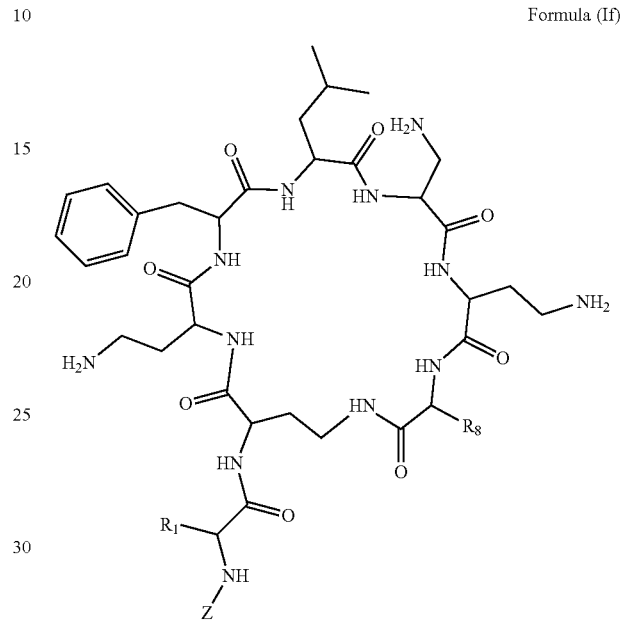

Formula (If)

wherein, $R_1$, and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and Z is selected from

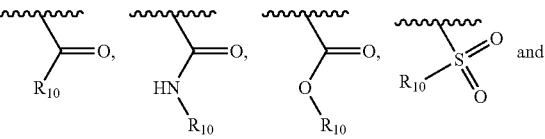

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In an embodiment, the compound of formula (I), (Ia), (Ib), or (Ic) may be selected from a compound of formula (Ig) or a salt or stereoisomer thereof:

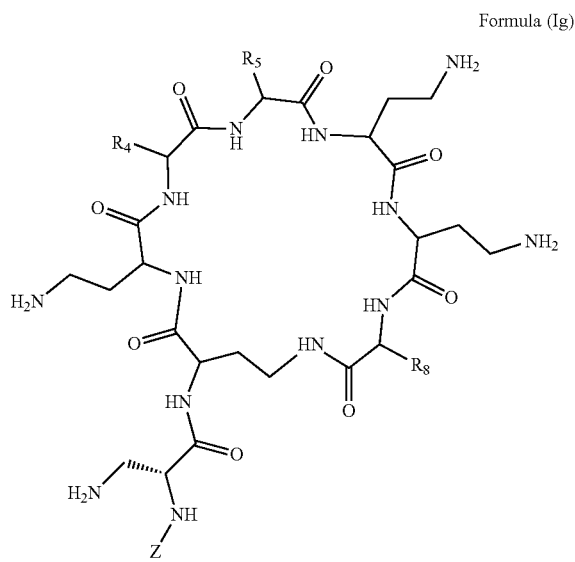

Formula (Ig)

wherein,
$R_4$, $R_5$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and Z is selected from

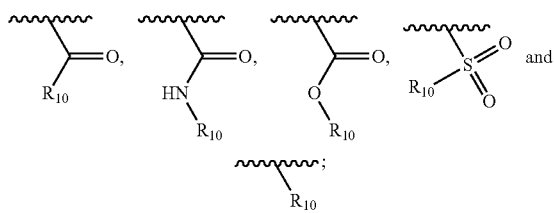

wherein
$R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In a second aspect, the invention resides in a pharmaceutical composition comprising a compound of the first aspect, or a pharmaceutically acceptable salt, solvate or prodrug thereof, and a pharmaceutically acceptable carrier, diluent and/or excipient.

In one embodiment, the pharmaceutical composition further comprises a therapeutic agent. The therapeutic agent being selected from the group consisting of antibiotic agents, antifungal agents, antivirulence agents, biofilm-disrupting agents, anti-inflammatory agents and agents known to potentiate antibiotic efficacy.

In a third aspect, the invention resides in a method of treatment or prevention of a disease, disorder or condition in a subject including the step of administering an effective amount of a compound of the first aspect, or a pharmaceutically acceptable salt, solvate or prodrug thereof, or the pharmaceutical composition of the second aspect, to the subject to thereby treat or prevent the disease, disorder or condition.

Suitably, the disease, disorder or condition is associated with a bacterial or fungal infection.

In an embodiment, the compound of the first aspect further includes the step of administering therapeutic agents. The therapeutic agent being selected from the group consisting of antibiotic agents, antifungal agents, antivirulence agents, biofilm-disrupting agents, anti-inflammatory agents and agents known to potentiate antibiotic efficacy. In one embodiment, the therapeutic agent is co-administered with, administered prior or administered after the compound of the first aspect.

In a fourth aspect, the invention resides in the use of a compound of the first aspect, or a pharmaceutically acceptable salt, solvate or prodrug thereof, or the pharmaceutical composition of the second aspect, in the manufacture of a medicament for the treatment of a disease, disorder or condition.

In another aspect, the invention resides in a compound of the first aspect for use in the treatment of a disease, disorder or condition.

Suitably, the disease, disorder or condition is associated with a bacterial or fungal infection.

The various features and embodiments of the present invention referred to in the individual sections above apply, as appropriate, to other sections, mutatis mutandis. Consequently, features specified in one section may be combined with features specified in other sections as appropriate.

Further features and advantages of the present invention will become apparent from the following detailed description.

BRIEF DESCRIPTION OF THE DRAWINGS

To assist in understanding the invention and to enable a person skilled in the art to put the invention into practical effect, the invention will be described by way of example only with reference to the accompanying drawing, in which.

DETAILED DESCRIPTION OF THE INVENTION

Figure 1A:
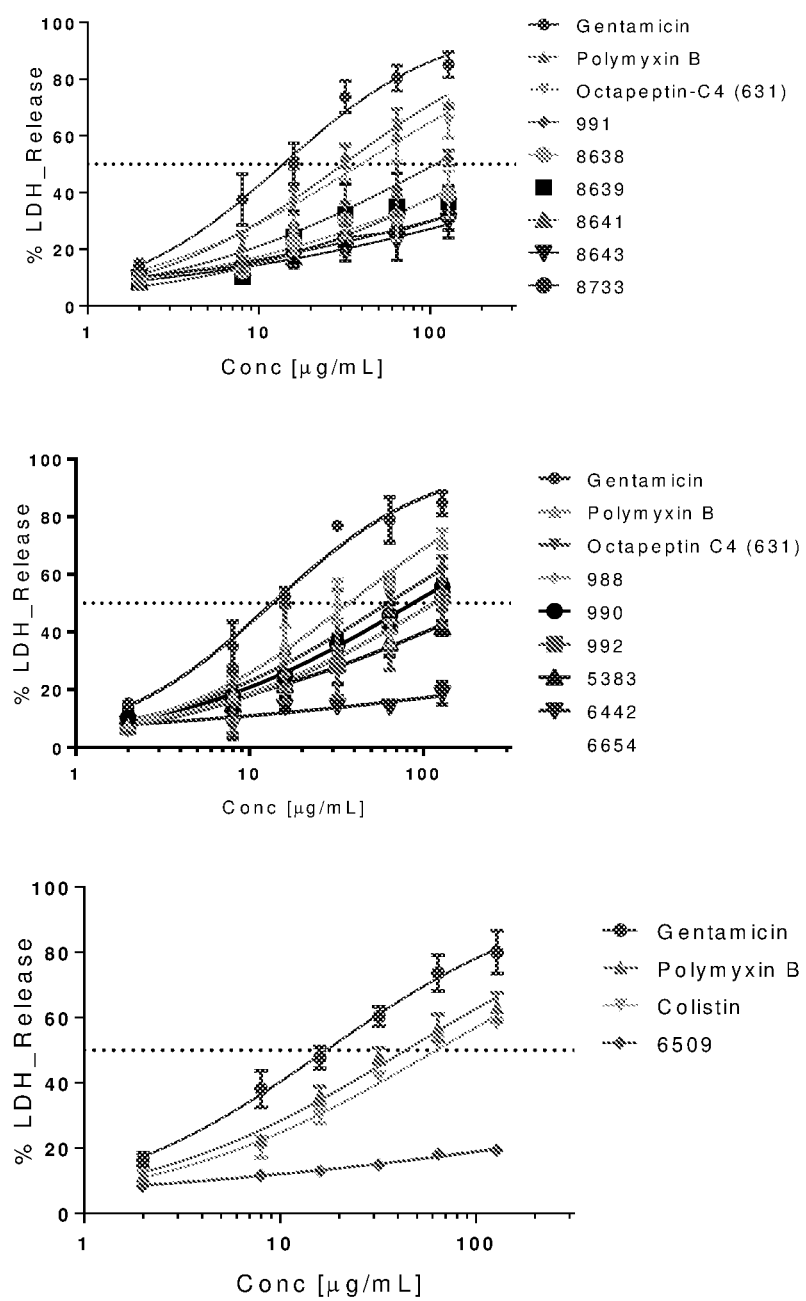
FIG. 1 shows the in vitro nephrotoxicity studies measuring the clinically-validated markers of drug-induced kidney injury Lactate Dehydrogenase (LDH) (A), Gamma-Glutamyl Transferase (GGT) (B), Neutrophil Gelatinase-Associated Lipocalin (NGAL) (C) and Kidney Injury Molecule-1 (KIM-1) (D) release from primary human kidney cells in response to exemplary compounds of the present invention as well as polymyxin B, octapeptin-C4 and gentamicin.
Figure 1B:
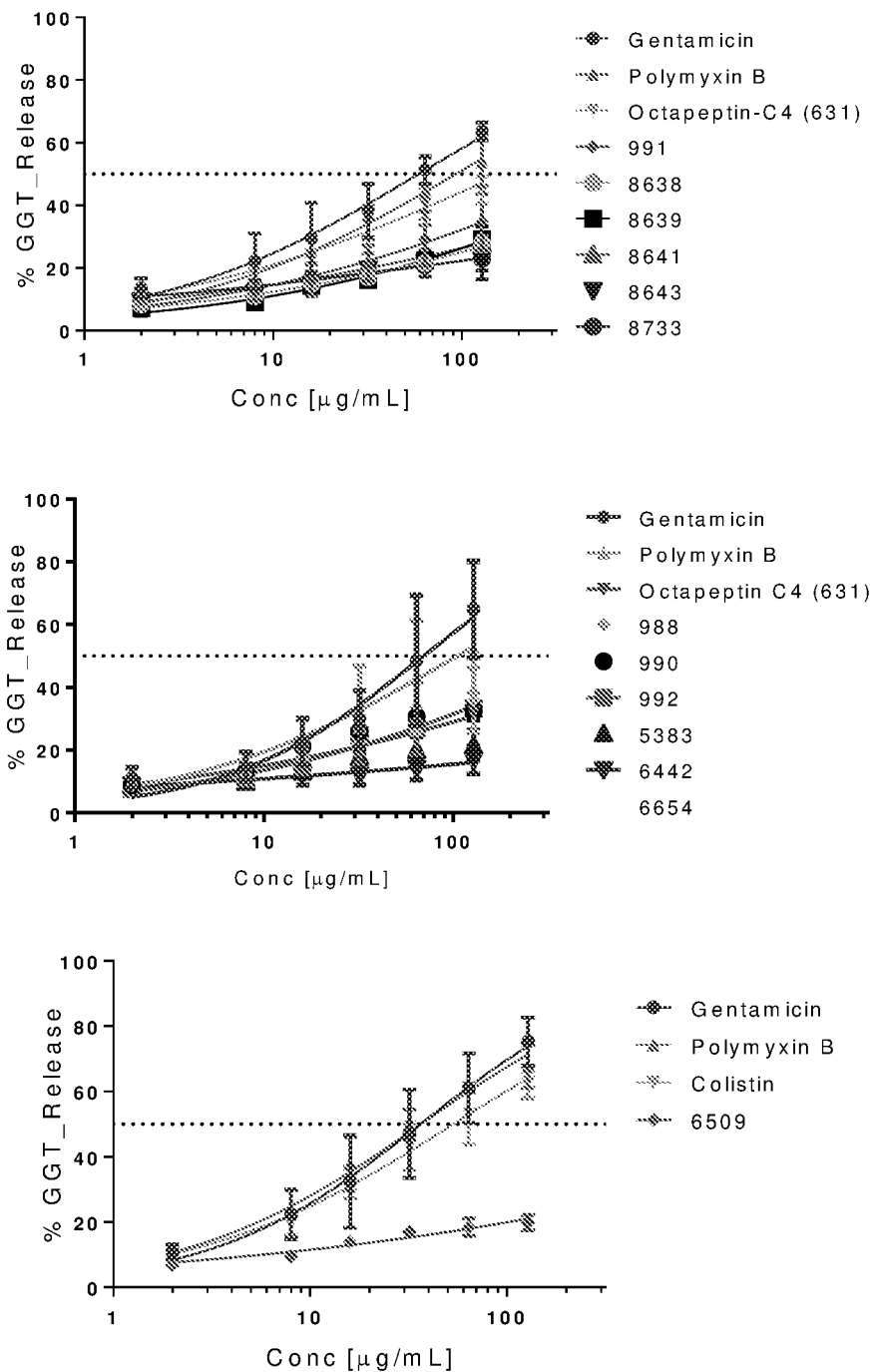
Figure 1C:
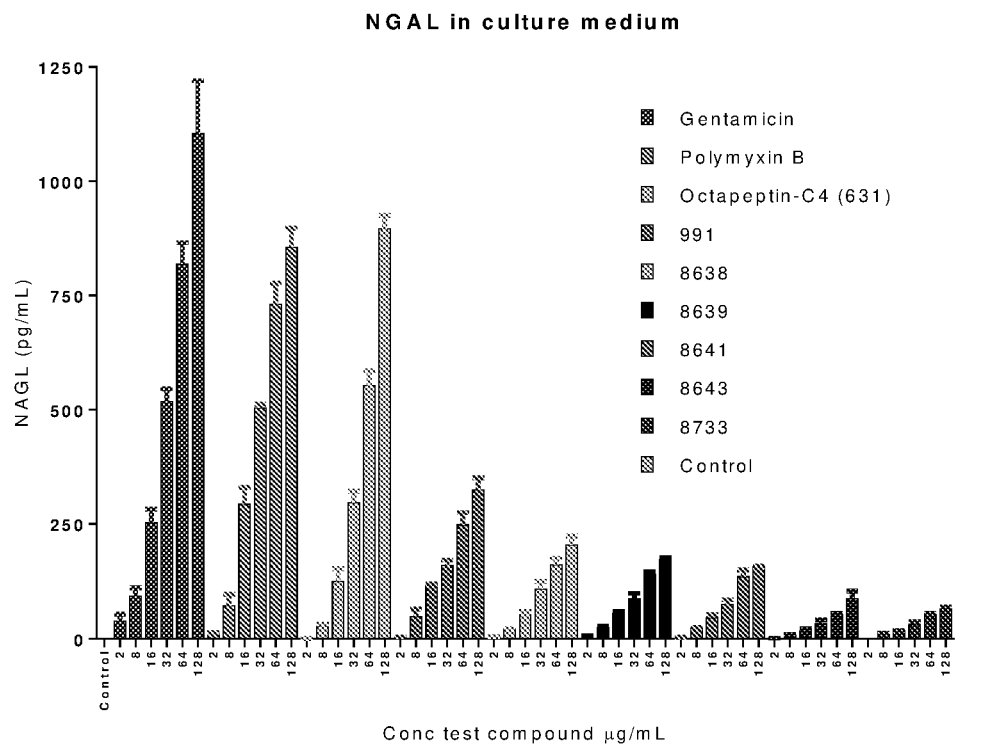
Figure 1C:
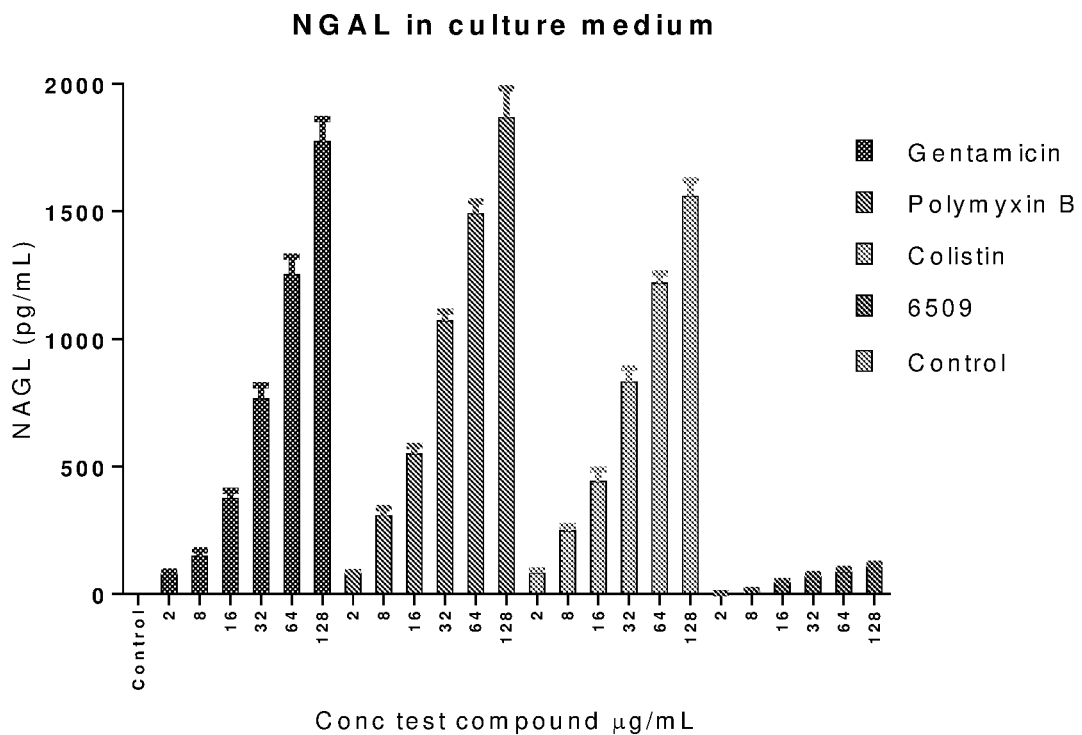
Figure 1D:
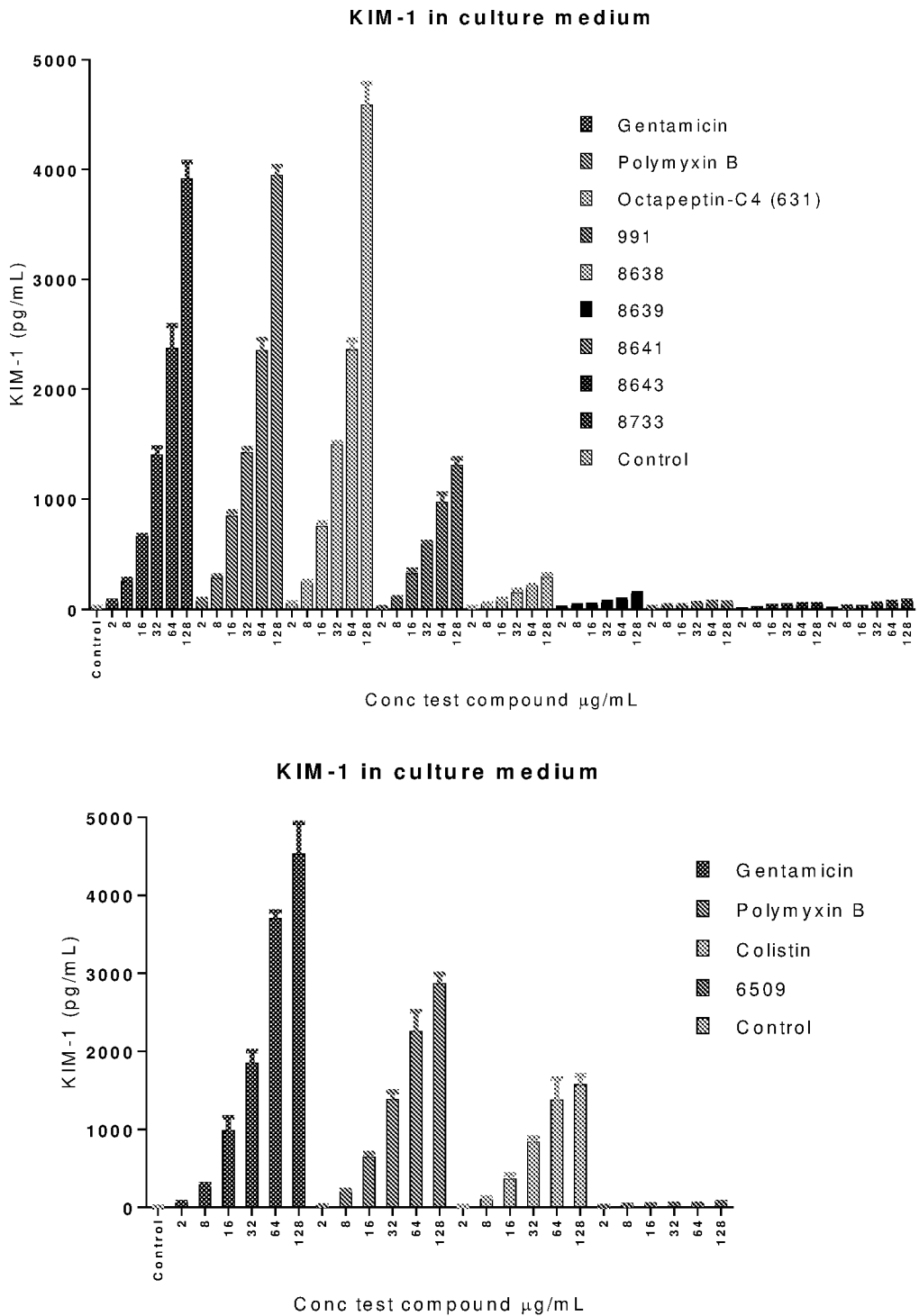

Embodiments of the present invention reside primarily in novel cyclic peptide compounds.

Definitions

In this specification, adjectives such as at least one, and one or more, and the like may be used solely to distinguish one element or action from another element or action without necessarily requiring or implying any actual such relationship or order.

As used herein, the term 'about' means the amount is nominally the number following the term 'about' but the actual amount may vary from this precise number to an unimportant degree.

In this patent specification, the terms 'comprises', 'comprising', 'includes', 'including', or similar terms are intended to mean a non-exclusive inclusion, such that a method or groups that comprises a list of elements does not include those elements solely, but may well include other elements not expressly listed.

Unless defined otherwise, all technical and scientific terms used herein have the same meaning as would be commonly understood by those of ordinary skill in the art to which this invention belongs.

The term "substituted" in each incidence of its use herein, and in the absence of an explicit listing for any particular moiety, refers to substitution of the relevant moiety, for example an alkyl chain or ring structure, with one or more groups selected from $C_1$-$C_{12}$ alkyl, $C_2$-$C_{12}$ alkenyl, $C_1$-$C_{12}$ haloalkyl, $C_1$-$C_{12}$ alkoxy, CN, OH, SH, SeH, S-alkyl, oxo, $NH_2$, NH—C(=NH)—$NH_2$, —NH—C(=NH)—NH—$NO_2$; —NH—C(=NH)-Me; —NH—$SO_2$-Me; —NH—C(=O)Me; monoalkyl ammonium, dialkyl ammonium, trialkylammonium, tetraalkylammonium, —NH—C(=NH)—NHMe; —NH—C(=NMe)-NHMe; —NH—C(=NH)—N(Me)$_2$; —NH—C(=NH)—NHCN; —NH—C(=O)—$NH_2$; —NH—C(=NH)—NH—OMe; —NH—C(=NH)—NHOH; $(CH_2)_2$—O—NH—C(=NH)—$NH_2$; $(CH_2)_3$—$ONH_2$, N($R_1$)—C(=$N_2$)—N($R_3R_4$) ($R_1$-$R_4$=H, alkyl) Cl, F, Br, I, COOH, cycloalkyl, imine, amide, aryl and heterocyclyl, each of which may themselves be optionally substituted. Furthermore, when any substituent is present, each substituent may be substituted with moieties that are independently selected from the group consisting of: halogen (e.g. chlorine, fluorine, bromine or iodine), =O, =S, —CN, —$NO_2$, —$CF_3$, —$OCF_3$, alkyl, alkenyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, aryl heteroalkyl, heteroaryl heteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkyl-aminocarbonyl, alkenyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)Ra, C(=O)O$R_a$, C(=O)N$R_aR_b$, C(=NOH)$R_a$, C(=N$R_a$)N$R_bR_c$, N$R_aR_b$, N$R_a$C(=O)$R_b$, N$R_a$C(=O)O$R_b$, N$R_a$C(=O)N$R_bR_c$, N$R_a$C(=N$R_b$) N$R_cR_d$, N$R_a$S$O_2R_b$, —SRa, $SO_2$NRaRb, —O$R_a$, OC(=O)N$R_aR_b$, OC(=O)$R_a$ and acyl, wherein $R_a$, $R_b$, $R_c$ and $R_d$ are each independently selected from the group consisting of H, $C_1$-$C_{12}$ alkyl, $C_1$-$C_{12}$ haloalkyl, $C_2$-$C_{12}$ alkenyl, $C_1$-$C_{10}$ heteroalkyl, $C_3$-$C_{12}$ cycloalkyl, $C_3$-$C_{12}$ cycloalkenyl, $C_1$-$C_{12}$ heterocycloalkyl, $C_1$-$C_{12}$ heterocycloalkenyl, $C_6$-$C_{18}$aryl, $C_1$-$C_{18}$ heteroaryl, and acyl, or any two or more of $R_a$, $R_b$, $R_c$ and $R_d$, when taken together with the atoms to which they are attached form a heterocyclic ring system with 3 to 12 ring atoms.

The term "alkyl" refers to a straight-chain or branched alkyl substituent containing from, for example, 1 to about 18 carbon atoms, preferably 1 to about 10 carbon atoms, more preferably 1 to about 8 carbon atoms, even more preferably from 1 to about 6 carbon atoms, still yet more preferably from 1 to 2 carbon atoms. Examples of such substituents include methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methyl pentyl, 3-methyl pentyl, 4-methyl pentyl, 2-ethylbutyl, 3-ethylbutyl, octyl, nonyl, decyl, undecyl, dodecyl and the like. The number of carbons referred to relate to the carbon backbone and carbon branching but does not include carbon atoms belonging to any substituents, for example the carbon atoms of an alkoxy substituent branching off the main carbon chain. Substituted alkyl includes alkyl substituted with one or more moieties selected from the group consisting of halo (e.g., Cl, F, Br, and I); other alkyl groups, halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; cyano; thio; sulfonic acid; sulfate; phosphonic acid; phosphate; and phosphonate as well as those described under the definition of 'substituted'.

The term "alkenyl" refers to optionally substituted unsaturated linear or branched hydrocarbon groups, having 2 to 18 carbon atoms, preferably 2 to 9 carbon atoms, more preferably 2 to 6 carbon atoms and having at least one carbon-carbon double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. The number of carbons referred to relates to the carbon backbone and carbon branching but does not include carbon atoms belonging to any substituents. Examples of such substituents may be selected from the group consisting of ethenyl, propenyl, isopropenyl, butenyl, s- and t-butenyl, pentenyl, hexenyl, hept-1,3-diene, hex-1,3-diene, non-1,3,5-triene and the like. Substituted alkenyl includes alkenyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; cyano; thio; sulfonic acid; sulfate; phosphonic acid; phosphate; and phosphonate as well as those described under the definition of 'substituted'.

The term "alkoxy" as used herein means optionally substituted straight or branched chain alkyl groups linked by an oxygen atom (i.e., —O-alkyl), wherein alkyl is as described above. In particular embodiments, alkoxy refers to oxygen-linked groups comprising 1 to 18 carbon atoms ("C1-18 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy"). Included within the scope of the term 'alkoxy' is a straight or branched chain alkenyl linked by an oxygen atom (i.e., —O-alkenyl).

The terms "cycloalkyl" and "cycloalkenyl" refers to optionally substituted saturated and unsaturated mono-cyclic, bicyclic or tricyclic carbon groups. Where appropriate, the cycloalkyl or cycloalkenyl group may have a specified number of carbon atoms, for example, $C_3$-$C_6$ cycloalkyl or cycloalkenyl includes within its scope a carbocyclic group having 3, 4, 5 or 6 carbon atoms. Examples of such substituents may be selected from the group consisting of cyclopropyl, cyclobutyl, cyclopentyl, cyclopentenyl, cyclohexyl, cyclohexenyl, cyclohexadienyl and the like. Substituted cycloalkyl or cycloalkenyl includes substitutions with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; cyano; thio; sulfonic acid;

sulfate; phosphonic acid; phosphate; and phosphonate as well as those described under the definition of 'substituted'.

The term "amino" or "amine" as used herein means a moiety represented by the structure —$NH_2$, —$NHR_1$, —$NR_1R_2$, and $N^+R_1R_2,R_3$, includes primary, secondary, tertiary and quaternary amines/ammonium substituted by alkyl (i.e., alkylamino). Examples of such substituents ($R_1$-$R_3$) include alkyl, alkenyl, alkoxy, aryl, cycloalkyl, cycloalkenyl, heterocyclyl, and heteroaryl.

The term "amide" as used herein means a moiety represented by the structure $R_1C(=O)NR_2R_3$, and include primary amides, secondary amides and tertiary amides substituted with alkyl moieties (alkylamides). $R_1$-$R_3$ may suitably be independently selected from hydrogen, alkyl, alkenyl, cycloalkyl, aryl, aralkyl, heterocyclic or heteroaryl.

The term "aryl" refers to an unsubstituted or substituted aromatic carbocyclic substituent, as commonly understood in the art. It is understood that the term aryl applies to cyclic substituents that are planar and comprise 4n+2 π electrons, according to Hückel's Rule. C-5 or C-6 aryl is preferred. The term 'aryl' also includes within its scope aryl group as defined above linked to the molecule through an alkyl group as defined above. Non-limiting examples of aryl may be selected from phenyl, benzyl, naphthyl, biphenyl and phenol. The aryl groups may also be fused with one or more cycloalkyl groups and linked to the molecule through the cycloalkyl group.

The terms "heterocyclic" and "heterocyclyl" as used herein refers to a non-aromatic ring having 5 to 7 atoms in the ring and of those atoms 1 to 4 are heteroatoms, said ring being isolated or fused to a second ring wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated. Non-limiting examples of heterocyclic may be selected from pyrazole, imidazole, indole, isoindole, triazole, benzotriazole, tetrazole, pyrimidine, pyridine, pyrazine, diazine, triazine, tetrazine, pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

The term "heteroaryl" refers to an aryl group containing from one or more (particularly one to four) non-carbon atom(s) (particularly N, O or S) or a combination thereof, which heteroaryl group is optionally substituted at one or more carbon or nitrogen atom(s). Heteroaryl rings may also be fused with one or more cycloalkyl, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. "Substituted heteroaryl" means a heteroaryl having one or more non-interfering groups as substituents.

Whenever a range of the number of atoms in a structure is indicated (e.g., a $C_1$-$C_{12}$, $C_1$-$C_{10}$, $C_1$-$C_9$, $C_1$-$C_6$, $C_1$-$C_4$, alkyl, etc.), it is specifically contemplated that any sub-range or individual number of carbon atoms falling within the indicated range also can be used. Thus, for instance, the recitation of a range of 1-12 carbon atoms (e.g., $C_1$-$C_{12}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In this specification, the indefinite articles "a" and "an" may refer to one entity or a plurality of entities (e.g. components) and are not to be read of understood as being limited to a single entity.

The present invention is predicated, at least in part, on the finding that certain cyclic peptides, related to octapeptins and related compounds, have advantageous properties including activity against certain polymyxin-resistant bacteria. Additionally, the compounds may demonstrate further advantageous properties such as improved stability and/or efficacy, reduced nephrotoxicity and reduced cytotoxicity.

Octapeptins are a class of naturally occurring cyclic lipopeptides, which are a relatively unexplored class of molecules. These compounds may demonstrate a broad-spectrum antibacterial and antifungal activity and it is shown herein that octapeptin related compounds may be active against the emerging polymyxin-resistant bacteria. Additionally, it is postulated that these compounds may have anti-protozoan, helmetic, aoemeba or other antiparasitic activity. Furthermore, these compounds are postulated to be 'resistance breakers' in combination with other antibiotics. In other words, these compounds may be useful when used in conjunction with other antibiotics.

In a first aspect, although it need not be the only or indeed the broadest aspect, the invention resides in a compound of formula (I), or a salt or stereoisomer thereof:

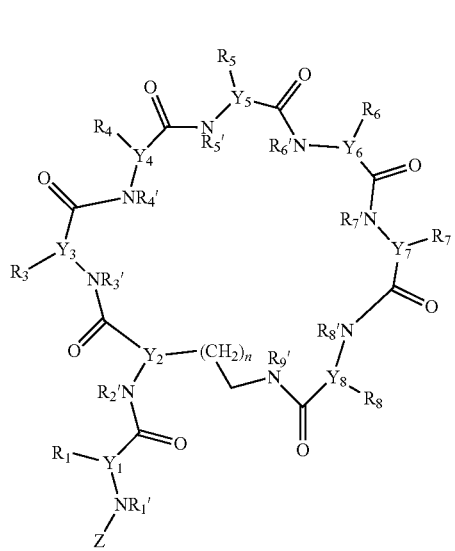

Formula (I)

wherein, $Y_1$, $Y_2$, $Y_3$, $Y_4$, $Y_5$, $Y_6$, $Y_7$ and $Y_8$ are independently selected from the group consisting of C and N;

$R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

$R_1'$, $R_2'$, $R_3'$, $R_4'$, $R_5'$, $R_6'$, $R_7'$, $R_8'$ and $R_9'$ are independently selected from the group consisting of hydrogen and substituted or unsubstituted alkyl, or each pair of $R_1'$ and $R_1$, $R_3'$ and $R_3$, $R_4'$ and $R_4$, $R_5'$ and $R_5$, $R_6'$ and $R_6$, $R_7'$ and $R_7$, and $R_8'$ and $R_8$ may together form a cycloalkyl;

n is an integer selected from 0, 1, 2, or 3; and

Z is selected from

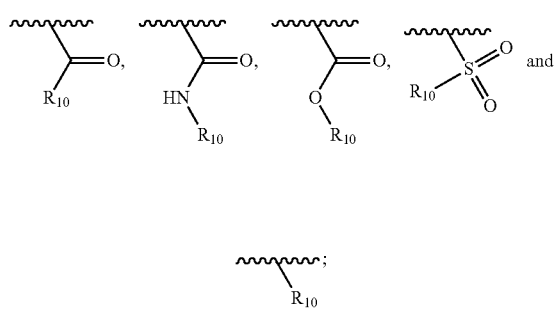

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In one embodiment, the compound of formula (I) may be selected from a compound of formula (Ia), or a salt or stereoisomer thereof:

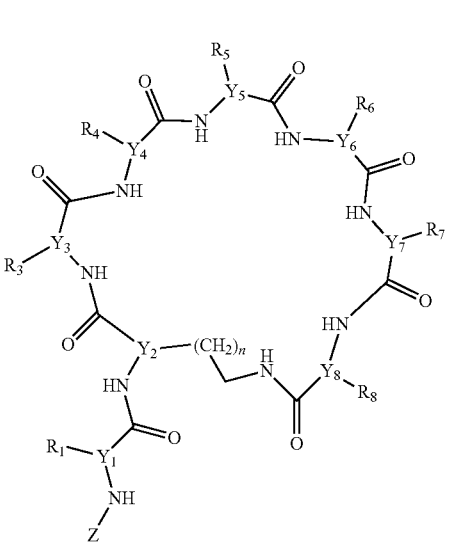

Formula (Ia)

wherein, $Y_1$, $Y_2$, $Y_3$, $Y_4$, $Y_5$, $Y_6$, $Y_7$ and $Y_8$ are independently selected from the group consisting of C and N;

$R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

n is an integer selected from 0, 1, 2, or 3; and

Z is selected from

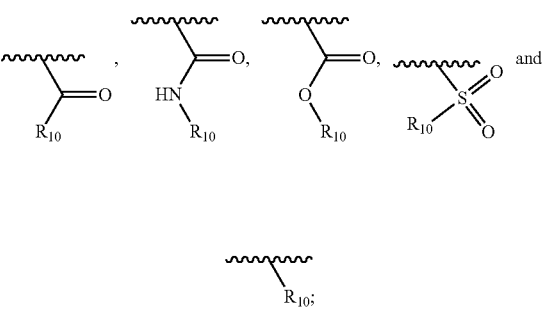

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In a preferred embodiment, the compound of formula (I) or (Ia) may be selected from a compound of formula (Ib), or a salt or stereoisomer thereof:

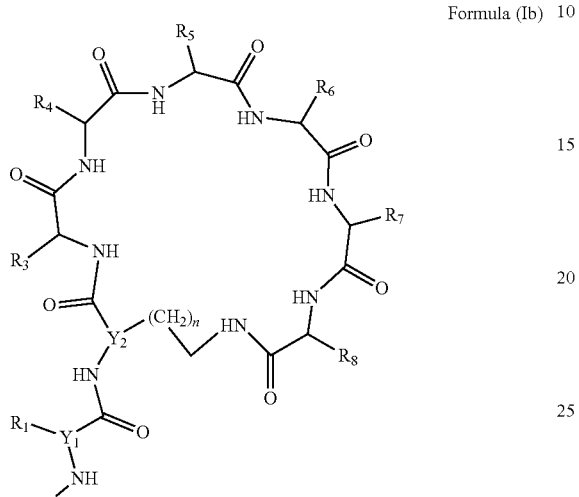

Formula (Ib)

wherein, $Y_1$ and $Y_2$ are independently selected from the group consisting of C and N;

$R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

n is an integer selected from 0, 1, 2, or 3; and

Z is selected from

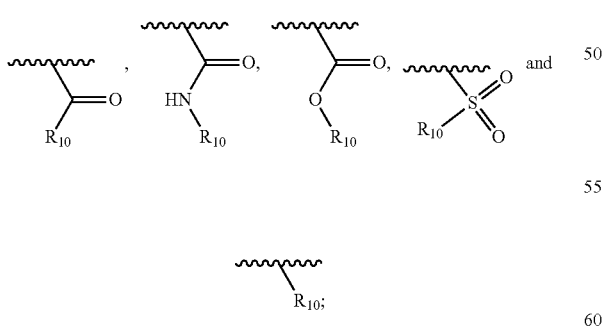

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In a preferred embodiment, the compound of formula (I), (Ia) or (Ib) may be selected from a compound of formula (Ic), or a salt or stereoisomer thereof:

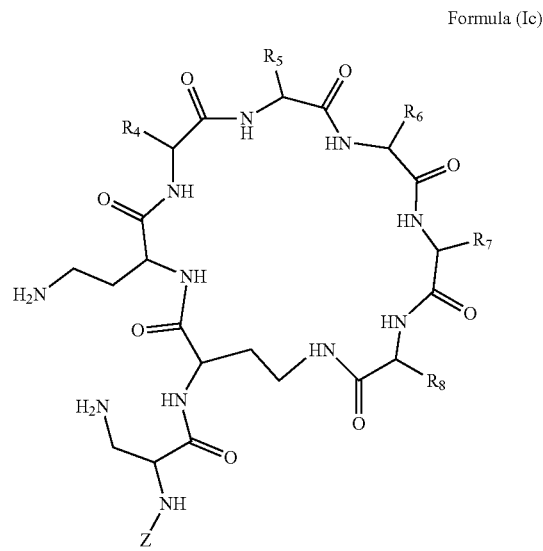

Formula (Ic)

wherein, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and Z is selected from

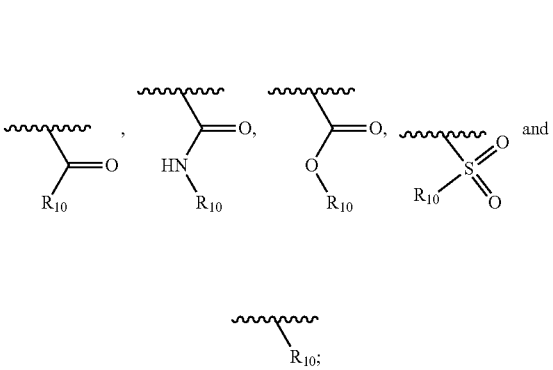

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In another preferred embodiment, the compound of formula (I), (Ia), (Ib) or (Ic) may be selected from a compound of formula (Id), or a salt or stereoisomer thereof:

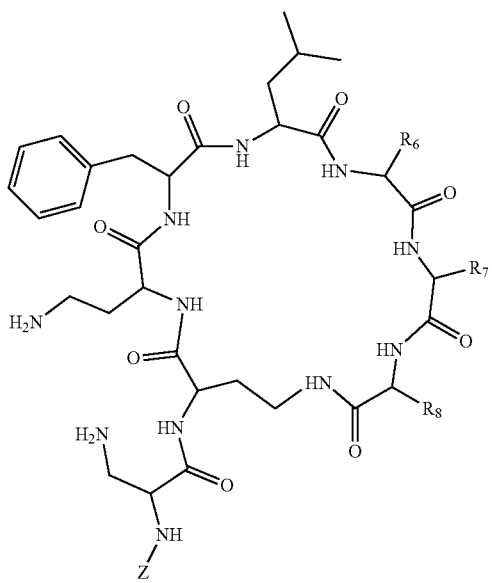

Formula (Id)

wherein $R_6$, $R_7$, and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and Z is selected from

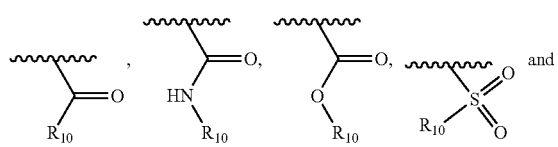

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted;

In another embodiment, the compound of formula (I) may be selected from a compound of formula (Ie), or a salt or stereoisomer thereof:

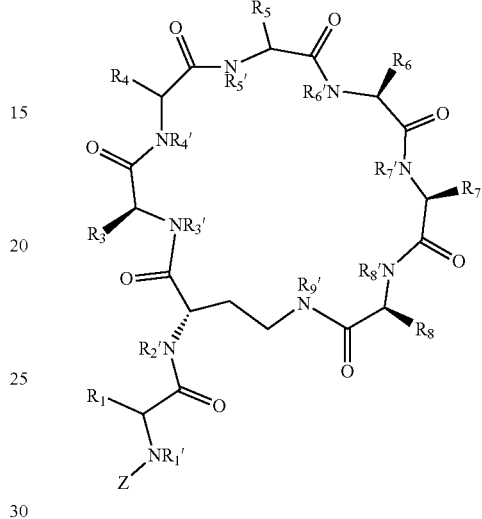

Formula (Ie)

wherein, $R_1$, $R_3$, $R_4$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted;

$R_1'$, $R_2'$, $R_3'$, $R_4'$, $R_5'$, $R_6'$, $R_7'$, $R_8'$ and $R_9'$ are independently selected from the group consisting of hydrogen and substituted or unsubstituted alkyl, or wherein each pair of $R_1'$ and $R_1$, $R_3'$ and $R_3$, $R_4'$ and $R_4$, $R_5'$ and $R_5$, $R_6'$ and $R_6$, $R_7'$ and $R_7$, and $R_8'$ and $R_8$ may together form a cycloalkyl;

Z is selected from

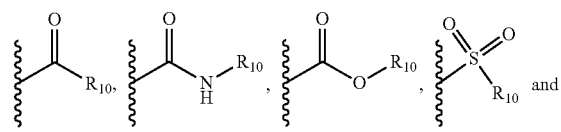

and wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In an embodiment, the compound of formula (I), (Ia), (Ib), (Ic), or (Id) may be selected from a compound of formula (If), or a salt or stereoisomer thereof:

Formula (If)

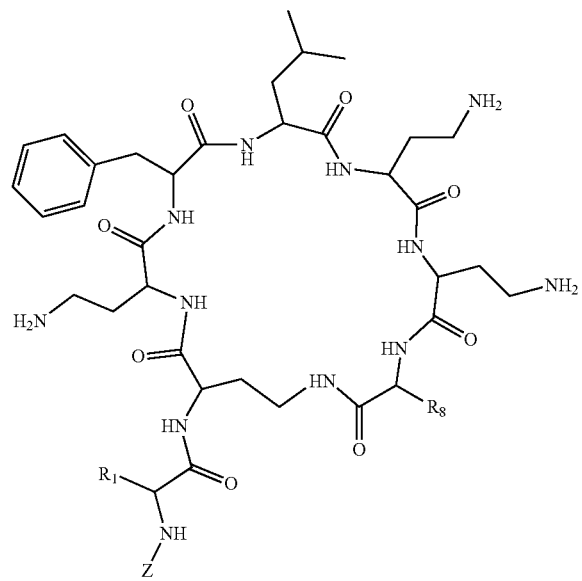

wherein,
$R_1$, and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and
Z is selected from

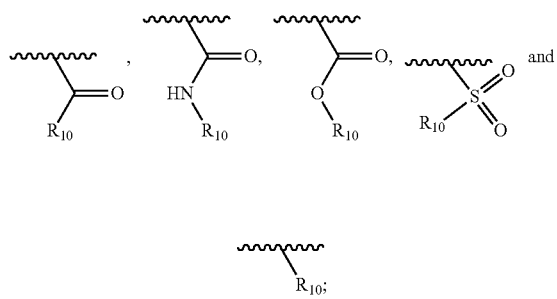

wherein
$R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In an embodiment, the compound of formula (I), (Ia), (Ib), or (Ic) may be selected from a compound of formula (Ig) or a salt or stereoisomer thereof:

Formula (Ig)

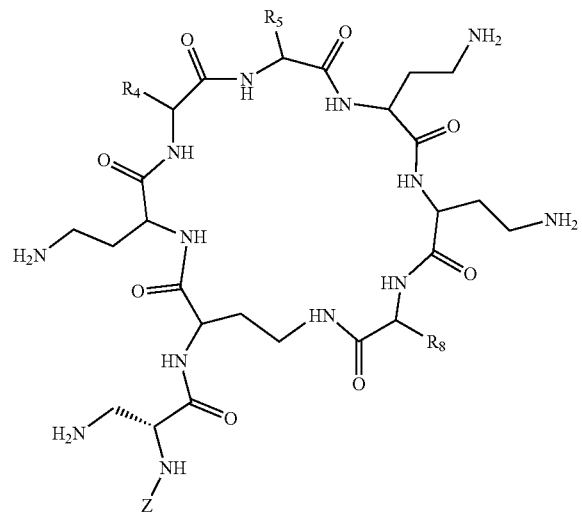

wherein,
$R_4$, $R_5$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; and
Z is selected from

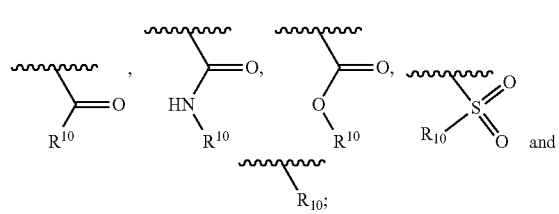

wherein
$R_{10}$ is selected from the group consisting of hydrogen, alkyl, alkenyl, cycloalkyl, cycloalkenyl, heterocyclyl, aryl and heteroaryl, each of which groups may be substituted or unsubstituted.

In an embodiment of formula (I), $Y_4$ and $Y_8$ are C, preferably CH.

In one embodiment of formula (I), $Y_1$, $Y_2$, $Y_3$, $Y_4$, $Y_5$, $Y_6$, $Y_7$ and $Y_8$ are C, preferably CH.

In another embodiment of formula (I), $R_1'$, $R_2'$, $R_3'$, $R_4'$, $R_5'$, $R_6'$, $R_7'$, $R_8'$ and $R_9'$ are independently selected from H, methyl, ethyl and propyl.

In a preferred embodiment of formula (I), at least one of the R groups in the pairs of $R_1$ and $R_1'$, $R_3$ and $R_3'$, $R_4$ and $R_4'$, $R_5$ and $R_5'$, $R_6$ and $R_6'$, $R_7$ and $R_7'$, and $R_8$ and $R_8'$, is hydrogen.

In a particularly preferred embodiment of formula (I), $Y_1$, $Y_2$, $Y_3$, $Y_4$, $Y_5$, $Y_6$, $Y_7$ and $Y_8$ are CH, and $R_1'$, $R_2'$, $R_3'$, $R_4'$, $R_5'$, $R_6'$, $R_7'$, $R_8'$ and $R_9'$ are H.

In one embodiment of formula (I), (Ia), (Ib), (Ic), (Id), (Ie), (If), or (Ig), Z is

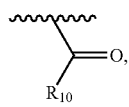

wherein $R_{10}$ is selected from alkyl, alkenyl, alkoxy, cycloalkyl, heterocyclyl, aryl and heteroaryl, each of which groups may themselves be substituted or unsubstituted.

In one embodiment of formula (I), (Ia) and (Ib), n is an integer selected from 0, 1 and 2. Suitably, n is 0 or 1. Preferably, n is 1.

Suitably, Z is

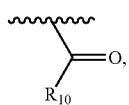

wherein $R_{10}$ is selected from C1-C18 alkyl, C2-C18 alkenyl, C1-C6 cycloalkyl, heterocyclyl, aryl and heteroaryl, each of which groups may be substituted or unsubstituted. In one embodiment, $R_{10}$ is a substituted or unsubstituted C1-C13 alkyl group. In one embodiment, $R_{10}$ is a substituted or unsubstituted C4-C13 alkyl group.

Preferably, Z, in any embodiment of the compound of formula (I), (Ia), (Ib), (Ic), (Id), (Ie), (If), or (Ig), may be selected from the group consisting of:

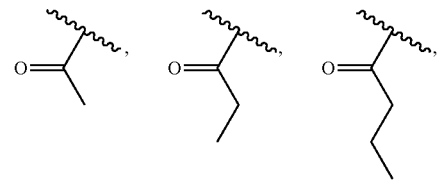

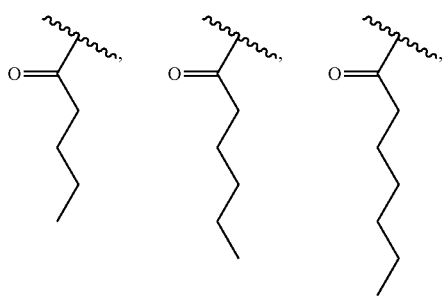

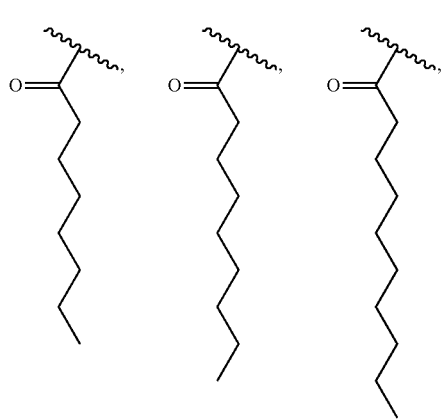

-continued

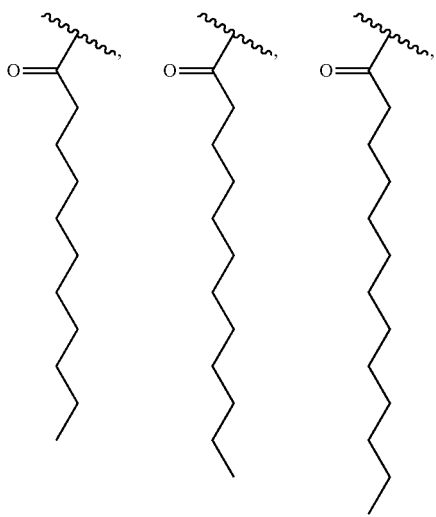

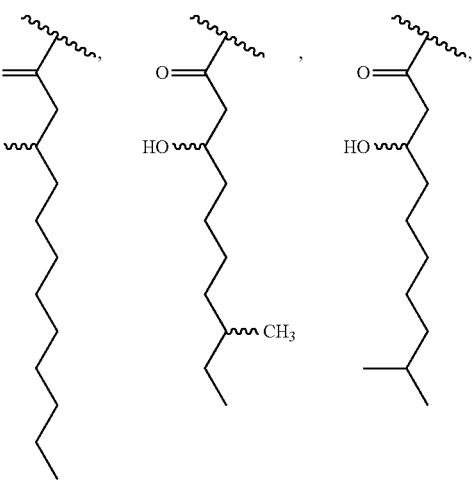

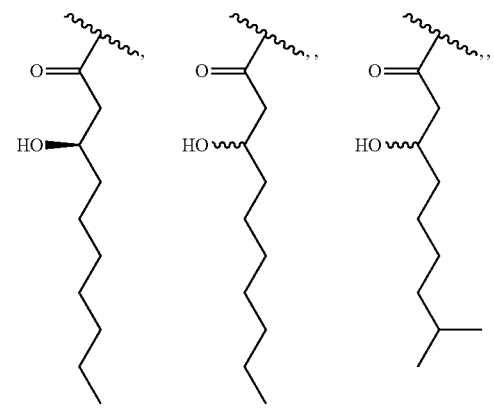
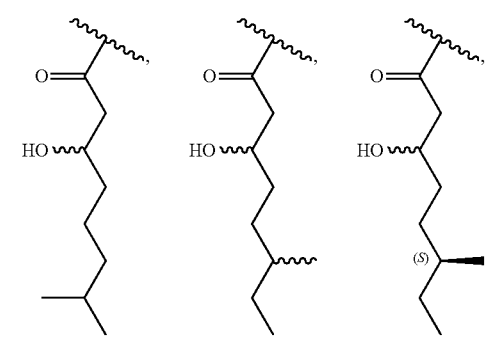
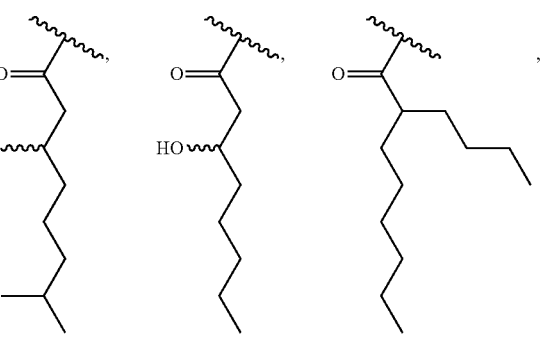
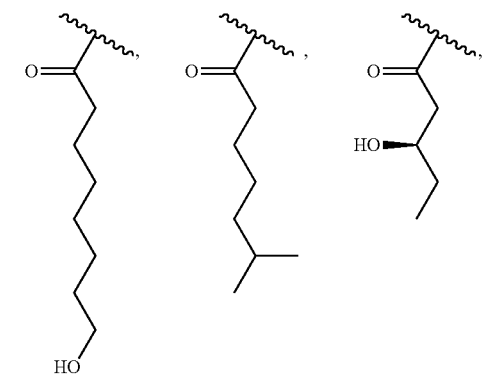
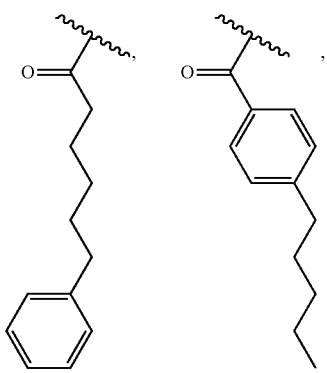
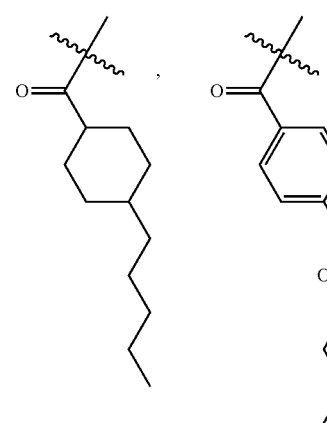
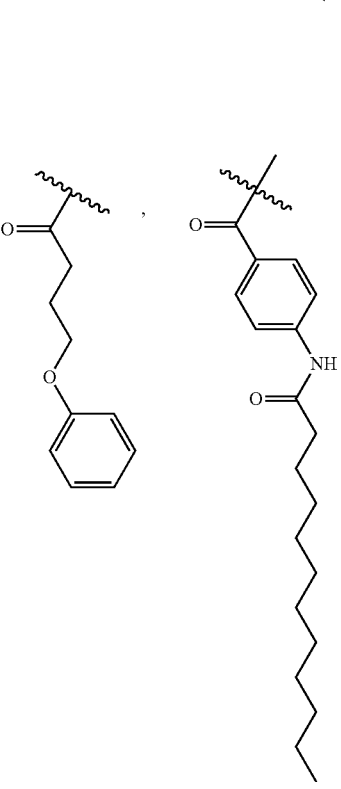

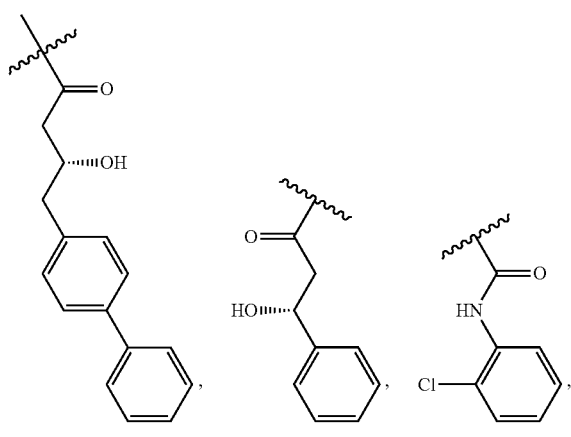
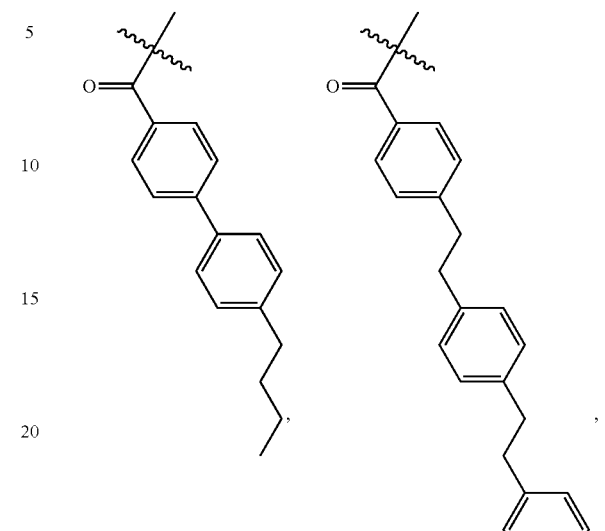
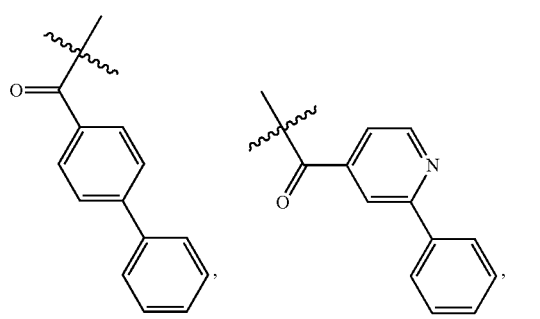
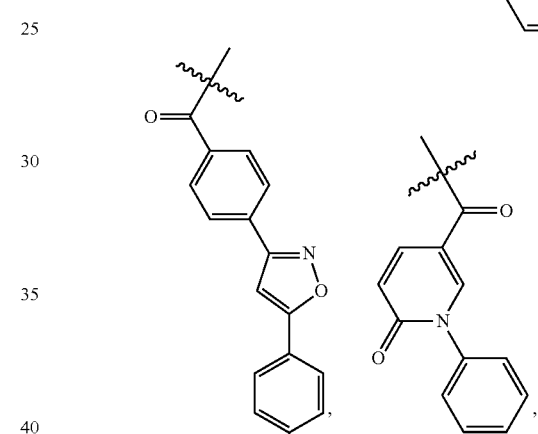
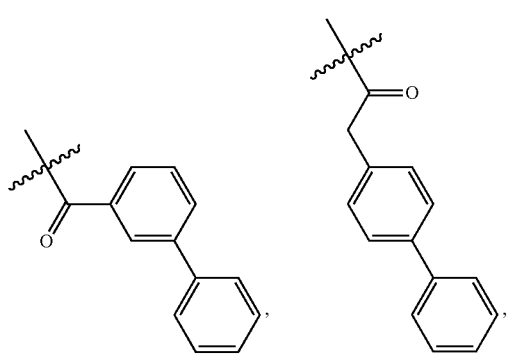
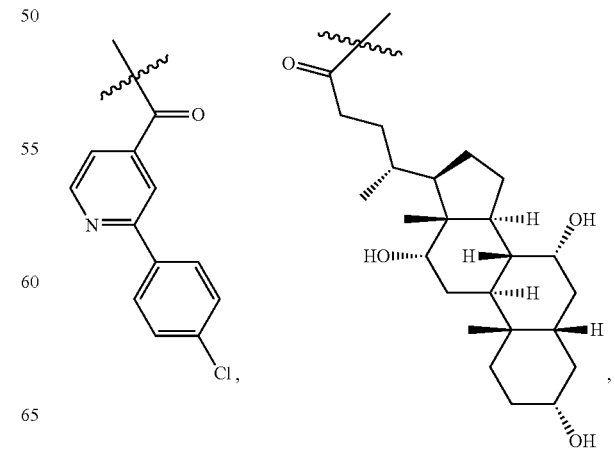

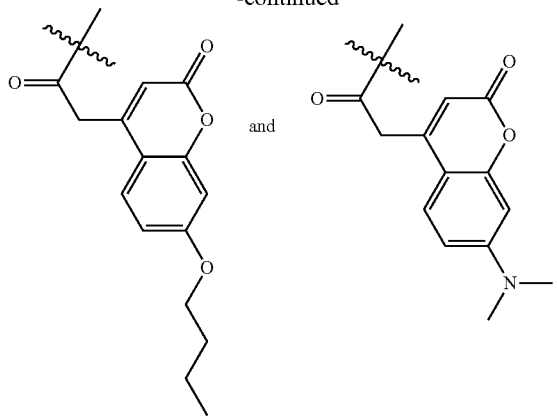

In one embodiment of formula (I), (Ia), (Ib), (Ic), (Id), (Ie), (If), or (Ig), Z is a 3-hydroxyl substituted acyl group or an acetyl group, each of which may be further substituted or unsubstituted. Preferably, Z is:

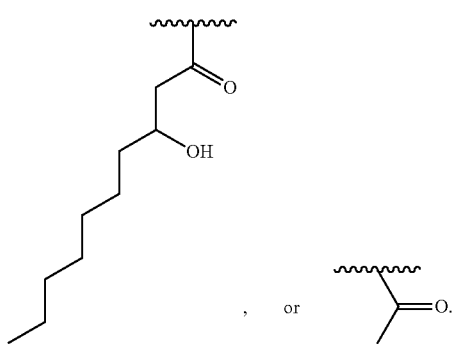

In one embodiment of formula (I), (Ia), (Ib), (Ic), (Id), (Ie), (If), or (Ig), Z does not contain more than one (1) amino acids. In other words, Z does not comprise more than one (1) peptide linkage or bond. That is to say, when Z is

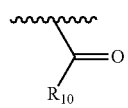

then $R_{10}$ does not have the structure

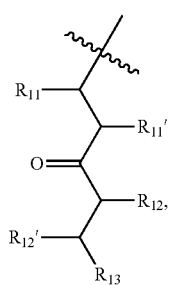

wherein $R_{11}$, $R_{11}'$, $R_{12}$, $R_{12}'$ and $R_{13}$ are independently selected from the group consisting of independently selected from the group consisting of hydrogen, alkyl, alkenyl, cycloalkyl, cycloalkenyl, heterocyclyl, aryl and heteroaryl, each of which groups may be substituted or unsubstituted.

In another embodiment of formula (I), (Ia), (Ib), (Ic), (Id), (Ie), (If), or (Ig), when Z is

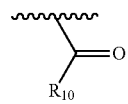

then $R_{10}$ does not have the structure

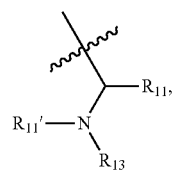

wherein $R_{11}$, $R_{11}'$, and $R_{13}$ are independently selected from the group consisting of independently selected from the group consisting of hydrogen, alkyl, alkenyl, cycloalkyl, cycloalkenyl, heterocyclyl, aryl and heteroaryl, each of which groups may be substituted or unsubstituted. In another embodiment, Z does not contain any amino acids or any peptide linkage or bond.

In one embodiment of formula (I), (Ia), (Ib), (Ic), (Id), (Ie), (If), or (Ig), as appropriate, $R_1$, $R_3$, $R_4$, $R_5$, $R_6$, $R_7$, $R_8$, are independently selected from the group consisting of:

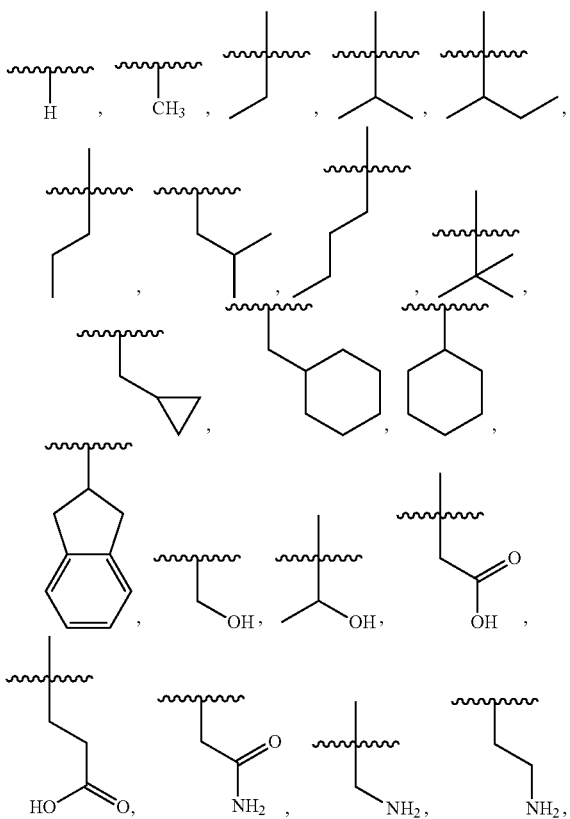

-continued

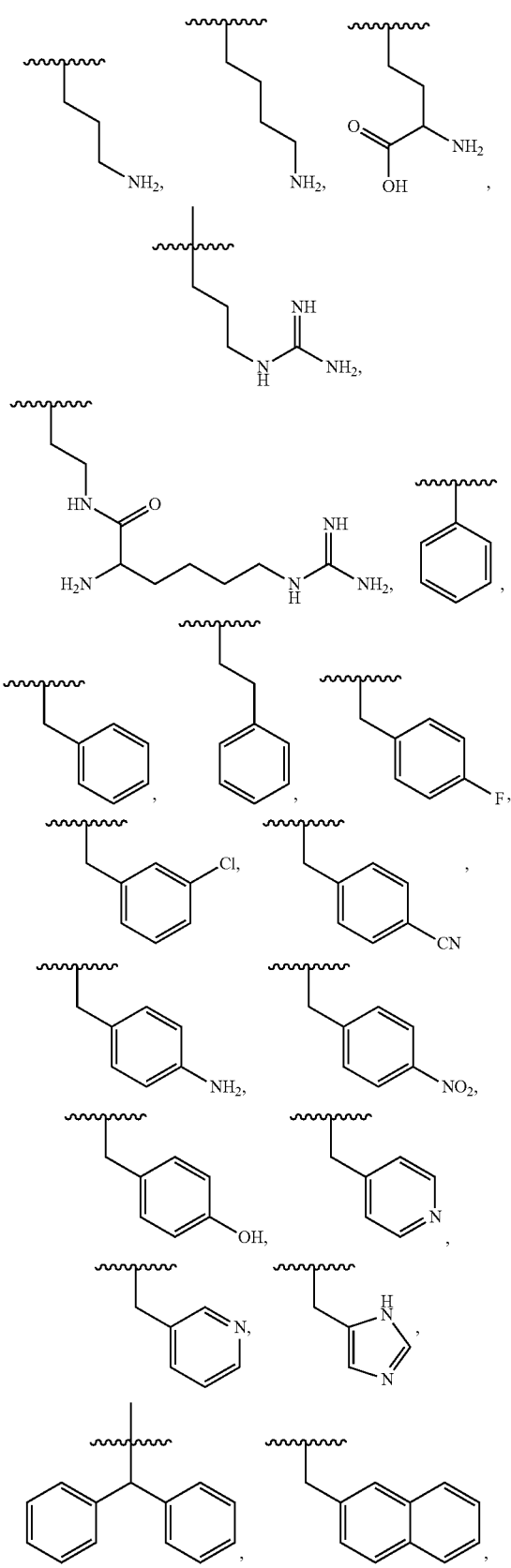

-continued

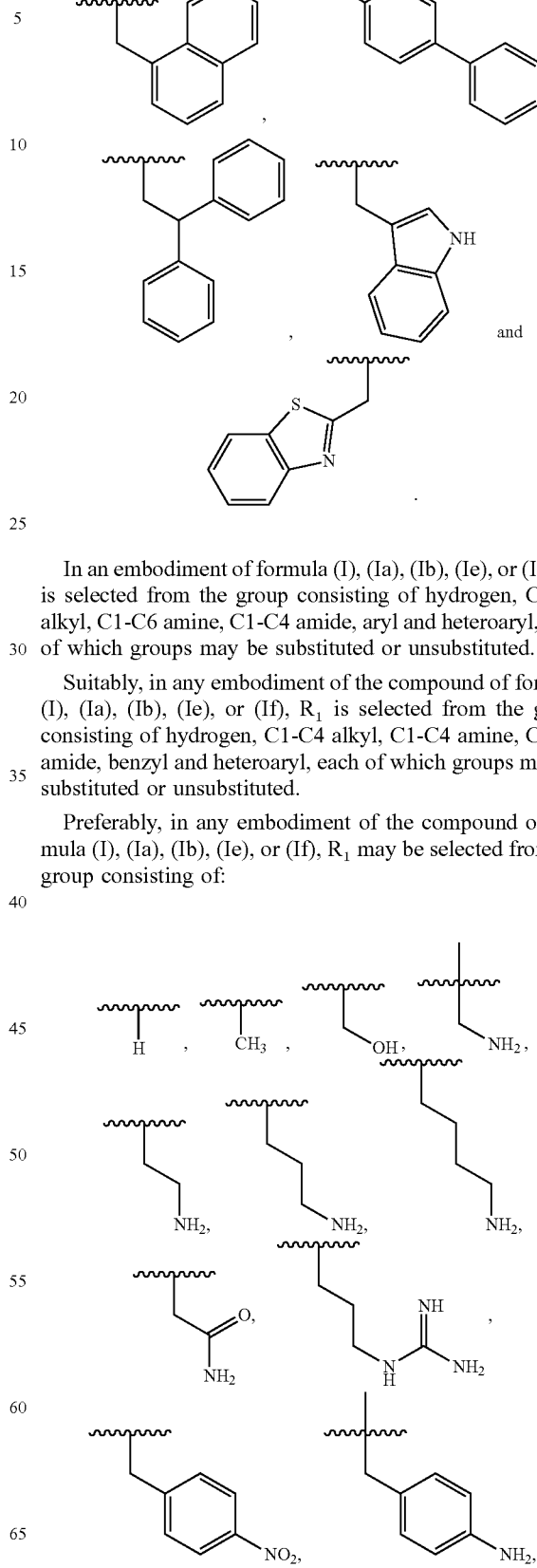

In an embodiment of formula (I), (Ia), (Ib), (Ie), or (If), $R_1$ is selected from the group consisting of hydrogen, C1-C6 alkyl, C1-C6 amine, C1-C4 amide, aryl and heteroaryl, each of which groups may be substituted or unsubstituted.

Suitably, in any embodiment of the compound of formula (I), (Ia), (Ib), (Ie), or (If), $R_1$ is selected from the group consisting of hydrogen, C1-C4 alkyl, C1-C4 amine, C1-C4 amide, benzyl and heteroaryl, each of which groups may be substituted or unsubstituted.

Preferably, in any embodiment of the compound of formula (I), (Ia), (Ib), (Ie), or (If), $R_1$ may be selected from the group consisting of:

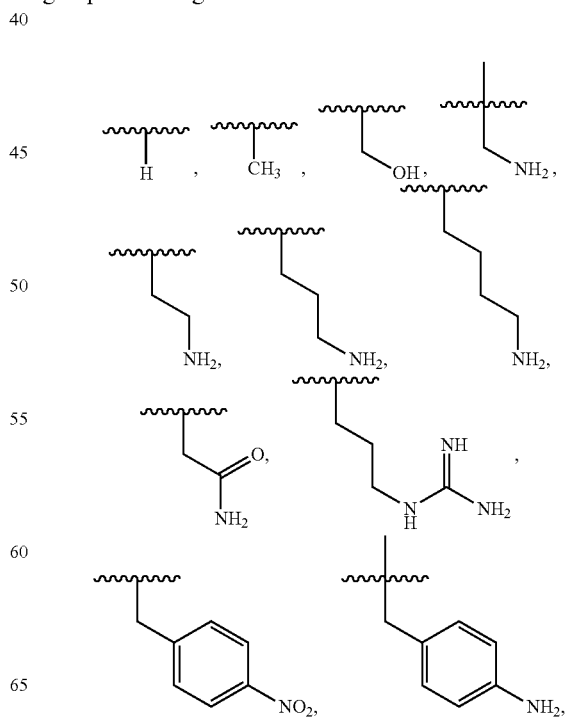

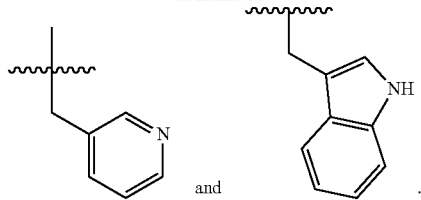

In one preferred embodiment of formula (I), (Ia), (Ib) or (Ie), $R_1$ is selected from the group consisting of:

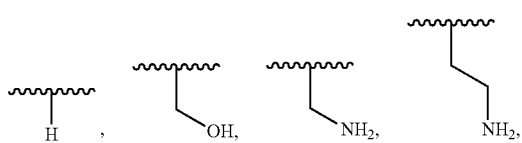

In one embodiment of formula (I), (Ia), (Ib) or (Ie), $R_3$ is selected from the group consisting of hydrogen, C1-C6 alkyl, C1-C6 amine, C1-C6 amide, aryl and heteroaryl, each of which groups may be substituted or unsubstituted.

Suitably, in any embodiment of the compound of formula (I), (Ia), (Ib) or (Ie), $R_3$ is selected from the group consisting of hydrogen, C1-C4 alkyl, C1-C4 amine, C1-C4 amide and benzyl, each of which groups may be substituted or unsubstituted.

Preferably, in any embodiment of the compound of formula (I), (Ia), (Ib) or (Ie), $R_3$ may be selected from the group consisting of:

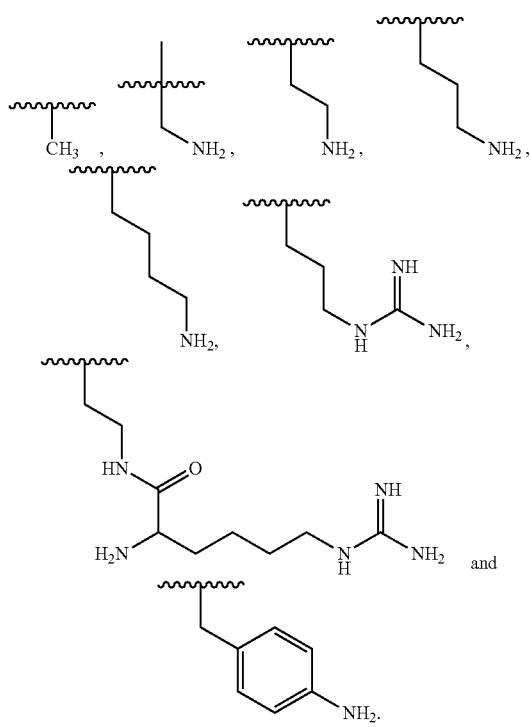

In one preferred embodiment of formula (I), (Ia), (Ib) or (Ie), $R_3$ is

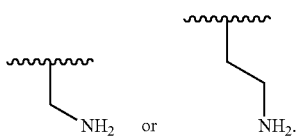

In an embodiment of formula (I), (Ia), (Ib), (Ic), (Ie), or (Ig), $R_4$ is selected from the group consisting of hydrogen, C1-C6 alkyl, C1-C6 amine, C1-C6 amide, C3-C10 cycloalkyl, heterocyclic, aryl and heteroaryl, each of which groups may be substituted or unsubstituted.

Suitably, in any embodiment of the compound of formula (I), (Ia), (Ib), (Ic), (Ie), or (Ig), $R_4$ is selected from the group consisting of hydrogen, C1-C4 alkyl, C3-C9 cycloalkyl, phenyl, benzyl, naphthyl, and heteroaryl, each of which groups may be substituted or unsubstituted.

Preferably, in any embodiment of the compound of formula (I), (Ia), (Ib), (Ic), (Ie), or (Ig), $R_4$ is selected from the group consisting of:

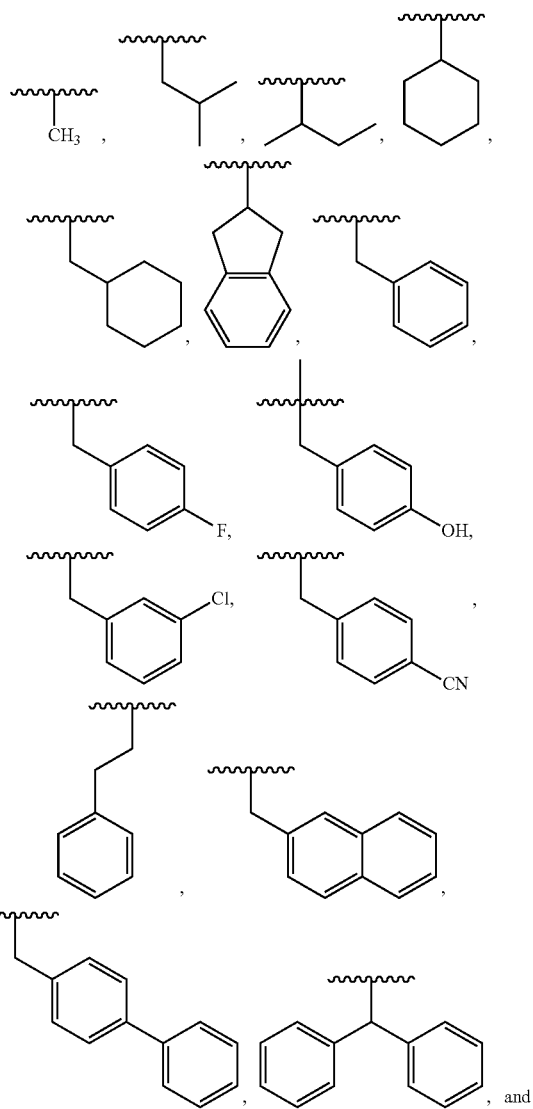

-continued

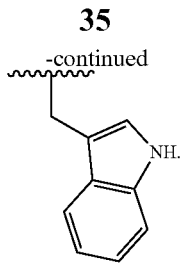

In a preferred embodiment, in any embodiment of the compound of formula (I), (Ia), (Ib), (Ic), (Ie), or (Ig), $R_4$ is selected from the group consisting of:

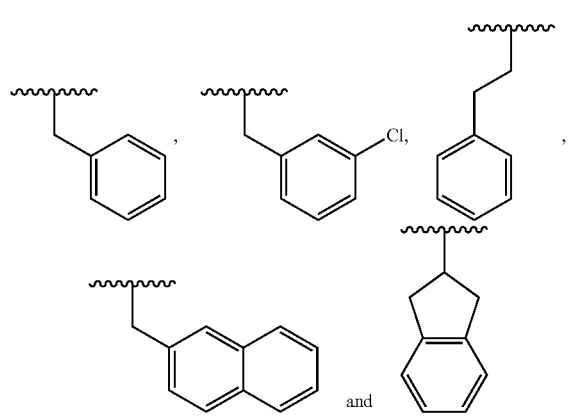

In an embodiment of the compound of formula (I), (Ia), (Ib), (Ic), (Ie), or (Ig), $R_5$ is selected from the group consisting of hydrogen, C1-C6 alkyl, C1-C6 amine, C1-C6 amide, C3-C10 cycloalkyl, heterocyclic, aryl and heteroaryl, each of which groups may be substituted or unsubstituted.

Suitably, in any embodiment of the compound of formula (I), (Ia), (Ib), (Ic), (Ie), or (Ig), $R_5$ is selected from the group consisting of hydrogen, C1-C6 alkyl, C1-C6 amine, C1-C6 amide, C3-C9 cycloalkyl, phenyl, benzyl, and naphthyl, each of which groups may be substituted or unsubstituted.

Preferably, in any embodiment of the compound of formula (I), (Ia), (Ib), (Ic), (Ie), or (Ig), $R_5$ is selected from the group consisting of:

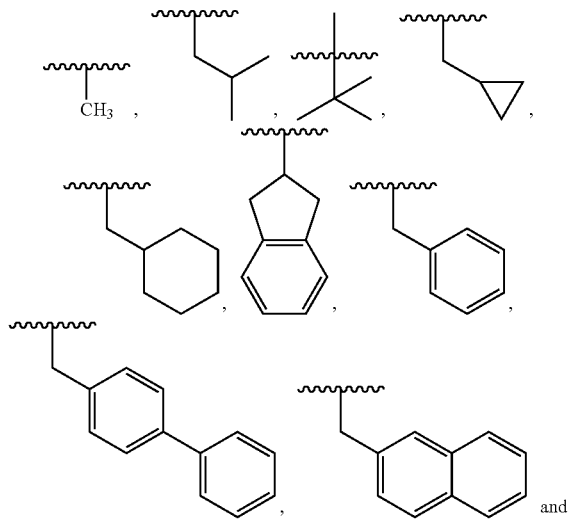

-continued

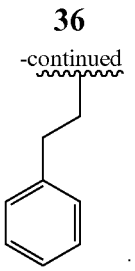

Preferably, in one preferred embodiment of compound of formula (I), (Ia), (Ib), (Ic), (Ie), or (Ig), $R_5$ is selected from the group consisting of:

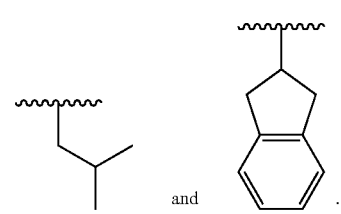

In one embodiment of formula (I), (Ia), (Ib), (Ic), (Id) or (Ie), $R_6$ is selected from the group consisting of hydrogen, C1-C6 alkyl, C1-C6 amine, C1-C6 amide, aryl, heteroaryl and heterocyclic each or which groups may be substituted or unsubstituted.

Suitably, in any embodiment of the compound of formula (I), (Ia), (Ib), (Ic), (Id) or (Ie), $R_6$ is selected from the group consisting of hydrogen, C1-C4 alkyl, C1-C4 amine, C1-C4 amide, and benzyl, each of which groups may be substituted or unsubstituted.

Preferably, in any embodiment of the compound of formula (I), (Ia), (Ib), (Ic), (Id) or (Ie), $R_6$ may be selected from the group consisting of:

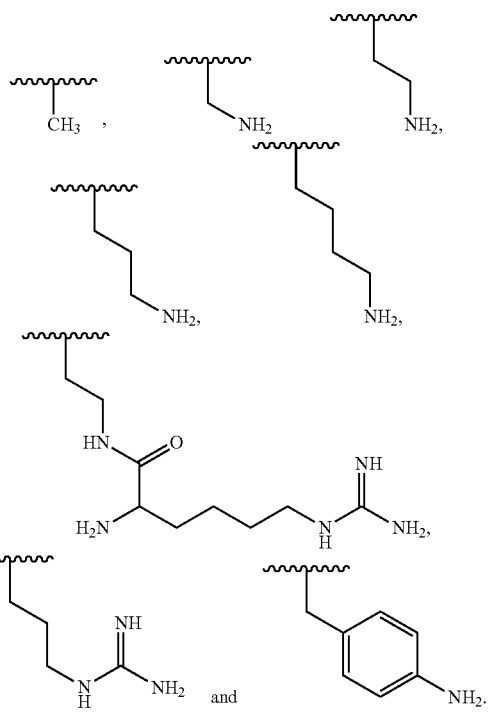

In one preferred embodiment of formula (I), (Ia), (Ib), (Ic), (Id) or (Ie), $R_6$ is selected from the group consisting of:

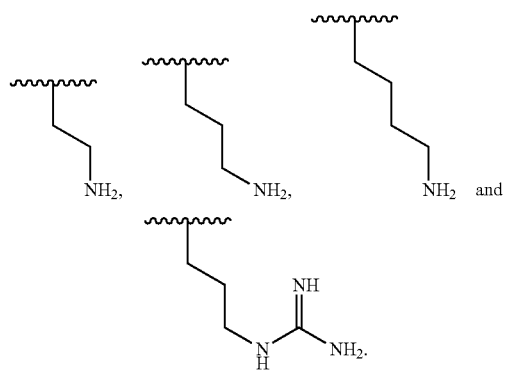

In an embodiment of the compound of formula (I), (Ia), (Ib), (Ic), (Id) or (Ie), $R_7$ is selected from the group consisting of hydrogen, C1-C6 alkyl, C1-C6 amine, C1-C6 amide, C3-C10 cycloalkyl, aryl and heteroaryl each or which groups may be substituted or unsubstituted.

Suitably, in any embodiment of the compound of formula (I), (Ia), (Ib), (Ic), (Id) or (Ie), $R_7$ is selected from the group consisting of hydrogen, C1-C4 alkyl, C1-C4 amine, C3-C9 cycloalkyl, benzyl, naphthyl and heteroaryl, each of which groups may be substituted or unsubstituted.

In a preferred embodiment of formula (I), (Ia), (Ib), (Ic), (Id) or (Ie), $R_7$ may be selected from the group consisting of:

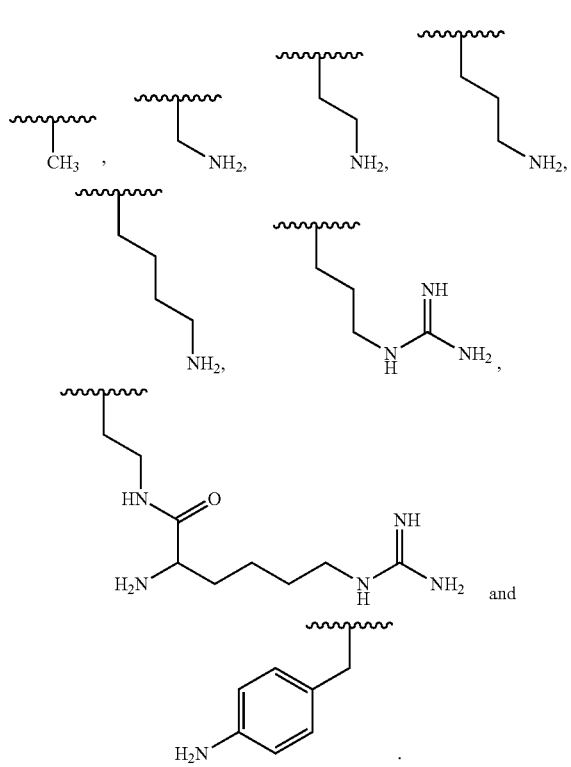

In a preferred embodiment of formula (I), (Ia), (Ib), (Ic), (Id) or (Ie), $R_7$ is selected from the group consisting of:

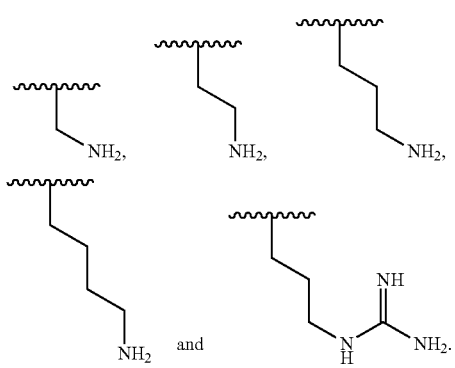

In an embodiment of formula (I), (Ia), (Ib), (Ic), (Id), (Ie), (If), or (Ig), $R_8$ is selected from the group consisting of hydrogen, C1-C6 alkyl, C1-C6 amine, C1-C6 amide, aryl and heteroaryl, each or which groups may be substituted or unsubstituted.

Suitably, in formula (I), (Ia), (Ib), (Ic), (Id), (Ie), (If), or (Ig), $R_8$ is selected from the group consisting of hydrogen, C1-C4 alkyl, C1-C4 amine, phenyl, benzyl, naphthyl and heteroaryl, each of which groups may be substituted or unsubstituted.

Preferably, in any embodiment of the compound of formula (I), (Ia), (Ib), (Ic), (Id), (Ie), (If), or (Ig), $R_8$ may be selected from the group consisting of:

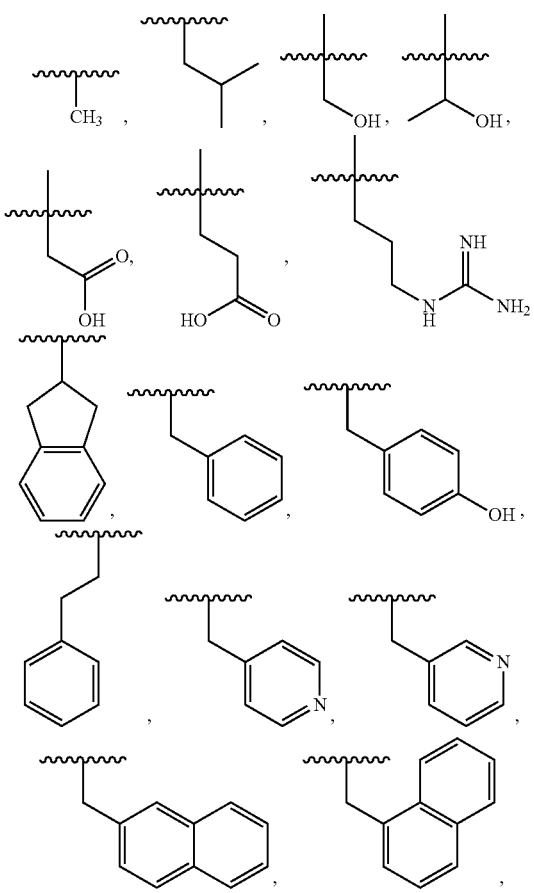

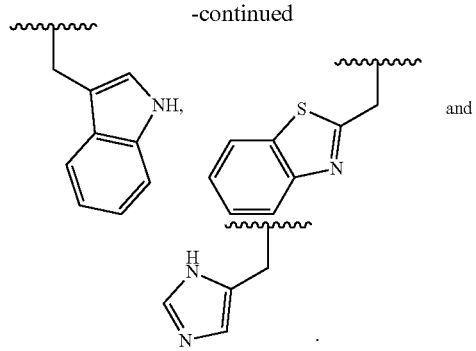

In a preferred embodiment of formula (I), (Ia), (Ib), (Ic), (Id), (Ie), (If), or (Ig), $R_8$ is selected from the group consisting of:

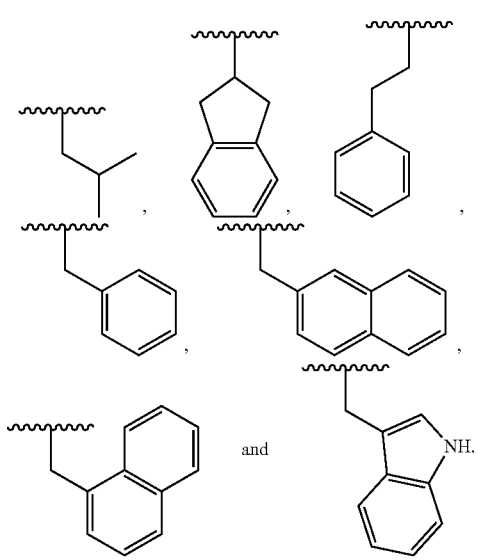

In an alternative embodiment, the compound of the present invention can be viewed as a compound of formula (II), or a salt or stereoisomer thereof:

Formula (II)

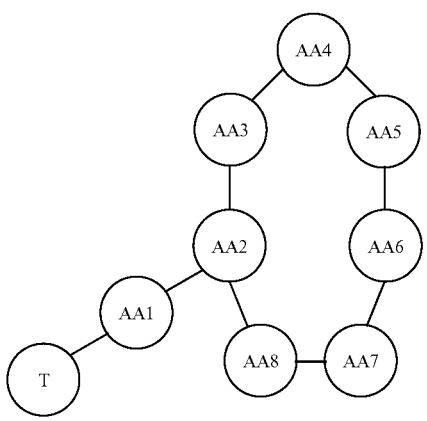

wherein,

AA1 is an amino acid selected from the group consisting of aza-Dab, 3PyPhe, 4NH₂Phe, 4NO₂Phe, Ala, Asn, Dab, Dap, Lys, Orn, Ser, Trp, Gly and Arg;

AA2 is an amino acid selected from the group consisting of Dap, Dab, Orn, Lys, aza-Dap, aza-Dab, aza-Orn and aza-Lys;

AA3 is an amino acid selected from the group consisting of Dab; aza-Dab, 4NH₂Phe, Ala, Arg, Dab(Arg), Dap, Lys and Orn;

AA4 is an amino acid selected from the group consisting of IndanylGly, Phe, Leu; 4CNPhe, 4FPhe, Ala, Ala(3,3'-diphenyl), Bip, Cha, Ile, 2-napthylAla, Trp, Tyr, 3-Cl-Phe, HPhe, cyclohexylglycine and aza-Phe;

AA5 is an amino acid selected from the group consisting of Leu, Phe, aza-Leu, Ala, Bip (biphenylalanine), cyclohexylalanine, cyclopropylalanine, indanylglycine, HPhe (homophenylalanine), 2-napthylAla, and tert-leucine;

AA6 is an amino acid selected from the group consisting of Dab; 4-NH₂Phe, aza-Dab, Ala, Arg; Dab(Arg), Dap, Lys and Orn;

AA7 is an amino acid selected from the group consisting of Dab, Dap, Orn, Lys, Ala, Dab(Arg), 4NH₂Phe, Arg and aza-Dab;

AA8 is an amino acid selected from the group consisting of Leu, Thr, Trp, Phe, Ala, Arg, Ser, Tyr, Glu, Asp, 4PyAla, 3PyAla, 2-napthylAla, 1-napthylAla, Ala(Bth), His, HPhe, indanylGly and aza-Leu; and T is derived from carboxylic acids, sulfonyl chlorides, chloroformates, aldehydes, or isocyanates. Suitably, T is derived from a carboxylic acid selected from the group consisting of acetic acid, pentanoic acid, octanoic acid, nonanoic acid, decanoic acid, 3,7-dimethyloctanoic acid, 3OH-pentanoic acid, 3OH-octanoic acid, 3OH-decanoic acid, 3OH-dodecanoic acid, 3OH-tetradecanoic acid, 8OH-octanoic acid, 3OH-6Me-octanoic acid, 3OH-7Me-octanoic acid, 3OH-8Me-nonanoic acid, 3OH-8Me-decanoic acid, 3OH-9Me-decanoic acid, 3-hydroxy-3-phenylpropanoic acid; 4-[1,1'-biphenyl]-4-yl)-3-hydroxybutanoic acid, 4-phenoxybutanoic acid, 4-(pentyloxy)benzoic acid; [1,1'-biphenyl]-4-carboxylic acid; 4-phenoxybenzoic acid; 4-(heptylamino)benzoic acid; 2-phenylisonicotinic acid; 1-heptylpiperidine-4-carboxylic acid, 4-pentylcyclohexane-1-carboxylic acid and cholic acid The amino acids are connected to one another by a peptide bond or linkage. The amino acids discussed herein can be either the D- or L-amino acid. For example, Dab can be either D-Dab or L-Dab.

For ease of description, the following embodiments of the compound of the first aspect are described in amino acid sequence. The structures of the compounds described in amino acid sequence can be found in the experimental data for synthesized compounds hereinafter. It will be appreciated that the naming of these compounds correlate to the T moiety (or the compound in which T is derived) and AA1-AA8. For example, the following naming convention is used [T]-(AA1)-cyc[(AA2)-(AA3)-(AA4)-(AA5)-(AA6)-(AA7)-(AA8)] For Example, compound 631 (Octapeptin C4) is recited as 3(R)OH-nC9CO-D-Dab-cyc[L-Dab-L-Dab-D-Phe-L-Leu-L-Dab-L-Dab-L-Leu] and this correlates to 3(R)OH-nC9CO[T]-D-Dab[AA1]-cyc[L-Dab[AA2]-L-Dab[AA3]-D-Phe[AA4]-L-Leu[AA5]-L-Dab[AA6]-L-Dab[AA7]-L-Leu[AA8]]. In preferred embodiments, the compound of formula (I), (Ia), (Ib), (Ic), (Id), (Ie), (If) and/or (II) is selected from the group consisting of:

(633) -3(R)OH-nC9CO-D-Dab-cyc[L-Dap-L-Dab-D-Leu-L-Leu-L-Dab-L-Dab-L-Leu];

(754) -3(R)OH-nC9CO-D-Ser-cyc[L-Dab-L-Dab-D-Phe-L-Leu-L-Dab-L-Dab-L-Thr];

(918) -3(R)OH-nC9CO-D-Ser-cyc[L-Dab-L-Dab-D-Phe-L-Leu-L-Dab-L-Dab-L-Leu];

(919) -C4CO-D-Dab-cyc[L-Dab-L-Dab-D-Phe-L-Leu-L-Dab-L-Dab-L-Leu]

(987) -3(R)OH-nC9CO-D-Dab-cyc[L-Dab-L-Dab-D-Phe-L-Leu-L-Dab-L-Dap-L-Leu];

(988) -3(R)OH-nC9CO-D-Dab-cyc[L-Dab-L-Dab-D-Phe-L-Leu-L-Dab-L-Orn-L-Leu];

(989) -3(R)OH-nC9CO-D-Dab-cyc[L-Dab-L-Dab-D-Phe-L-Leu-L-Dab-L-Lys-L-Leu];

(990) -3(R)OH-nC9CO-D-Dab-cyc[L-Dab-L-Dab-D-Phe-L-Leu-L-Dap-L-Dab-L-Leu];

(991) -3(R)OH-nC9CO-D-Dab-cyc[L-Dab-L-Dab-D-Phe-L-Leu-L-Orn-L-Dab-L-Leu];

(992) -3(R)OH-nC9CO-D-Dab-cyc[L-Dab-L-Dab-D-Phe-L-Leu-L-Lys-L-Dab-L-Leu];

(993) -3(R)OH-nC9CO-D-Dab-cyc[L-Dab-L-Dap-D-Phe-L-Leu-L-Dab-L-Dab-L-Leu];

(994) -3(R)OH-nC9CO-D-Dab-cyc[L-Dab-L-Orn-D-Phe-L-Leu-L-Dab-L-Dab-L-Leu];

(995) -3(R)OH-nC9CO-D-Dab-cyc[L-Dab-L-Lys-D-Phe-L-Leu-L-Dab-L-Dab-L-Leu];

(4943) -3(R)OH-nC9CO-D-Dab-cyc[L-Dab-L-Dab-D-Phe-L-Leu-L-Dab-L-Dab-L-Ala];

(4944) -3(R)OH-nC9CO-D-Dab-cyc[L-Dab-L-Dab-D-Phe-L-Leu-L-Dab-L-Ala-L-Leu];

(4945) -3(R)OH-nC9CO-D-Dab-cyc[L-Dab-L-Dab-D-Phe-L-Leu-L-Ala-L-Dab-L-Leu];

(4946) -3(R)OH-nC9CO-D-Dab-cyc[L-Dab-L-Dab-D-Phe-L-Ala-L-Dab-L-Dab-L-Leu];

(4947) -3(R)OH-nC9CO-D-Dab-cyc[L-Dab-L-Dab-L-Ala-L-Leu-L-Dab-L-Dab-L-Leu];

(4948) -3(R)OH-nC9CO-D-Dab-cyc[L-Dab-L-Ala-D-Phe-L-Leu-L-Dab-L-Dab-L-Leu];

(4950) -3(R)OH-nC9CO-L-Ala-cyc[L-Dab-L-Dab-D-Phe-L-Leu-L-Dab-L-Dab-L-Leu];

(4951) -3(R)OH-nC9CO-D-Ala-cyc[L-Dab-L-Dab-D-Phe-L-Leu-L-Dab-L-Dab-L-Leu];

(5002) -3(R)OH-nC9CO-D-Dab-cyc[L-Dab-L-Dab-L-Phe-L-Leu-L-Dab-L-Dab-L-Leu];

(5003) -3(R)OH-nC9CO-D-Dab-cyc[L-Dab-L-Dab-D-Phe-L-Phe-L-Dab-L-Dab-L-Leu];

(5004) -3(R)OH-nC9CO-D-Dab-cyc[L-Dab-L-Dab-D-Phe-L-Leu-L-Dab-L-Dab-L-Phe];

(5005) -3(R)OH-nC9CO-D-Dab-cyc[L-Dab-L-Dab-D-Phe-L-Phe-L-Dab-L-Dab-L-Phe];

(5006) -3(R)OH-nC9CO-D-Dab-cyc[L-Dab-L-Dab-D-Ala-L-Leu-L-Dab-L-Dab-L-Leu];

(5008) -3(R)OH-nC9CO-D-Dab-cyc[L-Dab-L-Dab-D-Tyr-L-Leu-L-Dab-L-Dab-L-Leu];

(5010) -3(R)OH-nC9CO-D-Dab-cyc[L-Dab-L-Dab-D-Bip-L-Leu-L-Dab-L-Dab-L-Leu];

(5012) -3OH-nC7CO-D-Dab-cyc[L-Dab-L-Dab-D-Phe-L-Leu-L-Dab-L-Dab-L-Leu];

(5013) -3OH-nC9CO-D-Dab-cyc[L-Dab-L-Dab-D-Phe-L-Leu-L-Dab-L-Dab-L-Leu];

(5014) -3OH-nC11CO-D-Dab-cyc[L-Dab-L-Dab-D-Phe-L-Leu-L-Dab-L-Dab-L-Leu];

(5015) -3OH-nC13CO-D-Dab-cyc[L-Dab-L-Dab-D-Phe-L-Leu-L-Dab-L-Dab-L-Leu];

(5016) -cholic acid-D-Dab-cyc[L-Dab-L-Dab-D-Phe-L-Leu-L-Dab-L-Dab-L-Leu];

(5017) -nC9CO-D-Dab-cyc[L-Dab-L-Dab-D-Phe-L-Leu-L-Dab-L-Dab-L-Leu];

(5381) -3(R)OH-nC9CO-D-Lys-cyc[L-Dab-L-Dab-D-Phe-L-Leu-L-Dab-L-Dab-L-Leu];

(5382) -3(R)OH-nC9CO-D-Dab-cyc[L-Lys-L-Dab-D-Phe-L-Leu-L-Dab-L-Dab-L-Leu];

(5383) -3(R)OH-nC9CO-D-Dab-cyc[L-Dab-L-Dab-D-Bip-L-Leu-L-Dab-L-Dap-L-Leu];

(5384) -3(R)OH-nC9CO-D-Dab-cyc[L-Dab-L-Dab-D-Bip-L-Leu-L-Dab-L-Dap-L-Phe];

(5385) -3(R)OH-nC9CO-D-Dab-cyc[L-Dab-L-Dab-D-Phe-L-Leu-L-Dab-L-Dap-L-Phe];

(5386) -3(R)OH-nC9CO-D-Dab-cyc[L-Dab-L-Dab-D-Phe-L-Leu-L-Dab-L-Dap-L-Thr];

(5561) -3(R)OH-nC9CO-L-Dap-cyc[L-Dab-L-Dab-D-Phe-L-Leu-L-Dab-L-Dab-L-Leu];

(5562) -3(R)OH-nC9CO-L-Lys-cyc[L-Dab-L-Dab-D-Phe-L-Leu-L-Dab-L-Dab-L-Leu];

(5563) -3(R)OH-nC9CO-L-Dab-cyc[L-Dab-L-Dab-D-Phe-L-Ala-L-Dab-L-Dab-L-Leu];

(5564) -3(R)OH-nC9CO-L-Dab-cyc[L-Dab-L-Dab-D-Phe-L-Leu-L-Dab-L-Dap-L-Leu];

(5565) -3(R)OH-nC9CO-L-Dab-cyc[L-Dab-L-Dab-D-Bip-L-Leu-L-Dab-L-Dap-L-Leu];

(5566) -nC5(7-Me)CH(OH)CH2CO-L-Dab-cyc[L-Dab-L-Dab-D-Phe-L-Leu-L-Dab-L-Dab-L-Leu];

(5567) -nC7(8-Me)CH(OH)CH2CO-L-Dab-cyc[L-Dab-L-Dab-D-Phe-L-Leu-L-Dab-L-Dab-L-Leu];

(5568) -nC9CO-L-Dab-cyc[L-Dab-L-Dab-D-Phe-L-Leu-L-Dab-L-Dab-L-Leu];

(5603) -3(R)OH-nC9CO-D-Dab-cyc[L-Dab-L-Dab-D-Phe-L-Leu-L-Dab-L-Dab(L-Arg)-L-Thr];

(5605) -3(R)OH-nC9CO-D-Dab-cyc[L-Dab-L-Dab-D-Phe-L-Leu-L-Dab-L-4NH2Phe-L-Thr];

(5606) -3(R)OH-nC9CO-D-Dab-cyc[L-Dab-L-Dab-D-Phe-L-Leu-L-Dab-L-Arg-L-Thr];

(5607) -3(R)OH-nC9CO-D-Dab-cyc[L-Dab-L-Dab-D-Phe-L-Bip-L-Dab-L-Dab-L-Thr];

(5608) -3(R)OH-nC9CO-D-Dab-cyc[L-Dab-L-Dab-D-Bip-L-Leu-L-Dab-L-Dab-L-Thr];

(6371) -nC5(6-Me)CH(OH)CH2CO-D-Dab-cyc[L-Dab-L-Dab-L-Leu-L-Phe-L-Dab-L-Dab-L-Leu];

(6394) -3(R)OH-nC9CO-D-Trp-cyc[L-Dab-L-Dab-D-Phe-L-Leu-L-Dab-L-Dab-L-Thr];

(6395) -3(R)OH-nC9CO-D-Dap-cyc[L-Dab-L-Dab-D-Phe-L-Leu-L-Dab-L-Dab-L-Thr];

(6396) -3(R)OH-nC9CO-D-Orn-cyc[L-Dab-L-Dab-D-Phe-L-Leu-L-Dab-L-Dab-L-Thr];

(6397) -3(R)OH-nC9CO-D-4NH2Phe-cyc[L-Dab-L-Dab-D-Phe-L-Leu-L-Dab-L-Dab-L-Thr];

(6398) -3(R)OH-nC9CO-D-3PyPhe-cyc[L-Dab-L-Dab-D-Phe-L-Leu-L-Dab-L-Dab-L-Thr];

(6399) -nC7CO-D-Dab-cyc[L-Dab-L-Dab-D-Phe-L-Leu-L-Dab-L-Dab-L-Thr];

(6403) -4(C7H15NH)PheCO-D-Dab-cyc[L-Dab-L-Dab-D-Phe-L-Leu-L-Dab-L-Dab-L-Thr];

(6404) -C11H21CO-D-Dab-cyc[L-Dab-L-Dab-D-Phe-L-Leu-L-Dab-L-Dab-L-Thr];

(6405) -3Phe4-PyCO-D-Dab-cyc[L-Dab-L-Dab-D-Phe-L-Leu-L-Dab-L-Dab-L-Thr];

(6426) -3(R)OH-nC9CO-D-Trp-cyc[L-Dab-L-Dab-D-Leu-L-Phe-L-Dab-L-Dab-L-Leu];

(6427) -3(R)OH-nC9CO-D-Dap-cyc[L-Dab-L-Dab-D-Leu-L-Phe-L-Dab-L-Dab-L-Leu];

(6428) -3(R)OH-nC9CO-D-Orn-cyc[L-Dab-L-Dab-D-Leu-L-Phe-L-Dab-L-Dab-L-Leu];

(6429) -3(R)OH-nC9CO-D-4NH2Phe-cyc[L-Dab-L-Dab-D-Leu-L-Phe-L-Dab-L-Dab-L-Leu];

(6430) -3(R)OH-nC9CO-D-3PyPhe-cyc[L-Dab-L-Dab-D-Leu-L-Phe-L-Dab-L-Dab-L-Leu];

-continued (6431) -3(R)OH-nC9CO-Gly-cyc[L-Dab-L-Dab-D-Leu-L-Phe-L-Dab-L-Dab-L-Leu];

(6432) -3(R)OH-nC9CO-D-Asn-cyc[L-Dab-L-Dab-D-Leu-L-Phe-L-Dab-L-Dab-L-Leu];

(6433) -3(R)OH-nC9CO-D-4NO2Phe-cyc[L-Dab-L-Dab-D-Leu-L-Phe-L-Dab-L-Dab-L-Leu];

(6441) -3(R)OH-nC9CO-D-Trp-cyc[L-Dab-L-Dab-D-Phe-L-Leu-L-Dab-L-Dab-L-Leu];

(6442) -3(R)OH-nC9CO-D-Dap-cyc[L-Dab-L-Dab-D-Phe-L-Leu-L-Dab-L-Dab-L-Leu];

(6443) -3(R)OH-nC9CO-D-Orn-cyc[L-Dab-L-Dab-D-Phe-L-Leu-L-Dab-L-Dab-L-Leu];

(6444) -3(R)OH-nC9CO-D-4NH2Phe-cyc[L-Dab-L-Dab-D-Phe-L-Leu-L-Dab-L-Dab-L-Leu];

(6445) -3(R)OH-nC9CO-D-3PyPhe-cyc[L-Dab-L-Dab-D-Phe-L-Leu-L-Dab-L-Dab-L-Leu];

(6446) -3(R)OH-nC9CO-Gly-cyc[L-Dab-L-Dab-D-Phe-L-Leu-L-Dab-L-Dab-L-Leu];

(6447) -3(R)OH-nC9CO-D-Asn-cyc[L-Dab-L-Dab-D-Phe-L-Leu-L-Dab-L-Dab-L-Leu];

(6448) -3(R)OH-nC9CO-D-4NO2Phe-cyc[L-Dab-L-Dab-D-Phe-L-Leu-L-Dab-L-Dab-L-Leu];

(6508) -3(R)OH-nC9CO-D-Dab-cyc[L-Dab-L-Dab-D-Phe-L-Leu-L-Dab-L-Dab-L-Arg];

(6509) -3(R)OH-nC9CO-D-Dab-cyc[L-Dab-L-Dab-D-Phe-L-Leu-L-Dab-L-Dab-L-Trp];

(6510) -3(R)OH-nC9CO-D-Dab-cyc[L-Dab-L-Dab-D-Phe-L-Leu-L-Dab-L-Dab-L-Ser];

(6511) -3(R)OH-nC9CO-D-Dab-cyc[L-Dab-L-Dab-D-Phe-L-Leu-L-Dab-L-Dab-L-Tyr];

(6512) -3(R)OH-nC9CO-D-Dab-cyc[L-Dab-L-Dab-D-Phe-L-Leu-L-Dab-L-Dab-L-Glu];

(6513) -3(R)OH-nC9CO-D-Dab-cyc[L-Dab-L-Dab-D-Phe-L-Leu-L-Dab-L-Dab-L-Asp];

(6514) -8OH-nC7CO-D-Dab-cyc[L-Dab-L-Dab-D-Leu-L-Phe-L-Dab-L-Dab-L-Leu];

(6515) -3,7-dimethyloctanoic acid-D-Dab-cyc[L-Dab-L-Dab-D-Leu-L-Phe-L-Dab-L-Dab-L-Leu];

(6516) -1-heptylpiperidine-4-carboxylic acid-D-Dab-cyc[L-Dab-L-Dab-D-Leu-L-Phe-L-Dab-L-Dab-L-Leu];

(6517) -3Phe4-PyCO-D-Dab-cyc[L-Dab-L-Dab-D-Leu-L-Phe-L-Dab-L-Dab-L-Leu];

(6518) -Ph-4-PhCO-D-Dab-cyc[L-Dab-L-Dab-D-Leu-L-Phe-L-Dab-L-Dab-L-Leu];

(6519) -Ph-4-OPhCO-D-Dab-cyc[L-Dab-L-Dab-D-Leu-L-Phe-L-Dab-L-Dab-L-Leu];

(6520) -4-(pentyloxy)benzoic acid-D-Dab-cyc[L-Dab-L-Dab-D-Leu-L-Phe-L-Dab-L-Dab-L-Leu];

(6521) -4-phenoxybutanoic cid-D-Dab-cyc[L-Dab-L-Dab-D-Leu-L-Phe-L-Dab-L-Dab-L-Leu];

(6522) -8OH-nC7CO-D-Dab-cyc[L-Dab-L-Dab-D-Phe-L-Leu-L-Dab-L-Dab-L-Leu];

(6523) -3,7-dimethyloctanoic acid-D-Dab-cyc[L-Dab-L-Dab-D-Phe-L-Leu-L-Dab-L-Dab-L-Leu];

(6524) -1-heptylpiperidine-4-carboxylic acid-D-Dab-cyc[L-Dab-L-Dab-D-Phe-L-Leu-L-Dab-L-Dab-L-Leu];

(6525) -3Phe4-PyCO-D-Dab-cyc[L-Dab-L-Dab-D-Phe-L-Leu-L-Dab-L-Dab-L-Leu];

(6526) -Ph-4-PhCO-D-Dab-cyc[L-Dab-L-Dab-D-Phe-L-Leu-L-Dab-L-Dab-L-Leu];

-continued (6527) -Ph-4-OPhCO-D-Dab-cyc[L-Dab-L-Dab-D-Phe-L-Leu-L-Dab-L-Dab-L-Leu];

(6528) -4-(pentyloxy)benzoic acid-D-Dab-cyc[L-Dab-L-Dab-D-Phe-L-Leu-L-Dab-L-Dab-L-Leu];

(6529) -4-phenoxybutanoic acid-D-Dab-cyc[L-Dab-L-Dab-D-Phe-L-Leu-L-Dab-L-Dab-L-Leu];

(6653) -3(R)OH-nC9CO-D-Dab-cyc[L-Dab-L-Dab-D-Phe-L-Leu-L-Dab-L-Dab(L-Arg)-L-Leu];

(6654) -3(R)OH-nC9CO-D-Dab-cyc[L-Dab-L-Dab-D-Phe-L-Leu-L-Dab(L-Arg)-L-Dab-L-Leu];

(6655) -3(R)OH-nC9CO-D-Dab-cyc[L-Dab-L-Dab(L-Arg)-D-Phe-L-Leu-L-Dab-L-Dab-L-Leu];

(6656) -3(R)OH-nC9CO-D-Dab-cyc[L-Dab-L-Dab-D-Phe-L-Leu-L-Dab(L-Arg)-L-Dab-L-Thr];

(6657) -3(R)OH-nC9CO-D-Dab-cyc[L-Dab-L-Dab(L-Arg)-D-Phe-L-Leu-L-Dab-L-Dab-L-Thr];

(6658) -3(R)OH-nC9CO-L-Dab-cyc[D-Dab-L-Dab-D-Phe-L-Leu-L-Dab-L-Dab-L-Leu];

(6660) -3(R)OH-nC9CO-L-Dab-cyc[D-Dab-L-Dab-D-Phe-L-Ala-L-Dab-L-Dab-L-Leu];

(6661) -3(R)OH-nC9CO-L-Dab-cyc[D-Dab-L-Dab-D-Bip-L-Leu-L-Dab-L-Dab-L-Leu];

(7037) -3(R)OH-nC9CO-D-Dab-cyc[L-Dab-D-Dab-L-Dab-D-Leu-L-Leu-L-Dab-L-Dab-L-Leu];

(7038) -3(R)OH-nC9CO-D-Dab-cyc[L-Dab-D-Dab-L-Dab-D-Leu-L-Phe-L-Dab-L-Dab-L-Leu];

(7039) -3(R)OH-nC9CO-D-Dab-cyc[L-Dab-D-Dab-L-Dab-L-Leu-D-Phe-L-Dab-L-Dab-L-Leu];

(7040) -3(R)OH-nC9CO-D-Dab-cyc[L-Dab-D-Dab-L-Dab-D-Phe-L-Leu-L-Dab-L-Dab-L-Leu];

(8099) -3(R)OH-nC9CO-D-Dab-cyc[L-Dab-L-Dab-D-Phe-L-Ala(cycloprop)-L-Dab-L-Dab-L-Trp];

(8101) -3(R)OH-nC9CO-D-Dab-cyc[L-Dab-L-Dab-L-Dab-D-Phe-L-Ala(cyclohexyl)-L-Dab-L-Dab-L-Trp];

(8103) -3(R)OH-nC9CO-D-Dab-cyc[L-Dab-L-Dab-L-Dab-D-Phe-L-indanylgly-L-Dab-L-Dab-L-Trp];

(8105) -3(R)OH-nC9CO-D-Dab-cyc[L-Dab-L-Dab-L-Dab-D-Phe(4-CN)-L-Leu-L-Dab-L-Dab-L-Trp];

(8109) -3(R)OH-nC9CO-D-Dab-cyc[L-Dab-L-Dab-L-Dab-D-Ala(3,3'-diphenyl)-L-Leu-L-Dab-L-Dab-L-Trp];

(8113) -3(R)OH-nC9CO-D-Dab-cyc[L-Dab-L-Dab-L-Dab-D-Ala(2-Na)-L-Leu-L-Dab-L-Dab-L-Trp];

(8119) -3(R)OH-nC9CO-D-Dab-cyc[L-Dab-L-Dab-L-Dab-D-Phe(4-F)-L-Leu-L-Dab-L-Dab-L-Trp];

-continued (8127)-3(R)OH-nC9CO-D-Dab-cyc[L-Dab-L-Dab-L-Dab-D-Trp-L-Leu-L-Dab-L-Dab-L-Trp];

(8129)-3(R)OH-nC9CO-D-Dab-cyc[L-Dab-L-Dab-L-Dab-D-hPhe-L-Leu-L-Dab-L-Dab-L-Trp];

(8634)-3(R)OH-nC9CO-D-Dab-cyc[L-Dab-L-Arg-D-Phe-L-Leu-L-Dab-L-Dab-L-Leu];

(8635)-3(R)OH-nC9CO-D-Dab-cyc[L-Dab-L-4NH2Phe-D-Phe-L-Leu-L-Dab-L-Dab-L-Leu];

(8636)-3(R)OH-nC9CO-D-Dab-cyc[L-Dab-azaDAB-D-Phe-L-Leu-L-Dab-L-Dab-L-Leu];

(8638)-3(R)OH-nC9CO-L-Dab-cyc[L-Dab-L-DAB-D-Phe-L-Leu-L-Dab-L-Dab-L-Leu];

(8639)-3(R)OH-nC9CO-azaDab-cyc[L-Dab-L-DAB-D-Phe-L-Leu-L-Dab-L-Dab-L-Leu];

(8640)-3(R)OH-nC9CO-D-Dab-cyc[L-Dab-L-DAB-D-Phe-D-Leu-L-Dab-L-Dab-L-Leu];

(8641)-3(R)OH-nC9CO-D-Dab-cyc[L-Dab-L-DAB-D-Phe-L-Leu-azaDab-L-Dab-L-Leu];

(8642)-3(R)OH-nC9CO-D-Dab-cyc[L-Dab-L-DAB-D-Phe-L-Leu-L-4NH2Phe-L-Dab-L-Leu];

(8643)-3(R)OH-nC9CO-D-Dab-cyc[L-Dab-L-DAB-D-Phe-L-Leu-L-Dab-L-Arg-L-Leu];

(8644)-3(R)OH-nC9CO-D-Dab-cyc[L-Dab-L-DAB-D-Phe-L-Leu-L-Dab-L-4NH2Phe-L-Leu];

(8733)-3(R)OH-nC9CO-D-Dab-cyc[L-Dab-L-DAB-D-Phe-L-Leu-L-Arg-L-Dab-L-Leu];

(8782)-3(R)OH-nC9CO-D-Dab-cyc[L-Dab-L-DAB-D-Phe-L-Leu-L-Dab-azaDab-L-Leu];

(8803)-3(R)OH-nC9CO-D-Dab-cyc[L-Dab-L-DAB-D-Phe-azaLeu-L-Dab-L-Dab-L-Leu];

(8826)-nC10-3(R)OH-D-Dab-cyc[L-Dab-L-Dab-D-indanylgyl-L-Leu-L-Dab-L-Dab-L-Trp];

(8832)-nC10-3(R)OH-D-Dab-cyc[L-Dab-L-Dab-D-Phe-L-2-NaphthylAla-L-Dab-L-Dab-L-Trp];

(8834)-nC10-3(R)OH-D-Dab-cyc[L-Dab-L-Dab-D-Phe-L-hPhe-L-Dab-L-Dab-L-Trp];

(8884)-nC10-3(R)OH-D-Arg-cyc[L-Dab-L-Dab-D-Phe-L-Leu-L-Dab-L-Dab-L-Trp];

(8886)-3(R)OH-nC9CO-D-Dap-cyc[L-Dab-L-Dab-D-Phe-L-Leu-L-Dab-L-Dab-L-Trp];

(8887)-nC7CO-D-Dap-cyc[L-Dab-L-Dab-D-Phe-L-Leu-L-Dab-L-Dab-L-Trp];

(8888)-3(R)OH-nC9CO-D-Dap-cyc[L-Dab-L-Dab-D-Phe-L-indanylgly-L-Lys-L-Arg-L-Trp];

(8890)-3(R)OH-nC9CO-D-Dap-cyc[L-Dab-L-Dab-D-Phe-L-indanylgly-L-Arg-L-Lys-L-Trp];

(8892)-3(R)OH-nC9CO-D-Dap-cyc[L-Dab-L-Dab-D-Bip-L-tert-Leu-L-Lys-L-Arg-L-Trp];

(8896)-3(R)OH-nC9CO-D-Dap-cyc[L-Dab-L-Dab-D-indanylgly-L-Leu-L-Lys-L-Arg-L-Trp];

-continued (8897) -3(R)OH-nC9CO-D-Dap-cyc[L-Dab-L-Dab-D-indanylgly-L-indanylgly-L-Dab-L-Dab-L-Trp];

(8898) -nC7CO-D-Dab-cyc[L-Dab-L-Dab-D-Phe-L-indanylgly-L-Dab-L-Dab-L-Trp];

(8899) -3(R)OH-nC9CO-D-Dab-cyc[L-Dab-L-Dab-D-Chg-L-Leu-L-Dab-L-Dab-L-Trp];

(8900) -nC7CO-D-Dab-cyc[L-Dab-L-Dab-D-indanylgly-L-Leu-L-Dab-L-Dab-L-Trp];

(8901) -nC7CO-D-Dab-cyc[L-Dab-L-Dab-D-Phe-L-Leu-L-Dab-L-Dab-L-Trp];

(8906) -3(R)OH-nC9CO-D-Dab-cyc[L-Dab-L-Dab-D-Phe-L-Leu-L-Dab-L-Dab-L-Ala(4py)];

(8907) -3(R)OH-nC9CO-D-Dab-cyc[L-Dab-L-Dab-D-Phe-L-Leu-L-Dab-L-Dab-L-Ala(3py)];

(8908) -3(R)OH-nC9CO-D-Dab-cyc[L-Dab-L-Dab-D-Phe-L-Leu-L-Dab-L-Dab-L-Ala(2Naphthyl)];

(8909) -3(R)OH-nC9CO-D-Dab-cyc[L-Dab-L-Dab-D-Phe-L-Leu-L-Dab-L-Dab-L-Ala(1Naphthyl)];

(8910) -3(R)OH-nC9CO-D-Dab-cyc[L-Dab-L-Dab-D-Phe-L-Leu-L-Dab-L-Dab-L-Ala(Bth)];

(8911) -3(R)OH-nC9CO-D-Dab-cyc[L-Dab-L-Dab-D-Phe-L-Leu-L-Dab-L-Dab-L-His];

(8912) -3(R)OH-nC9CO-D-Dab-cyc[L-Dab-L-Dab-D-Phe-L-Leu-L-Dab-L-Dab-L-indanylgly];

(8913) -3(R)OH-nC9CO-D-Dab-cyc[L-Dab-L-Dab-D-Phe-L-Leu-L-Dab-L-Dab-L-hPhe];

(8914) -3(R)OH-nC9CO-D-Dab-cyc[L-Dab-L-Dab-D-Phe(3-Cl)-L-Leu-L-Dab-L-Dab-L-Trp];

(8942) -3(R)OH-nC9CO-D-Dab-cyc[L-Dab-L-Dab-azaPhe-L-Leu-L-Dab-L-Dab-L-Trp];

(8976) -nC7CO-D-Dap-cyc[L-Dab-L-Dab-D-Phe-L-Leu-L-Dab-L-Dab-L-Leu];

(8977) -nC10-3(R)OH-D-Dap[L-Dab-L-Dab-D-Leu-L-Leu-L-Dab-L-Dab-L-Leu];

(8978) -nC7CO-D-Dap-cyc[L-Dab-L-Dab-D-Leu-L-Leu-L-Dab-L-Dab-L-Leu];

(8980) -Ac-D-Dap-cyc[L-Dab-L-Dab-D-Phe-L-Leu-L-Dab-L-Dab-L-Leu];

(8981) -Ac-D-Dab-cyc[L-Dab-L-Dab-D-Phe-L-Leu-L-Dab-L-Dab-L-Trp];

(9032) -nC8CO-L-Dab-L-Thr-L-Dab-cyc[L-Dab-L-Dab-D-Phe-L-Leu-L-Dab-L-Dab-L-Trp].

(9188) -2-ClPh-NHCO-D-Dap-cyc[L-Dab-L-Dab-D-Phe-L-Leu-L-Dab-L-Dab-L-Dab];

(9189) -4-(1-Ph-pyridinone)-D-Dap-cyc[L-Dab-L-Dab-D-Phe-L-Leu-L-Dab-L-Dab-L-Dab];

(9190) -nC6CO-D-Dap-cyc[L-Dab-L-Dab-D-Phe-L-Leu-L-Dab-L-Dab-L-Leu];

(9191) -nC8CO-D-Dap-cyc[L-Dab-L-Dab-D-Phe-L-Leu-L-Dab-L-Dab-L-Leu];

(9192) -nC9CO-D-Dap-cyc[L-Dab-L-Dab-D-Phe-L-Leu-L-Dab-L-Dab-L-Leu];

-continued (9193) -3(R)-OH-nC9CO-D-Dap-cyc[L-Dab-L-Dab-D-Phe-L-Leu-L-Ser-L-Dab-L-Leu];

(9194) -3(R)-OH-nC9CO-D-Dab-cyc[L-Dab-L-Dab-L-Leu-D-Phe-L-Dab-L-Dab-L-Leu];

(9289) -3(R)OH-nC9CO-D-Ddab-cyc[L-Dab-L-Dab-D-phe-L-Thr-L-Dab-L-Dab-L-Leu];

(9290) -6Me-nC6CO-D-Dab-cyc[L-Dab-L-Dab-D-Phe-L-Leu-L-Dab-L-Dab-L-Leu];

(9291) -3(R)OH-nC9CO-D-Dap-cyc[L-Dab-L-Dab-D-Phe-L-Val-L-Dab-L-Dab-L-Leu];

(9292) -3(R)OH-nC9CO-D-Dap-cyc[L-Dab-L-Dab-D-Phe-L-Abu-L-Dab-L-Dab-L-Leu];

(9293) -3(R)OH-nC9CO-D-Dap-cyc[L-Dab-L-Dab-D-Phe-L-NorVal-L-Dab-L-Dab-L-Leu];

(9294) -3(R)OH-nC9CO-D-Dap-cyc[L-Dab-L-Dab-D-Phe-L-NorLeu-L-Dab-L-Dab-L-Leu];

(9295) -3(R)OH-nC9CO-D-Dap-cyc[L-Dab-L-Dab-D-Phe-L-Thr-L-Dab-L-Dab-L-Leu];

(9296) -nC10CO-D-Dap-cyc[L-Dab-L-Dab-D-phe-L-Leu-L-Dab-L-Dab-L-Leu];

(9297) -nC11CO-D-Dap-cyc[L-Dab-L-Dab-D-phe-L-Leu-L-Dab-L-Dab-L-Leu];

(9416) -3(R)OH-nC9CO-D-Dab-cyc[L-Dab-L-Dab-D-Phe-L-Leu-L-Dab-L-Dab-(aza-Leu)];
and (9417) -3(R)OH-nC9CO-D-Dab-cyc[(aza-Dab)-L-Dab-D-Phe-L-Leu-L-Dab-L-Dab-L-Leu].

In one embodiments, the compound of formula (I), (Ia), (Ib), (Ic), (Id), (Ie) and/or (II) is selected from the group consisting of:

(6442) -3(R)OH-nC9CO-D-Dap-cyc[L-Dab-L-Dab-D-Phe-L-Leu-L-Dab-L-Dab-L-Leu];

(8980) -Ac-D-Dap-cyc[L-Dab-L-Dab-D-Phe-L-Leu-L-Dab-L-Dab-L-Leu];
and (8981) -Ac-D-Dab-cyc[L-Dab-L-Dab-D-Phe-L-Leu-L-Dab-L-Dab-L-Trp];

In one embodiment, the compound of the first aspect is not selected from a compound where $R_4$ is

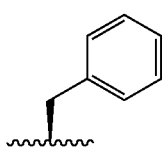

$R_5$ is

$R_8$ is

and Z is selected from the group consisting of:

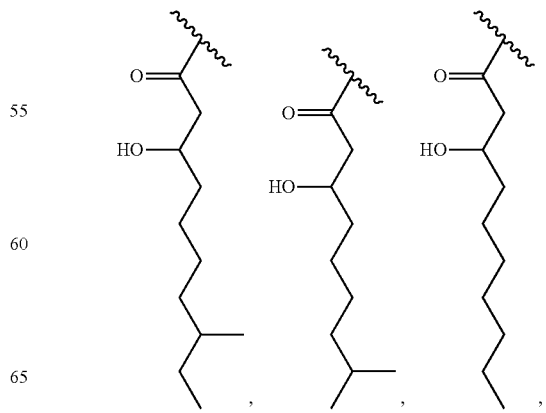

-continued
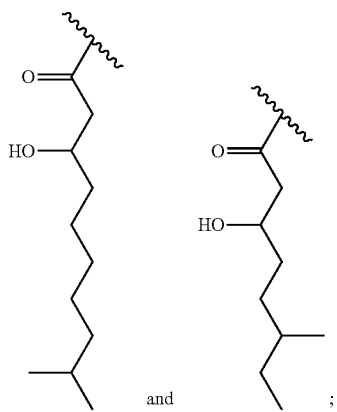
and ;
or
preferably Z is selected from the group consisting of:
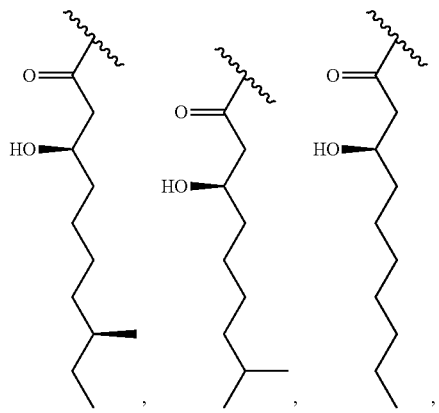
and .
In one embodiment, the compound of the first aspect is not selected from a compound where $R_4$ is
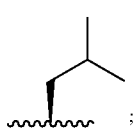
;
$R_5$ is
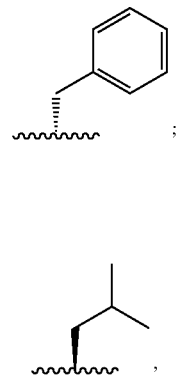
;
$R_8$ is
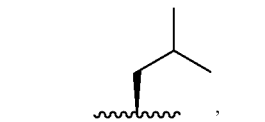
,
and Z is selected from the group consisting of:
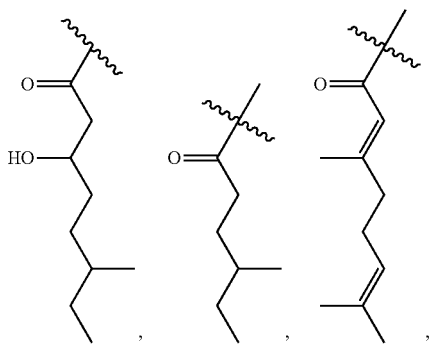
and .
In another embodiment, the compound of the first aspect is not selected from a compound where $R_4$ is
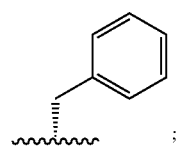
;

$R_5$ is
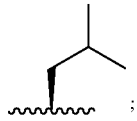;
$R_8$ is
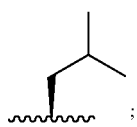;
and Z is selected from the group consisting of:
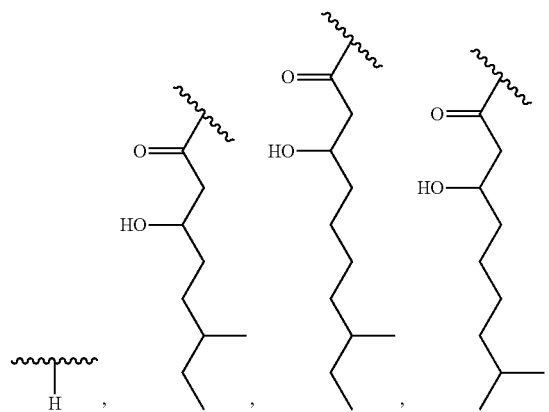
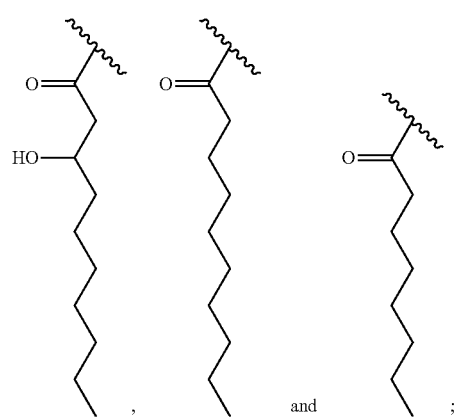
or
preferably Z is selected from the group consisting of:
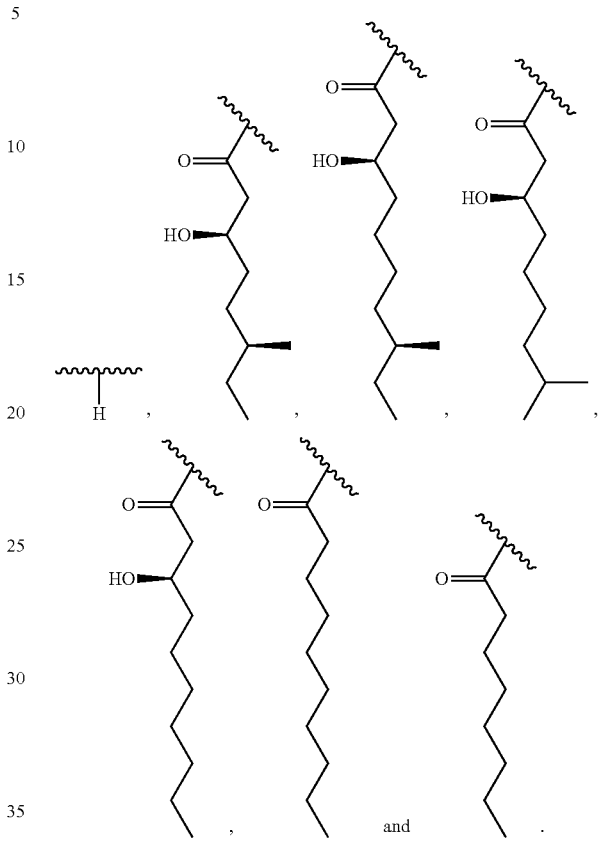
In another embodiment, the compound of the first aspect is not selected from a compound where $R_4$ is
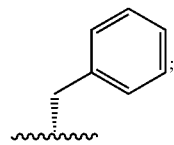;
$R_5$ is
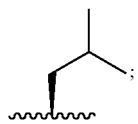;
$R_8$ is
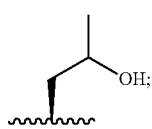;

and Z is selected from the group consisting of:
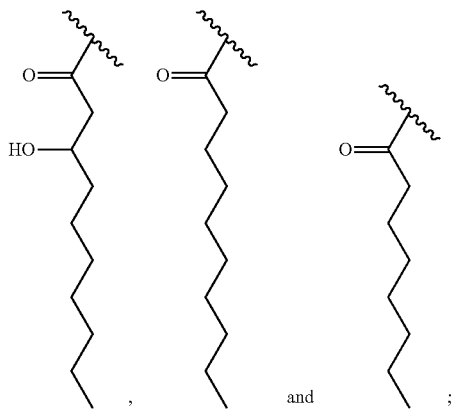
or
preferably Z is selected from the group consisting of:
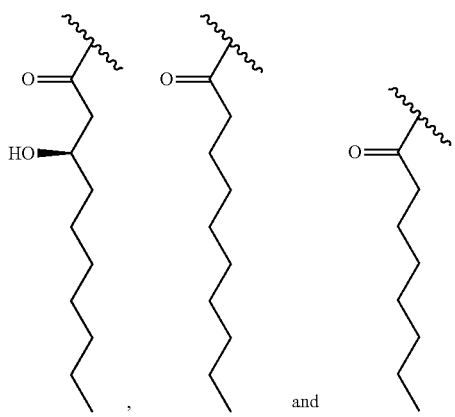
In another embodiment, the compound of the first aspect is not selected from a compound where $R_1$ is
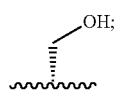
$R_4$ is
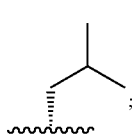
$R_5$ is
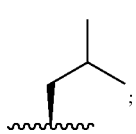
$R_8$ is
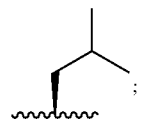
and Z is selected from the group consisting of:
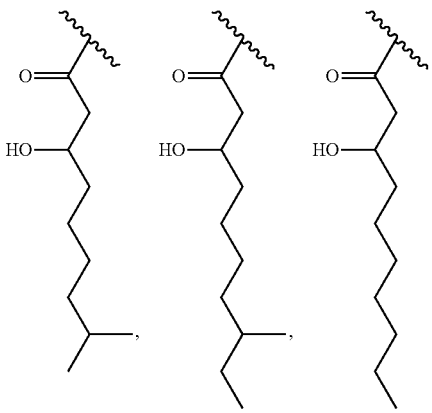
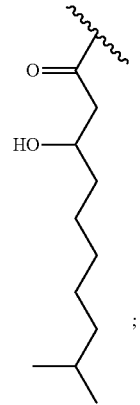
or
preferably Z is selected from the group consisting of:
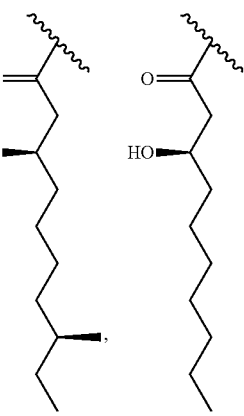

-continued

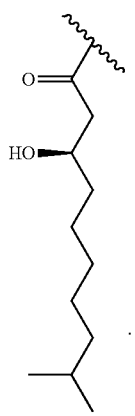

In another embodiment, the compound of the first aspect is not selected from a compound where $R_4$ is

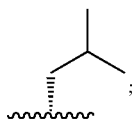

$R_5$ is

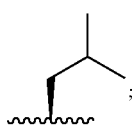

$R_8$ is

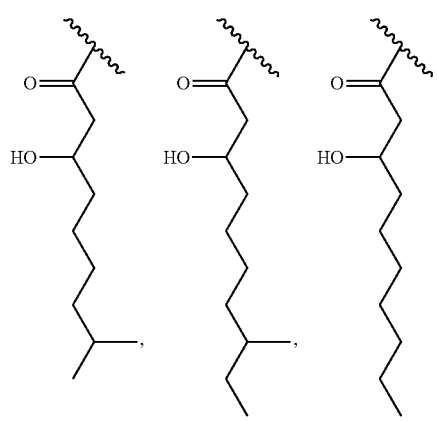

and Z is selected from the group consisting of:

-continued

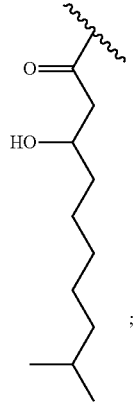

or preferably Z is selected from the group consisting of:

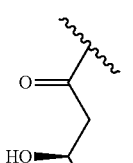 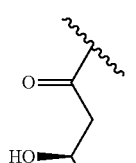 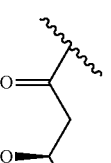 and

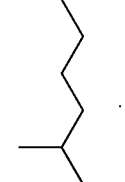

In one embodiment, the compound of the first aspect is not selected from a compound where $R_{10}$ is hydrogen.

In one embodiment, the compound of formula (II) is not selected from a compound where AA4 is D-Leu, AA5 is L-Phe, AA8 is L-Leu, and T is derived from a carboxylic acid selected from the group consisting of:

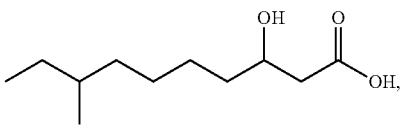

-continued

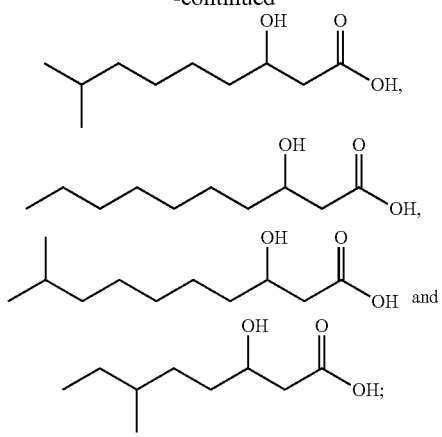

or
preferably T is derived from a carboxylic acid from the group consisting of:

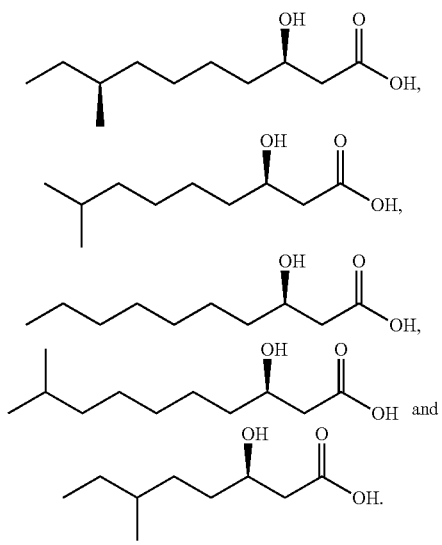

In an embodiment the compound of formula (II) is not selected from a compound where AA4 is L-Leu, AA5 is D-Phe, AA8 is L-Leu, and T is derived from a carboxylic acid selected from the group consisting of

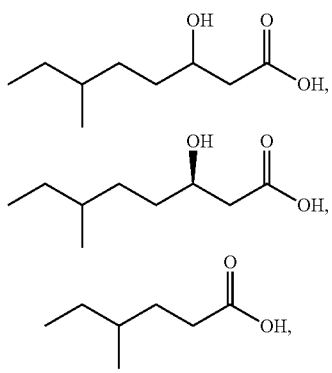

-continued

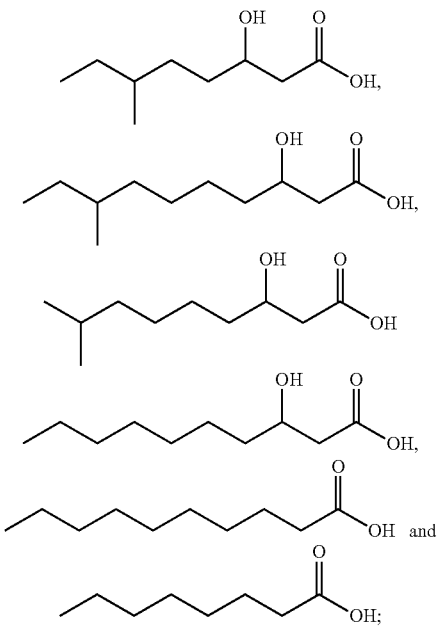

In one embodiment, the compound of formula (II) is not selected from a compound where AA4 is D-Phe, AA5 is L-Leu, AA8 is L-Leu; and T is hydrogen or derived from a carboxylic acid selected from the group consisting of:

or
preferably T is derived from a carboxylic acid from the group consisting of:

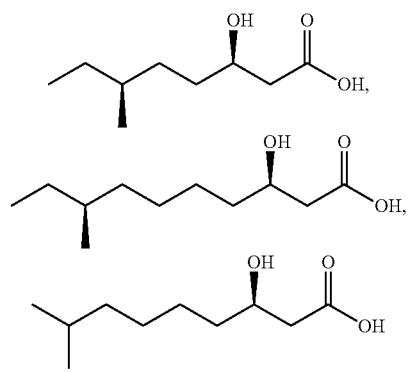

-continued

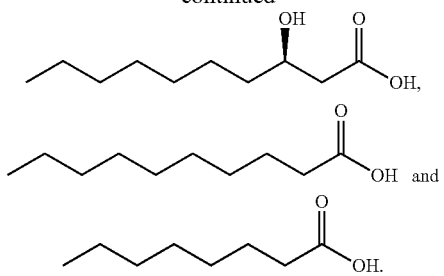

In one embodiment, the compound of formula (II) is not selected from a compound where AA4 is D-Phe, AA5 is L-Leu, AA8 is L-Thr; and T is derived from a carboxylic acid selected from the group consisting of:

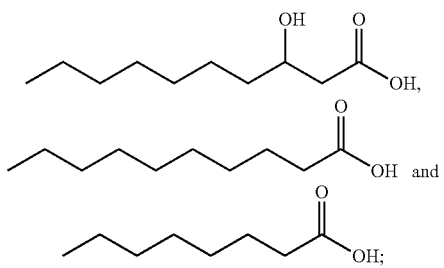

or
preferably T is derived from a carboxylic acid from the group consisting of:

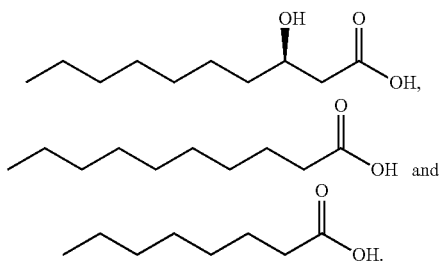

In one embodiment, the compound of formula (II) is not selected from a compound where AA1 is D-Ser, AA4 is D-Leu, AA5 is L-Leu, AA8 is L-Leu; and T is derived from a carboxylic acid selected from the group consisting of:

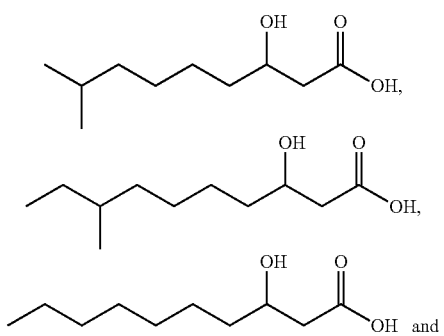

-continued

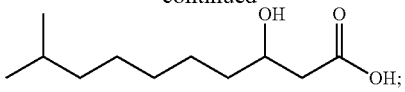

or
preferably T is derived from a carboxylic acid selected from the group consisting of:

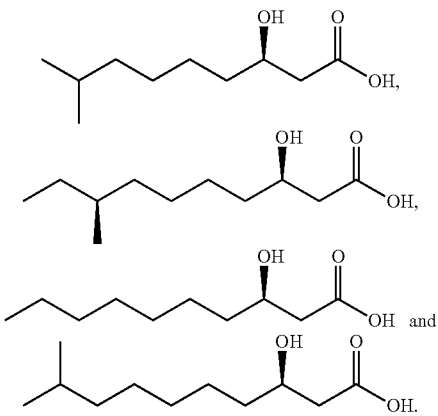

In one embodiment, the compound of formula (II) is not selected from a compound where AA4 is D-Leu, AA5 is L-Leu, AA8 is L-Leu; and T is derived from a carboxylic acid selected from the group consisting of:

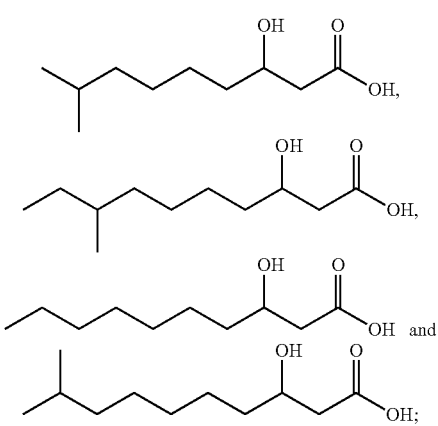

or
preferably T is derived from a carboxylic acid from the group consisting of:

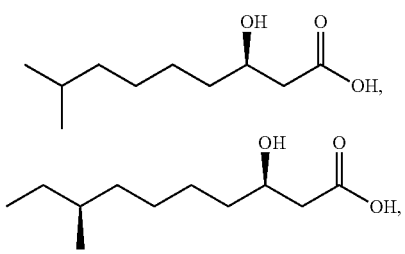

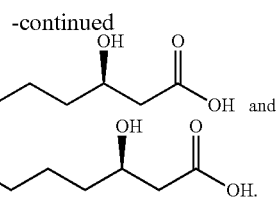

In one embodiment, the compound of formula (II) is not selected from a compound where T is hydrogen, or derived from formic acid, isocyanic acid, chloroformic acid, hydrogen sulphonyl halide or formaldehyde, For ease of description, the following the compound of formula (I), (Ia), (Ib), (Ic), (Id), (Ie), (If) and/or (II) are not selected from the following compounds described in amino acid sequence:

(A1)-
aC11-3OH-D-Dab-cyc[L-Dab-L-Dab-D-Leu-L-Leu-L-Dab-L-Dab-L-Leu]

(A2)-
iC10-3OH-D-Dab-cyc[L-Dab-L-Dab-D-Leu-L-Leu-L-Dab-L-Dab-L-Leu]

(A3)-
nC10-3OH-D-Dab-cyc[L-Dab-L-Dab-D-Leu-L-Leu-L-Dab-L-Dab-L-Leu]

(A4)-
iC11-3OH-D-Dab-cyc[L-Dab-L-Dab-D-Leu-L-Leu-L-Dab-L-Dab-L-Leu]

(B1)-
aC11-3OH-D-Dab-cyc[L-Dab-L-Dab-D-Leu-L-Phe-L-Dab-L-Dab-L-Leu]

(B2)-
iC10-3OH-D-Dab-cyc[L-Dab-L-Dab-D-Leu-L-Phe-L-Dab-L-Dab-L-Leu]

(B3)-
nC10-3OH-D-Dab-cyc[L-Dab-L-Dab-D-Leu-L-Phe-L-Dab-L-Dab-L-Leu]

(B4)-
iC11-3OH-D-Dab-cyc[L-Dab-L-Dab-D-Leu-L-Phe-L-Dab-L-Dab-L-Leu]

(XYZ)-
aC9-3OH-D-Dab-cyc[L-Dab-L-Dab-D-Leu-L-Phe-L-Dab-L-Dab-L-Leu]

(B5)-
aC9-3OH-D-Dab-cyc[L-Dab-L-Dab-L-Leu-D-Phe-L-Dab-L-Dab-L-Leu]

(C0)-
H-D-Dab-cyc[L-Dab-L-Dab-D-Phe-L-Leu-L-Dab-L-Dab-L-Leu]

(C1)-
aC9-3OH-D-Dab-cyc[L-Dab-L-Dab-D-Phe-L-Leu-L-Dab-L-Dab-L-Leu]

(C2)-
aC11-3OH-D-Dab-cyc[L-Dab-L-Dab-D-Phe-L-Leu-L-Dab-L-Dab-L-Leu]

(C3)-
iC10-3OH-D-Dab-cyc[L-Dab-L-Dab-D-Phe-L-Leu-L-Dab-L-Dab-L-Leu]

(C4)-
nC10-3OH-D-Dab-cyc[L-Dab-L-Dab-D-Phe-L-Leu-L-Dab-L-Dab-L-Leu]

(D1)-
aC11-3OH-D-Ser-cyc[L-Dab-L-Dab-D-Leu-L-Leu-L-Dab-L-Dab-L-Leu]

(D2)-
iC10-3OH-D-Ser-cyc[L-Dab-L-Dab-D-Leu-L-Leu-L-Dab-L-Dab-L-Leu]

(D3)-
nC10-3OH-D-Ser-cyc[L-Dab-L-Dab-D-Leu-L-Leu-L-Dab-L-Dab-L-Leu]

(D4)-
iC11-3OH-D-Ser-cyc[L-Dab-L-Dab-D-Leu-L-Leu-L-Dab-L-Dab-L-Leu]

(5387)-
3(R)OH-nC9CO-D-Dab-cyc[L-Dab-L-Dab-D-Phe-L-Leu-L-Dab-L-Dab-L-Thr];

(FADDI-115)-
nC9CO-D-Dab-cyc[L-Dab-L-Dab-D-Phe-L-Leu-L-Dab-L-Dab-L-Leu];

(FADDI-116)-
nC9CO-D-Dab-cyc[L-Dab-L-Dab-D-Phe-L-Leu-L-Dab-L-Dab-L-Thr];

(FADDI-117)-
nC7CO-D-Dab-cyc[L-Dab-L-Dab-D-Phe-L-Leu-L-Dab-L-Dab-L-Leu];

(FADDI-118)-
nC7CO-D-Dab-cyc[L-Dab-L-Dab-D-Phe-L-Leu-L-Dab-L-Dab-L-Thr];

(JMC-12)-
Fmoc-D-Dab-cyc[L-Dab-L-Dab-L-Leu-D-Phe-L-Dab-L-Dab-L-Leu]

(JMC-13)-
4Me-nC5CO-D-Dab-cyc[L-Dab-L-Dab-L-Leu-D-Phe-L-Dab-L-Dab-L-Leu]

(JMC-14)-
geranyl-D-Dab-cyc[L-Dab-L-Dab-L-Leu-D-Phe-L-Dab-L-Dab-L-Leu]

(JMC-15)-
nC13CO-D-Dab-cyc[L-Dab-L-Dab-L-Leu-D-Phe-L-Dab-L-Dab-L-Leu]

(JMC-16)-
4Me-nC5CO-D-Lys-cyc[L-Lys-L-Lys-L-Leu-D-Phe-L-Dab-L-Dab-L-Leu]
In one embodiment, the compound of formula (I), (Ia), (Ib), (Ic), (Id), (Ie) and (II) is not a compound selected from the group consisting of:
C1
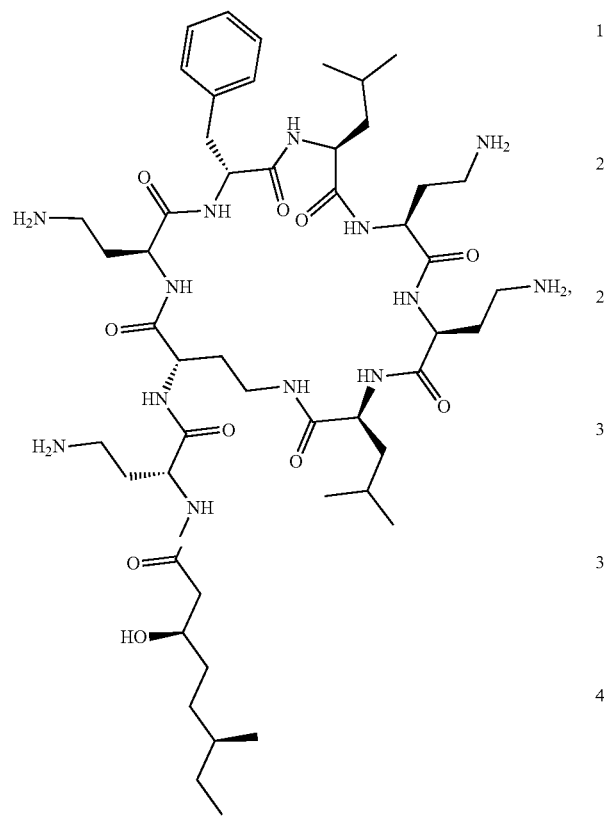
C2
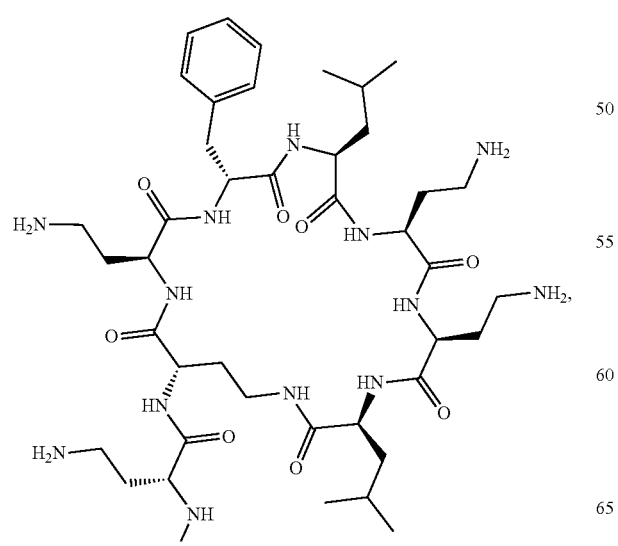
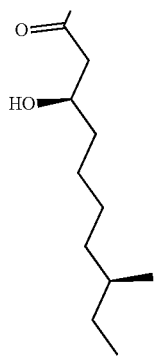
C3
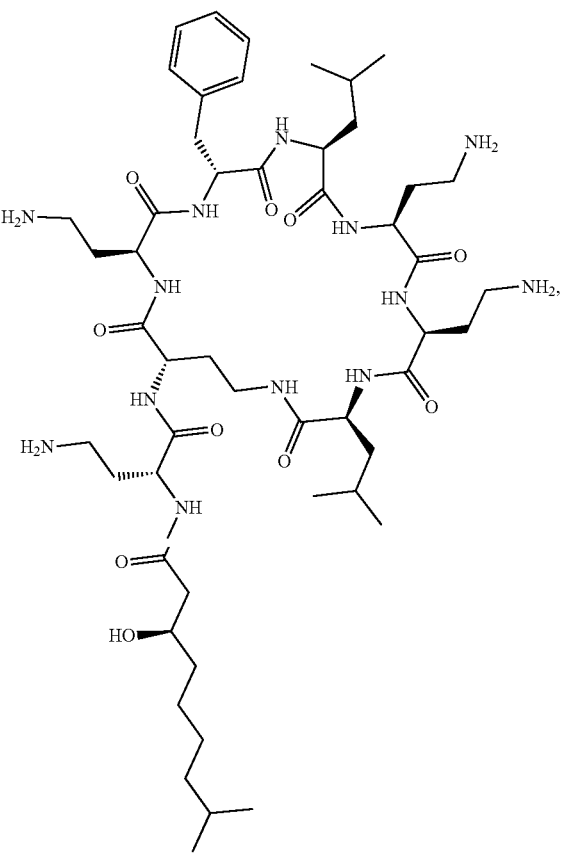

C4
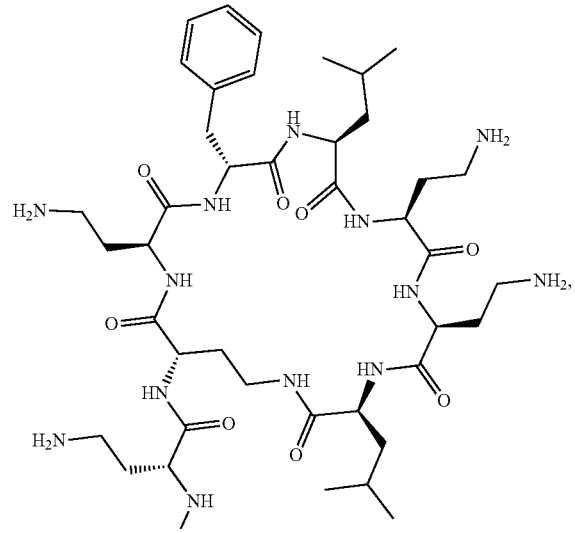
C0
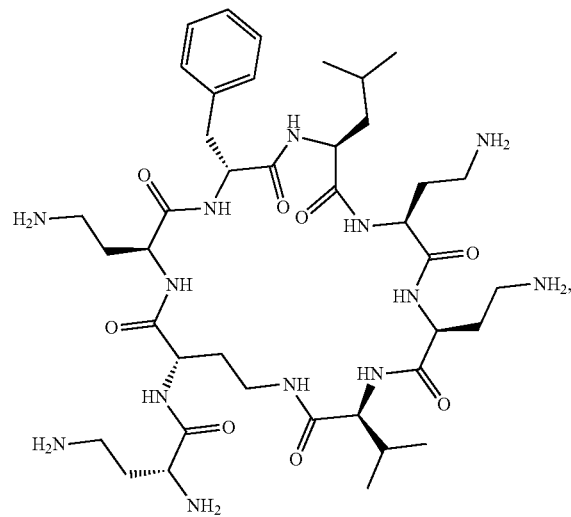
D1
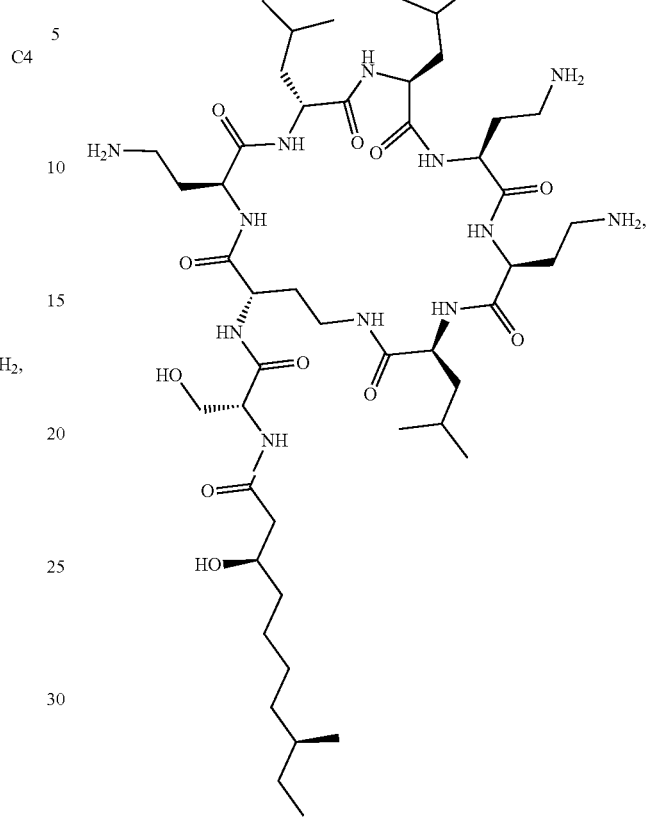
D2
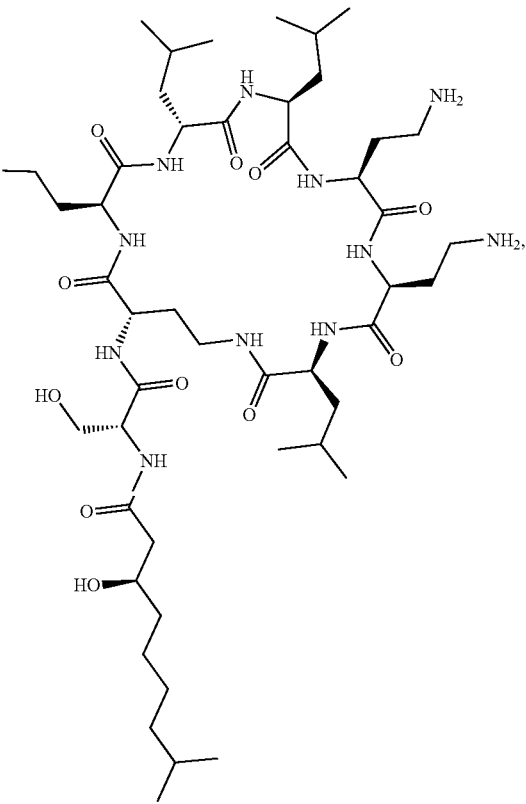

73
-continued
74
-continued
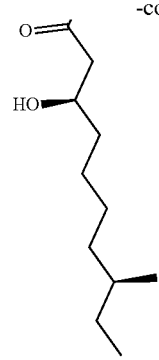
D3
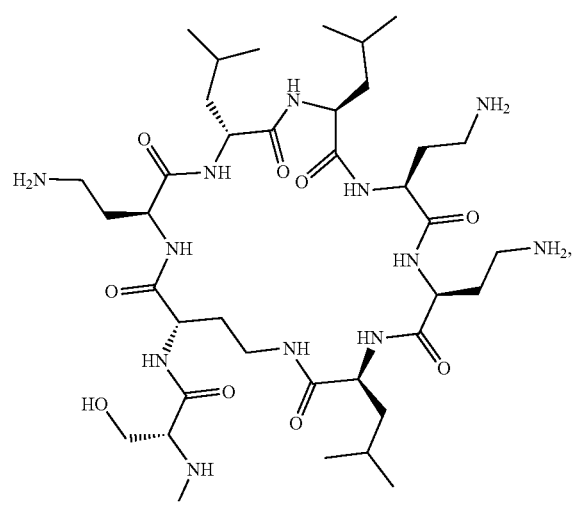
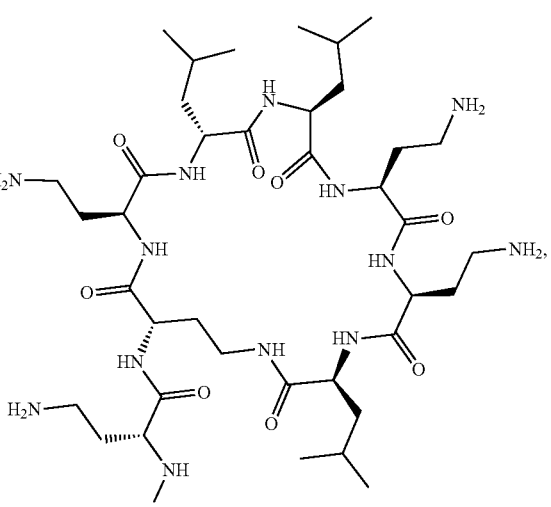
A2
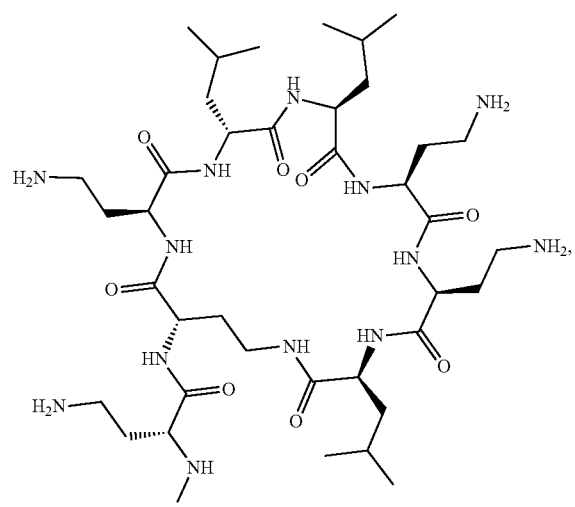
A1
A3

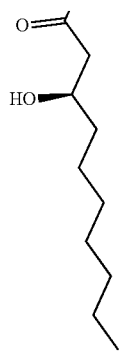
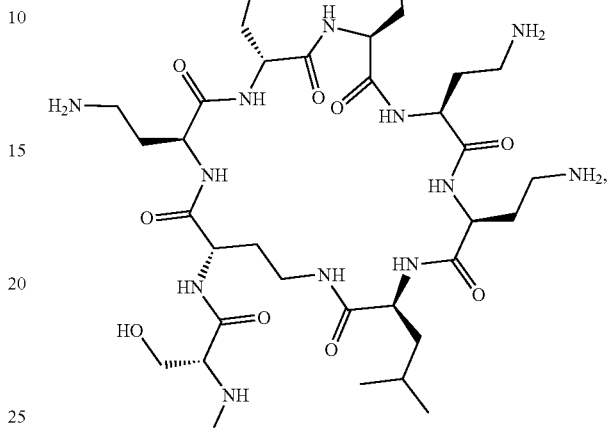
A4
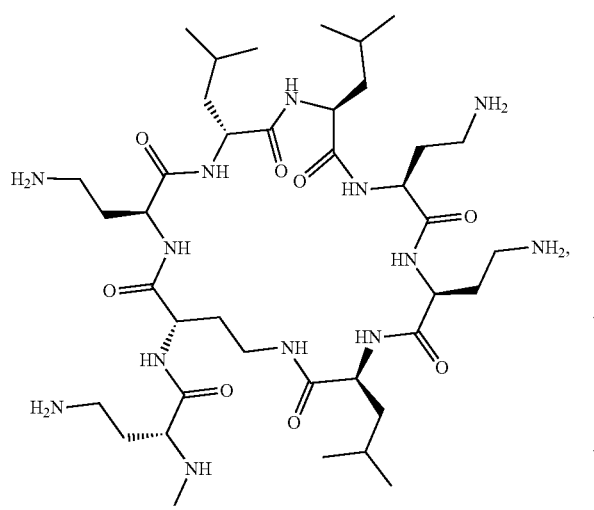
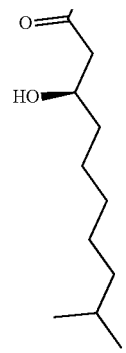
B1
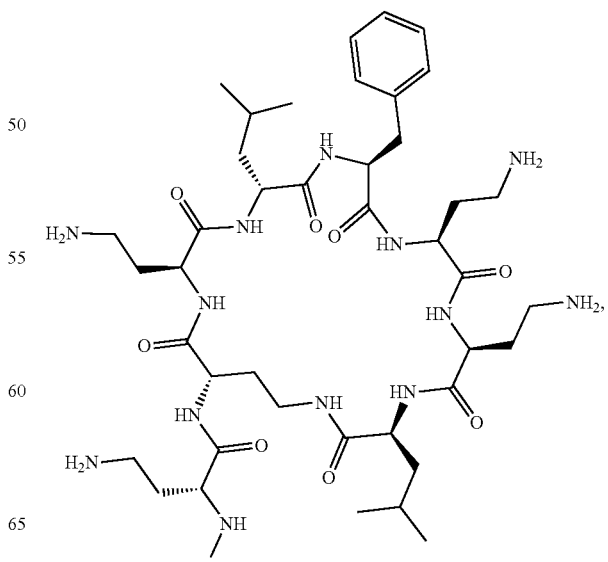
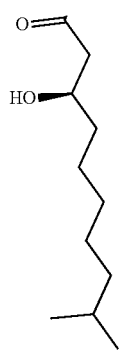

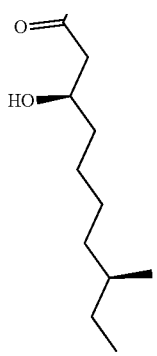
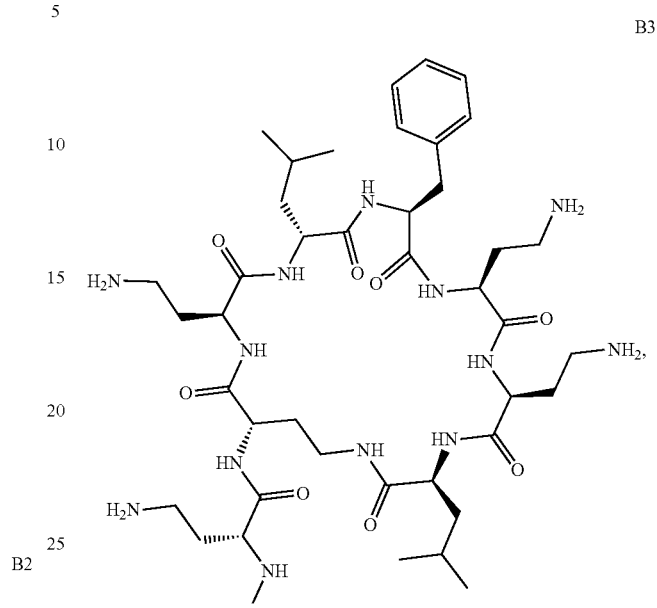
B2
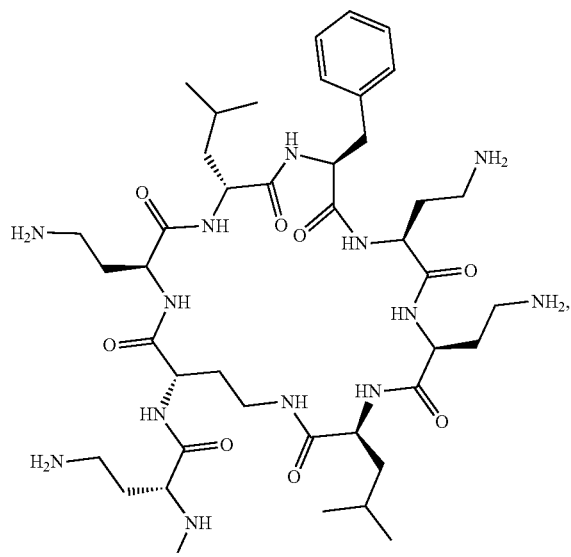
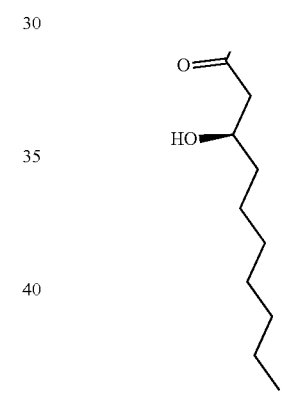
B3
B4
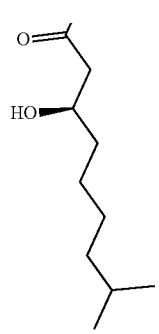
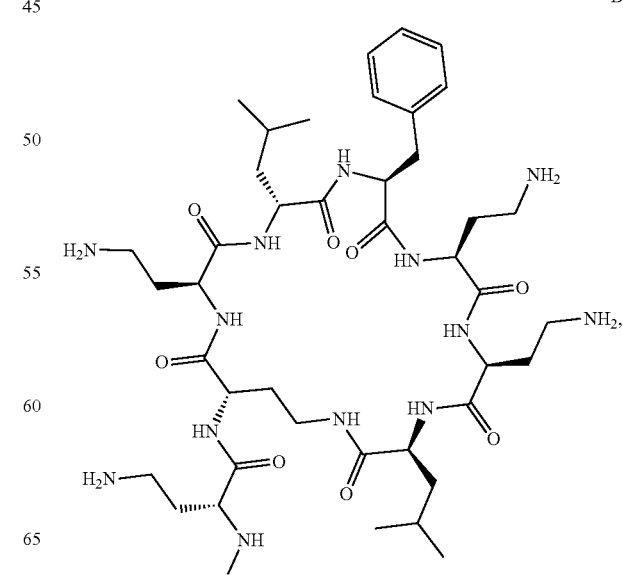

79
-continued
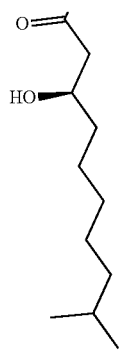
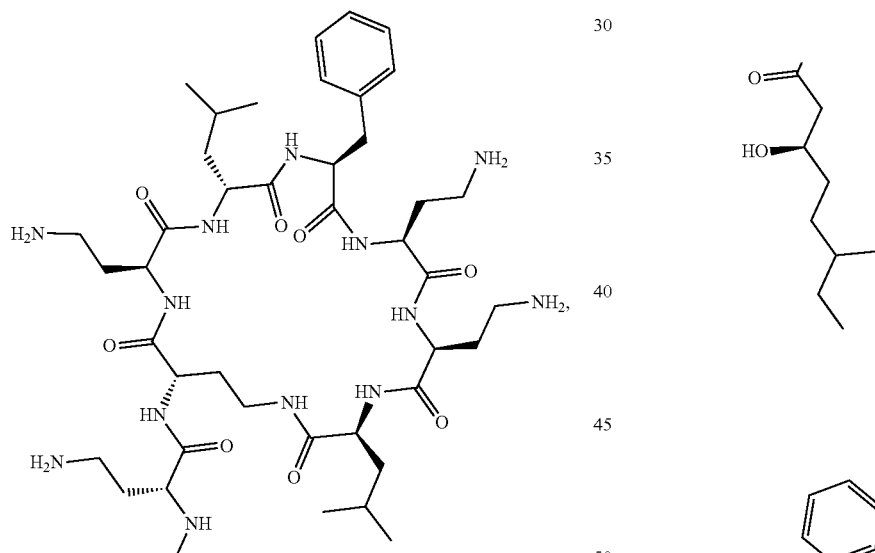
XYZ
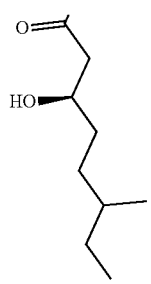
80
-continued
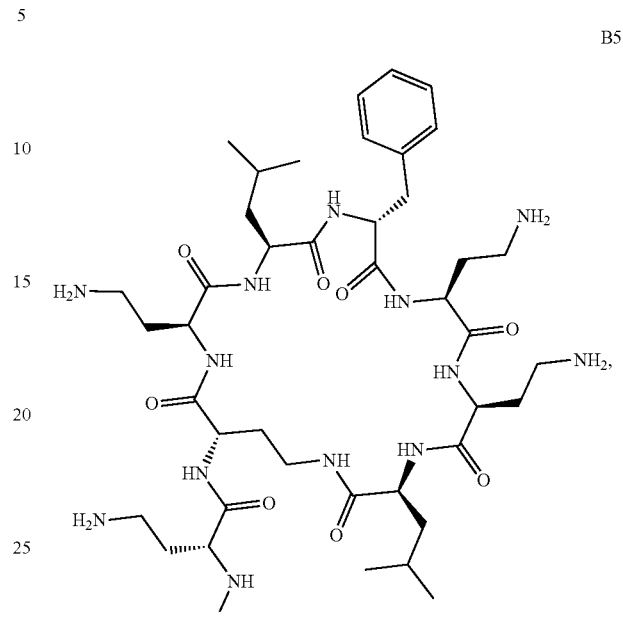
B5
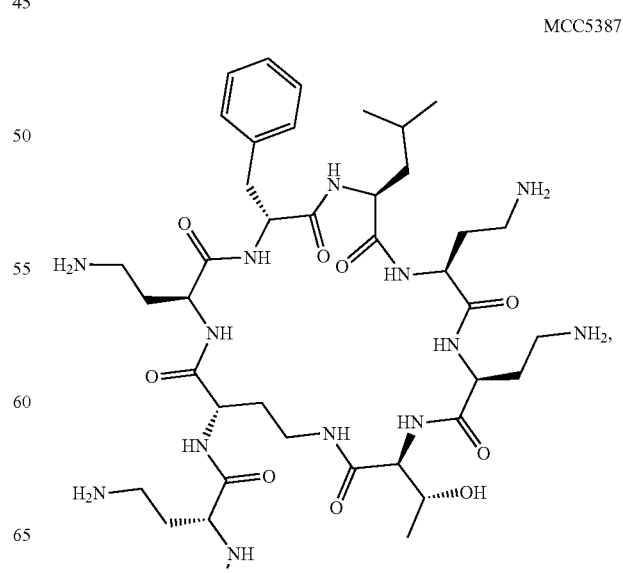
MCC5387

-continued
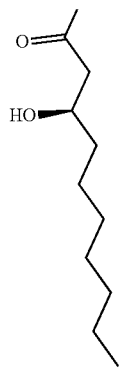
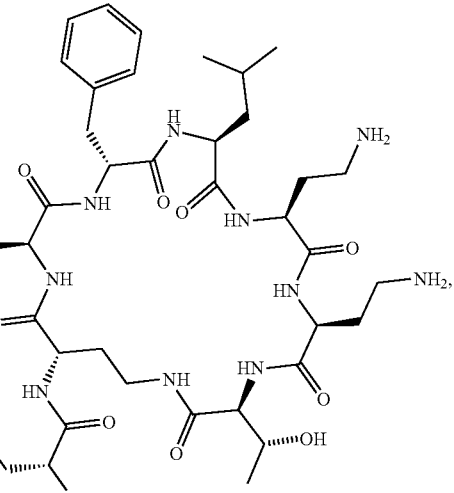
FADDI-116
FADDI-115
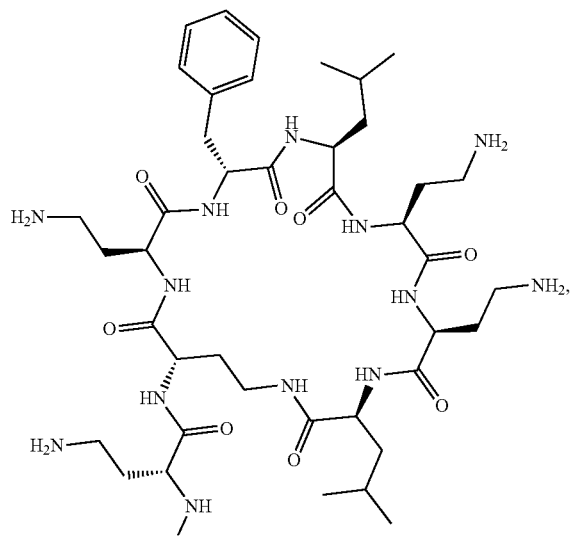
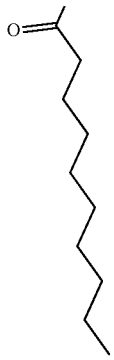
FADDI-117
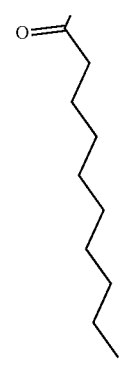
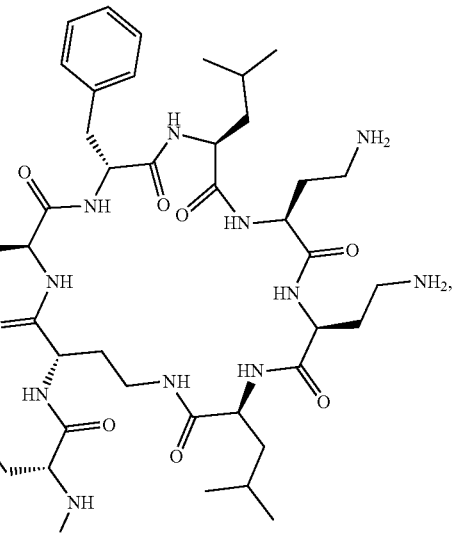

83
-continued
FADDI-118
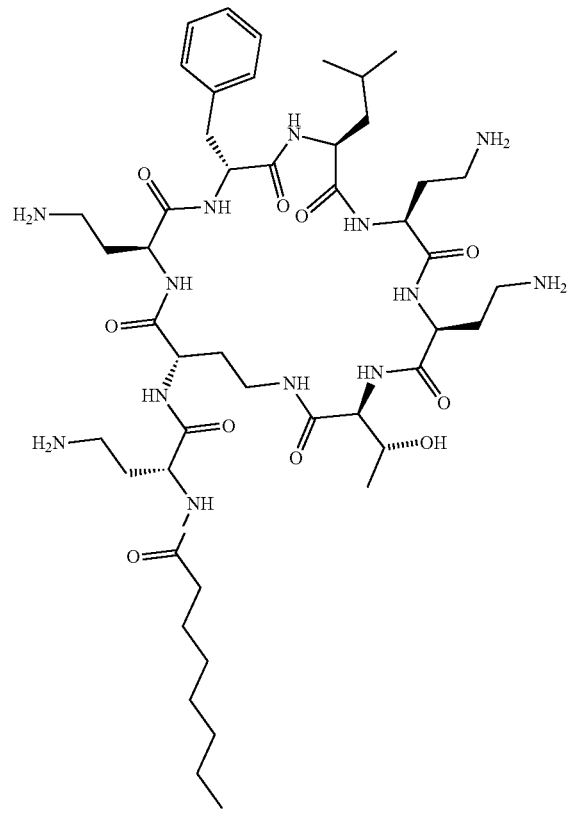
JMC-12
84
-continued
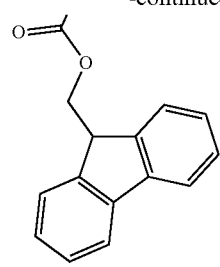
JMC-13
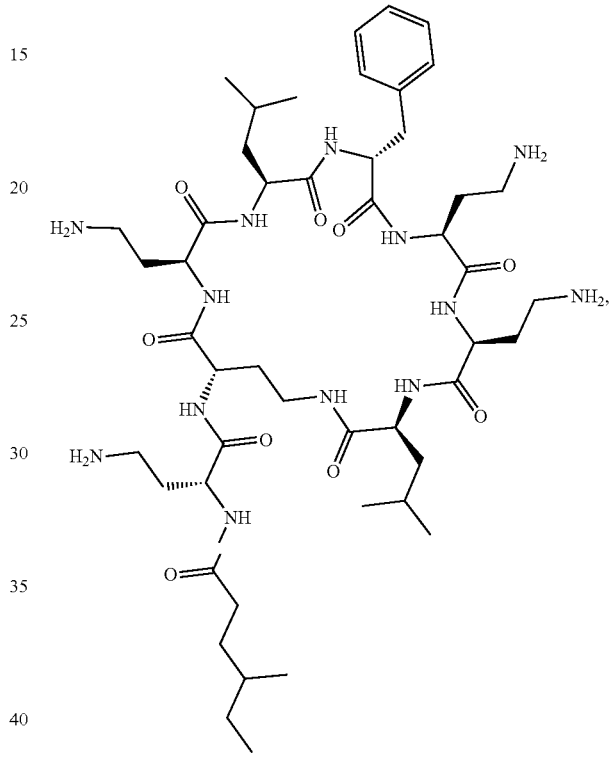
JMC-14
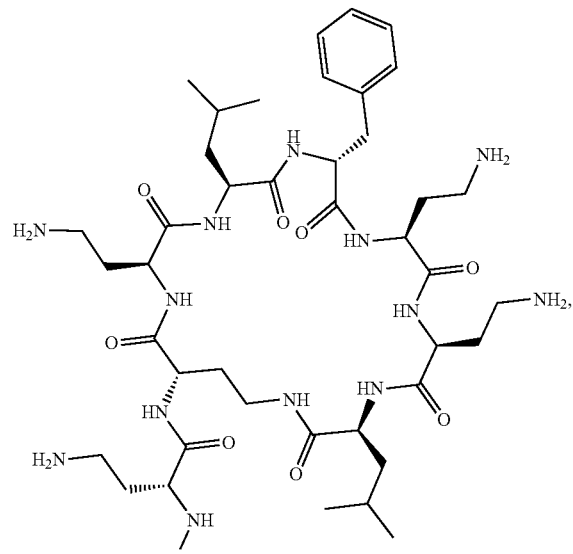
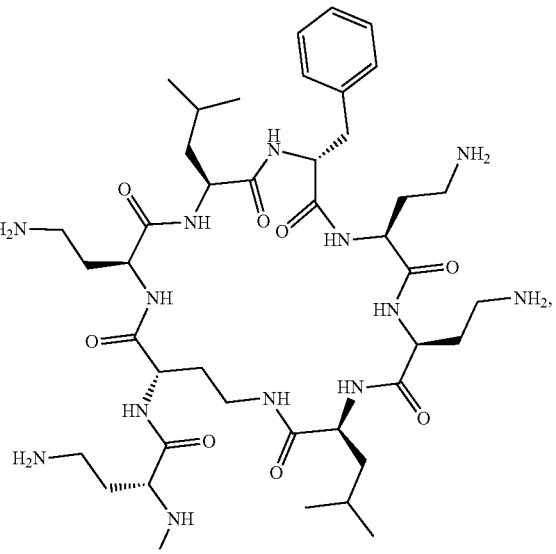

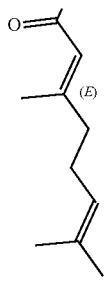

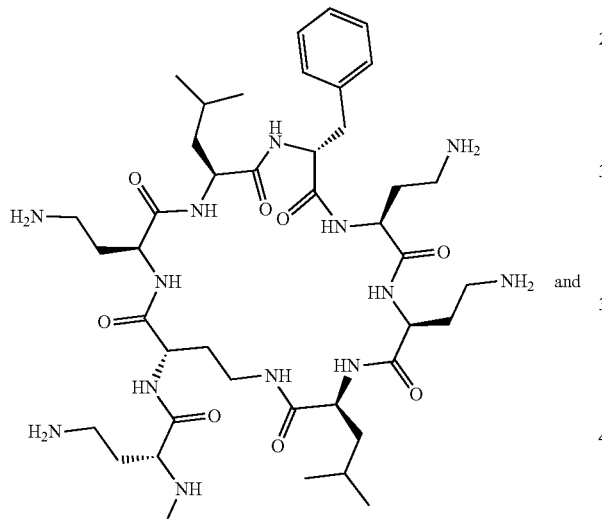

JMC-15

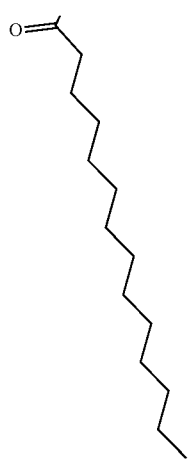

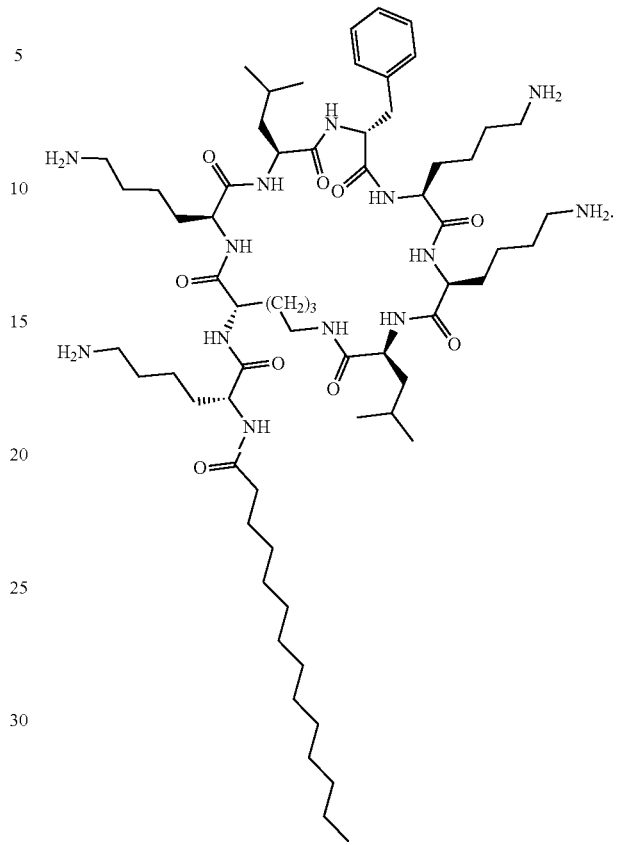

JMC-16

The compounds of formula (I), (Ia), (Ib), (Ic), (Id), (Ie), (If) and (II) may be viewed as potent peptide antibiotics. The data presented in the experimental section supports this view. Some of the compounds of formula (I), (Ia), (Ib), (Ic), (Id), (Ie), (If) and (II) have shown superior properties in terms of predicted nephrotoxicity based on activity against certain cells. Non-limiting examples of these cells include freshly isolated human proximal tubular epithelial kidney cells, HK2 (LDH), HEK293 and HepG2 cells. Additionally, certain compounds of formula (I), (Ia), (Ib), (Ic), (Id), (Ie), (If) and (II) have shown superior minimum inhibitory concentration (MIC) values against polymyxin-resistant bacteria when compared to polymyxin B and polymyxin E.

Additionally, the compounds of formula (I), (Ia), (Ib), (Ic), (Id), (Ie), (If) and (II) may display inhibitory and/or biocidal activity against Gram-positive bacteria and/or Gram-negative bacteria. Further to this, these compounds can also display such activity against yeasts, fungi and protozoa.

It is one advantage of the present compounds that they may demonstrate improved stability, improved efficacy against polymyxin-resistant bacteria, lower nephrotoxicity and lower cytotoxicity when compared to any one or more of octapeptin C4, polymyxin B and polymyxin E.

In some embodiments of the present invention, therapeutically inactive prodrugs of the compounds of the first aspect are provided.

Prodrugs are compounds which, when administered to a mammal, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, may reduce polarity and allow for the compound's passage into cells. Examples of substituent groups that can replace one or more hydrogen atoms on a free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphatidylcholine; phosphocholine; amino acid residues or derivatives; amino acid acyl residues or derivatives; peptides; cholesterols; or other pharmaceutically acceptable leaving groups which, when administered in vivo, provide the free amine. Any of these moieties can be used in combination with the disclosed active agents to achieve a desired effect. Preferred prodrugs for these compounds are where the basic amine/guanidine groups are masked by a prodrug to reduce overall positive charge. A non-limiting example is the methanesulfonate group which is used in a prodrug for colistin methanesulfonate (colistimethate sodium). Reference is made to Prodrugs, Challenges and Rewards Parts 1 and 2, Stella, V., Borchardt, R., Hageman, M., Oliyai, R., Maag, H., Tilley, J. (Eds.) Springer-Verlag New York, which provides non-limiting examples of prodrugs which may be useful according to the invention.

In some embodiments, compounds with one or more chiral centers are provided. While racemic mixtures of compounds of the invention may be active, selective, and bioavailable, isolated isomers may be of interest as well.

Various methods are known in the art for preparing optically active forms and determining activity. Such methods include standard tests described herein and other similar tests which are well known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compounds of the first aspect may contain chiral centers, which may be either of the (R) or (S) configuration, or which may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

The compound optionally may be provided in a composition that is diastereomerically enriched, such as a mixture of diastereomerics in which one diastereomer is present in excess, in particular, to the extent of 95% or more, 96% or more, 97% or more, 98% or more, or 99% or more, including 100%.

The terms (R), (S), (R,R), (S,S), (R,S) and (S,R) as used herein mean that the composition contains a greater proportion of the named isomer of the compound in relation to other isomers. The person skilled in the art will appreciate that this description can be extended to compounds with more than 2 chiral centres. In this regard, compounds of the first aspect can have greater than 2, 3, 4, 5, 6, 7 and 8 chiral centers depending on the $R_1$-$R_8$ and Z moieties. In a preferred embodiment, these terms indicate that the composition contains at least 90% by weight of the named isomer and 10% by weight or less of the one or more other isomers; or more preferably about 95% by weight of the named isomer and 5% or less of the one or more other isomers. In some embodiments, the composition may contain at least 99% by weight of the named isomer and 1% or less by weight of the one or more other isomers, or may contain 100% by weight of the named isomer and 0% by weight of the one of more other isomers. These percentages are based on the total amount of the compound of the present invention present in the composition.

The compounds of the first aspect may be utilized per se or in the form of a pharmaceutically acceptable ester, amide, salt, solvate, prodrug, or isomer, as appropriate. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenyl propionates, phenyl butyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound or prodrug useful according to the present invention may be prepared in a similar manner using a pharmaceutically acceptable base, such as sodium hydroxide, potassium hydroxide, ammonium hydroxide, calcium hydroxide, triethylamine, or the like.

Esters of the compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from an anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound of the first aspect is an acid, the desired salt may be prepared by any suitable method known in the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

Another advantage of the compounds of formula (I), (Ia), (Ib), (Ic), (Id), (Ie), (If) and (II) is that they can be synthesized relatively easily. In this regard, the person skilled in the art will appreciate that the compounds of formula (I), (Ia), (Ib), (Ic), (Id), (Ie), (If) and (II) are cyclic lipopeptides and can be synthesized by utilizing standard solid phase peptide synthesis protocols known in the art.

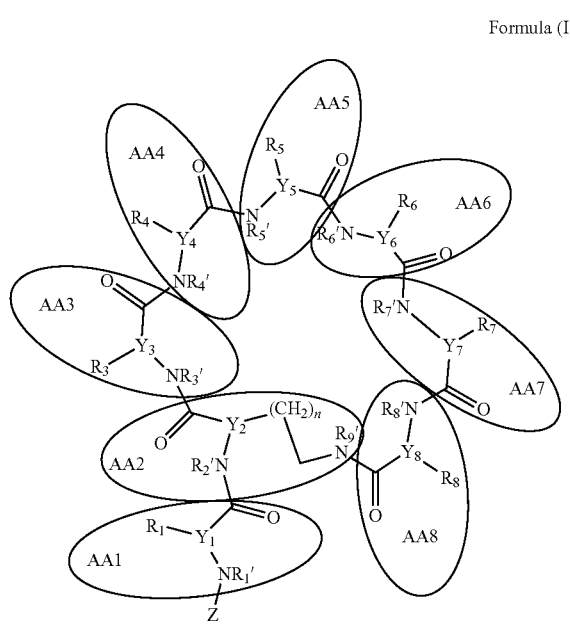

Formula (I)

The above chemical structure of the compound of Formula (I) can be disseminated into separate components. For instance, when $Y_1$-$Y_8$ are CH and $R_1'$-$R_8'$ are H, then a compound of formula (I) can be produced by cyclizing a polypeptide that comprises 8 amino acids. This polypeptide can be formed using standard solid phase peptide synthesis protocols, such as Fmoc chemistry and HBTU as a coupling agent. The person skilled in the art will appreciate that the compounds of formula (I), (Ia), (Ib), (Ic), (Id), (Ie), (If) and (II) can be synthesized using other techniques known in the art, and that the synthetic techniques discussed herein are only an example of how these compounds can be obtained.

The R ($R_1$ and $R_3$-$R_8$) groups can be simply incorporated into the ring structure through selection of the amino acid or equivalent compound, and their position in the linear polypeptide precursor. Specific protecting groups can be chosen so that the reactive centers of AA2 and/or AA8 can be selectively deprotected to cyclize the linear polypeptide into the cyclic polypeptide. Non-limiting examples of these protecting groups include 9-fluorenylmethoxy carbonyl (Fmoc), tert-butyloxycarbonyl (Boc), benzyl (Bn), allyloxycarbonyl (alloc), 1-(4,4-Dimethyl-2,6-dioxo-cyclohexylidene)-3-methyl-butyl (ivDde) and tertbutyl (tBu) protecting groups. In this regard, the other R groups (side chains) of the other amino acids can be protected, if required, so that they do not participate in the cyclization process. As such, functionalized R groups (side chains) can be protected using protecting groups.

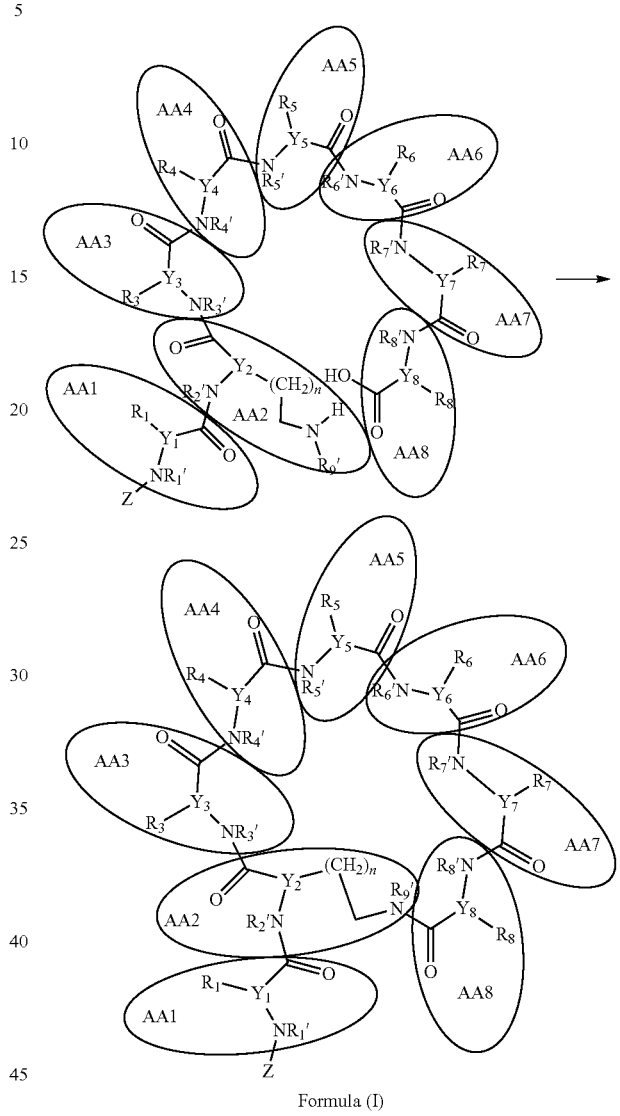

Formula (I)

Cyclization reaction to form compound of formula (I)

It will be appreciated that any one of the amino acids (AA1-AA8) can be substituted with an N-alkyl amino acid to provide a functional moiety off the nitrogen center. For instance, AA1-AA8 may be replaced with N-methyl substituted amino acids to give R' ($R_1'$-$R_8'$) as a methyl moiety. In this regard, the N-alkyl amino acids can be simply incorporated into the linear polypeptide during solid phase peptide synthesis.

Furthermore, it will be appreciated that the amino acids may be aza amino acids to allow for the Y ($Y_1$-$Y_8$) groups to be N. These changes in the structure of the compound can be easily made during the solid phase peptide synthesis of the linear polypeptide so that the desired cyclic polypeptide can be obtained after cyclisation.

It will also be appreciated that the size of the cyclic peptide can be modified by changing AA2. In this regard, Dap, Dab, Orn, Lys, aza-Dap, aza-Dab, aza-Orn or aza-Lys can be used in the AA2 position to change the ring size of the resultant cyclic peptide. For example, when Dap is used then n (in formula (I), (Ia) and (Ib)) is 0, when Dab is used then n is 1, and when Orn is used then n is 2.

The Z moiety can be easily derived from a carboxylic acid to form an amide, a sulfonyl chloride to form a sulphonamine, a chloroformate to form a urethane, an aldehyde to form an aminoalkyl, and an isocyanate to form a urea.

These moieties can be attached during the solid phase synthetic pathway. It will be appreciated that there are a wide range of suitable commercially available carboxylic acids, sulfonyl chlorides, chloroformates, aldehydes, and isocyanates that can be used, and those not easily available can be synthesised by methods well known to the person of skill in the art. For instance, a carboxylic acid, sulfonyl chloride, chloroformate, aldehydes or isocyanate can be coupled to the amine (—NR$_1$') during the solid phase synthetic pathway to form the desired Z moiety. It will be appreciated by the person skilled in the art that this synthetic technique provides a simple synthetic pathway for many derivatives to be produced. The Z precursor can easily be synthesized and some examples are demonstrated in the Examples hereinafter.

For instance, when Z is an alkyl group then an aminoalkyl is formed, which can be formed by simply introducing an aldehyde followed by reductive amination during solid phase peptide synthesis. Alternatively, when Z is an acyl group then an amine is formed, which can be achieved through peptide synthesis. Furthermore, when Z is sulfonyl group then a sulfonamide is formed, which can be formed by simply introducing a sulphonyl halide during solid phase peptide synthesis.

It will be appreciated that any number of amino acids, aza amino acids and N-alkylated amino acids can be incorporated into the linear polypeptide. Further to this, the Z moiety can be easily incorporated into the linear polypeptide. The amino acids, aza amino acids and/or N-alkylated amino acids can be incorporated into any position by virtue of the synthesis of the linear polypeptide. It will be appreciated by the person skilled in the art that these modifications allow all compounds within the structure of formula (I), (IIb), (Ic), (Id), (Ie) and (II) to be accessible.

As previously mentioned, the present synthetic method allows for a large number of octapeptin-like compounds to be accessible due to the ease of modification through using different amino acids. Non-limiting examples of the amino acids used to form the compounds of the first aspect include:

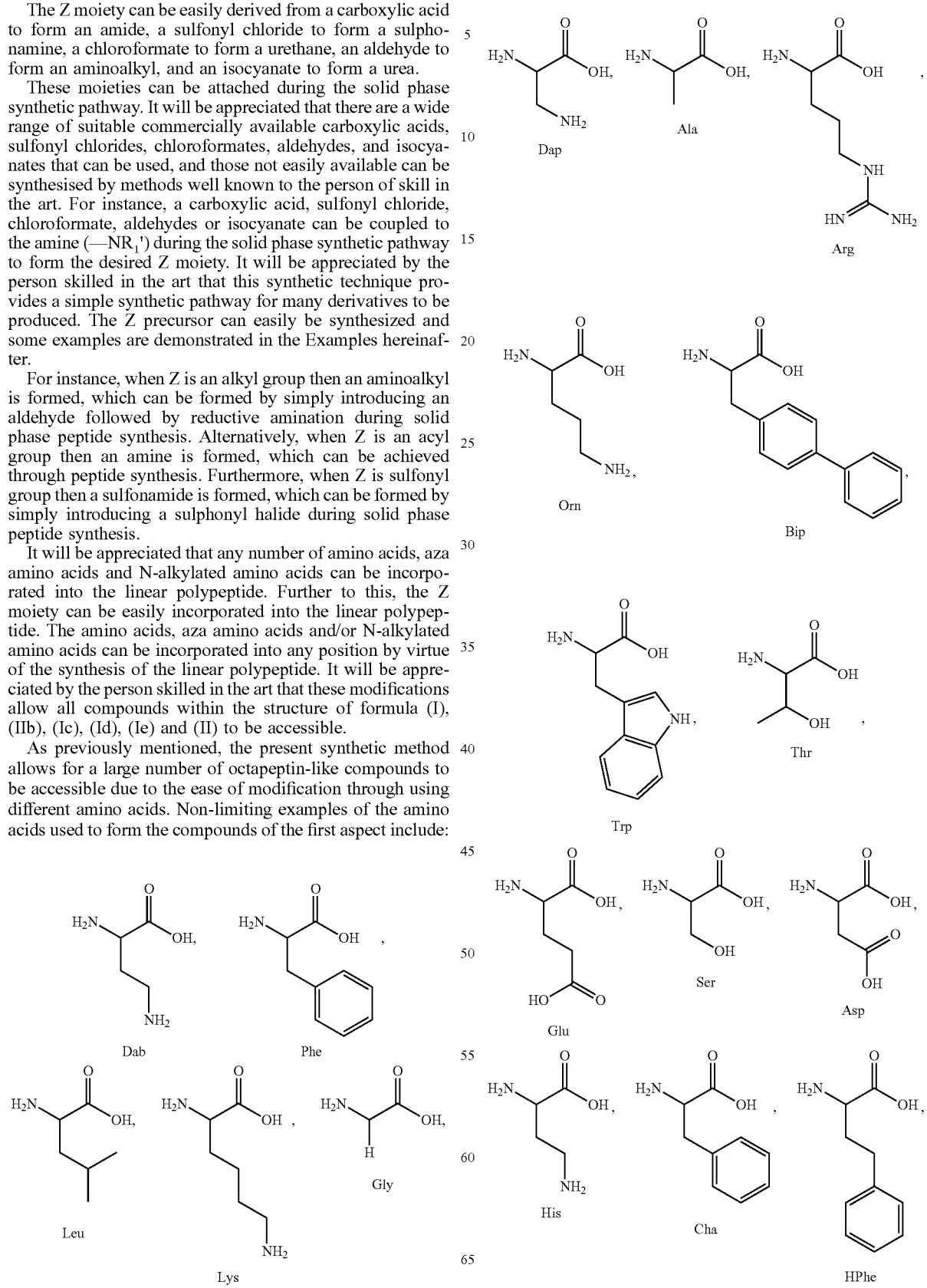

-continued

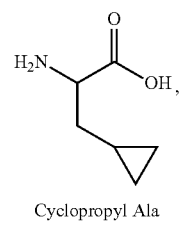
Cyclopropyl Ala

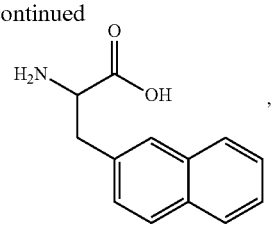
2-Napththyl Ala

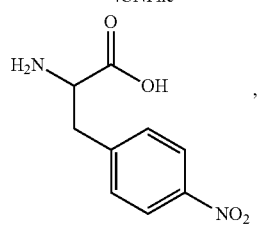
4CNPhe

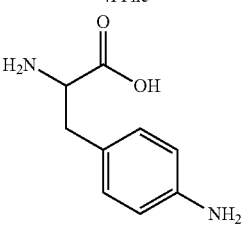
4FPhe

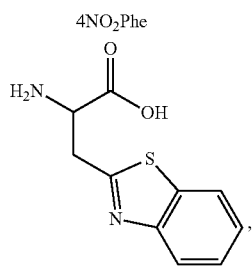
4NO₂Phe

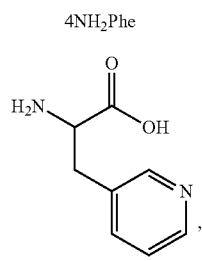
4NH₂Phe

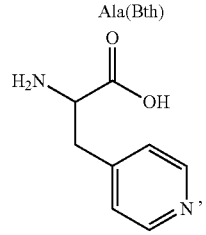
Ala(Bth)

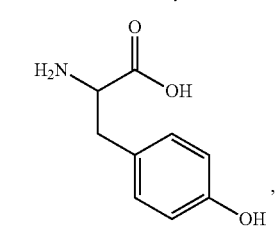
3PyAla

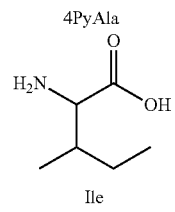
4PyAla

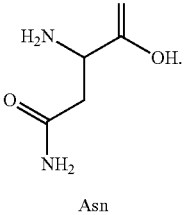
Tyr

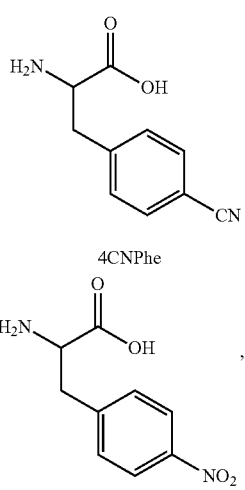
Ile and

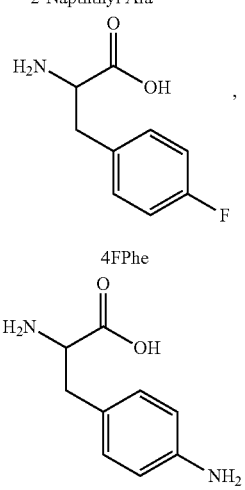
Asn

These amino acids may be D- or L-amino acids; that is with (R)- or (S)-configuration/chirality at the alpha-center. In other words, D- and L-amino acids can be used to synthesize compounds of formula (I), (Ia), (Ib), (Ic), (Id), (Ie), (If) or (II).

As previously mentioned, aza amino acids can be used in the synthesis of the linear polypeptide. Non-limiting examples of aza amino acids are aza-glycine (aza-Gly), aza-diaminobutric acid (aza-Dab) and aza-leucine (aza-Leu). The structure of aza-glycine is

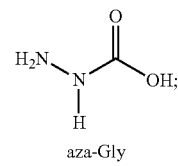
aza-Gly the structure of aza-diaminobutyric acid is

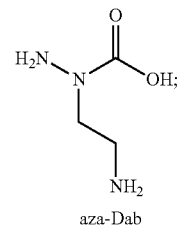
aza-Dab and the structure of aza-leucine is

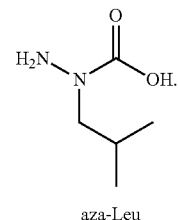
aza-Leu

In one embodiment, AA1 is aza-Dab. In an embodiment, AA3 is aza-Dab. In one embodiment, AA5 is aza-Leu. In an embodiment, AA6 is aza-dab. In another embodiment, AA7 is aza-Dab. In a further embodiment, AA8 is aza-Leu. In yet another embodiment, AA4 is aza-Phe.

A non-limiting example of a standard solid phase peptide synthesis approach to form a compound of formula (I), (Ia), (Ib), (Ic), (Id), (Ie), (If) and (II) is shown below:

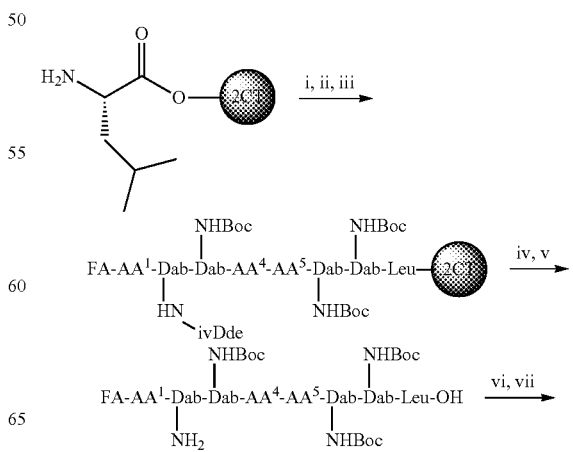

-continued

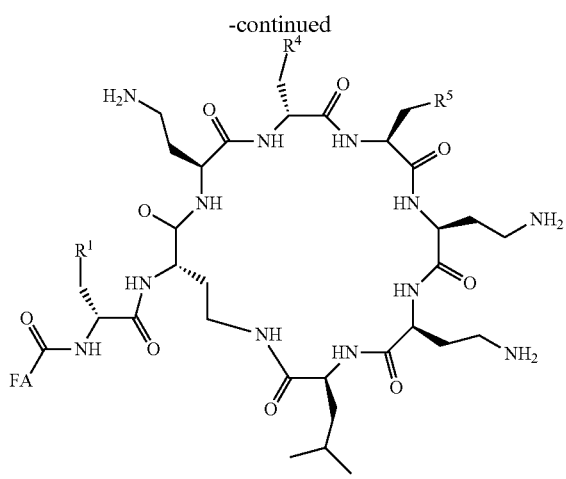

i) amino acid, HCTU, 2,4,6-collidine, DMF;
ii) 30% piperidine in DMF;
iii) FA, HCTU, 2,4,6-collidine, DMF;
iv) 4% hydrazine hydrate in DMF;
v) 20% HFIP in DCM;
vi) DPPA, NaHCO$_3$, DMF, 0.008 M;
vii) TFA/H$_2$O/$^i$Pr$_3$SiH.

It will be appreciated that the above figure shows the protected Dab side chains as —NHBoc, with the exception of Dab$^2$ (AA2 being DAB), which is —NHivDde, to exemplify the protecting groups. In this example, the carboxylic acid functional group for cyclization is unmasked when the peptide is cleaved from the 2-chlorotrityl (2-Ct) resin. The ivDde group is selectively removed by treatment with hydrazine prior to cleavage form the resin. The other functionalized side chains are protected by Boc groups which are not removed in the reaction conditions, and as such do not participate in cyclization. This is one possible combination of orthogonal protecting groups. It will be appreciated by the person skilled in the art that other combinations can also be used to produce the same final product.

According to a second aspect, the invention resides in a pharmaceutical composition comprising a compound of formula (I), (Ia), (Ib), (Ic), (Id), (Ie), (If) or (II), or a pharmaceutically acceptable salt, solvate or prodrug thereof, and a pharmaceutically acceptable carrier, diluent and/or excipient.

The compounds of the first aspect can additionally be combined with other compounds to provide an operative combination. It is intended to include any chemically compatible combination of pharmaceutically-active agents, as long as the combination does not eliminate the activity of the compound of the first aspect. In one embodiment, the compounds of the first aspect are used in combination with other therapeutical agents. In an embodiment, the compounds of the first aspect are used in combination with a therapeutic agent selected from antibiotic agents, antifungal agents, antivirulence agents, biofilm-disrupting agents, anti-inflammatory agents and agents known to potentiate antibiotic efficacy. Non-limiting examples of therapeutic agents include rifampicin (rifampin), minocycline, clarithromycin, azithromycin, fusidic acid, mupirocin, retapamulin, meropenem, aztreonam, clarithromycin, erythromycin, novobiocin, telithromycin, colistin, polymyxin B, fosfomycin, ciprofloxacin, tetracycline, gentamycin, vancomycin, quinupristin-dalfopristin, ramoplanin, teicoplanin, levofloxacin, octapeptin C4, arenicin-3, linezolid and antimicrobial peptides.

The invention thus provides in a further aspect a combination comprising a compound of the first aspect of a pharmaceutically acceptable salt or derivative thereof together with another therapeutically active agent which, in one non-limiting embodiment, may be an antibiotic. As such, it will be appreciated that the pharmaceutical composition may further comprise at least one other pharmaceutically-active agent. Suitably, the pharmaceutically-active agent may be selected from antibiotic agents and antifungal agents.

Compounds 6442, 8980 or 8981 appear to provide an operative combination with pharmaceutically-active agents such as, but not limited to, rifampicin and minocycline. In one embodiment, compounds 6442, 8980 or 8981 can be combined with rifampicin and minocycline. It will be appreciated that the compounds of the first aspect may be combined with a number of known pharmaceutically-active agents known to the person skilled in the art. In other words, the pharmaceutical composition may further comprise at least one other pharmaceutically-active agent selected from the group consisting of rifampicin (rifampin), minocycline, meropenem, colistin, polymyxin B, fosfomycin, ciprofloxacin, levofloxacin, tetracycline, gentamicin, erythromycin, azithromycin, clarithromycin, arenicin-3 and linezolid. It is postulated that the compounds of the first aspect can provide an operative combination with a number of pharmaceutically-act agents.

The combinations referred to above may conveniently be presented for use in the form of a pharmaceutical formulation, and thus formulations comprising a combination as defined above together with a pharmaceutically acceptable carrier therefore comprise a further aspect of the invention.

Suitably, the pharmaceutically acceptable carrier, diluent and/or excipient may be or include one or more of diluents, solvents, pH buffers, binders, fillers, emulsifiers, disintegrants, polymers, lubricants, oils, fats, waxes, coatings, viscosity-modifying agents, glidants and the like.

The salt forms of the compounds of the invention may be especially useful due to an improved solubility.

Diluents may include one or more of microcrystalline cellulose, lactose, mannitol, calcium phosphate, calcium sulfate, kaolin, dry starch, powdered sugar, and the like. Binders may include one or more of povidone, starch, stearic acid, gums, hydroxypropylmethyl cellulose and the like. Disintegrants may include one or more of starch, croscarmellose sodium, crospovidone, sodium starch glycolate and the like. Solvents may include one or more of ethanol, methanol, isopropanol, chloroform, acetone, methylethyl ketone, methylene chloride, water and the like. Lubricants may include one or more of magnesium stearate, zinc stearate, calcium stearate, stearic acid, sodium stearyl fumarate, hydrogenated vegetable oil, glyceryl behenate and the like. A glidant may be one or more of colloidal silicon dioxide, talc or cornstarch and the like. Buffers may include phosphate buffers, borate buffers and carbonate buffers, although without limitation thereto. Fillers may include one or more gels inclusive of gelatin, starch and synthetic polymer gels, although without limitation thereto. Coatings may comprise one or more of film formers, solvents, plasticizers and the like. Suitable film formers may be one or more of hydroxypropyl methyl cellulose, methyl hydroxyethyl cellulose, ethyl cellulose, hydroxypropyl cellulose, povidone, sodium carboxymethyl cellulose, polyethylene glycol, acrylates and the like. Suitable solvents may be one or more of water, ethanol, methanol, isopropanol, chloroform, acetone, methylethyl ketone, methylene chloride and the like. Plasticizers may be one or more of propylene glycol, castor oil, glycerin, polyethylene glycol, polysorbates, and the like.

Reference is made to the Handbook of Excipients 6$^{th}$ Edition, Eds. Rowe, Sheskey & Quinn (Pharmaceutical Press), which provides non-limiting examples of excipients which may be useful according to the invention.

It will be appreciated that the choice of pharmaceutically acceptable carriers, diluents and/or excipients will, at least in part, be dependent upon the mode of administration of the formulation. By way of example only, the composition may be in the form of a tablet, capsule, caplet, powder, an injectable liquid, a suppository, a slow release formulation, an osmotic pump formulation or any other form that is effective and safe for administration.

Suitably, the pharmaceutical composition is for the treatment or prevention of a disease, disorder or condition in a mammal caused by a bacterial infection and/or fungal infection.

In a third aspect, the invention resides in a method of treatment or prevention of a disease, disorder or condition in a subject including the step of administering an effective amount of a compound of the first aspect, or a pharmaceutically acceptable salt, solvate or prodrug thereof, or the pharmaceutical composition of the second aspect, to the subject to thereby treat or prevent the disease, disorder or condition. Suitably, the disease, disorder or condition is associated with a bacterial or fungal infection.

As discussed hereinabove, it will be appreciated that the method of treatment can further include the step of administering other compounds to provide an operative combination. This further active agent can be co-administered with, administered prior or administered after the compound of the first aspect.

It is intended to include any chemically compatible combination of pharmaceutically-active agents, as long as the combination does not eliminate the activity of the compound of the first aspect. In one embodiment, the compounds of the first aspect are used in combination with other therapeutical agents. The therapeutic agent may be selected from the group consisting of antibiotic agents, antifungal agents, antivirulence agents, biofilm-disrupting agents, antiinflammatory agents and agents known to potentiate antibiotic efficacy. In an embodiment, the compounds of the first aspect are used in combination with other antibiotics.

In one embodiment, the invention resides in a method of treating or preventing a disease, disorder or condition in a subject including the step of administering an effective amount of a compound of the first aspect, or a pharmaceutically acceptable salt, solvate or prodrug thereof, or the pharmaceutical composition of the second aspect, to the subject in combination with another active agent or therapeutic agent, to thereby treat or prevent the disease, disorder or condition more effectively than either compound alone.

In a fourth aspect, the invention resides in the use of a compound of the first aspect, or a pharmaceutically acceptable salt, solvate or prodrug thereof, or the pharmaceutical composition of the second aspect, in the manufacture of a medicament for the treatment of a disease, disorder or condition. Suitably, the disease, disorder or condition is associated with a bacterial or fungal infection.

The medicament can further comprise a further active agent. The active agent can suitably be other therapeutic agents. The therapeutic agent may be selected from the group consisting of antibiotic agents, antifungal agents, antivirulence agents, biofilm-disrupting agents, antiinflammatory agents and agents known to potentiate antibiotic efficacy.

It is postulated that the compounds of formula (I), (Ia), (Ib), (Ic), (Id), (Ie), (If) or (II), can have improved efficacy against different strains of bacteria. In one embodiment, the disease, disorder or condition is caused by, or is associated with, a pathogen. The pathogen may be a virus, a bacterium, a protist, a worm or a fungus or any other organism capable of infecting a mammal, although without limitation thereto. Such bacteria include both gram-positive and gram-negative bacteria.

Non-limiting examples of the bacteria include *Escherichia coli, Klebsiella pneumoniae, Pseudomonas aeruginosa, Acinetobacter baumannii*, and *Staphylococcus aureus*. Further non-limiting examples of the bacteria include *E. coli* ATCC 25922; *K. pneumoniae* ATCC 13883; *K. pneumoniae* ATCC 700603, MDR; *K. pneumoniae* ATTC BAA-2146, NDM-1 pos; *A. baumannii* ATCC 19606; *P. aeruginosa* ATCC 27853; *P. aeruginosa* GN_043, PmxR; *P. aeruginosa* GN_105, PmxR; *A. baumannii* GN_093, PmxR; *K. pneumoniae* GN_102, PmxR; *K. pneumoniae* GN_106, PmxR; and *S. aureus* ATCC 25923, MSSA. Other non-limiting examples of bacteria include bacteria from the genus *Bacillus* (such as *Bacillus anthracis* and *Bacillus cereus*); *Bartonella* (such as *Bartonella henselae* and *Bartonella quintana*); *Bordetella* (such as *Bordetella pertussis*); *Borrelia* (such as *Borrelia burgdorferi, Borrelia garinii, Borrelia afzelii* and *Borrelia recurrentis*); *Brucella* (such as *Brucella abortus, Brucella canis, Brucella melitensis, Brucella suis*); *Campylobacter* (such as *Campylobacter jejuni*); *Chlamydia* (such as *Chlamydia pneumoniae* and *Chlamydia trachomatis*); *Chlamydophila* (such as *Chlamydophila psittaci*); *Clostridium* (such as *Clostridium botulinum, Clostridium difficile, Clostridium perfringens* and *Clostridium tetani*); *Corynebacterium* (such as *Corynebacterium diphtheriae*); Enterobacteriaceae (such as *Enterobacter* spp., *Citrobacter* spp., *Escherichia coli, Klebsiella pneumoniae*, and *Salmonella typhimurium*) *Enterococcus* (such as *Enterococcus faecalis* and *Enterococcus faecium*); *Escherichia* (such as *Escherichia coli*); *Francisella* (such as *Francisella tularensis*); *Haemophilus* (such as *Haemophilus influenzae*); *Helicobacter* (such as *Helicobacter pylori*); *Legionella* (such as *Legionella pneumophila*); *Leptospira* (such as *Leptospira interrogans, Leptospira santarosai, Leptospira weilii* and *Leptospira noguchii*); *Listeria* (such as *Listeria monocytogenes*); *Mycobacterium* (such as *Mycobacterium leprae, Mycobacterium tuberculosis* and *Mycobacterium ulcerans*); *Mycoplasma* (such as *Mycoplasma pneumoniae*); *Neisseria* (such as *Neisseria gonorrhoeae* and *Neisseria meningitidis*); *Proteus* (such as *Proteus Mirabilis*); *Pseudomonas* (such as *Pseudomonas aeruginosa*); *Rickettsia* (such as *Rickettsia rickettsii*); *Salmonella* (such as *Salmonella typhi* and *Salmonella typhimurium*); *Serratia* (such as *Serratia Marcescens*); *Shigella* (such as *Shigella sonnei*); *Staphylococcus* (such as *Staphylococcus aureus, Staphylococcus epidermidis* and *Staphylococcus saprophyticus*); *Streptococcus* (such as *Streptococcus agalactiae, Streptococcus pneumoniae* and *Streptococcus pyogenes*); *Treponema* (such as *Treponema pallidum*); *Ureaplasma* (such as *Ureaplasma urealyticum*); *Vibrio* (such as *Vibrio cholerae*) and *Yersinia* (such as *Yersinia pestis, Yersinia enterocolitica* and *Yersinia pseudotuberculosis*).

Non limiting examples of fungi include *Aspergillus* (such as *Aspergillus fumigatus, Aspergillus flavus* and *Aspergillus clavatus*), *Blastomyces, Candida* spp., *Coccidioides, Cryptococcus* (such as *Cryptococcus neoformans, Cryptococcus*

*laurentii, Cryptococcus* albidu and *Cryptococcus gattii*), *Histoplasma* (such as *Histoplasma capsulatum*), *Pneumocystis* (such as *Pneumocystis jirovecii*), *Sporothrix, Stachybotrys* (such as *Stachybotrys chartarum*), *Exserohilum* and *Cladosporium*.

As generally used herein, the terms "administering" or "administration", and the like, describe the introduction of the compound or composition to a subject such as by a particular route or vehicle. Routes of administration may include topical, parenteral and enteral which include oral, buccal, sub-lingual, nasal, anal, gastrointestinal, subcutaneous, intramuscular and intradermal routes of administration, although without limitation thereto.

By "treat", "treatment" or treating" is meant administration of the compound or composition to a subject to at least ameliorate, reduce or suppress existing signs or symptoms of the disease, disorder or condition experienced by the subject.

By "prevent", "preventing" or "preventative" is meant prophylactically administering the formulation to a subject who does not exhibit signs or symptoms of a disease disorder or condition, but who is expected or anticipated to likely exhibit such signs or symptoms in the absence of prevention. Preventative treatment may at least lessen or partly ameliorate expected symptoms or signs.

As used herein, "effective amount" refers to the administration of an amount of the relevant compound or composition sufficient to prevent the occurrence of symptoms of the condition being treated, or to bring about a halt in the worsening of symptoms or to treat and alleviate or at least reduce the severity of the symptoms.

The effective amount will vary in a manner which would be understood by a person of skill in the art with patient age, sex, weight etc. An appropriate dosage or dosage regime can be ascertained through routine trial.

As used herein, the terms "subject" or "individual" or "patient" may refer to any subject, particularly a vertebrate subject, and even more particularly a mammalian subject, for whom treatment is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment for a disease, disorder or condition. Particularly one related to bacterial or fungal infection.

Additionally, it is postulated that the compounds of formula (I), (Ia), (Ib), (Ic), (Id), (Ie), (If) or (II), are efficacious when administered subcutaneously, topically, intramuscularly and intravenously. Some exemplary compounds were tested in a mouse thigh infection model with results shown in FIGS. 3 and 4. Please note that the following abbreviations are used in FIGS. 3 and 4: 'b.i.d' is 'bis in die' and means administration was completed twice a day; 'q.d' is 'quaque die' and means administration was once a day; 'IV' mean intravenous therapy; and 'SC' means subcutaneous injection.

Some exemplary compounds were tested to determine their MIC against a panel of sensitive and resistant bacteria, and to determine their cytotoxicity (CC50) and nephrotoxicity against HK2, HEK293, HEPG2 cells and primary kidney cells. These results are shown in the following tables (Tables 1-12).

It will be appreciated that these general embodiments defined according to broad categories of diseases, disorders and conditions are not mutually exclusive. In this regard any particular disease, disorder or condition may be categorized according to more than one of the above general embodiments.

TABLE 1

Minimum inhibitory concentration (MIC, μg/mL) values for octapeptin compounds possessing AA1 = D-Dab, AA3 = AA6 = AA7 = L-Dab, FA = 3(R)-hydroxydecanoic acid, with variation at positions AA4, and/or AA5 and/or AA8. Amino acids are L-configuration unless indicated otherwise.

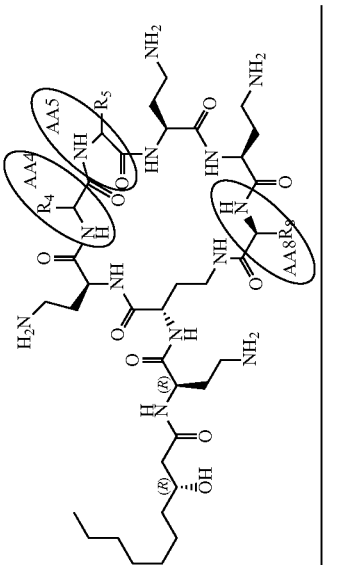

| ID | AA4 | AA5 | AA8 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293- CC50 (μM) | HK2 (LDH)- CC50 (μM) | Hep G2- CC50 (μM) |
|---|---|---|---|---|---|---|---|---|---|---|---|---|---|---|---|---|---|---|
| | | | | | | | | | MIC (μg/mL) | | | | | | | | | |
| Colistin | | | | 0.25 | 0.25 | 0.25 | 0.25 | 0.25 | 0.5 | 128 | 128 | >64 | >128 | 64 | >128 | >300 | 266 | >300 |
| PolymyxinB | | | | 0.25 | 0.5 | 1 | 0.25 | 0.25 | 0.5 | 64 | >128 | 64 | 64 | 64 | >64 | >300 | 125 | >300 |
| Octapeptin C4 (631) | | | | 4 | 8 | 8 | 8 | 4 | 2 | 2 | 16 | 32 | 2 | 4 | 16 | 41 | 148 | 118 |
| 4943 | D-Phe | Leu | Ala | 8 | 8 | 16 | 8 | >32 | 1 | 0.5 | 8 | 4 | 8 | 16 | >32 | nd | >300 | nd |
| 5004 | D-Phe | Leu | Phe | 8 | 8 | 4 | 8 | 4 | 4 | 2 | 2 | 32 | nd | nd | nd | nd | 23 | nd |
| 5387 | D-Phe | Leu | Thr | 2 | 2 | 2 | 1 | 8 | 1 | 2 | 2 | >32 | >32 | >32 | nd | nd | 210 | nd |
| 6508 | D-Phe | Leu | Arg | 16 | 16 | >64 | >64 | >64 | 2 | >32 | >32 | >32 | >32 | >32 | >32 | nd | 142 | nd |
| 6509 | D-Phe | Leu | Trp | 4 | 2 | 4 | 4 | 8 | 2 | 1 | 1 | 8 | 4 | 4 | 4 | 71 | nd | 76 |
| 6510 | D-Phe | Leu | Ser | 1 | 4 | 64 | 4 | >64 | 2 | 1 | 16 | >32 | >32 | >32 | >64 | nd | 149 | nd |
| 6511 | D-Phe | Leu | Tyr | 8 | 4 | 8 | 2 | 32 | 2 | 1 | 4 | 32 | 8 | 8 | 32 | nd | 76 | nd |
| 6512 | D-Phe | Leu | Glu | >64 | 64 | >64 | >64 | >64 | 8 | >32 | >32 | >32 | >32 | >32 | >32 | nd | >300 | nd |
| 6513 | D-Phe | Leu | Asp | >64 | 64 | >64 | >64 | >64 | 4 | 8 | >32 | >32 | >32 | >32 | >32 | nd | >300 | nd |
| 8906 | D-Phe | Leu | Ala(4py) | 4 | 4 | 4 | 8 | >32 | 1 | 0.5 | 1 | >32 | 16 | 16 | 4 | >300 | nd | nd |
| 8907 | D-Phe | Leu | Ala(3py) | 4 | 4 | 2 | 4 | >32 | 1 | 4 | 2 | >32 | 32 | 8 | 2 | >300 | nd | nd |
| 8908 | D-Phe | Leu | Ala(2Na) | 2 | 2 | 2 | 4 | 4 | 4 | 4 | 2 | 4 | 4 | 4 | 4 | 39 | nd | nd |
| 8909 | D-Phe | Leu | Ala(1Na) | 2 | 2 | 2 | 4 | 4 | 4 | 2 | 2 | 4 | 8 | 4 | 2 | 26 | nd | nd |
| 8910 | D-Phe | Leu | His | 4 | 4 | 4 | 4 | 8 | 2 | 2 | 16 | 4 | >32 | >32 | >32 | 47 | nd | nd |
| 8911 | D-Phe | Leu | indanylgly | 8 | 8 | >32 | 16 | >32 | 2 | 4 | 2 | 4 | 2 | 2 | 2 | >300 | nd | nd |
| 8912 | D-Phe | Leu | hPhe | 2 | 4 | 4 | 4 | 4 | 2 | 2 | 2 | 4 | 2 | 2 | 2 | 28 | nd | nd |
| 8913 | D-Phe | Leu | Phe | 2 | 4 | 2 | 4 | 8 | 4 | 4 | 4 | 4 | 2 | 2 | 4 | 32 | nd | nd |
| 5005 | D-Phe | L-Phe | Phe | 8 | 8 | 4 | 4 | >32 | 4 | 4 | nd | nd | nd | nd | nd | nd | 54 | nd |
| 5384 | D-Bip | Leu | Phe | 4 | 8 | 4 | 4 | 8 | 4 | 4 | 4 | 16 | 16 | 8 | 4 | nd | 24 | nd |
| 5385 | D-Phe | Leu | Phe | 4 | 8 | 4 | 4 | 8 | 2 | 2 | 2 | 16 | 8 | 16 | 8 | nd | 41 | nd |

TABLE 2

Minimum inhibitory concentration (MIC, μg/mL) values for octapeptin compounds possessing AA1 = D-Dab, AA3 = AA6 = AA7 = L-Dab, AA8 = L-Trp, FA = 3(R)-hydroxydecanoic acid, with variation at positions AA4 or AA5. Amino acids are L-configuration unless indicated otherwise.

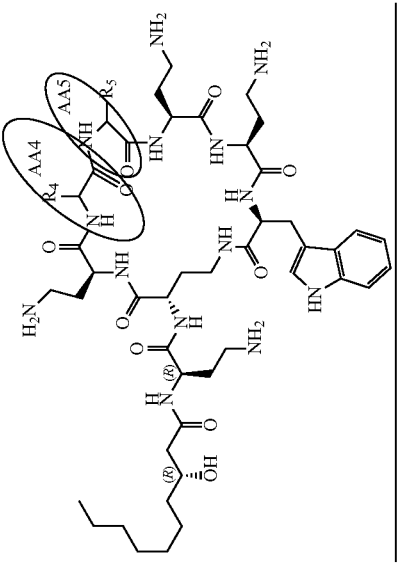

| ID | AA4 | AA5 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093 PmxR | K. pneumoniae GN_102 PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|
| | Colistin | | 0.25 | 0.25 | 0.25 | 0.25 | 0.25 | 0.5 | 128 | 128 | >64 | >128 | 64 | >128 | >300 | 266 | >300 |
| | PolymyxinB | | 0.25 | 0.5 | 1 | 0.25 | 0.25 | 0.5 | 64 | >128 | 64 | 64 | 64 | >64 | >300 | 125 | >300 |
| | Octapeptin C4 (631) | Ala(cycloprop) | 4 | 8 | 8 | 4 | 4 | 2 | 2 | 2 | 16 | 2 | 4 | 16 | 41 | 148 | 118 |
| 8099 | D-Phe | Ala(cyclohex) | 8 | 8 | 8 | 8 | 8 | 2 | 2 | >32 | 16 | 8 | 4 | 4 | 73 | nd | nd |
| 8101 | D-Phe | indanylgly | 2 | 2 | 4 | 8 | 4 | 4 | 4 | 4 | 8 | 8 | 8 | 2 | nd | nd | 24 |
| 8103 | D-Phe | Ala(2-Na) | 8 | 8 | 16 | 8 | 8 | 2 | 4 | 8 | 16 | 4 | 4 | 4 | 34 | nd | nd |
| 8832 | D-Phe | hPhe | 8 | 8 | 4 | 8 | 8 | 4 | 4 | 32 | 8 | 16 | 8 | 4 | 26 | nd | nd |
| 8834 | D-Phe | Leu | 4 | 8 | 8 | 8 | 8 | 2 | 2 | 2 | 16 | 4 | 8 | 4 | nd | nd | nd |
| 8105 | D-Phe(4-CN) | Leu | 4 | 16 | 32 | 16 | 32 | 4 | 4 | 8 | 32 | >32 | >32 | 4 | 107 | nd | nd |
| 8109 | D-Ala(3,3'diph) | Leu | 8 | 8 | 4 | 4 | 8 | 4 | 2 | 4 | 8 | 8 | 8 | 4 | 55 | nd | 70 |
| 8113 | D-Ala(2-Na) | Leu | 2 | 4 | 16 | 4 | 16 | 4 | 2 | 2 | 32 | 16 | 4 | 16 | 28 | nd | nd |
| 8119 | D-Phe(4-F) | Leu | 2 | 4 | 8 | 4 | 4 | 2 | 4 | 2 | 4 | 4 | 4 | 2 | 64 | nd | nd |
| 8127 | D-Trp | Leu | 8 | 8 | 8 | 4 | 8 | 4 | 4 | 4 | 16 | 8 | 8 | 4 | 63 | nd | nd |
| 8129 | D-hPhe | Leu | 4 | 4 | 8 | 4 | 8 | 2 | 4 | 4 | 8 | 4 | 4 | 2 | 37 | nd | nd |
| 8826 | D-indanylgly | Leu | 8 | 8 | 8 | 4 | 16 | 4 | 4 | 4 | 16 | 8 | 8 | 8 | 38 | nd | nd |
| 8899 | D-Chg | Leu | 4 | 4 | 2 | 4 | 2 | 4 | 4 | 2 | 16 | 16 | 16 | 2 | 64 | nd | nd |
| 8914 | D-Phe(3-Cl) | Leu | 2 | 2 | 2 | 4 | 4 | 2 | 4 | 1 | 4 | 4 | 4 | 2 | 25 | nd | nd |

TABLE 3

Minimum inhibitory concentration (MIC, µg/mL) values for octapeptin compounds possessing AA3 = L-Dab, AA8 = L-Trp with variation at positions AA1, and/or AA4 and/or AA5 and/or AA6 and/or AA7 and/or fatty acid (FA). Amino acids are L-configuration unless indicated otherwise.

| ID | FA | AA1 | AA4 | AA5 | AA6 | AA7 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (µM) | HK2 (LDH)-CC50 (µM) | Hep G2-CC50 (µM) |
|---|---|---|---|---|---|---|---|---|---|---|---|---|---|---|---|---|---|---|---|---|---|
| | | Colistin | | | | | 0.25 | 0.25 | 0.25 | 0.25 | 0.25 | 0.5 | 128 | 128 | >64 | >128 | 64 | >128 | >300 | 266 | >300 |
| | | PolymyxinB | | | | | 0.25 | 0.5 | 1 | 0.25 | 0.25 | 0.5 | 64 | >128 | 64 | 64 | 64 | >64 | >300 | 125 | >300 |
| | | Octapeptin C4 (631) | | | | | 4 | 8 | 8 | 8 | 4 | 2 | 2 | 2 | 4 | 2 | 4 | 16 | 41 | 148 | 118 |
| 8888 | FA1 | D-Dap | D-Phe | indanylgly | Lys | Arg | 2 | 2 | 4 | 2 | 4 | 2 | 4 | 2 | 8 | 4 | 4 | 2 | 67 | nd | nd |
| 8890 | FA1 | D-Dap | D-Phe | indanylgly | Arg | Lys | 4 | 4 | 2 | 4 | 8 | 4 | 4 | 2 | 8 | 4 | 8 | 2 | 67 | nd | nd |
| 8892 | FA1 | D-Dap | D-Bip | tert-Leu | Lys | Arg | 4 | 4 | 8 | 2 | 8 | 8 | 8 | 4 | 8 | 8 | 4 | 4 | >300 | nd | nd |
| 8896 | FA1 | D-Dap | D-indanylgly | Leu | Lys | Arg | 2 | 2 | 4 | 4 | 4 | 4 | 4 | 2 | 16 | 16 | 4 | 2 | 102 | nd | nd |
| 8897 | FA1 | D-Dap | D-indanylgly | indanylgly | Dab | Dab | 4 | 4 | 4 | 2 | 2 | 2 | 2 | 2 | 4 | 32 | 4 | 2 | 27 | nd | nd |
| 8884 | FA1 | D-Arg | D-Phe | Leu | Dab | Dab | 2 | 4 | 16 | 8 | 32 | 4 | 4 | 16 | 32 | 32 | 16 | 16 | 73 | nd | nd |
| 8886 | FA1 | D-Dap | D-Phe | Leu | Dab | Dab | 2 | 4 | 4 | 8 | 8 | 2 | 2 | 1 | 8 | 4 | 4 | 4 | 95 | nd | nd |
| 8887 | FA2 | D-Dap | D-Phe | Leu | Dab | Dab | 8 | 4 | 16 | 8 | 32 | 4 | 2 | 8 | >32 | 32 | 16 | 8 | 190 | nd | nd |
| 8898 | FA2 | D-Dap | D-Phe | indanylgly | Dab | Dab | 4 | 4 | 8 | 8 | 16 | 4 | 4 | 4 | 16 | 4 | 8 | 4 | 90 | nd | nd |
| 8900 | FA2 | D-Dap | D-indanylgly | Leu | Dab | Dab | 4 | 8 | 16 | 8 | 32 | 4 | 4 | 8 | >32 | 16 | 16 | 8 | 115 | nd | nd |
| 8901 | FA2 | D-Dap | D-Phe | Leu | Dab | Dab | 8 | 8 | 8 | 8 | 32 | 2 | 2 | 8 | >32 | 32 | 32 | 16 | >300 | nd | nd |

TABLE 3-continued

Minimum inhibitory concentration (MIC, μg/mL) values for octapeptin compounds possessing AA3 = L-Dab, AA8 = L-Trp with variation at positions AA1, and/or AA4 and/or AA5 and/or AA6 and/or AA7 and/or fatty acid (FA). Amino acids are L-configuration unless indicated otherwise.

| ID | FA | AA1 | AA4 | AA5 | AA6 | AA7 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (μM) | HK2 (LDH)-CC50 (μM) | HepG2-CC50 (μM) |
|---|---|---|---|---|---|---|---|---|---|---|---|---|---|---|---|---|---|---|---|---|---|
| | | | | | | | | | | | | | MIC (μg/mL) | | | | | | | | |
| 9032 | FA2 | D-Dap | D-Phe | Leu | Dab | Dab | 4 | 8 | 8 | 8 | 8 | 2 | 1 | 2 | 8 | 4 | 4 | 16 | nd | nd | nd |
| 8981 | FA3 | D-Dap | D-Phe | Leu | Dab | Dab | 32 | 16 | >32 | 16 | >32 | 4 | 32 | >32 | 32 | >32 | >32 | >32 | nd | nd | nd |

FA3 = CH₃

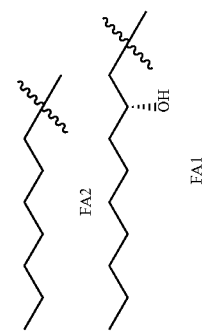

FA2

FA1

TABLE 4

Minimum inhibitory concentration (MIC, μg/mL) values for octapeptin compounds possessing AA3 = AA6 = L-Dab, AA5 = AA8 = L-Leu, FA = 3(R)-hydroxydecanoic acid, with variation at positions AA1, and/or AA4 and/or AA7. Amino acids are L-configuration unless indicated otherwise.

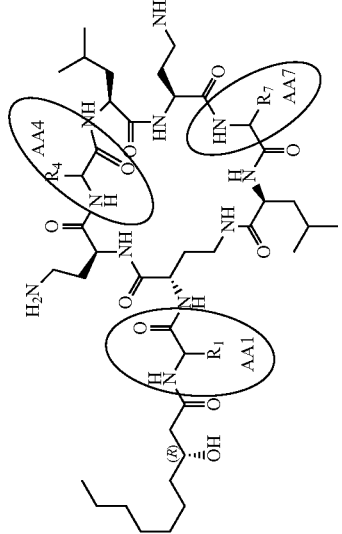

| ID | AA1 | AA4 | AA7 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102 PmxR | K. pneumoniae GN_106, PmxB | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|---|
| | | | | | | | | | MIC (μg/mL) | | | | | | | | | |
| | Colistin | | | 0.25 | 0.25 | 0.25 | 0.25 | 0.25 | 0.5 | 128 | 128 | >64 | >128 | 64 | >128 | >300 | 266 | >300 |
| | PolymyxinB | | | 0.25 | 0.5 | 1 | 0.25 | 0.25 | 0.5 | 64 | >128 | 64 | 64 | 64 | >64 | >300 | 125 | >300 |
| | Octapeptin C4 (631) | | | 4 | 8 | 8 | 8 | 4 | 2 | 2 | 2 | 4 | 2 | 4 | 16 | 41 | 148 | 118 |
| 987 | D-Dab | D-Phe | Dap | 8 | 4 | 4 | 4 | 1 | 2 | 2 | 2 | 8 | 16 | 16 | 16 | >300 | 49 | 265 |
| 988 | D-Dab | D-Phe | Orn | 2 | 2 | 2 | 2 | 4 | 2 | 2 | 2 | 16 | 2 | 2 | 16 | 104 | 48 | 84 |
| 989 | D-Dab | D-Phe | Lys | 4 | 2 | 4 | 2 | 8 | 2 | 2 | 2 | 8 | 4 | 4 | 16 | >300 | 82 | 293 |
| 4944 | D-Dab | D-Phe | Ala | 16 | 16 | 16 | 8 | 32 | 8 | 4 | 4 | >32 | 8 | 32 | >32 | 60 | 111 | nd |
| 6653 | D-Dab | D-Phe | Dab(Arg) | 16 | 8 | 8 | 8 | 16 | 4 | 2 | 16 | 16 | >32 | 16 | 32 | >300 | 64 | >300 |
| 8644 | D-Dab | D-Phe | 4NH2Phe | 16 | 8 | 2 | 4 | 4 | 8 | 8 | 8 | >32 | 2 | 8 | 32 | 205 | 91 | 149 |
| 8643 | D-Dab | D-Phe | Arg | 1 | 2 | 2 | 8 | >32 | 2 | 2 | | 16 | 2 | 2 | 16 | 91 | 137 | 104 |
| 5564 | Dab | D-Phe | Dap | 8 | 16 | 4 | 16 | 8 | 4 | 2 | 32 | 32 | 4 | 8 | 32 | >300 | 44 | 296 |
| 5565 | Dab | D-Bip | Dap | 4 | 8 | 4 | 4 | 4 | 4 | 2 | 4 | 16 | 32 | 16 | 2 | 30 | 11 | 34 |
| 5383 | D-Dab | D-Bip | Dap | 4 | 4 | 4 | 4 | 4 | 2 | 2 | 2 | 4 | 8 | 8 | 2 | 40 | 13 | 38 |

TABLE 5

Minimum inhibitory concentration (MIC, μg/mL) values for octapeptin compounds possessing AA1 = D-Dab, AA4 = L-Phe, AA5 = AA8 = L-Leu, FA = 3(R)-hydroxydecanoic acid, with variation at positions AA3 or AA6. Amino acids are L-configuration unless indicated otherwise.

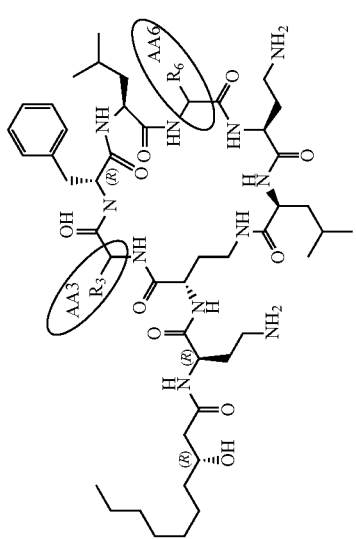

| ID | AA1 | AA3 | AA6 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa FADDI-PA070, PmxR | P. aeruginosa PA9704 PmxR | A. baumannii Cl Ptyela 10073 4512-2, PmxR | K. pneumoniae Cl Koprana 10065 0661:1, PmxR | K. pneumoniae Cl 138- 16347- 20362, PmxR | S. Aureus ATCC 25923, MSSA | HEK-293- CC50 (μM) | HK2 (LDH)- CC50 (μM) | Hep G2- CC50 (μM) |
|---|---|---|---|---|---|---|---|---|---|---|---|---|---|---|---|---|---|---|
| | | | | | | | | | | | MIC (μg/mL) | | | | | | | |
| | Colistin | | | 0.25 | 0.25 | 0.25 | 0.25 | 0.25 | 0.5 | 128 | 128 | >64 | >128 | 64 | >128 | >300 | 266 | >300 |
| | PolymyxinB | | | 0.25 | 0.5 | 1 | 0.25 | 0.25 | 0.5 | 64 | >128 | 64 | 64 | 64 | >64 | >300 | 125 | >300 |
| | Octapeptin C4 (631) | | | 4 | 8 | 8 | 8 | 4 | 2 | 2 | 2 | 4 | 2 | 4 | 16 | 41 | 148 | 118 |
| 990 | D-Dab | Dab | Dap | 4 | 4 | 4 | 4 | 8 | 2 | 2 | 4 | 16 | 2 | 2 | 32 | >300 | 95 | 292 |
| 991 | D-Dab | Dab | Orn | 2 | 2 | 2 | 2 | 4 | 2 | 2 | 1 | 8 | 1 | 2 | 8 | 114 | 39 | 97 |
| 992 | D-Dab | Dab | Lys | 2 | 2 | 2 | 2 | 2 | 2 | 2 | 4 | 8 | 4 | 4 | 4 | 135 | 21 | 92 |
| 4945 | D-Dab | Dab | Ala | 16 | 8 | 16 | 8 | 16 | 4 | 4 | 8 | 32 | 4 | 16 | 32 | nd | 181 | nd |
| 6654 | D-Dab | Dab | Dab(Arg) | 4 | 4 | 4 | 4 | 8 | 4 | 8 | 2 | 8 | 8 | 16 | 16 | 228 | 31 | 163 |
| 8642 | D-Dab | Dab | 4NH2Phe | 4 | 4 | 2 | 4 | 8 | 2 | 2 | 8 | 16 | 2 | 16 | 8 | 133 | 52 | 73 |
| 8733 | D-Dab | Dab | Arg | 2 | 2 | 2 | 2 | 4 | 2 | 2 | 2 | 8 | 2 | 4 | 8 | 69 | 47 | 129 |
| 9193 | D-Dab | Dab | Ser | >32 | >32 | >32 | >32 | 32 | 32 | >32 | >32 | >32 | >32 | >32 | >32 | >300 | nd | nd |
| 993 | D-Dap | Dap | Dab | 2 | 4 | 4 | 8 | 8 | 2 | 2 | 2 | 16 | 2 | 2 | 8 | 235 | 56 | 154 |
| 994 | D-Dab | Orn | Dab | 8 | 8 | 8 | 8 | 32 | 4 | >32 | 8 | 32 | 4 | 4 | 32 | >300 | 53 | 152 |
| 995 | D-Dab | Lys | Dab | 8 | 16 | 16 | 8 | >32 | 4 | 8 | >32 | >32 | 8 | 8 | 32 | >300 | 57 | 195 |
| 4948 | D-Dab | Ala | Dab | 16 | 16 | 16 | 16 | 32 | 1 | 1 | >32 | >32 | 16 | 16 | >32 | nd | 112 | nd |
| 6655 | D-Dab | Dab(Arg) | Dab | 8 | 8 | 32 | 16 | 32 | 4 | 4 | 4 | >32 | 16 | >32 | 16 | >300 | 40 | 295 |
| 8635 | D-Dab | 4NH2Phe | Dab | 16 | 32 | >32 | 16 | >32 | 16 | 16 | >32 | >32 | >32 | >32 | 32 | >300 | 219 | >300 |
| 8634 | D-Dab | Arg | Dab | 8 | 4 | 8 | 8 | 16 | 4 | 2 | 4 | 32 | 4 | >32 | 16 | 188 | nd | 162 |

TABLE 6

Minimum inhibitory concentration (MIC, μg/mL) values for octapeptin compounds possessing AA3 = AA6 = AA7 = L-Dab, AA4 = L-Phe, AA5 = AA8 = L-Leu, with variation at positions AA1 and/or fatty acid (FA). Amino acids are L-configuration unless indicated otherwise.

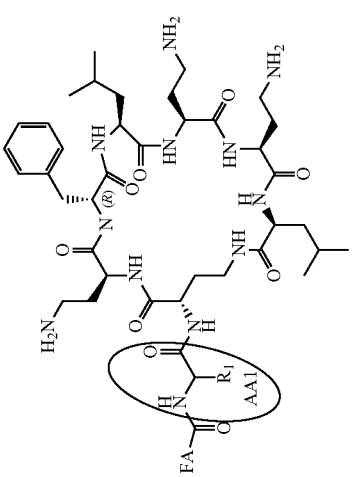

| ID | FA | AA1 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093 PmxR | K. pneumoniae GN_102 PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|
| | Colistin | | 0.25 | 0.25 | 0.25 | 0.25 | 0.25 | 0.5 | 128 | 128 | >64 | >128 | 64 | >128 | >300 | 266 | >300 |
| | PolymyxinB | | 0.25 | 0.5 | 1 | 0.25 | 0.25 | 0.5 | 64 | >128 | 64 | 64 | 64 | >64 | >300 | 125 | >300 |
| | Octapeptin C4 (631) | | 4 | 8 | 8 | 8 | 4 | 2 | 2 | 2 | 4 | 2 | 4 | 16 | 41 | 148 | 118 |
| 918 | 3(R)—OH-nC9CO | D-Ser | 8 | 8 | 16 | 16 | 32 | 8 | >32 | 16 | nd | nd | nd | nd | nd | 113 | nd |
| 4951 | 3(R)—OH-nC9CO | D-Ala | 16 | 16 | 16 | 16 | 32 | 8 | 8 | 16 | 32 | 4 | 8 | 32 | nd | 120 | nd |
| 4950 | 3(R)—OH-nC9CO | Ala | 32 | 16 | 8 | 16 | >32 | 16 | 16 | 32 | >32 | 2 | 32 | >32 | nd | 286 | 176 |
| 5381 | 3(R)—OH-nC9CO | D-Lys | 8 | 4 | 8 | 8 | 16 | 4 | 2 | 4 | 8 | 4 | 4 | >32 | >300 | 160 | 238 |
| 5562 | 3(R)—OH-nC9CO | Lys | 8 | 4 | 4 | 8 | >32 | 2 | 4 | >32 | 32 | 4 | 2 | 32 | 234 | 39 | 162 |
| 6442 | 3(R)—OH-nC9CO | D-Dap | 2 | 8 | 4 | 8 | 4 | 2 | 2 | 2 | 8 | 4 | 4 | 16 | >300 | 40 | 271 |
| 5561 | 3(R)—OH-nC9CO | Dap | 4 | 8 | 8 | 8 | 16 | 2 | 2 | 2 | 16 | 8 | 4 | 16 | >300 | 24 | 78 |
| 6441 | 3(R)—OH-nC9CO | D-Trp | 16 | 8 | 16 | 8 | 16 | 16 | 8 | 16 | 32 | 4 | 4 | 8 | 117 | 44 | 177 |
| 6443 | 3(R)—OH-nC9CO | D-Orn | 8 | 8 | 4 | 8 | 16 | 2 | 2 | 2 | 16 | 8 | 4 | 32 | >300 | 41 | 146 |
| 6444 | 3(R)—OH-nC9CO | D-4NH2Phe | 8 | 8 | 4 | 8 | 32 | 16 | 32 | 16 | 32 | 4 | 8 | >32 | 186 | 58 | 151 |
| 6445 | 3(R)—OH-nC9CO | D-3pyAla | 8 | 4 | 8 | 8 | 32 | 4 | 8 | 8 | >32 | 2 | 4 | >32 | 237 | 76 | 154 |
| 6446 | 3(R)—OH-nC9CO | Gly | 8 | 8 | 8 | 8 | 32 | 4 | 4 | 4 | >32 | 4 | 4 | >32 | 246 | 74 | 150 |
| 6447 | 3(R)—OH-nC9CO | D-Asn | 4 | 4 | 4 | 8 | 16 | 4 | 4 | 4 | 8 | 4 | 4 | 32 | 292 | 54 | 61 |
| 6448 | 3(R)—OH-nC9CO | D-4NO2Phe | 8 | 8 | 8 | 8 | 8 | 2 | 8 | 2 | 8 | 8 | 8 | 16 | 82 | 24 | 151 |
| 5566 | 3(RS)OH,7Me-nC7CO | Dab | 4 | 8 | 4 | 16 | 4 | 2 | 2 | 2 | 16 | 32 | 16 | 2 | 237 | 76 | 150 |
| 5567 | 3(RS)OH,8(RS)Me-nC9CO | Dab | 8 | 8 | 8 | 8 | 8 | 4 | 2 | 2 | 16 | 8 | 4 | 32 | 292 | 54 | 61 |
| 5568 | nC9CO | Dab | 8 | 8 | 4 | 8 | 16 | 1 | 8 | 4 | >32 | nd | 16 | 8 | 82 | 24 | 162 |
| 8638 | 3(R)OH,nC9CO | D-Dap | 2 | 4 | 8 | 8 | 32 | 2 | 2 | 2 | 32 | 4 | 4 | 16 | 158 | 57 | nd |
| 8976 | nC7CO | D-Dap | 4 | 8 | 8 | 8 | >32 | 2 | 8 | 4 | 8 | 16 | 16 | >32 | >300 | nd | nd |
| 8980 | Ac | D-Dap | >32 | 32 | >32 | 32 | >32 | 4 | >32 | >32 | >32 | >32 | >32 | >32 | >300 | nd | nd |

TABLE 7

Minimum inhibitory concentration (MIC, μg/mL) for octapeptin compounds possessing AA3 = AA6 = AA7 = L-Dab, AA8 = L-Leu, with variation at positions AA1, and/or AA4 and/or AA5 and/or fatty acid (FA) with additional variation in ring size (AA2). Amino acids are L-configuration unless indicated otherwise.

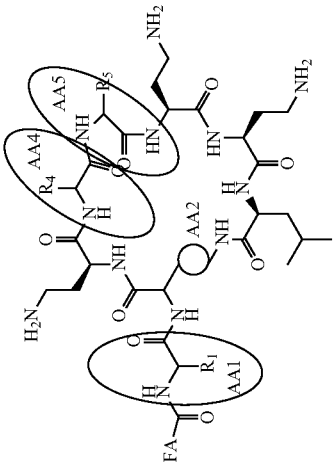

| ID | FA | AA1 | AA2 | AA4 | AA5 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|---|---|---|
| | | Colistin | | | | 0.25 | 0.25 | 0.25 | 0.25 | 0.25 | 0.5 | 128 | 128 | >64 | >128 | 64 | >128 | >300 | 266 | >300 |
| | | PolymyxinB | | | | 0.25 | 0.5 | 1 | 0.25 | 0.25 | 0.5 | 64 | >128 | >64 | 64 | 64 | >64 | >300 | 125 | >300 |
| | | Octapeptin C4 (631) | | | | 4 | 8 | 8 | 8 | 4 | 2 | 0.5 | 2 | 4 | 2 | 4 | 16 | 41 | 148 | 118 |
| 4946 | FA1 | D-Dab | Dab | D-Phe | Ala | 16 | 16 | >32 | 16 | 16 | 1 | >32 | 16 | 16 | 4 | 16 | >32 | nd | 107 | nd |
| 5563 | FA1 | Dab | Dab | D-Phe | Ala | 32 | 16 | 4 | 16 | >32 | 2 | 32 | 32 | >32 | 32 | 32 | >32 | >300 | 158 | >300 |
| 5003 | FA1 | D-Dab | Dab | D-Phe | Phe | 8 | 16 | 32 | 32 | >32 | 16 | 8 | 2 | 8 | 4 | 4 | 8 | 193 | 65 | 113 |
| 5006 | FA1 | D-Dab | Dab | D-Ala | Leu | 16 | >32 | >32 | >32 | >32 | 32 | >32 | 2 | >32 | >32 | 32 | >32 | nd | 277 | nd |
| 4947 | FA1 | D-Dab | Dab | Ala | Leu | >32 | >32 | >32 | >32 | >32 | 32 | >32 | >32 | >32 | >32 | >32 | >32 | nd | 213 | >300 |
| 6371 | FA1 | D-Dab | Dab | Leu | Phe | >32 | >32 | >32 | >32 | >32 | 8 | 4 | 2 | >32 | >32 | >32 | >32 | >300 | >300 | >300 |
| 6514 | FA1 | D-Dab | Dab | D-Leu | Phe | 2 | 4 | 8 | 8 | >32 | 2 | 2 | 4 | >32 | 16 | >32 | 32 | >300 | 80 | >300 |
| 6515 | FA1 | D-Dab | Dab | D-Leu | Phe | 16 | >32 | >32 | 32 | >32 | 1 | 0.5 | 2 | 16 | nd | nd | 32 | nd | 223 | >300 |
| 6516 | FA1 | D-Dab | Dab | D-Leu | Phe | 8 | 8 | 16 | 16 | >32 | 2 | 4 | 4 | >32 | >32 | >32 | 32 | >300 | >300 | 300 |
| 6517 | FA1 | D-Dab | Dab | D-Leu | Phe | 2 | 8 | 16 | 16 | 16 | 4 | 1 | 2 | >32 | >32 | >32 | 32 | >300 | 180 | 300 |
| 6518 | FA1 | D-Dab | Dab | D-Leu | Phe | 2 | 8 | 32 | 16 | >32 | 2 | 4 | 4 | 32 | 32 | >32 | 32 | >300 | 163 | 236 |
| 6519 | FA1 | D-Dab | Dab | D-Leu | Phe | 8 | 8 | 32 | 8 | >32 | 4 | 4 | 4 | 32 | 32 | >32 | 32 | >300 | 76 | >300 |
| 6520 | FA1 | D-Dab | Dab | D-Leu | Phe | 4 | 16 | 32 | 16 | >32 | 8 | 8 | 16 | 16 | 16 | 4 | 8 | 86 | 290 | 76 |
| 6521 | FA1 | D-Trp | Dab | D-Leu | Phe | 4 | 8 | 16 | 8 | 8 | 2 | 2 | 2 | 16 | 4 | 4 | 32 | >300 | 32 | >300 |
| 6426 | FA1 | D-Dap | Dab | D-Leu | Phe | 16 | 8 | 16 | 16 | 32 | 4 | 4 | 4 | 16 | 2 | 4 | 32 | >300 | 123 | >300 |
| 6427 | FA1 | D-Orn | Dab | D-Leu | Phe | 16 | 8 | 16 | 16 | 32 | 4 | 16 | 32 | 16 | 8 | 8 | 32 | >300 | 137 | 285 |
| 6428 | FA1 | D-4NH2Phe | Dab | D-Leu | Phe | 16 | 8 | 16 | 16 | 32 | 32 | 16 | 32 | 32 | >32 | 4 | >32 | >300 | 187 | 291 |
| 6429 | FA1 | D-3PyPhe | Dab | D-Leu | Phe | 16 | 8 | 16 | 16 | 32 | 32 | 32 | 32 | 32 | 8 | 8 | >32 | >300 | 177 | 296 |
| 6430 | FA1 | Gly | Dab | D-Leu | Phe | 16 | 16 | 32 | 16 | 32 | 16 | 4 | 8 | 32 | 2 | 4 | >32 | >300 | 125 | 296 |
| 6431 | FA1 | D-Asn | Dab | D-Leu | Phe | 8 | 8 | 16 | 8 | 32 | 16 | 4 | 8 | 32 | 4 | 4 | >32 | >300 | 230 | >300 |
| 6432 | FA1 | D-4NO2Phe | Dab | D-Leu | Phe | 4 | 16 | 16 | 16 | 8 | 4 | 4 | 2 | 16 | 2 | 4 | 8 | 157 | 31 | 89 |
| 6433 | FA1 | D-Dab | Dab | Phe | D-Leu | 16 | 32 | 8 | >32 | 32 | 16 | >32 | 8 | 16 | 8 | >32 | 32 | >300 | nd | 300 |
| 8640 | FA1 | D-Dab | D-Dab | D-Phe | Leu | >32 | >32 | 16 | >32 | >32 | 8 | >32 | >32 | >32 | >32 | >32 | >32 | >300 | 89 | >300 |
| 6658 | FA1 | Dab | D-Dab | D-Phe | Ala | >32 | >32 | 32 | >32 | 32 | 32 | 32 | 32 | >32 | >32 | >32 | >32 | >300 | >300 | >300 |
| 6660 | FA1 | D-Dab | Lys | D-Phe | Leu | 4 | 8 | 8 | 8 | 32 | 4 | 2 | 2 | >32 | 4 | >32 | 32 | >300 | 58 | 154 |
| 5382 | FA1 | | | | | | | | | | | | | | | | | | | |

TABLE 7-continued

Minimum inhibitory concentration (MIC, µg/mL) for octapeptin compounds possessing AA3 = AA6 = AA7 = L-Dab, AA8 = L-Leu, with variation at positions AA1, and/or AA4 and/or AA5 and/or fatty acid (FA) with additional variation in ring size (AA2). Amino acids are L-configuration unless indicated otherwise.

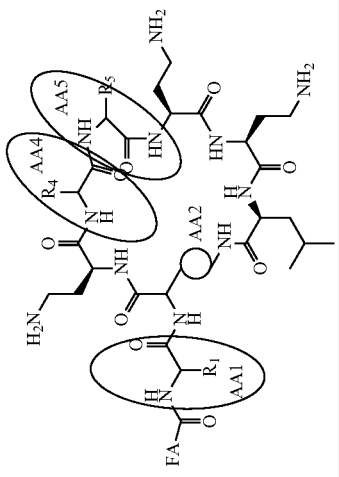

| ID | FA | AA1 | AA2 | AA4 | AA5 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102 PmxR | K. pneumoniae GN_106, PmxR | S. aureus ATCC 25923, MSSA | HEK-293-CC50 (µM) | HK2 (LDH)-CC50 (µM) | Hep G2-CC50 (µM) |
|---|---|---|---|---|---|---|---|---|---|---|---|---|---|---|---|---|---|---|---|---|
| | | | | | | | | | | | | | MIC (µg/mL) | | | | | | | |
| 5002 | FA1 | D-Dab | Dab | Phe | Leu | 32 | 16 | >32 | 16 | >32 | 4 | 8 | >32 | >32 | 32 | >32 | 32 | >300 | 80 | 197 |
| 5010 | FA1 | D-Dab | Dab | D-Bip | Leu | 2 | 4 | 2 | 4 | 4 | 4 | 2 | 2 | 4 | 4 | 2 | 2 | nd | 75 | nd |
| 6661 | FA1 | Dab | D-Dab | D-Bip | Leu | 32 | 32 | 32 | 32 | >32 | 8 | >32 | 8 | >32 | >32 | >32 | 8 | 157 | 84 | 146 |
| 8977 | FA1 | D-Dap | Dab | D-Leu | Leu | 4 | 4 | 8 | 8 | 8 | 4 | 2 | 2 | 8 | 2 | 4 | 32 | nd | nd | nd |
| 8978 | FA1 | D-Dap | Dap | D-Leu | Leu | 4 | 16 | 16 | 16 | 32 | 2 | 4 | 2 | >32 | 32 | 32 | >32 | nd | 104 | >300 |
| 633 | FA2 | D-Dab | Dap | D-Leu | Leu | 16 | 32 | >32 | 8 | >32 | 1 | 16 | >32 | 8 | >32 | >32 | 32 | >300 | 106 | >300 |
| 5008 | FA1 | D-Dap | Dab | D-Tyr | Leu | 8 | 8 | 16 | 16 | 32 | 2 | 2 | 16 | 32 | 16 | 16 | 32 | >300 | nd | nd |
| 9188 | FA12 | D-Dap | Dab | D-Phe | Leu | 8 | 32 | >32 | 32 | >32 | 4 | >16 | >16 | >16 | >32 | >32 | >16 | >300 | nd | nd |
| 9189 | FA13 | D-Dap | Dab | D-Phe | Leu | >32 | 16 | 16 | 16 | >32 | 2 | 4 | 16 | >32 | >32 | >32 | >32 | >300 | nd | nd |
| 9190 | FA14 | D-Dap | Dab | D-Phe | Leu | 8 | 8 | 8 | 8 | >32 | 4 | 4 | 8 | 16 | 32 | 16 | 32 | >300 | nd | nd |
| 9191 | FA15 | D-Dap | Dab | D-Phe | Leu | 4 | 4 | 8 | 8 | 32 | 4 | 4 | 8 | 4 | 8 | 8 | 8 | 224 | nd | nd |
| 9192 | FA17 | D-Dap | Dab | D-Phe | D-Phe | 32 | >32 | >32 | >32 | >32 | 32 | >32 | >32 | >32 | >32 | >32 | 32 | >300 | nd | nd |
| 9194 | FA1 | D-Dap | Dab | Leu | Thr | 2 | 2 | 2 | 2 | 2 | 1 | 1 | 16 | 16 | >32 | 4 | nd | >300 | nd | nd |
| 9289 | FA16 | D-Dap | Dab | D-Phe | Leu | 8 | 8 | 8 | 4 | 16 | 2 | 2 | 32 | 32 | 4 | 32 | nd | >300 | nd | nd |
| 9290 | FA1 | D-Dap | Dab | D-Phe | Val | 2 | 4 | 4 | 4 | >32 | 2 | 2 | 4 | 8 | 2 | 4 | nd | >300 | nd | nd |
| 9291 | FA1 | D-Dap | Dab | D-Phe | Abu | 4 | 4 | 4 | 4 | 8 | 2 | 1 | 4 | 4 | 2 | 2 | nd | >300 | nd | nd |
| 9292 | FA1 | D-Dap | Dab | D-Phe | NorVal | 4 | 4 | 4 | 4 | 8 | 2 | 2 | 4 | 4 | 2 | 2 | nd | >300 | nd | nd |
| 9293 | FA1 | D-Dap | Dab | D-Phe | NorLeu | 4 | 4 | 4 | 4 | 4 | 2 | 1 | 4 | 4 | 2 | 2 | nd | 193 | nd | nd |
| 9294 | FA1 | D-Dap | Dab | D-Phe | NorLeu | 4 | 4 | 4 | 4 | 8 | 2 | 2 | 4 | 4 | 2 | 2 | nd | >300 | nd | nd |
| 9295 | FA1 | D-Dap | Dab | D-Phe | Thr | 2 | 4 | 4 | 4 | 4 | 2 | 2 | 4 | 4 | 4 | 4 | nd | >300 | nd | nd |

TABLE 7-continued

Minimum inhibitory concentration (MIC, μg/mL) for octapeptin compounds possessing AA3 = AA6 = AA7 = L-Dab, AA8 = L-Leu, with variation at positions AA1, and/or AA4 and/or AA5 and/or fatty acid (FA) with additional variation in ring size (AA2). Amino acids are L-configuration unless indicated otherwise.

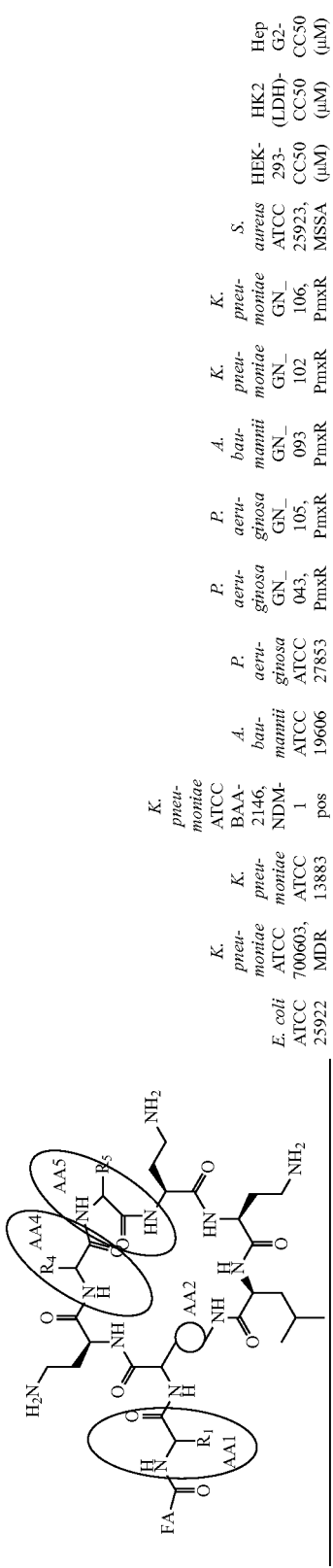

| ID | FA | AA1 | AA2 | AA4 | AA5 | E. coli ATCC 25922 | K. pneu- moniae ATCC 700603, MDR | K. pneu- moniae ATCC 13883 | K. pneu- moniae ATCC BAA- 2146, NDM- 1 pos | A. bau- mannii ATCC 19606 | P. aeru- ginosa ATCC 27853 | P. aeru- ginosa GN_ 043, PmxR | P. aeru- ginosa GN_ 105, PmxR | A. bau- mannii GN_ 093, PmxR | K. pneu- moniae GN_ 102, PmxR | K. pneu- moniae GN_ 106, PmxR | S. aureus ATCC 25923, MSSA | HEK- 293- CC50 (μM) | HK2 (LDH)- CC50 (μM) | Hep G2- CC50 (μM) |
|---|---|---|---|---|---|---|---|---|---|---|---|---|---|---|---|---|---|---|---|---|
| | | | | | | | | | | | | | MIC (μg/mL) | | | | | | | |
| 9296 | FA18 | D-Dap | Dab | D-Phe | Leu | 4 | 2 | 4 | 4 | 16 | 2 | 1 | 32 | 32 | 2 | 4 | nd | 63 | nd | nd |
| 9297 | FA19 | D-Dap | Dab | D-Phe | Leu | 2 | 4 | 4 | 8 | 16 | 4 | 2 | 8 | 8 | 8 | 8 | nd | 33 | nd | nd |

TABLE 7-continued

Minimum inhibitory concentration (MIC, µg/mL) for octapeptin compounds possessing AA3 = AA6 = AA7 = L-Dab, AA8 = L-Leu, with variation at positions AA1, and/or AA4 and/or AA5 and/or fatty acid (FA) with additional variation in ring size (AA2). Amino acids are L-configuration unless indicated otherwise.

| | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (µM) | HK2 (LDH)-CC50 (µM) | Hep G2-CC50 (µM) |
|---|---|---|---|---|---|---|---|---|---|---|---|---|---|---|---|
| | | | | | | MIC (µg/mL) | | | | | | | | | |

| ID | FA | AA1 | AA2 | AA4 | AA5 |

TABLE 7-continued

Minimum inhibitory concentration (MIC, µg/mL) for octapeptin compounds possessing AA3 = AA6 = AA7 = L-Dab, AA8 = L-Leu, with variation at positions AA1, and/or AA4 and/or AA5 and/or fatty acid (FA) with additional variation in ring size (AA2). Amino acids are L-configuration unless indicated otherwise.

| ID | FA | AA1 | AA2 | AA4 | AA5 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (µM) | HK2 (LDH)-CC50 (µM) | Hep G2-CC50 (µM) |
|----|----|-----|-----|-----|-----|-----|-----|-----|-----|-----|-----|-----|-----|-----|-----|-----|-----|-----|-----|-----|
| | | | | | | | | | | | MIC (µg/mL) | | | | | | | | | |

TABLE 7-continued

Minimum inhibitory concentration (MIC, μg/mL) for octapeptin compounds possessing AA3 = AA6 = AA7 = L-Dab, AA8 = L-Leu, with variation at positions AA1, and/or AA4 and/or AA5 and/or fatty acid (FA) with additional variation in ring size (AA2). Amino acids are L-configuration unless indicated otherwise.

| ID | FA | AA1 | AA2 | AA4 | AA5 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|---|---|---|

MIC (μg/mL)

TABLE 7-continued

Minimum inhibitory concentration (MIC, μg/mL) for octapeptin compounds possessing AA3 = AA6 = AA7 = L-Dab, AA8 = L-Leu, with variation at positions AA1, and/or AA4 and/or AA5 and/or fatty acid (FA) with additional variation in ring size (AA2). Amino acids are L-configuration unless indicated otherwise.

| ID | FA | AA1 | AA2 | AA4 | AA5 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|---|---|---|
| | | | | | | | | | | | MIC (μg/mL) | | | | | | | | | |
| FA18 | | | | | | | | | | | | | | | | | | | | |
| FA19 | | | | | | | | | | | | | | | | | | | | |

TABLE 8

Minimum inhibitory concentration (MIC, μg/mL) values for octapeptin compounds possessing AA1 = D-Dab, AA3 = L-Dab, AA8 = L-Thr, FA = 3(R)-hydroxydecanoic acid, with variation at positions AA4 and/or AA5 and/or AA6 and/or AA7. Amino acids are L-configuration unless indicated otherwise.

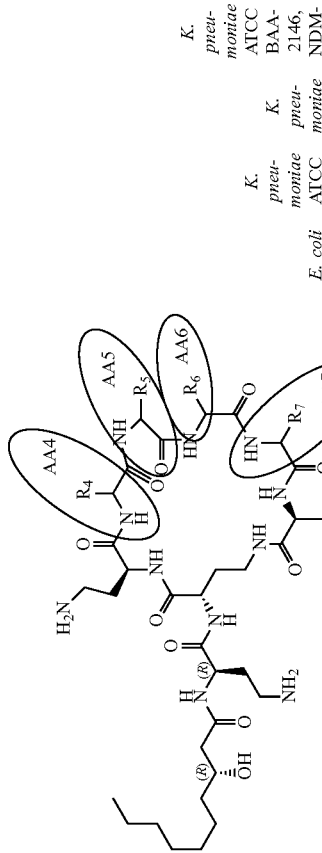

| ID | AA4 | AA5 | AA6 | AA7 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|---|---|
| | | | | | | | | | | | | MIC (μg/mL) | | | | | | | |
| Colistin | | | | | 0.25 | 0.25 | 0.25 | 0.25 | 0.25 | 0.5 | 128 | 128 | >64 | >128 | 64 | >128 | >300 | 266 | >300 |
| PolymyxinB | | | | | 0.25 | 0.5 | 1 | 0.25 | 0.25 | 0.5 | 64 | >128 | 64 | 64 | 64 | >64 | >300 | 125 | >300 |
| Octapeptin C4 (631) | | | | | 4 | 8 | 8 | 8 | 4 | 4 | 2 | 2 | 4 | 2 | 4 | 16 | 41 | 148 | 118 |
| 5386 | D-Phe | Leu | Dab | Dap | 2 | 2 | 16 | 4 | >32 | 2 | 1 | 4 | >32 | 32 | >32 | >32 | nd | 154 | nd |
| 5605 | D-Phe | Leu | Dab | 4-NH2Phe | 16 | 32 | 16 | 16 | nd | 8 | nd | nd | nd | nd | nd | nd | nd | 115 | nd |
| 5606 | D-Phe | Leu | Dab | Arg | >32 | 16 | 32 | >32 | >32 | 2 | 32 | 32 | >32 | >32 | >32 | >32 | nd | 137 | nd |
| 5603 | D-Phe | Leu | Dab | Dab(Arg) | 32 | 16 | >32 | >32 | 16 | 8 | 8 | 16 | 16 | 32 | >32 | >32 | nd | 103 | nd |
| 6656 | D-Phe | Leu | Dab(Arg) | Dab | 8 | 4 | 16 | 4 | 8 | 4 | 2 | 4 | 4 | 4 | 32 | 4 | nd | >300 | nd |
| 5607 | D-Phe | Bip | Dab | Dab | 2 | 2 | 2 | 2 | 4 | 2 | 1 | 2 | 16 | 4 | 8 | 4 | nd | 19 | nd |
| 5608 | D-Bip | Leu | Dab | Dab | | | | | | | | | | | | | | 37 | |

TABLE 9

Minimum inhibitory concentration (MIC, μg/mL) values for octapeptin compounds possessing AA6 = AA7 = L-Dab, AA4 = L-Phe, AA5 = L-Leu, AA8 = L-Thr, with variation at positions or AA1 and/or AA3 and/or fatty acid (FA). Amino acids are L-configuration unless indicated otherwise.

| ID | FA | AA1 | AA3 | E. coli ATCC 25922 | K. pneu-moniae ATCC 700603, MDR | K. pneu-moniae ATCC 13883 | K. pneu-moniae ATCC BAA-2146, NDM-1 pos | A. bau-mannii ATCC 19606 | P. aeru-ginosa ATCC 27853 | P. aeru-ginosa GN_043, PmxR | P. aeru-ginosa GN_105, PmxR | A. bau-mannii GN_093, PmxR | K. pneu-moniae GN_102, PmxR | K. pneu-moniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|---|
| | | | | | | | | | | | MIC (μg/mL) | | | | | | | |
| | | Colistin | | 0.25 | 0.25 | 0.25 | 0.25 | 0.25 | 0.5 | 128 | 128 | >64 | >128 | 64 | >128 | >300 | 266 | >300 |
| | | PolymyxinB | | 0.25 | 0.5 | 1 | 0.25 | 0.25 | 0.5 | 64 | >128 | 64 | 64 | 64 | >64 | >300 | 125 | >300 |
| | | Octapeptin C4 (631) | Dab(Arg) | 4 | 8 | 8 | 8 | 4 | 2 | 2 | 2 | 4 | 2 | 4 | 16 | 41 | 148 | 118 |
| 6657 | FA1 | D-Dab | Dab | >32 | 32 | >32 | >32 | >32 | 16 | >32 | nd | >32 | nd | >32 | >32 | nd | >300 | nd |
| 754 | FA1 | D-Ser | Dab | 32 | 32 | 32 | 32 | 16 | 4 | >32 | >32 | >32 | nd | >32 | nd | nd | 154 | nd |
| 6394 | FA1 | D-Trp | Dab | >64 | >64 | >64 | >64 | >64 | 64 | >32 | >32 | >32 | 16 | >32 | >32 | nd | >300 | nd |
| 6395 | FA1 | D-Dap | Dab | 2 | 1 | 8 | 2 | 16 | 2 | 2 | 2 | >32 | >32 | >32 | >32 | nd | >300 | nd |
| 6396 | FA1 | D-Orn | Dab | 16 | 16 | >64 | 32 | >64 | 16 | 16 | 16 | >32 | 16 | >32 | >32 | nd | >300 | nd |
| 6397 | FA1 | D-4NH2Phe | Dab | >64 | >64 | >64 | >64 | >64 | >64 | >32 | >64 | >32 | 32 | >32 | >32 | nd | >300 | nd |
| 6398 | FA1 | D-3PyPhe | Dab | >64 | 16 | >32 | >32 | >32 | 32 | 8 | 2 | >32 | 32 | >32 | >32 | nd | >300 | nd |
| 6399 | FA2 | D-Dab | Dab | 8 | >64 | >64 | >64 | >64 | 1 | 32 | 16 | >32 | >32 | >32 | >32 | nd | >300 | nd |
| 6403 | FA12 | D-Dab | Dab | >64 | >64 | >64 | >64 | >64 | 16 | >32 | >32 | >32 | >32 | >32 | >32 | nd | >300 | nd |
| 6404 | FA13 | D-Dab | Dab | 1 | 0.5 | 16 | 1 | 64 | 0.25 | 32 | 2 | >32 | >32 | >32 | 8 | nd | 38 | nd |
| 6405 | FA7 | D-Dab | Dab | >64 | >64 | >64 | >64 | >64 | 8 | >32 | >32 | >32 | >32 | >32 | >32 | nd | >300 | nd |

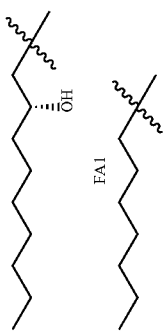

TABLE 9-continued

Minimum inhibitory concentration (MIC, μg/mL) values for octapeptin compounds possessing AA6 = AA7 = L-Dab, AA4 = L-Phe, AA5 = L-Leu, AA8 = L-Thr, with variation at positions or AA1 and/or AA3 and/or fatty acid (FA). Amino acids are L-configuration unless indicated otherwise.

| ID | FA | AA1 | AA3 | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093, PmxR | K. pneumoniae GN_102, PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|---|---|
| | | | | | | | | | | MIC (μg/mL) | | | | | | | | |

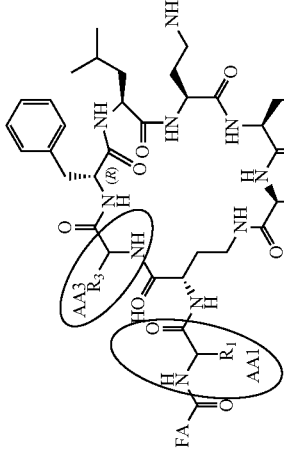

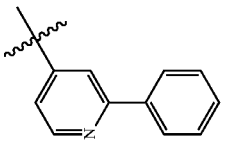

FA7

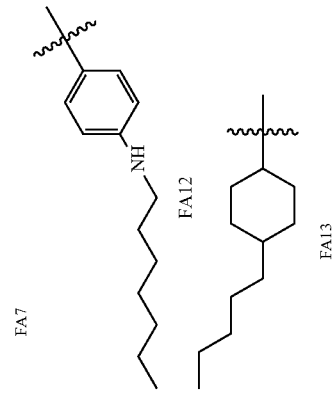

FA12

FA13

TABLE 10

Minimum inhibitory concentration (MIC, μg/mL) values for octapeptin compounds possessing AA1 = D-Dab, AA3 = AA6 = AA7 = L-Dab, AA4 = L-Phe, AA5 = AA8 = L-Leu, with variation of the fatty acid (FA). Amino acids are L-configuration unless indicated otherwise.

| ID | FA | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa GN_043, PmxR | P. aeruginosa GN_105, PmxR | A. baumannii GN_093 PmxR | K. pneumoniae GN_102 PmxR | K. pneumoniae GN_106, PmxR | S. aureus ATCC 25923, MSSA | HEK-293-CC50 (μM) | HK2 (LDH)-CC50 (μM) | Hep G2-CC50 (μM) |
|---|---|---|---|---|---|---|---|---|---|---|---|---|---|---|---|---|
| | Colistin | 0.25 | 0.25 | 0.25 | 0.25 | 0.25 | 0.5 | 128 | 128 | >64 | >128 | 64 | >128 | >300 | 266 | >300 |
| | PolymyxinB | 0.25 | 0.5 | 1 | 0.25 | 0.25 | 0.5 | 64 | >128 | 64 | 64 | 64 | >64 | >300 | 125 | >300 |
| | Octapeptin C4 (631) | 4 | 8 | 8 | 8 | 4 | 2 | 2 | 2 | 4 | 2 | 4 | 16 | 41 | 148 | 118 |
| 919 | C4CO | 32 | >32 | 32 | 16 | 16 | 2 | >32 | nd | nd | nd | nd | nd | nd | >300 | nd |
| 5012 | 3OH-nC7CO | 32 | 16 | 8 | 32 | 16 | 4 | 4 | 4 | >32 | nd | >32 | >32 | nd | 130 | nd |
| 5013 | 3OH-nC9CO | 8 | 8 | 4 | 16 | 16 | 2 | 2 | 2 | 8 | 4 | 16 | 16 | nd | 69 | 174 |
| 5014 | 3OH-nC11CO | 2 | 8 | 4 | 16 | 8 | 2 | 4 | 32 | nd | nd | nd | 4 | nd | 19 | nd |
| 5015 | 3OH-nC13CO | 4 | 8 | 4 | 8 | 4 | 2 | 4 | 4 | 8 | 8 | 4 | 4 | 39 | 12 | 38 |
| 5016 | cholic acid | 8 | 4 | 4 | 8 | 16 | 2 | 4 | 4 | 8 | 8 | 16 | 32 | 48 | 17 | 46 |
| 5017 | nC9CO | 4 | 16 | 8 | 16 | 8 | 2 | 2 | 2 | 16 | 32 | 16 | 16 | 169 | 45 | 102 |
| 6522 | 8OH-nC7CO | >32 | >32 | >32 | >32 | >32 | 2 | >32 | >32 | >32 | >32 | >32 | >32 | >300 | 208 | >300 |
| 6523 | 3(RS),7-diMeOctanoic acid | 1 | 8 | 4 | 8 | >32 | 4 | 2 | 2 | 16 | 16 | 32 | 32 | nd | 41 | 138 |
| 6524 | 1-heptylpiperidine-4-carboxylic acid | 32 | >32 | >32 | 32 | >32 | 1 | 0.5 | 8 | >32 | >32 | >32 | 32 | >300 | 106 | >300 |
| 6525 | 2Ph-4-PyCO | 4 | 8 | 16 | 16 | >32 | 2 | 2 | 4 | 16 | 16 | 16 | 32 | >300 | >300 | >300 |
| 6526 | Ph-4-PhCO | 8 | 8 | 8 | 8 | >32 | 2 | 1 | 4 | >32 | 32 | 32 | >32 | >300 | 94 | 292 |
| 6527 | Ph-4-OPhCO | 2 | 16 | 16 | 16 | >32 | 1 | 1 | 2 | >32 | 32 | 32 | >32 | 296 | 89 | 195 |
| 6528 | 4-(pentyloxy)benzoic acid | 2 | 16 | 8 | 8 | >32 | 2 | 1 | 4 | >32 | 32 | 32 | >32 | 259 | 52 | 143 |
| 6529 | 4-phenoxybutanoic acid | 8 | 32 | 16 | 32 | >32 | 2 | 1 | 16 | >32 | >32 | >32 | >32 | >300 | 199 | >300 |

TABLE 11

Minimum inhibitory concentration (MIC, μg/mL) values for mono-substituted aza-octapeptin compounds where each amino acid position in octapeptin-C4 has been substituted with its aza-amino acid equivalent. Amino acids are L-configuration unless indicated otherwise.

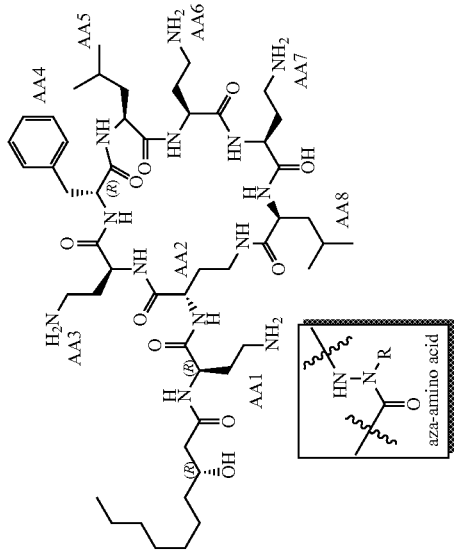

| ID | AAn | E. coli ATCC 25922 | K. pneumoniae ATCC 700603, MDR | K. pneumoniae ATCC 13883 | K. pneumoniae ATCC BAA-2146, NDM-1 pos | A. baumannii ATCC 19606 | P. aeruginosa ATCC 27853 | P. aeruginosa FADDI-PA070, PmxR | P. aeruginosa PA9704, PmxR | A. baumannii Cl Ptyela 10073 4512:2, PmxR | K. pneumoniae Cl Koprana 10065 0661:1 PmxR | K. pneumoniae Cl 183-16357-20352, PmxR | S. aureus ATCC 25923, MSSA | HEK-293- CC50 (μM) | HK2 (LDH)- CC50 (μM) | Hep G2- CC50 (μM) |
|---|---|---|---|---|---|---|---|---|---|---|---|---|---|---|---|---|
| | Colistin | 0.25 | 0.25 | 0.25 | 0.25 | 0.25 | 0.5 | 128 | 128 | >64 | >128 | 64 | >128 | >300 | 266 | >300 |
| | PolymyxinB | 0.25 | 0.5 | 1 | 0.25 | 0.25 | 0.5 | 64 | >128 | 64 | 64 | 64 | >64 | >300 | 125 | >300 |
| | Octapeptin C4 (631) | 4 | 8 | 8 | 8 | 4 | 2 | 2 | 2 | 4 | 2 | 4 | 16 | 41 | 148 | 118 |
| 9416 | AA8 = aza-Leu | 16 | 16 | 16 | 16 | >32 | 4 | >32 | >32 | >32 | >32 | >32 | 32 | >300 | nd | nd |
| 8782 | AA7 = aza-Dab | 16 | 32 | 32 | >32 | >32 | 2 | 8 | 32 | >32 | >32 | >32 | 16 | >300 | nd | >300 |
| 8641 | AA6 = aza-Dab | 4 | 4 | 4 | 8 | 8 | 2 | 2 | 2 | 32 | 2 | 4 | 32 | >300 | nd | >300 |
| 8803 | AA5 = aza-Leu | 2 | 8 | 8 | 8 | 8 | 4 | 1 | 2 | 32 | 2 | 4 | 16 | 26 | nd | 28 |
| 8942 | AA4 = aza-Phe | 32 | >32 | >32 | >32 | >32 | 4 | 16 | >32 | 32 | >32 | >32 | >32 | nd | nd | nd |
| 8636 | AA3 = aza-Dab | 16 | 16 | >32 | >32 | >32 | 16 | >32 | >32 | >32 | >32 | >32 | 32 | >300 | nd | >300 |
| 9417 | AA2 = aza-Dab | >32 | >32 | >32 | >32 | >32 | 2 | >32 | >32 | >32 | >32 | >32 | 8 | >300 | nd | nd |
| 8639 | AA1 = aza-Dab | 2 | 2 | 4 | 4 | 4 | 2 | 2 | 2 | 8 | 2 | 2 | 8 | 108 | nd | 117 |

TABLE 12

Minimum inhibitory concentration (MIC, μg/mL) values against
Neisseria gonorrhoeae for octapeptin compounds with sequences as indicated.

| ID | | N. gonor-rhoeae FA19 ATCC BAA-1838 | N. gonor-rhoeae FA1090 A25 ATCC 700825 | N. gonor-rhoeae H041 | N. gonor-rhoeae F89 |
|---|---|---|---|---|---|
| PolymyxinB | | 12.5 | 10.42 | 8.33 | 9.38 |
| Octapeptin C4 (631) | | 0.78 | 1.69 | 2.08 | 1.82 |
| 988 | 3(R)OH-nC9CO-D-Dab-cyc[L-Dab-L-Dab-D-Phe-L-Leu-L-Dab-L-Orn-L-Leu] | 0.78 | n.d. | n.d. | n.d. |
| 991 | 3(R)OH-nC9CO-D-Dab-cyc[L-Dab-L-Dab-D-Phe-L-Leu-L-Orn-L-Dab-L-Leu] | 0.39 | 1.56 | 2.08 | 1.3 |
| 6442 | 3(R)OH-nC9CO-D-Dap-cyc[L-Dab-L-Dab-D-Phe-L-Leu-L-Dab-L-Dab-L-Leu] | 1.56 | 1.3 | 1.56 | 1.56 |
| 6509 | 3(R)OH-nC9CO-D-Dab-cyc[L-Dab-L-Dab-D-Phe-L-Leu-L-Dab-L-Dab-L-Trp] | 0.78 | 0.65 | 1.69 | 1.04 |
| 8103 | 3(R)OH-nC9CO-D-Dab-cyc[L-Dab-L-Dab-L-Dab-D-Phe-L-indanylgly-L-Dab-L-Dab-L-Trp] | 0.2 | n.d. | n.d. | n.d. |
| 8639 | 3(R)OH-nC9CO-azaDab-cyc[L-Dab-L-DAB-D-Phe-L-Leu-L-Dab-L-Dab-L-Leu] | 0.78 | n.d. | n.d. | n.d. |
| 8643 | 3(R)OH-nC9CO-D-Dab-cyc[L-Dab-L-DAB-D-Phe-L-Leu-L-Dab-L-Arg-L-Leu] | 1.56 | n.d. | n.d. | n.d. |
| 8733 | 3(R)OH-nC9CO-D-Dab-cyc[L-Dab-L-DAB-D-Phe-L-Leu-L-Arg-L-Dab-L-Leu] | 0.78 | n.d. | n.d. | n.d. |
| 8886 | 3(R)OH-nC9CO-D-Dap-cyc[L-Dab-L-Dab-D-Phe-L-Leu-L-Dab-L-Dab-L-Trp] | 0.39 | 0.91 | 1.04 | 1.04 |
| 8909 | 3(R)OH-nC9CO-D-Dab-cyc[L-Dab-L-Dab-D-Phe-L-Leu-L-Dab-L-Dab-L-Ala (1Naphthyl)] | 0.78 | n.d. | n.d. | n.d. |
| 8912 | 3(R)OH-nC9CO-D-Dab-cyc[L-Dab-L-Dab-D-Phe-L-Leu-L-Dab-L-Dab-L-indanylgly] | 0.78 | n.d. | n.d. | n.d. |
| 8913 | 3(R)OH-nC9CO-D-Dab-cyc[L-Dab-L-Dab-D-Phe-L-Leu-L-Dab-L-Dab-L-hPhe] | 1.56 | n.d. | n.d. | n.d. |
| 8914 | 3(R)OH-nC9CO-D-Dab-cyc[L-Dab-L-Dab-D-Phe(3-Cl)-L-Leu-L-Dab-L-Dab-L-Trp] | 0.78 | n.d. | n.d. | n.d. |
| 9193 | 3(R)-OH-nC9CO-D-Dap-cyc[L-Dab-L-Dab-D-Phe-L-Leu-L-Ser-L-Dab-L-Leu] | 25 | n.d. | n.d. | n.d. |

TABLE 13

Potentiation summary of Octapeptin C4 with antibiotics rifampicin, minocycline, arenicin-3 and linezolid.

| | | | | MIC (μg/mL) with OctC4 at concn (μg/mL) of: | | | | |
|---|---|---|---|---|---|---|---|---|
| Antibiotic | | Strain | | 0 | 0.03 | 0.0625 | 0.125 | 0.25 |
| Rifampicin | GN_181 | E. coli | mcr-1 | 32 | NA | *1* | *0.25* | *0.25* |
| | GN_102 | K. pneumoniae | XDR/PmxR | 32 | NA | 32 | 32 | *0.25* |
| Minocycline | GN_007 | E. coli | ESBL | 0.25 | 0.25 | 0.125-0.25 | 0.125 | *0.06* |
| | GN_181 | E. coli | mcr-1 | 4 | 4 | 2-4 | *0.5-1* | *0.06-0.25* |
| | GN_045 | K. pneumoniae | NDM-1 | 32 | 32 | 32 | 32 | *0.25-1* |
| | GN_102 | K. pneumoniae | XDR/PmxR | 32 | 32 | 16 | 16 | *0.5-1* |
| | GN_105 | P. aeruginosa | PmxR | 8 | 8 | 4 | 4 | *0.06-0.125* |

TABLE 13-continued

Potentiation summary of Octapeptin C4 with antibiotics rifampicin, minocycline, arenicin-3 and linezolid.

| Antibiotic | Strain | | | MIC (µg/mL) with OctC4 at concn (µg/mL) of: | | | | |
|---|---|---|---|---|---|---|---|---|
| | | | | 0 | 0.03 | 0.0625 | 0.125 | 0.25 |
| Arenicin-3 | GN_093 | *A. baumannii* | XDR/PmxR | 0.5 | *0.002* | *0.004* | 0.008 | 0.016 |
| | GN_043 | *P. aeruginosa* | PmxR | 2 | | *0.004* | *0.008* | *0.016* |
| Linezolid | GN_181 | *E. coli* | mcr-1 | >32 | 8 | 4 | 4 | 0.25 |

*Where the compound combination has FICI value ≤0.5 value is marked in bold and italics to indicate synergy;
NA = No activity;
underlined value indicates an excluded value as the MIC of the potentiator is at this value.

TABLE 14

Potentiation summary of 6442 with antibiotics rifampicin and minocycline.

| Antibiotic | Strain | | | MIC (µg/mL) with 6442 at concn (µg/mL) of | | | | |
|---|---|---|---|---|---|---|---|---|
| | | | | 0 | 0.03 | 0.0625 | 0.125 | 0.25 |
| Rifampicin | GN_181 | *E. coli* | mcr-1 | 32 | NA | NA | *0.25* | 0.25 |
| | GN_102 | *K. pneumoniae* | XDR/PmxR | 32 | NA | NA | 16 | *0.25* |
| | GN_007 | *E. coli* | ESBL | 0.25 | 0.25 | 0.125 | *0.06* | *0.015* |
| | GN_181 | *E. coli* | mcr-1 | 4 | 4 | *1* | 1 | 0.06 |
| Minocycline | GN_045 | *K. pneumoniae* | NDM-1 | 32 | 32 | 32 | *8* | *0.25* |
| | GN_102 | *K. pneumoniae* | XDR/PmxR | 32 | 16 | 16 | *8* | *0.25* |
| | GN_105 | *P. aeruginosa* | PmxR | 8 | 4 | 2-4 | *1* | 0.06 |

*Where the compound combination has FICI value ≤0.5 value is marked in bold and italics to indicate synergy;
NA = No activity;
underlined value indicates an excluded value as the MIC of the potentiator is at this value

TABLE 15

Potentiation summary of 8980 with antibiotics rifampicin and minocycline.

| | Strain | | | MIC (µg/mL) with 8980 at conc (µg/mL) of | | | | |
|---|---|---|---|---|---|---|---|---|
| | | | | 0 | 1 | 2 | 4 | 8 |
| Rifampicin | GN_181 | *E. coli* | mcr-1 | 32 | 32 | 32 | 32 | *8* |
| | GN_102 | *K. pneumoniae* | XDR/PmxR | 32 | 16 | *8* | *2-4* | *2* |
| Minocycline | GN_007 | *E. coli* | ESBL | 0.25 | 0.125-0.25 | 0.125 | 0.06-0.125 | 0.06-0.125 |
| | GN_181 | *E. coli* | mcr-1 | 4 | 1-2 | 0.5-2 | 0.5-2 | 0.5-2 |
| | GN_045 | *K. pneumoniae* | NDM-1 | 32 | *0.25-1* | *0.25-0.5* | *0.25-0.5* | *0.25-1* |
| | GN_102 | *K. pneumoniae* | XDR/PmxR | 32 | *2-4* | *1-2* | *1-2* | *1-2* |
| | GN_019 | *A. baumannii* | CARB | 4 | *0.5-16* | *0.5-8* | *0.5-8* | *0.5-4* |
| | GN_093 | *A. baumannii* | XDR/PmxR | 8 | *2-32* | *2-16* | *1-16* | *1-16* |
| | GN_105 | *P. aeruginosa* | PmxR | 8 | *1* | 1 | 1 | *0.125-1* |

*Where the compound combination has FICI value ≤0.5 value is marked in bold and italics to indicate synergy.

TABLE 16

Potentiation summary of 8981 with antibiotics rifampicin and minocycline.

| Antibiotic | Strain | | | MIC (µg/mL) with 8981 at conc (µg/mL) of | | | | |
|---|---|---|---|---|---|---|---|---|
| | | | | 0 | 1 | 2 | 4 | 8 |
| Rifampicin | GN_181 | *E. coli* | mcr-1 | 32 | 32 | 32 | 32 | *8* |
| | GN_102 | *K. pneumoniae* | XDR/PmxR | 32 | 16-32 | 16 | 8-16 | *1-4* |
| Minocycline | GN_007 | *E. coli* | ESBL | 0.25 | 0.25 | 0.125-0.25 | 0.03-0.125 | 0.03-0.125 |
| | GN_181 | *E. coli* | mcr-1 | 4 | 1-2 | 1-2 | 0.5-2 | 0.5-2 |
| | GN_045 | *K. pneumoniae* | NDM-1 | 32 | *0.5-4* | *0.5-1* | *0.5-1* | *0.25-1* |
| | GN_102 | *K. pneumoniae* | XDR/PmxR | 32 | *4-8* | *4-8* | *4-8* | *4* |
| | GN_019 | *A. baumannii* | CARB | 4 | 2-16 | 2-16 | *2-16* | *2-16* |
| | GN_093 | *A. baumannii* | XDR/PmxR | 8 | 4-32 | 2-32 | *2-32* | *1-16* |
| | GN_105 | *P. aeruginosa* | PmxR | 8 | *1-2* | *1* | *1* | *0.125-1* |

*Where the compound combination has FICI value ≤0.5 value is marked in bold and italics to indicate synergy.

TABLE 17

Summary of cytotoxicity $CC_{50}$ data (HepG2 and HEK293 cell lines) and nephrotoxicity $CC_{50}$ data measuring LDH (A) and GGT (B) release from primary human kidney cells for representative compounds compared to control compounds (polymyxin B, octapeptin-C4 and gentamicin).

| Sample | HK2 (LDH) $CC_{50}$ (μM) | HEK293 $CC_{50}$ (μM) | HepG2 $CC_{50}$ (μM) | LDH release $CC_{50}$ (μg/mL) | GGT release $CC_{50}$ (μg/mL) |
|---|---|---|---|---|---|
| Gentamicin | >300 | >300 | >300 | 14 | 70 |
| Polymyxin B | 125 | >300 | >300 | 37 | 105 |
| Octapeptin C4 | 148 | 41 | 118 | 62 | >128 |
| 988 | 48 | 104 | 84 | 118 | >128 |
| 990 | 95 | >300 | 292 | 87 | >128 |
| 991 | 39 | 114 | 97 | 107 | >128 |
| 992 | 21 | 135 | 92 | 114 | >128 |
| 5383 | 13 | 40 | 38 | >128 | >128 |
| 6442 | 40 | >300 | 162 | >128 | >128 |
| 6509 | nd | 71 | 76 | >128 | >128 |
| 6654 | 31 | 228 | 163 | >128 | >128 |
| 8638 | 57 | 158 | 162 | >128 | >128 |
| 8639 | nd | 108 | 117 | >128 | >128 |
| 8641 | nd | >300 | >300 | >128 | >128 |
| 8643 | 137 | 91 | 104 | >128 | >128 |
| 8733 | 47 | 69 | 129 | >128 | >128 |

It should be clear from the above tables 1-12 that some of the compounds of formula (I), (Ia), (Ib), (Ic), (Id), (Ie), (If) and (II) show advantageous properties in relation to MIC against the abovementioned bacteria strains. Additionally, it should also be clear that the above compounds are accessible through the current synthetic route leading to many possible antibiotics.

It should be clear from the tables 13-16 that some compounds of formula (I), (Ia), (Ib), (Ic), (Id), (Ie), (If) and (II) show advantageous properties when used in combination with other antibiotics, showing synergy according to fractional inhibitory concentration index (FICI) determinations against several of the abovementioned bacteria strains.

FIG. 1 shows the in vitro nephrotoxicity studies measuring LDH (A) and GGT (B) and NGAL (C) and KIM-1 (D) release from primary human kidney cells using some compounds of the present invention as well as polymyxin B, octapeptin-C4 and gentamicin.

Figure 2:
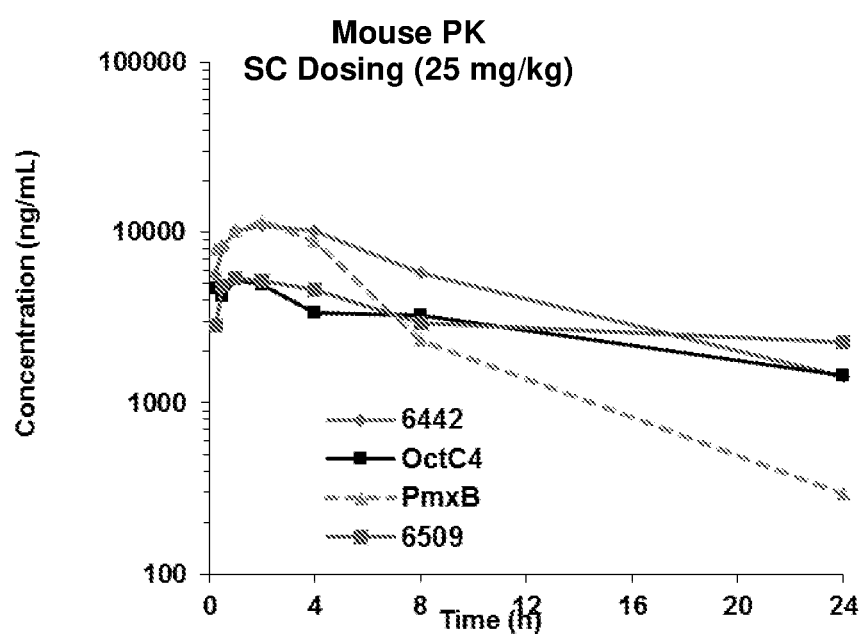
FIG. 2 shows the pharmacokinetic profile of exemplary compounds of the present invention dosed subcutaneously in mice, compared to polymyxin B and octapeptin C4.
Figure 3:
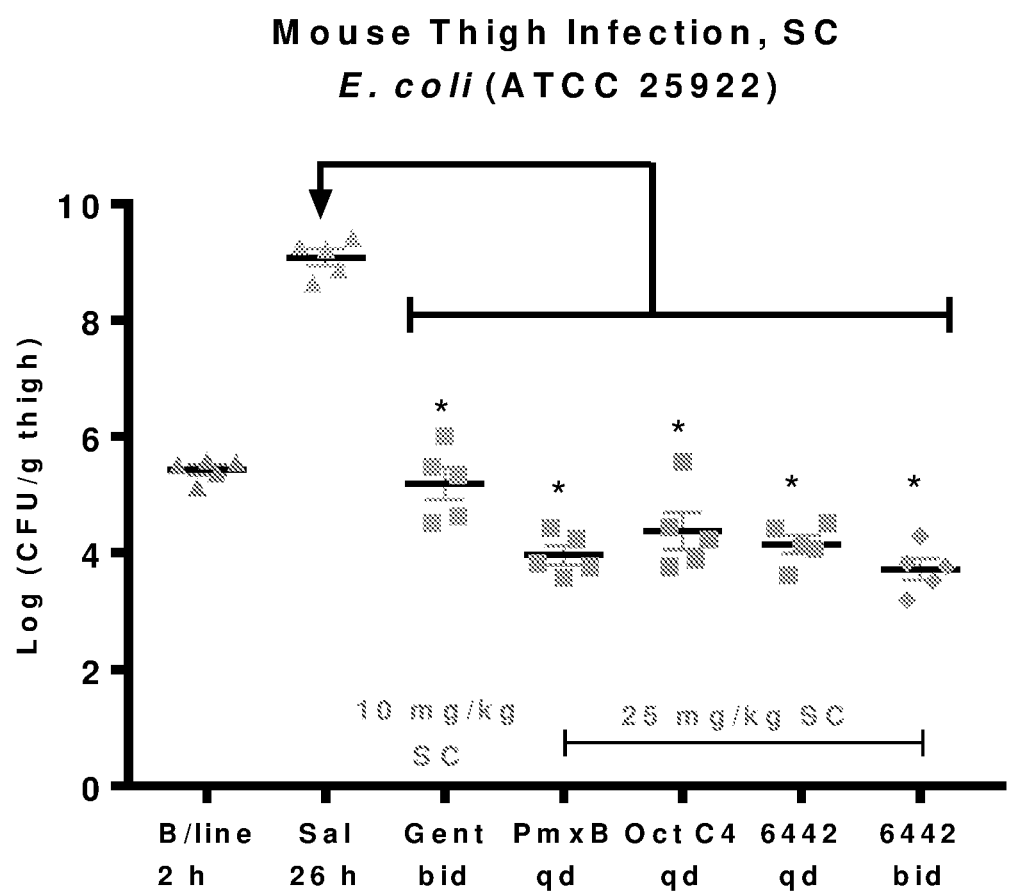
FIG. 3 shows in vivo efficacy studies with treatment of an *Escherichia coli* mouse thigh infection by subcutaneous administration of exemplary compounds of the present invention as well as polymyxin B, octapeptin-C4 and gentamicin, compared to an untreated control, measuring the cfu (colony forming units) of bacteria remaining in the thigh after 24 h.

FIG. 2 shows the pharmacokinetic profile of exemplary compounds of the present invention dosed subcutaneously in mice, compared to polymyxin B and octapeptin C4; and FIG. 3 shows in vivo efficacy studies with treatment of an *Escherichia coli* mouse thigh infection by subcutaneous administration of exemplary compounds of the present invention as well as polymyxin B, octapeptin-C4 and gentamicin, compared to an untreated control, measuring the cfu (colony forming units) of bacteria remaining in the thigh after 24 h.

Figure 4:
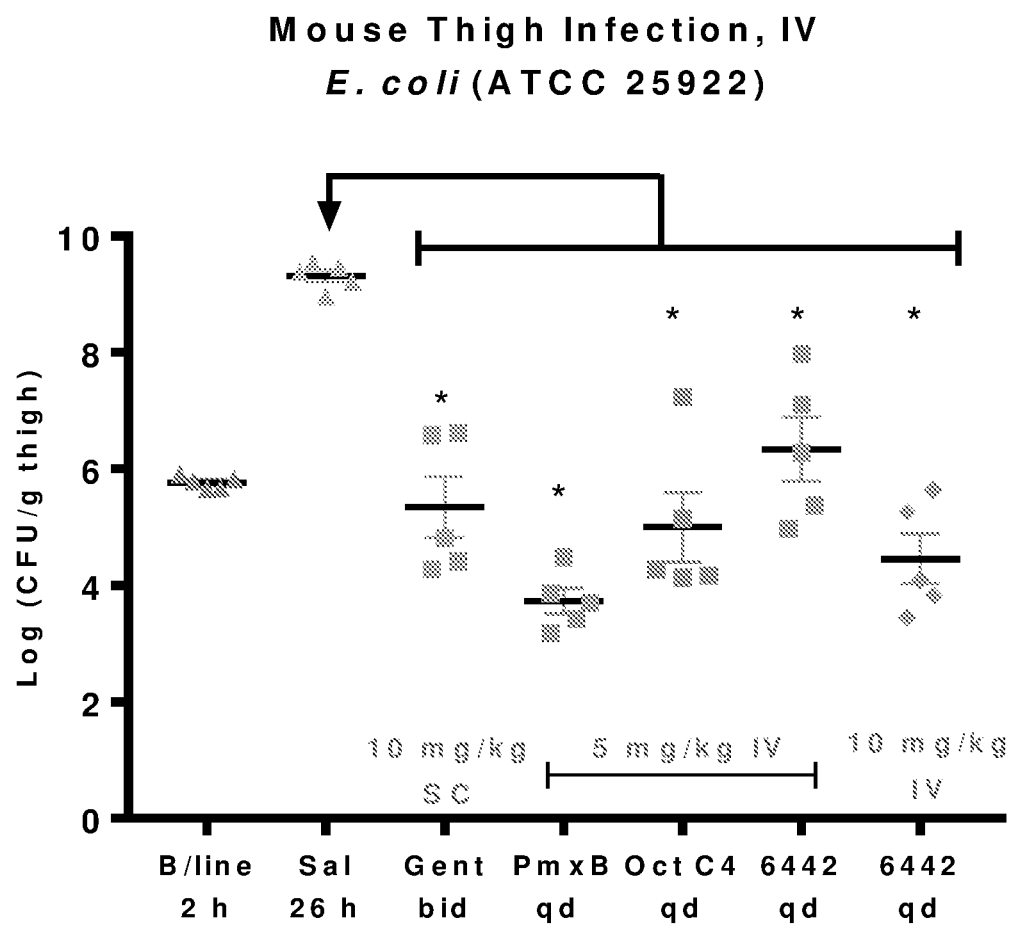
FIG. 4 shows in vivo efficacy studies with treatment of an *Escherichia coli* mouse thigh infection by intravenous administration of exemplary compounds of the present invention as well as polymyxin B, octapeptin-C4 and gentamicin, compared to an untreated control, measuring the cfu (colony forming units) of bacteria remaining in the thigh after 24 h

FIG. 4 shows in vivo efficacy studies with treatment of an *Escherichia coli* mouse thigh infection by intravenous administration of exemplary compounds of the present invention as well as polymyxin B, octapeptin-C4 and gentamicin, compared to an untreated control, measuring the cfu (colony forming units) of bacteria remaining in the thigh after 24 h.

EXPERIMENTAL

Material and Method

All chemicals were obtained from commercial suppliers and used without further purification. H-L-Leu-2-chlorotrityl resin and Fmoc α-amino acids were purchased from Chem-Impex International Inc. (Wood Dale, Ill., USA) or Iris Biotech (Marktredwitz, Germany) or Novabiochem (Merck). Peptide grade trifluoroacetic acid (TFA), piperidine, methanol and N,N-dimethylformamide (DMF) were purchased from AusPep (Melbourne, Australia). Gentamicin sulfate (USP grade), polymyxin B sulfate (USP grade) and vancomycin hydrochloride hydrate were purchased from Sigma-Aldrich (Sydney, Australia). 3-(R)-Hydroxydecanoic acid methyl ester was purchased from Toronto Research Chemicals, Inc. (Toronto, Canada). All other solvents were HPLC grade.

LC-MS analysis was conducted using Agilent Technologies 1200 Series Instrument with a G1316A variable wavelength detector set at λ=210 nm, 1200 Series ELSD, 6110 quadrupole ESI-MS, using an Agilent Eclipse XDB-Phenyl (3×100 mm, 3.5 μm particle size, flow rate 1 mL/min, the mobile phases 0.05% formic acid in water and 0.05% formic acid in acetonitrile). Compound purification was done using a Agilent 1260 Infinity Preparative HPLC with a G1365D multiple wavelength detector set at λ=210 nm. Eluent 1: 0.05% formic acid in water (A) and 0.05% formic acid in acetonitrile (B). Eluent 2: 0.05% trifluoroacetic acid in water (A) and 0.05% trifluoroacetic acid in acetonitrile (B). Eluent 3: water (A) and acetonitrile (B). HPLC columns—Column 1: Agilent Eclipse XDB phenyl; 4.6×150 mm, 5μ. Column 2: Agilent Eclipse XDB phenyl; 30×100 mm, 5μ. Column 3: Grace Reverleris C18 RP 12 g cartridge. HPLC methods—Method 1: eluant 1, column 1, flow 1 mL/min. Ratios refer to solvents A & B, respectively: 95:5, 0.5 min; 95:5 to 0:100, 8.5 min; 0:100, 2 min. Method 2: eluant 1, column 1, flow 1 mL/min. Ratios refer to solvents A & B, respectively: 95:5, 0.5 min; 95:5 to 0:100, 3 min; 0:100, 0.7 min. Method 3: eluant 2, column 2, flow 20 mL/min. Ratios refer to solvents A & B, respectively: 95:5 to 59:41, 16 min. Method 4: eluant 2, column 2, flow 20 mL/min. Ratios refer to solvents A & B, respectively: 95:5, 5 min; 95:5 to 75:25, 1 min; 75:25 to 70:30, 5 min; 70:30, 10 min. Method 5: eluant 3, column 3, flow 30 mL/min. Ratios refer to solvents A & B, respectively: 100:0, 1.9 min; 100:0 to 0:100, 9.5 min; 0:100, 3.4 min.

Final purity of more than 95% was confirmed using a combination of one or more of the following techniques: MS/MS, obtained using an API QSTAR™ Pulsar Hybrid LC-MS/MS System, high resolution mass spectrometry (HRMS), performed on a Bruker Micro TOF mass spectrometer using (+)-ESI calibrated to sodium formate as well as $^1$H (600 MHz), and 2D NMR spectra, obtained using a Bruker Avance-600 spectrometer equipped with a TXI cryoprobe in $D_2O$, referenced externally with NaOAc ($δ_H$ 1.90 and 8.44; 10 mg in 500 μL $D_2O$) and then internally with the HDO resonance at δ 4.77.

Generic Synthetic Method

The compounds of formula (I), (Ia), (Ib), (Ic), (Id), (Ie) and (II) were assembled using solid phase peptide synthesis using Fmoc chemistry and HBTU as a coupling reagent. A typical resin, such as 2-chlorotrityl (2-CT), was chosen as the solid support as it allows the selective cleavage from resin under mild acidic conditions which leave the Boc protecting group and t-butyl ethers on the side chains intact.

The 3-hydroxy fatty acids were synthesized using magnesium monoethylmalonate to form the corresponding b-keto esters from the starting acids, reduction of the ketones to the alcohols and hydrolysis of the ethyl esters.

General Procedure for Solid Phase Peptide Synthesis (Exemplified by Synthesis of Octapeptin C4)

General Method for Peptide Coupling:

The starting resin H-L-Leu-2CT (1006 mg, 0.674 mmol, 0.67 mmol/g) was pre-swollen in THF and then briefly washed with DCM (×3) and DMF (×3). The appropriate Fmoc-amino acid (2 equiv.) was dissolved in a solution of HCTU (0.279 M, 1.8 equiv.), treated with 2,4,6-collidine (4 equiv.), and allowed to stand for 5 min. The pre-activated amino acid solution was added to the resin. After shaking for 2 hr, the solvent was drained and the resin was washed with DMF (×3). Coupling efficiency was monitored by treatment of a small quantity of resin (1-3 mg) with 95:2.5:2.5 TFA/triisopropyl silane/H$_2$O (10 μL) for 15 min, followed by suspension in 1:1 acetonitrile/H$_2$O (1 mL), filtration and LC/MS analysis. In this manner, all couplings were deemed quantitative at each step. If the next amino acid was not scheduled for immediate coupling, the resin was washed with DCM (×3), IPA (×3) and dried under vacuum overnight before storage; otherwise Fmoc deprotection was effected by two successive treatments of the resin with a solution of 30% piperidine in DMF (ca. 10 mL per gram of resin) at ambient temperature (1×10 min, 1×20 min). The solvent was drained and the resin was washed with DMF (×3) between each treatment, and after completion of the sequence. Peptide synthesis was completed by acylation of the N-terminus of AA-1 with 3-(R)-hydroxydecanoic acid (1.5 equiv.) using the same protocol outlined above. The resin was washed with DMF (×3), DCM (×3), IPA (×3), DCM (×3), IPA (×3), and then dried under vacuum overnight. The final weight of the resin 1a was 2214 mg (SV 0.33 mmol/g).

Orthogonal N-Deprotection:

Resin 1a obtained above (2214 mg) was pre-swollen in THF for 30 min. The solvent was drained, and the resin was agitated with a solution of 4% hydrazine hydrate in DMF (6.5 mL, ca. 8 equiv.) for 1 h at ambient temperature. The solvent was drained, and the resin was successively washed with DMF (×3), THF (×3), IPA (×3), DCM (×3) and IPA (×3). The resulting deprotected resin was dried under vacuum overnight. The final weight of the resin 1b was 2030 mg (SV 0.354 mmol/g).

Resin Cleavage:

The resin obtained above (2030 mg, 0.354 mmol/g, 0.718 mmol) was treated with a solution of hexafluoroisopropanol (HFIP) in DCM (1:4, 45 mL) for 1 h. The solvent was drained and the resin was shaken with an additional volume of cleavage solution (25 mL) for a further 30 min. The solvent was drained, and the resin was washed with DCM (×3). The filtrates were pooled, evaporated and then dried under vacuum overnight to afford crude 1c (1.357 g, 129% of theoretical) as a cream solid. $t_R$ 6.7 (method 1). (ES) m/z 1462.9 (MH$^+$). The material was used without further purification.

Off-Resin Cyclization and Deprotection:

Crude 1c (1.357 g, assume 0.718 mmol) was dissolved in DMF (90 mL, 0.008 M) and the slightly turbid solution was filtered through a short bed of Celite. The resulting clear solution was treated with NaHCO$_3$ (1260 mg, ca. 20 equiv.) followed by DPPA (395 mg, 1.436 mmol, 2 equiv.). The mixture was stirred at ambient temperature overnight. Conversion was quantitative as monitored by LC/MS analysis ($t_R$ 6.7 linear, $t_R$ 7.5 cyclised, method 1). The mixture was filtered through a bed of Celite, and the solvent was evaporated. Traces of DMF were removed by co-evaporation from heptane (×3), and the resulting product was dried overnight under vacuum to afford crude cyclised product id (1697 mg). To remove the by-product arising from reaction between diphenylphosphoryl azide (DPPA) and residual HFIP from the resin cleavage step, the crude solid was suspended in excess petroleum spirit (40-60) and stirred overnight to produce a uniform off-white solid that was collected by filtration. The cake was washed with pentane and the solid was dried under vacuum overnight to afford the crude cyclised product id an off-white powder (1367 mg). At this stage, id was substantially free from any impurities other than diphenylphosphate, which was subsequently removed by rp-HPLC purification (method 5). The final yield of the fully protected octapeptin-C$_4$ precursor id was 600 mg (58% yield, >97% purity). $t_R$ 7.5 (method 1). (ES) m/z 1445.4 (MH$^+$), 1345.5 2 (MH$^+$-Boc).

Purification of Octapeptin Analogues.

Purified 1d (600 mg, 0.415 mmol) was dissolved in 94:5:1 TFA/H$_2$O/$^i$Pr$_3$iH (10 mL) and allowed to stand at ambient temperature for 1 h. Volatiles were removed under reduced pressure and the resulting residue was co-evaporated from heptane (×2). The crude octapeptin C4 thus obtained was lyophilised from water, and then re-lyophilised from 10 mM NH$_4$HCO$_3$ solution to give a white powder (605 mg). $t_R$ 3.4 (method 1). (ES) m/z 1067.0 (M+Na$^+$), 1045.1 (MH$^+$), 523.1 (MH$_2^{2+}$). Purification was achieved by rp-HPLC (method 4). The final yield of octapeptin C4 631 as its TFA salt was 386 mg (62%, >97% purity). HRMS exact mass (ESI microTOF-LC): calcd for C$_{51}$H$_{90}$N$_{13}$O$_{10}^+$ 1044.6928 (MH$_2^{2+}$). found 1044.6917. The overall yield of octapeptin C4 from H-L-Leu-2CT resin was 38%.

Solid Phase Synthesis and Off-Resin Cyclisation for Octapeptin C4

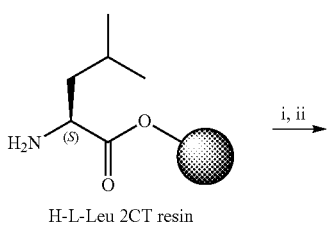

H-L-Leu 2CT resin

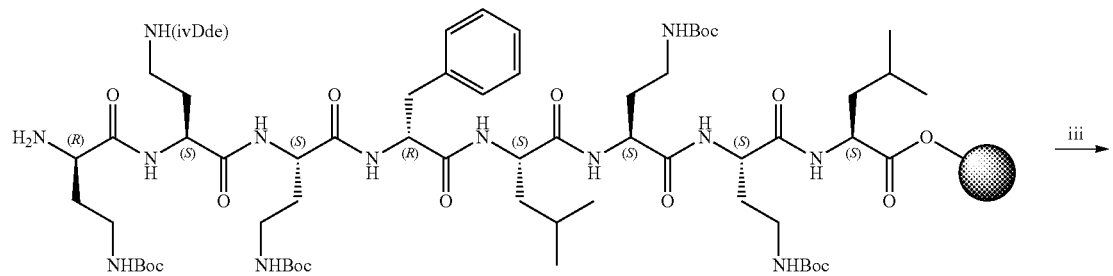

-continued

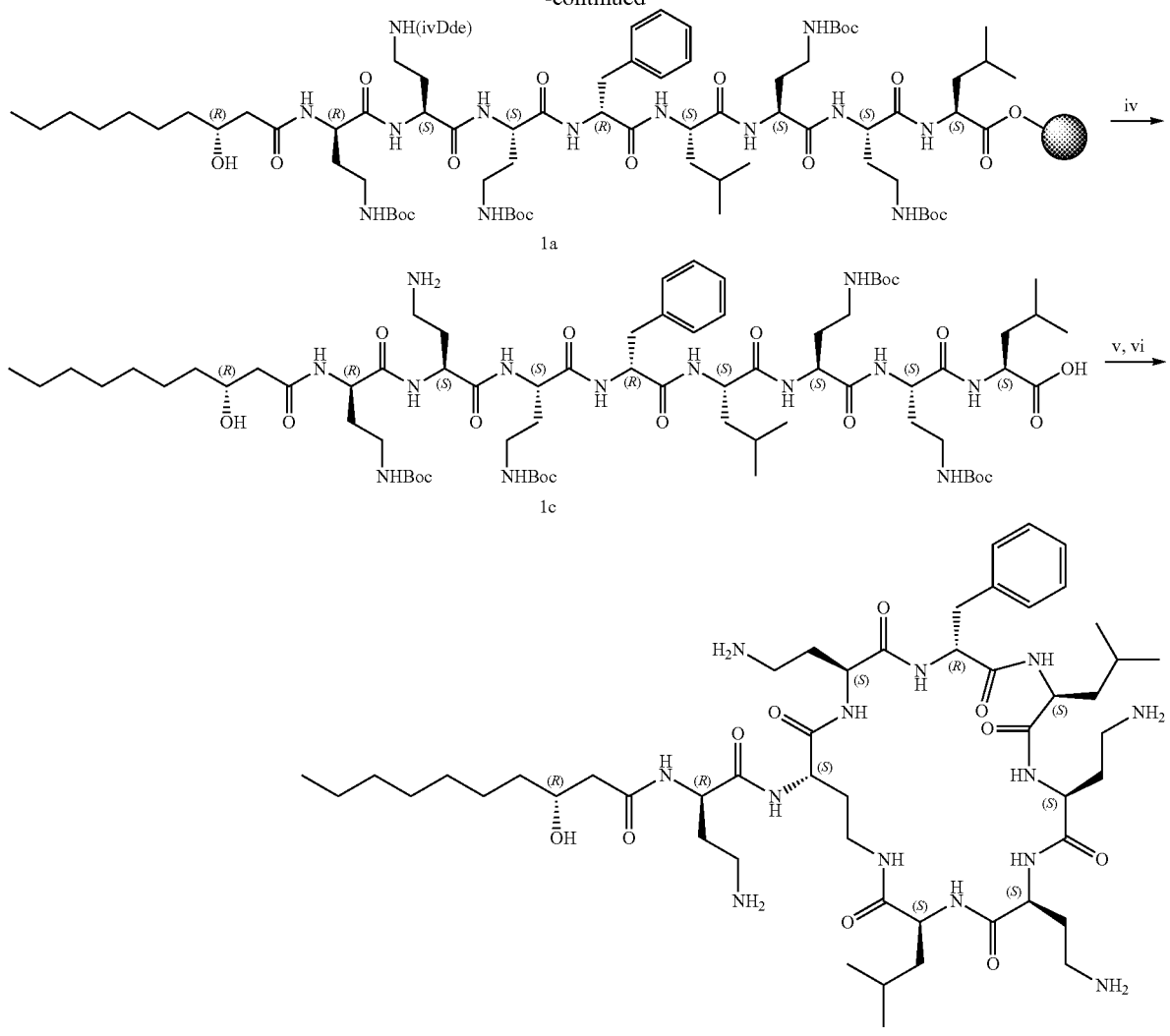

Reagent and Conditions:
i) Solid-phase peptide synthesis (SPPS) using 2 equivalents of corresponding amino acid (See Table 1), 1.8 equivalents of 0.28 M HCTU in DMF and 4 equivalents of 2,4,6-collidine;
ii) 30% piperidine, DMF;
iii) 1.5 equivalents of (R)-3-hydroxydecanoic acid (3(R)OH—$nC_9CO$), 1.8 equivalents of 0.28 M HCTU in DMF and 4 equivalents of 2,4,6-collidine;
iv) (a) 4% hydrazine hydrate in DMF; (b) HFIP in DCM;
v) DPPA, NaHCO$_3$, DMF;
vi) TFA/iPr$_3$SiH/H$_2$O (95:1:4).

General Procedure for Solid Phase Peptide Synthesis of Aza-Peptides (Exemplified by Synthesis of Aza-Leu$^4$-Octapeptin C4)

General method for coupling aza-amino acid to resin: The starting resin Fmoc-L-Dab-L-Dab-L-Leu-2CT (prepared previously in a separate step, 418 mg, 0.198 mmol, 0.473 mmol/g) was pre-swollen in THF and then briefly washed with DCM (×3) and DMF (×3). The resin was treated with a solution of 30% piperidine in DMF (ca. 10 mL per gram of resin) at ambient temperature (1×10 min, 1×20 min). The resin was washed with anhydrous DCM (×3) and then treated with Fmoc-aza-Leu-COCl, prepared as follows: Fmoc-aza-Leu (196 mg, 0.631 mmol) in anhydrous DCM (5 mL) was cooled to 0° C. and treated with a 20% solution of phosgene in toluene (665 μL, 1.26 mmol, 2 equiv.). After 15 min, TLC indicated the reaction had gone to completion. The solution was concentrated and dried under vacuum to yield a colourless oil. The oil was redissolved in a solution of DCM (4 mL) and DIPEA (220 μL), and the resultant solution was added to the peptide resin. After shaking for 2 hr, the resin was drained and successively washed with DCM, DMF, MeOH and DCM (×3 each), and dried under high vacuum overnight. The resin 2a yield was 420 mg (SV 0.458 mmol/g).

General Method for Coupling Fmoc-Amino Acid to Aza-Amino Acid:

Resin 2a (420 mg, ~0.19 mmol) was treated with a solution of 30% piperidine in DMF (ca. 10 mL per gram of resin) at ambient temperature (1×10 min, 1×20 min). The resin was washed with DMF followed by anhydrous THF (×3 each). The resin was suspended in a minimal volume of THF and treated with DIPEA (300 μL). After 1 min, the resin was drained, re-suspended in THF (minimal volume), and treated successively with DIPEA (300 μL) followed by Fmoc-Phe-COCl, prepared as follows: Fmoc-Phe-OH (234 mg, 0.604 mmol, ~3 equiv. wrt resin) and BTC (56 mg, 0.188 mmol) in anhydrous THF (2 mL) was cooled to 0° C. and treated with 2,4,6-collidine (260 µL, 1.98 mmol, 10 equiv. wrt resin). After 1 min, the solution was warmed to RT, stirred for 5 min and then added to the resin. After shaking for 3 hr, the resin was drained and successively washed with DMF and DCM (×3 each), and dried under high vacuum overnight. The coupling was incomplete by lc/ms analysis. A second coupling was performed for an additional 4 hr. After washing and drying, the resin 2b yield was 420 mg (SV 0.429 mmol/g). The remainder of the peptide was synthesised using the standard peptide coupling procedure outlined for octapeptin C4. The final weight of the resin 2c was 408 mg (SV 0.33 mmol/g).

Orthogonal N-Deprotection:

Resin 2c obtained above (408 mg) was pre-swollen in THF for 30 min. The solvent was drained, and the resin was agitated with a solution of 4% hydrazine hydrate in DMF (1.3 mL, ca. 8 equiv.) for 1 h at ambient temperature. The solvent was drained, and the process repeated with an additional volume of 4% hydrazine hydrate in DMF (2 mL). The resin was successively washed with DMF (×3), THF (×3), IPA (×3), DCM (×3) and IPA (×3). The resulting deprotected resin was dried under vacuum overnight. The final weight of the resin 2d was ~400 mg (SV 0.36 mmol/g).

Resin Cleavage:

The resin obtained above (400 mg, 0.36 mmol/g, 0.14 mmol) was treated with a solution of hexafluoroisopropanol (HFIP) in DCM (1:4, 15 mL) for 2 h. The solvent was drained, and the resin was washed with DCM (×3). The filtrates were pooled, evaporated and then dried under vacuum overnight to afford crude 2d (123 mg) as a cream solid. $t_R$ 6.8 (method 1). (ES) m/z 1463.8 (MH$^+$). The material was used without further purification.

Off-Resin Cyclization and Deprotection:

Crude 2d (123 mg, assume 0.08 mmol) was dissolved in DMF (10 mL, 0.008 M) and treated with NaHCO$_3$ (140 mg, ca. 20 equiv.) followed by DPPA (36 µL, 0.16 mmol, 2 equiv.). The mixture was stirred at ambient temperature overnight. The reaction was monitored by LC/MS analysis ($t_R$ 6.8 linear, $t_R$ 7.5 cyclised, method 1). The mixture was filtered through a bed of Celite, and the solvent was evaporated. Traces of DMF were removed by co-evaporation from heptane (×3), and the resulting product was dried overnight under vacuum. To remove the by-product arising from reaction between diphenylphosphoryl azide (DPPA) and residual HFIP from the resin cleavage step, the crude solid was suspended in excess pentane and stirred overnight to produce a uniform off-white solid that was collected by filtration. The cake was washed with pentane and the solid was dried under vacuum overnight to afford the crude cyclised product 2e an off-white powder (145 mg). At this stage, 2e was substantially free from any impurities other than diphenylphosphate, which was subsequently removed by rp-HPLC purification (method 5). The final yield of the fully protected aza-Leu$^4$-octapeptin-C$_4$ precursor 2e was 26 mg (22% yield, 95% purity). $t_R$ 7.5 (method 1). (ES) m/z 1446.2 (MH$^+$), 1346.2 (MH$^+$-Boc).

Purification of Octapeptin Analogues.

Purified 2e (26 mg, 0.018 mmol) was dissolved in 94:5:1 TFA/H$_2$O/$^i$Pr$_3$iH (4 mL) and allowed to stand at ambient temperature for 1 h. Volatiles were removed under reduced pressure and the resulting residue was co-evaporated from heptane (×2). The crude 8803 thus obtained was lyophilised from water to give a white powder (23.7 mg). $t_R$ 3.5 (method 1). (ES) m/z 1068.0 (M+Na$^+$), 1046.1 (MH$^+$), 523.5 (MH$_2^{2+}$). Purification was achieved by rp-HPLC (method 4). The final yield of 8803 as its TFA salt was 15.8 mg (58%, >97% purity). HRMS exact mass (ESI microTOF-LC): calcd for C$_{50}$H$_{90}$N$_{14}$O$_{10}^{2+}$ 524.3549 (MH$_2^{2+}$). found 524.3489. The overall yield of 8803 from Fmoc-L-Dab-L-Dab-L-Leu-2CT resin was 5.3%.

General Procedure for Solid Phase Synthesis and Off-Resin Cyclisation for an Aza Compound of Formula (I)

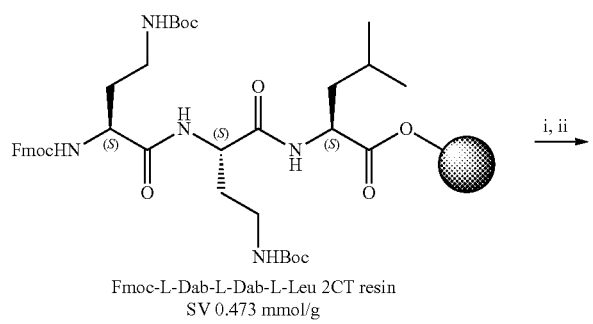

Fmoc-L-Dab-L-Dab-L-Leu 2CT resin
SV 0.473 mmol/g

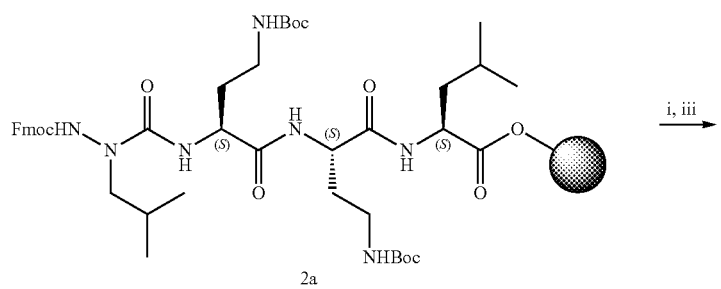

2a

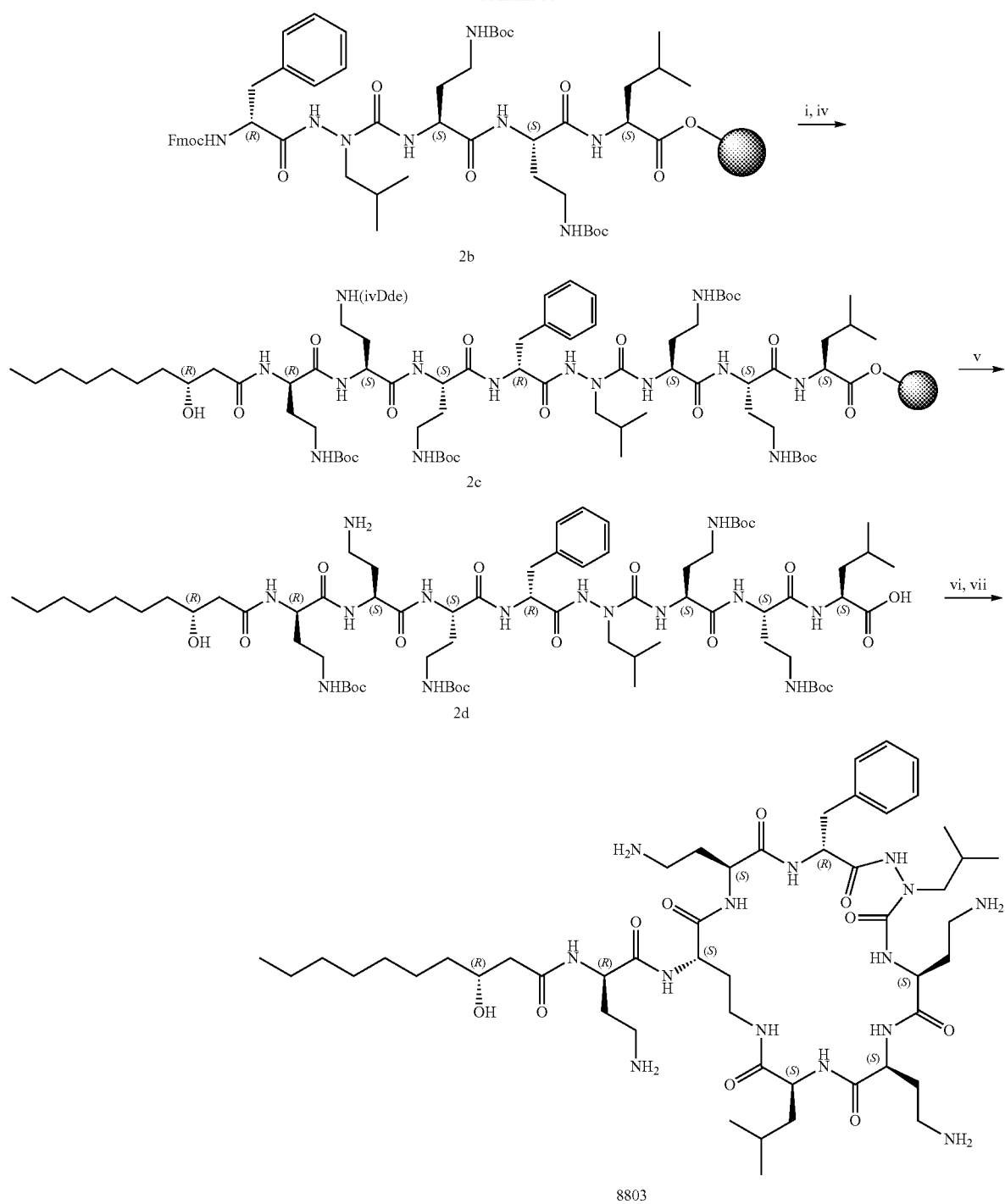
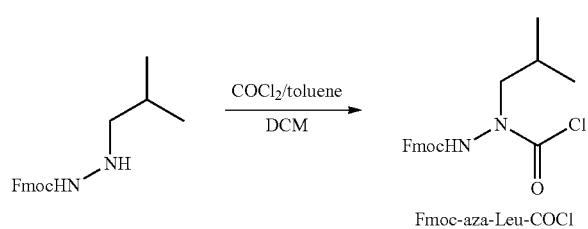

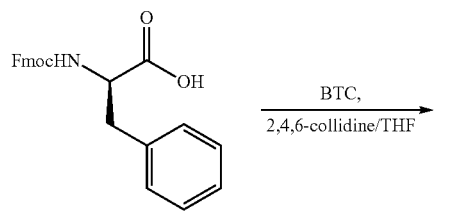 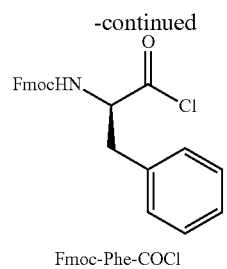

Reagent and Conditions:
i) 30% piperidine, DMF;
ii) Fmoc-aza-Leu-COCl, DIPEA, DCM;
iii) Fmoc-Phe-COCl, THF;
iv) (a) solid-phase peptide synthesis (SPPS) using 2 equivalents of corresponding amino acid, 1.8 equivalents of 0.28 M HCTU in DMF and 4 equivalents of 2,4,6-collidine; (b) 1.5 equivalents of (R)-3-hydroxydecanoic acid (3(R)OH—$nC_9CO$), 1.8 equivalents of 0.28 M HCTU in DMF and 4 equivalents of 2,4,6-collidine;
v) (a) 4% hydrazine hydrate in DMF; (b) HFIP in DCM;
vi) DPPA, NaHCO$_3$, DMF;
vii) TFA/iPr$_3$SiH/H$_2$O (95:1:4).

Solid Phase Synthesis and Off-Resin Cyclisation for Another Compound of Formula (I)

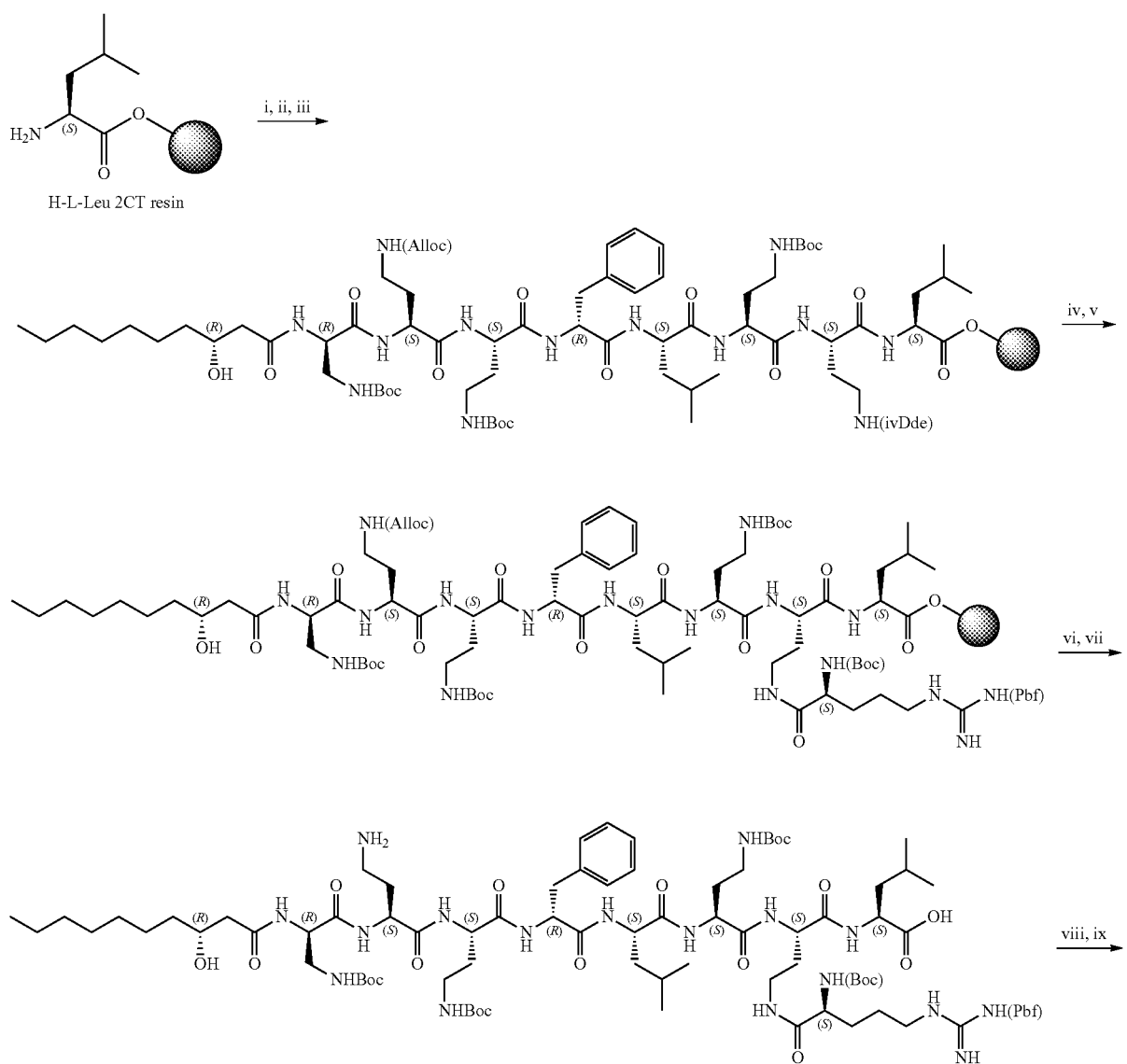

-continued

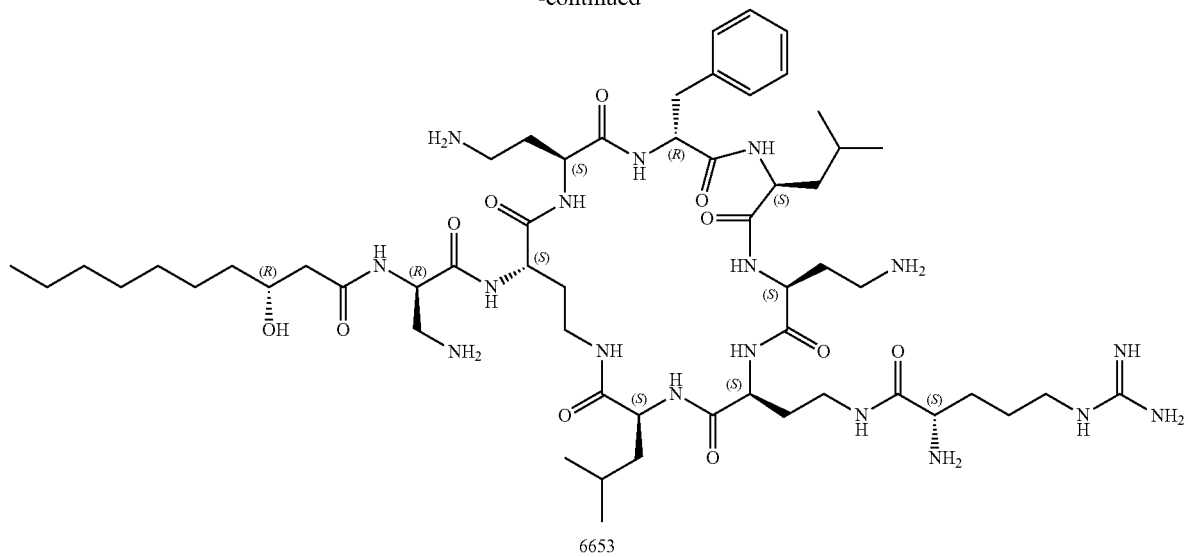

6653

Reagent and Conditions:
i) Solid-phase peptide synthesis (SPPS) using 2 equivalents of corresponding amino acid, 2 equivalents of 0.5 M HCTU in DMF and 4 equivalents of DIPEA;
ii) 30% piperidine, DMF;
iii) 1.2 equivalents of (R)-3-hydroxydecanoic acid (3(R)OH—$n$C$_9$CO), 2 equivalents of 0.5 M HCTU in DMF and 4 equivalents of DIPEA;
iv) 2% hydrazine hydrate in DMF;
v) Boc-Arg(Pbf)-OH, 2 equivalents of 0.5 M HCTU in DMF and 4 equivalents of DIPEA;
vi) Pd(PPh$_3$), PhSiH$_3$, DCM;
vii) 2% TFA in DCM;
viii) DPPA, DIPEA, DMF;
vii) TFA/H$_2$O/Et$_3$SiH (94:5:1).

Synthesis of β-hydroxy carboxylic acids (S)-(+)-6-Methyl-1-octanoic Acid, 2b

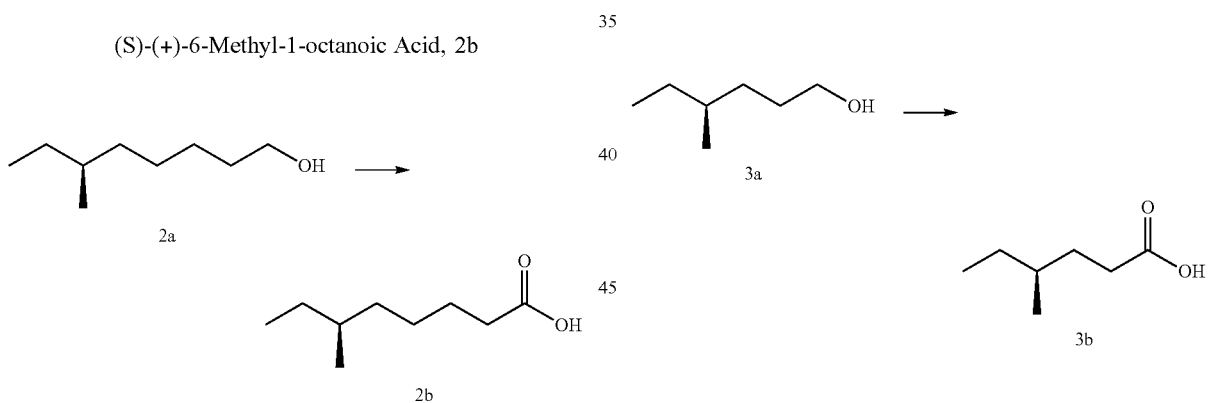

To a solution of (S)-(+)-6-methyl-1-octanol, 2a (3.14 g, 21.80 mmol) in DMF (57 mL) was added PDC (28.75 g, 76.43 mmol). This solution was stirred at room temperature under N$_2$ overnight. Water (60 mL) was added and the mixture was extracted with diethyl ether (2×100 mL). The organic phase was dried over MgSO$_4$. And the solvents removed in vacuo. The crude product was purified using column chromatography on silica with EtOAc: petroleum ether (1:1) as eluent to give a colourless oil; yield: 2.05 g, 59%; $^1$H NMR (400 MHz, CDCl$^3$) δ: 2.34-2.38 (2H, t, J 15.2 Hz), 1.54-1.68 (m, 2H), 1.24-1.39 (5H, m), 1.10-1.17 (2H, m), 0.84-0.86 (6H, m); $^{13}$C NMR (100 MHz, CDCl$_3$) δ: 179.9, 36.1, 34.0, 29.4, 26.5, 25.0, 19.1, 11.3. IR λmax, cm-1: 2927 (s,), 2673 (br), 1713 (s).

(S)-(+)-4-Methyl-1-hexanoic Acid, 3b

As described for 2b but using (S)-(+)-4-methyl-1-hexanol, 3a (3.15 g, 27.12 mmol) to give 3b as a colourless oil (1.56 g, 46% yield); $^1$H NMR (400 MHz, CDCl$_3$) δ: 2.29-2.43 (2H, m) 1.63-1.73 (1H, m) 1.27-1.50 (3H, m), 1.12-1.23 (1H, m), 0.88-0.92 (6H, m); $^{13}$C NMR (100 MHz, CDCl$_3$) δ: 180.2, 33.9, 31.8, 31.2, 29.1, 18.7, 11.2. IR λmax, cm-1: 2960 (s), 2673 (br), 1712 (s).

7-Methyl-1-octanoic Acid, 4b

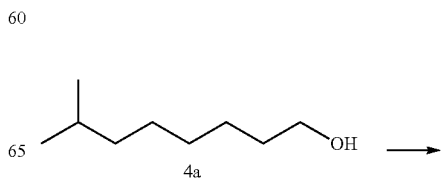

-continued

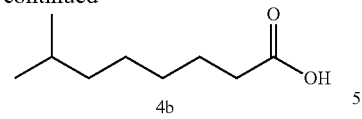
4b

As described for 2b but using 7-methyl-1-octanol, 4a (0.75 g, 5.21 mmol) to give 4b as a colourless oil (0.311 g, 38% yield); 1H NMR (400 MHz, CDCl$_3$) δ: 2.33-2.38 (2H, t, J 12 Hz), 1.42-1.68 (3H, m), 1.28-1.36 (4H, m), 1.16-1.24 (2H, m), 0.86-0.87 (6H, d, J 6.4 Hz). $^{13}$C NMR (100 MHz, CDCl$_3$) δ: 180.0, 38.7, 34.0, 29.3, 27.9, 27.0, 24.7, 22.6. IR λmax, cm-1=3348 (br), 1644 (s).

(S)-Ethyl-8-methyl-3-oxodecanoate, 5

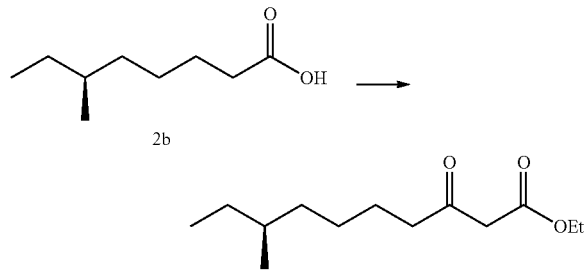

To a solution of (S)-(+)-6-methyl-1-octanoic acid, 2b (0.629 g, 15.66 mmol) in dry THF (19.9 mL), CDI (2.404 g, 14.82 mmol) was added and the solution stirred at ambient temperature under nitrogen overnight. Mg(OOCCH$_2$COOEt)$_2$ was prepared by adding magnesium ethoxide (1.96 g, 14.82 mmol) into a solution of mono ethyl malonate (0.933 g) in dry THF (11 mL) and stirring under nitrogen for 1 hour. The THF was evaporated in vacuo to give a colourless hygroscopic salt, to which the solution containing the activated (S)-(+)-6-methyl-1-octanoic acid was added and stirring under nitrogen was continued. 1M HCl was added after 1 h until the solution reach approximately pH 2-3. The mixture was extracted with DCM and the extract washed with sat. NaHCO$_3$, dried over MgSO$_4$, filtered and the solvents removed in vacuo. The crude product was purified by column chromatography on silica with EtOAc: petroleum ether (9:1) to give a yellowish oil. Yield: 2.34 g, 76%; $^1$H NMR (400 MHz, CDCl$_3$) δ: 4.17-4.23 (2H, q, J=7.2 Hz), 3.43 (2H, s), 2.52-2.59 (2H, t, J=7.2 Hz), 1.51-1.62 (2H, m), 1.21-1.46 (8H, m), 1.06-1.16 (2H, m), 0.83-0.90 (6H, m); $^{13}$C NMR (100 MHz, CDCl$_3$) δ: 203.0 (C$_3$), 167.3, 61.3, 49.3, 43.1, 36.3, 34.2, 29.4, 26.6, 23.8, 19.1, 14.1, 11.4. IR λmax, cm-1: 2873-2900 (s), 1747 (s), 1613 (s), 1150-1313 (m).

Ethyl-8-methyl-3-oxononanoate, 6

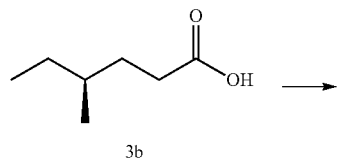
3b

-continued

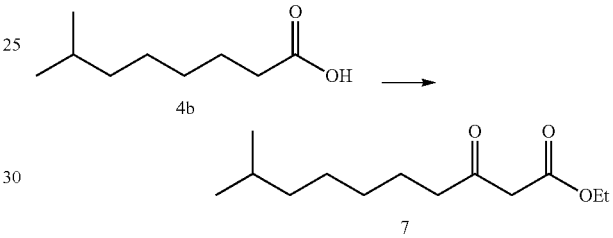
6

As described for 5, but using (S)-(+)-4-methyl-1-hexanoic acid, 3b (1.00 g, 6.934 mmol) to give 6 as a colourless oil (0.454 g, 59% yield); $^1$H NMR (400 MHz, CDCl$_3$) δ: 4.18-4.21 (2H, m, J=5.6 Hz), 3.44 (2H, s), 2.49-2.60 (2H, m), 1.58-1.67 (1H, m), 1.24-1.45 (6H, m), 1.12-1.23 (1H, m), 0.87-0.92 (6H, m); $^{13}$C NMR (100 MHz, CDCl$_3$) δ: 203.0, 167.2, 61.2, 49.2, 40.7, 33.8, 29.8, 29.1, 18.8, 14.0, 11.2. IR λmax, cm-1: 2875-2962 (s), 1739 (s), 1647 (s), 1074-1316 (s).

Ethyl-9-methyl-3-oxodecanoate, 7

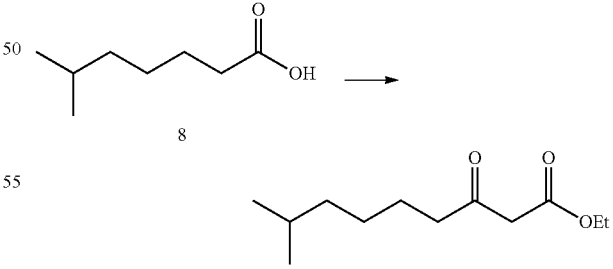

As described for 5 but using 7-methyl-1-octanoic acid, 4b (0.390 g, 2.46 mmol) to give 7 as a colourless oil (0.495 g, 94% yield); $^1$H NMR (400 MHz, CDCl$_3$) δ: 4.17-4.22 (2H, q, J=7.2 Hz), 3.43 (2H, s), 2.51-2.56 (2H, t, J=7.2), 1.46-1.63 (3H, m), 1.22-1.37 (7H, m), 1.11-1.20 (2H, m), 0.85-0.87 (6H, d, J=6.8 Hz); $^{13}$C NMR (100 MHz, CDCl$_3$) δ: 203.0, 167.2, 61.3, 49.3, 43.0, 38.7, 29.2, 27.9, 27.1, 23.5, 22.6, 14.1; IR λmax, cm-1: 2869-2954 (s), 1718-1746 (s), 1649 (s), 1095-1313 (s).

Ethyl-8-methyl-3-oxononanoate, 9

As described for 5 but using 6-methyl-heptanoic acid, 8 (1.00 g, 6.934 mmol) to give 9 as a colourless oil (0.6896 g, 50% yield); $^1$H NMR (400 MHz, CDCl$_3$) δ: 4.18-4.21 (2H, q, J=6.8 Hz), 3.43 (2H, s), 2.54-2.58 (2H, t, J=7.2 Hz), 1.44-1.65 (3H, m), 1.24-1.33 (5H, m), 1.12-1.18 (2H, m), 0.86-0.89 (6H, d, J=6.8 Hz). $^{13}$C NMR (100 MHz, CDCl$_3$)

δ: 202.9, 167.2, 61.2, 49.2, 43.0, 38.6, 27.7, 26.7, 23.6, 22.5, 14.0; IR λmax, cm-1: 2870-2955 (s), 1715-1747 (s), 1631-1646 (s), 1236-1314 (s).

(8S)-ethyl-3-hydroxy-8-methyldecanoate, 10

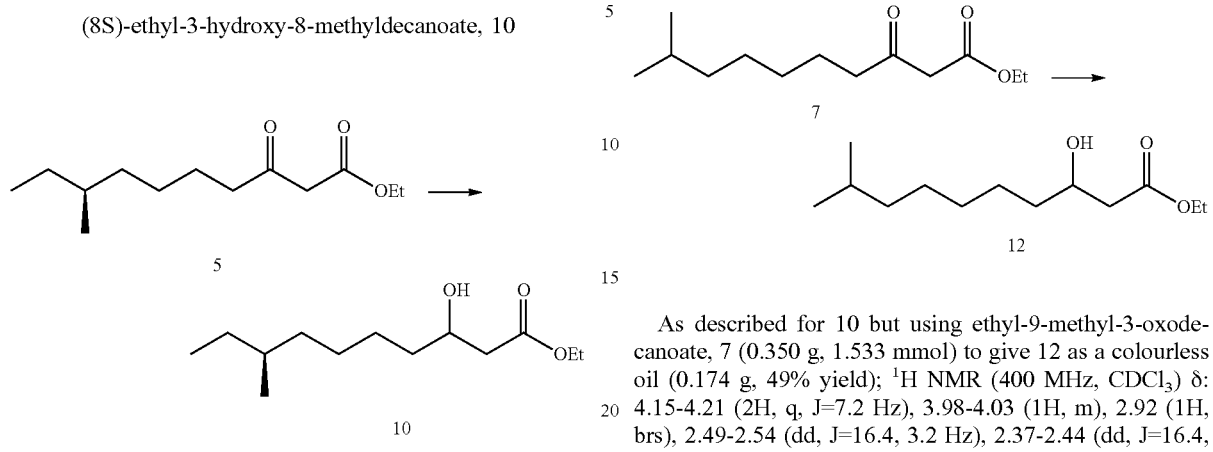

Sodium borohydride (0.083 g, 2.19 mmol) was added to a solution of (S)-ethyl-8-methyl-3-oxodecanoate, 5 (0.50 g, 2.19 mmol) in EtOH (25 mL). After stirring at 0° C. for 2.5 hours the EtOH was evaporated in vacuo, water (25 mL) was added and the mixture was extracted with DCM (2×15 mL). The combined extracts were dried over MgSO$_4$, filtered and the solvent removed in vacuo. The crude was purified by column chromatography on silica with 1:4 (EtOAc: petroleum ether) to give a colourless oil. Yield: 0.297 g, 59%; $^1$H NMR (400 MHz, CDCl$_3$) δ: 4.15-4.21 (2H, q, J=7.2 Hz), 4.00 (1H, m), 2.93 (1H, brs), 2.48-2.54 (dd, J=16.8, 3.2 Hz), 2.37-2.44 (dd, J=16.4, 8.8 Hz), 1.22-1.60 (12H, m), 1.09-1.17 (2H, m), 0.84-0.87 (6H, m); $^{13}$C NMR (100 MHz, CDCl$_3$) δ: 173.1, 68.0, 60.6, 41.2, 36.53, 36.47, 34.3, 29.4, 26.9, 25.8, 19.2, 14.1, 11.4. IR λmax, cm-1: 3460 (br), 2874-2961 (s), 1736 (s), 1186-1301 (s), 1031 (s).

(6S)-Ethyl-3-hydroxy-6-methyloctanoate, 11

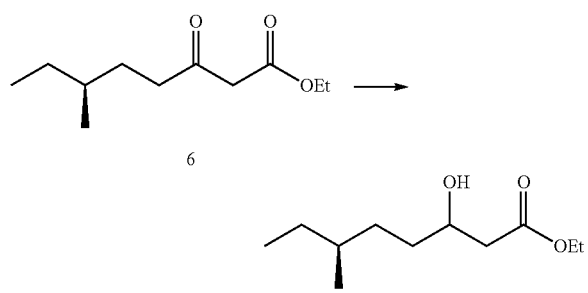

As described for 10 but using ethyl-6-methyl-3-oxooctanoate, 6 (0.385 g, 1.924 mmol) to give 11 as a colourless oil (0.248 g, 64% yield); $^1$H NMR (400 MHz, CDCl$_3$) δ: 4.15-4.20 (2H, q, J=7.2 Hz), 3.93-4.01 (1H, m), 2.92-2.95 (1H, m), 2.49-2.54 (dt, J=16.4, 2 Hz), 2.37-2.46 (dd, J=6.4, 2.8 Hz), 1.23-1.60 (8H, m), 1.08-1.20 (2H, m), 0.85-0.95 (6H, m); $^{13}$C NMR (100 MHz, CDCl$_3$) δ: 173.1, 68.5, 60.6, 41.3, 34.3, 34.0, 32.2, 29.4, 19.1, 14.2, 11.3. λmax, cm-1: 3461 (br), 2874-2961 (s), 1736 (s), 1175-1249 (s), 1031 (s).

3-Hydroxy-9-methyldecanoate, 12

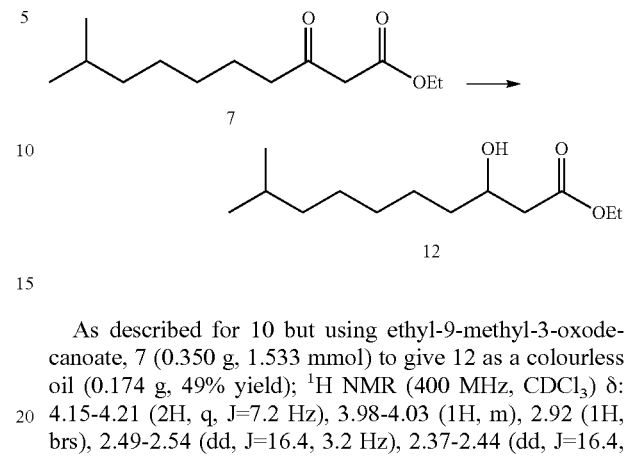

As described for 10 but using ethyl-9-methyl-3-oxodecanoate, 7 (0.350 g, 1.533 mmol) to give 12 as a colourless oil (0.174 g, 49% yield); $^1$H NMR (400 MHz, CDCl$_3$) δ: 4.15-4.21 (2H, q, J=7.2 Hz), 3.98-4.03 (1H, m), 2.92 (1H, brs), 2.49-2.54 (dd, J=16.4, 3.2 Hz), 2.37-2.44 (dd, J=16.4, 8.8 Hz), 1.16-1.57 (14H, m), 0.86-0.87 (6H, d, J=6.4 Hz); $^{13}$C NMR (100 MHz, CDCl$_3$) δ: 173.2, 68.1, 60.7, 41.3, 38.9, 36.5, 29.8, 28.0, 27.3, 25.5, 22.6, 14.2; λmax, cm-1: 3461 (br), 2857-2953 (s), 1736 (s), 1184-1260 (s), 1031 (m).

Ethyl-3-hydroxy-8-methylnonanoate, 13

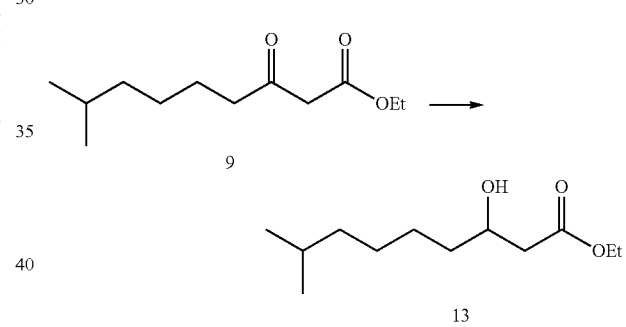

As described for 10 but using ethyl-8-methyl-3-oxononanoate, 9 (0.602 g, 2.807 mmol) to give 13 as a colourless oil (0.467 g, 77% yield); $^1$H NMR (400 MHz, CDCl$_3$) δ: 4.15-4.21 (2H, q, J=7.2 Hz), 3.99-4.02 (1H, m), 2.92 (1H, d), 2.48-2.53 (dd, J=16.4, 3.2 Hz), 2.37-2.43 (dd, J=16.8, 9.2 Hz), 1.161-1.59 (12H, m), 0.86-0.88 (6H, d, J=6.8 Hz); $^{13}$C NMR (100 MHz, CDCl$_3$) δ: 173.2, 68.0, 60.7, 41.3, 38.9, 36.6, 27.9, 27.3, 25.7, 22.6, 14.2; λmax, cm-1: 3460 (br), 2869-2954 (s), 1737 (s), 1169-1301 (s), 1030 (m).

(8S)-Ethyl-3-hydroxy-8-methyldecanoate, 14

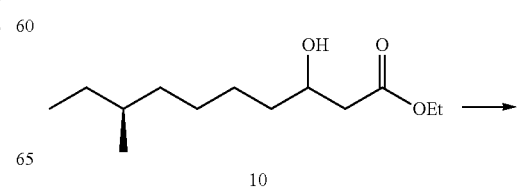

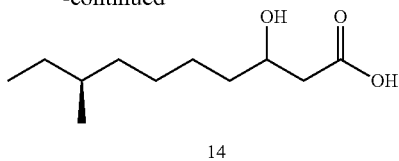

14

To a solution of (8S)-ethyl-3-hydroxy-8-methyldecanoate, 10 (0.287 g, 1.24 mmol) in 4.6 mL of THF/H₂O (1:1), LiOH (0.089 g, 3.73 mmol) was added and the mixture was stirred at ambient temperature overnight. 1M HCl was added to acidify the solution to pH 2-3. The solution was extracted with EtOAc (3×15 mL), the combined extracts dried over MgSO₄, filtered and the solvents removed in vacuo to give a pale yellowish oil. Yield: 0.237 g, 94%; $^1$H NMR (400 MHz, CDCl₃) δ: 4.01-4.06 (1H, m), 2.56-2.61 (dd, J=16.8, 3.2 Hz), 2.45-2.51 (dd, J=16.4, 8.8 Hz), 1.07-1.55 (11H, m), 0.84-0.88 (6H, m); $^{13}$C NMR (100 MHz, CDCl₃) δ: 177.4, 68.0, 41.0, 36.6, 36.5, 34.3, 29.5, 26.9, 25.8), 19.2, 11.4; IR λmax, cm-1: 3393 (br), 2932 (s), 2600 (br), 1715 (s), 1080-1192 (s).

(6S)-Ethyl-3-hydroxy-6-methyloctanoic Acid, 15

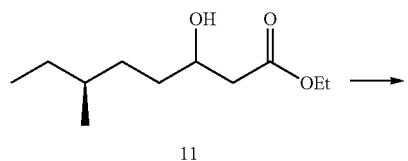

As described for 14 but using (6S)-ethyl-3-hydroxy-6-methyloctanoate, 11 (0.238 g, 1.176 mmol) to give 15 as a pale yellow oil (0.196 g, 96% yield); $^1$H NMR (400 MHz, CDCl₃) δ: 4.01-4.02 (1H, m), 2.57-2.62 (dd, J=16.4 Hz), 2.41-2.52 (dd, J=16.4, 8.8 Hz), 1.09-1.68 (7H, m), 0.86-0.93 (6H, m); $^{13}$C NMR (100 MHz, CDCl₃) δ: 177.2, 68.3, 41.5, 34.3, 34.0, 32.2, 29.4, 19.1, 11.3; IR λmax, cm-1: 3393 (br), 2874-2960 (s), 2600 (br), 1714 (s), 1042-1292 (s).

3-Hydroxy-9-methyldecanoic Acid, 16

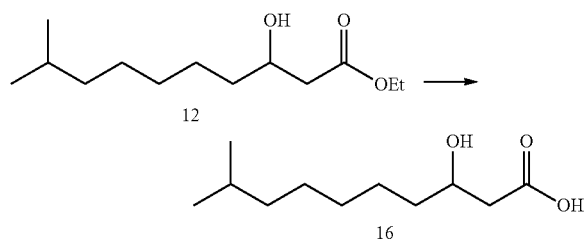

As described for 14 but using 3-hydroxy-9-methyldecanoate, 12 (0.171 g, 0.742 mmol) to give 16 as a yellow oil (0.144 g, 96% yield); $^1$H NMR (400 MHz, CDCl₃) δ: 4.01-4.07 (1H, m), 2.56-2.61 (dd, J=16.4, 3.2 Hz), 2.45-2.51 (dd, J=16.4, 8.8 Hz), 1.13-1.59 (11H, m), 0.86-0.87 (6H, m, J=6.4 Hz); $^{13}$C NMR (100 MHz, CDCl₃) δ: 177.4, 68.0, 41.0, 39.0, 36.5, 29.7, 28.0, 27.3, 25.5, 22.6. λmax, cm-1: 3393 (br) 2857-2953 (s), 2717 (br), 1714 (s), 1015-1190 (m).

Ethyl-3-hydroxy-8-methylnonanoic Acid, 17

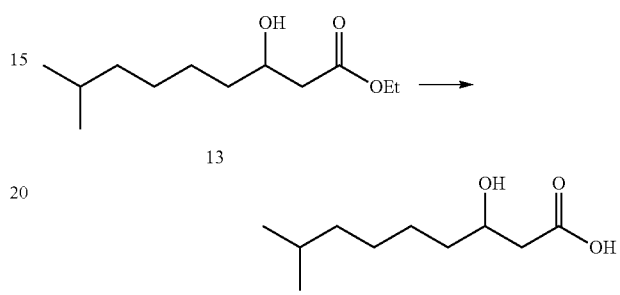

As described for 14 but using ethyl-3-hydroxy-8-methylnonanoate, 13 (0.462 g, 2.136 mmol) to give 17 as a yellow oil (0.393 g, 98% yield); $^1$H NMR (400 MHz, CDCl₃) δ: 4.01-4.07 (1H, m), 2.56-2.61 (dd, J=16.4, 2.8 Hz), 2.45-2.51 (dd, J=16.8, 9.2 Hz), 1.15-1.61 (9H, m), 0.86-1.01 (6H, m, J=6.4 Hz); $^{13}$C NMR (100 MHz, CDCl₃) δ: 177.5, 68.0, 41.0, 38.9, 36.6, 27.9, 27.2, 25.7, 22.6. λmax, cm-1: 3394 (br), 2868-2953 (s), 2717 (br), 1714 (s), 1058-1194 (m).

3-(R)-Hydroxydecanoic Acid, 19

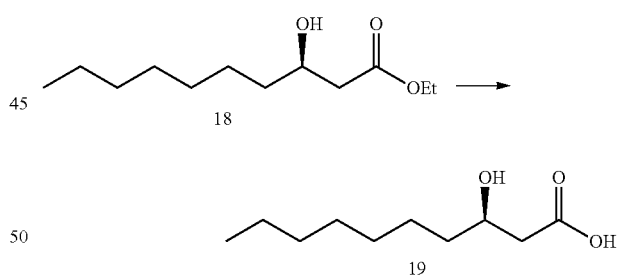

As described for 14, Ethyl-3-(R)-hydroxydecanoate, 18 (0.654 g, 3.232 mmol) gave 19 as a colorless solid (0.596 g, 98% yield); $^1$H NMR (400 MHz, CDCl₃) δ: 4.00-4.07 (1H, m, CH—OH), 2.51-2.60 (dd, J=16.4, 3.2 Hz), 2.45-2.51 (dd, J=16.8, 8.8 Hz), 1.22-1.59 (12H, m), 0.87-0.90 (3H, m). $^{13}$C NMR (100 MHz, CDCl₃) δ: 177.5, 68.0, 41.0, 36.5, 31.7, 29.4, 29.2, 25.4, 22.6, 14.0 (Consistent with literature: Wu, C.; Miller, P. A.; Miller, M. J., Syntheses and studies of amamistatin B analogs reveals that anticancer activity is relatively independent of stereochemistry, ester, or amide linkage and select replacement of one of the metal chelating groups. *Bioorg. Med. Chem. Lett.* 2011, 21, 2611-2615).

Experimental Data for Synthesized Compounds

| ID | Formula | Exact Mass | [M + nH]ⁿ⁺ found | [M + nH]ⁿ⁺ calc'd | [M + nH]ⁿ⁺ calc'd for |
|---|---|---|---|---|---|
| 631 | C51H89N13O10 | 1043.6855 | 522.8516 | 522.85 | [C51H91N13O10]2+ |

3(R)OH-nC9CO-D-Dab-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 633 | C47H89N13O10 | 995.6855 | 498.8522 | 498.85 | [C47H91N13O10]2+ |

3(R)OH-nC9CO-D-Dab-cyc[L-Dap-L-Dab-D-Leu-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 754 | C48H82N12O12 | 1018.6175 | 1019.6201 | 1019.6248 | [C48H83N12O12]1+ |

Structure: 3(R)OH-nC9CO-D-Ser-cyc[L-Dab-L-Dab-D-Phe-L-Leu-L-Dab-L-Dab-L-Thr]

-continued

| ID | Formula | Exact Mass | [M + nH]^n+ found | [M + nH]^n+ calc'd | calc'd for |
|---|---|---|---|---|---|
| 918 | C50H86N12O11 | 1030.6539 | 1031.6613 | 1031.6612 | [C50H87N12O11]1+ |

Structure: 3(R)OH-nC9CO-D-Ser-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 919 | C46H79N13O9 | 957.6124 | 479.8139 | 479.8135 | [C46H81N13O9]2+ |

C4CO-D-Dab-cyc[L-Dab-L-Dab-D-Phe-L-Leu-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 987 | C50H87N13O10 | 1029.6699 | 515.844 | 515.8422 | [C50H89N13O10]2+ |

Structure: 3(R)OH-nC9CO-D-Dab-cyc[L-Dab-L-Dab-D-Phe-L-Leu-L-Dab-L-Dap-L-Leu]

-continued

| ID | Formula | Exact Mass | [M + nH]^{n+} found | [M + nH]^{n+} calc'd | calc'd for |
|---|---|---|---|---|---|
| 988 | C52H91N13O10 | 1057.7012 | 529.8586 | 529.8579 | [C52H93N13O10]2+ |

3(R)OH-nC9CO-D-Dab-cyc[L-Dab-L-Dab-L-Dab-D-Phe-L-Leu-L-Dab-L-Orn-L-Leu]

-continued

| ID | Formula | Exact Mass | [M + nH]^n+ found | [M + nH]^n+ calc'd | calc'd for |
|---|---|---|---|---|---|
| 989 | C53H93N13O10 | 1071.7168 | 536.8657 | 536.8671 | [C53H95N13O10]2+ |

Structure: 3(R)OH-nC9CO-D-Dab-cyc[L-Dab-L-Dab-D-Phe-L-Leu-L-Dab-L-Lys-L-Leu]

| ID | Formula | Exact Mass | [M + nH]ⁿ⁺ found | [M + nH]ⁿ⁺ calc'd | calc'd for |
|---|---|---|---|---|---|
| 990 | C50H87N13O10 | 1029.6699 | 515.8425 | 515.8422 | [C50H89N13O10]2+ |

3(R)OH-nC9CO-D-Dab-cyc[L-Dab-L-Dab-D-Phe-L-Leu-L-Dap-L-Dab-L-Leu]

-continued

| ID | Formula | Exact Mass | [M + nH]^n+ found | [M + nH]^n+ calc'd | calc'd for |
|---|---|---|---|---|---|
| 991 | C52H91N13O10 | 1057.7012 | 529.8597 | 529.8579 | [C52H93N13O10]2+ |
| 992 | C53H93N13O10 | 1071.7168 | 536.8664 | 536.8657 | [C53H95N13O10]2+ |

991: 3(R)OH-nC9CO-D-Dab-cyc[L-Dab-L-Dab-L-Dab-D-Phe-L-Leu-L-Orn-L-Dab-L-Leu]

992: 3(R)OH-nC9CO-D-Dab-cyc[L-Dab-L-Dab-L-Dab-D-Phe-L-Leu-L-Lys-L-Dab-L-Leu]

-continued

| ID | Formula | Exact Mass | [M + nH]^n+ found | [M + nH]^n+ calc'd | calc'd for |
|---|---|---|---|---|---|
| 993 | C50H87N13O10 | 1029.6699 | 515.8445 | 515.8422 | [C50H89N13O10]2+ |

3(R)OH-nC9CO-D-Dab-cyc[L-Dab-L-Dap-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 994 | C52H91N13O10 | 1057.7012 | 529.8587 | 529.8579 | [C52H93N13O10]2+ |

3(R)OH-nC9CO-D-Dab-cyc[L-Dab-L-Orn-D-Phe-L-Leu-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 995 | C53H93N13O10 | 1071.7168 | 536.8671 | 536.8657 | [C53H95N13O10]2+ |
| 4943 | C48H83N13O10 | 1001.6386 | 334.886 | 334.8868 | [C48H86N13O10]3+ |

3(R)OH-nC9CO-D-Dab-cyc[L-Dab-L-Dab-L-Lys-D-Phe-L-Leu-L-Dab-L-Dab-L-Leu]

3(R)OH-nC9CO-D-Dab-cyc[L-Dab-L-Dab-D-Phe-L-Leu-L-Dab-L-Dab-L-Ala]

-continued
| ID | Formula | Exact Mass | [M + nH]$^{n+}$ found | [M + nH]$^{n+}$ calc'd | [M + nH]$^{n+}$ calc'd for |
|---|---|---|---|---|---|
| 4944 | C50H86N12O10 | 1014.659 | 339.2285 | 339.2269 | [C50H89N12O10]3+ |
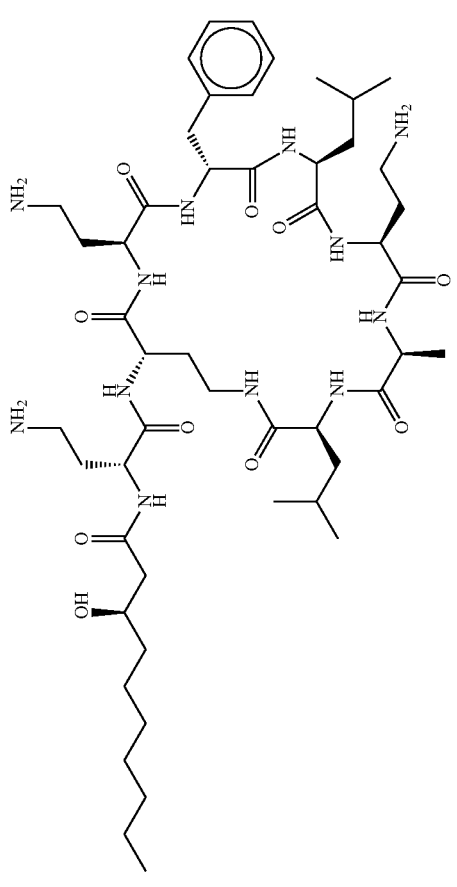
3(R)OH-nC9CO-D-Dab-cyc[L-Dab-L-Dab-D-Phe-L-Leu-L-Dab-L-Ala-L-Leu]

| ID | Formula | Exact Mass | [M + nH]$^{n+}$ found | [M + nH]$^{n+}$ calc'd | [M + nH]$^{n+}$ calc'd for |
|---|---|---|---|---|---|
| 4945 | C50H86N12O10 | 1014.659 | 339.2286 | 339.2269 | [C50H89N12O10]3+ |
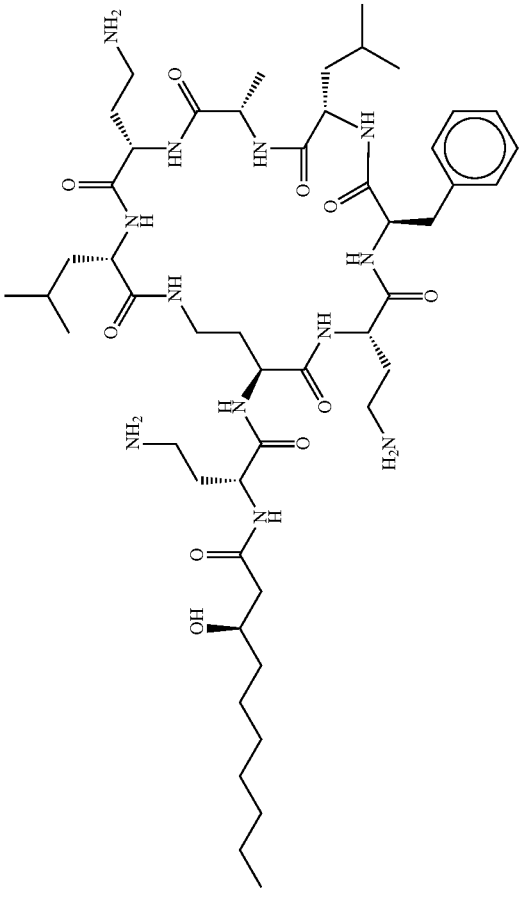
3(R)OH-nC9CO-D-Dab-cyc[L-Dab-L-Dab-D-Phe-L-Leu-L-Ala-L-Dab-L-Leu]

-continued
| ID | Formula | Exact Mass | [M + nH]ⁿ⁺ found | [M + nH]ⁿ⁺ calc'd | calc'd for |
|---|---|---|---|---|---|
| 4946 | C48H83N13O10 | 1001.6386 | 334.8874 | 334.8868 | [C48H86N13O10]3+ |
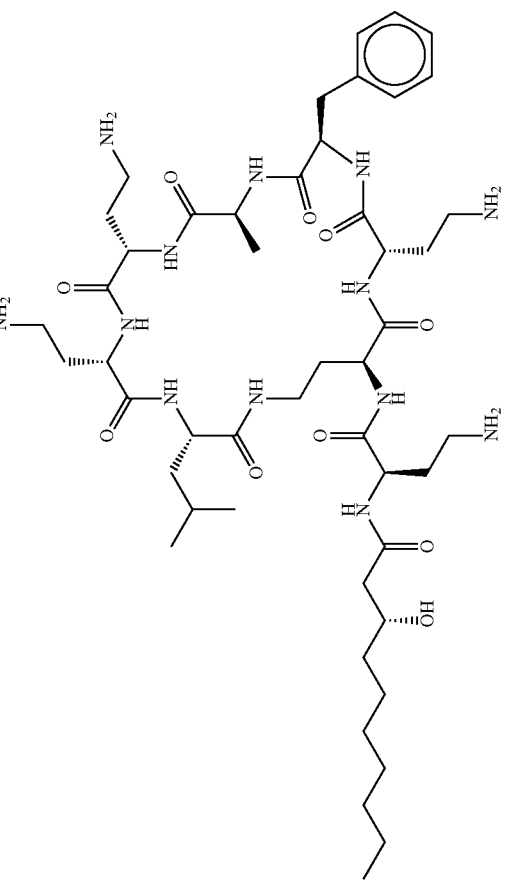
3(R)OH-nC9CO-D-Dab-D-Dab-cyc[L-Dab-L-Dab-D-Phe-L-Ala-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 4947 | C45H85N13O10 | 967.6542 | 323.56 | 323.5587 | [C45H88N13O10]3+ |

Structure:

3(R)OH-nC9CO-D-Dab-cyc[L-Dab-L-Dab-L-Dab-L-Ala-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 4948 | C50H86N12O10 | 1014.659 | 508.3361 | 508.3368 | [C50H88N12O10]2+ |

3(R)OH-nC9CO-D-Dab-cyc[L-Dab-L-Ala-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 4950 | C50H86N12O10 | 1014.659 | 339.2285 | 339.2269 | [C50H89N12O10]3+ |

Structure: 3(R)OH-nC9CO-L-Ala-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 4951 | C50H86N12O10 | 1014.659 | 339.2285 | 339.2269 | [C50H89N12O10]3+ |

Structure: 3(R)OH-nC9CO-D-Ala-cyc[L-Dab-L-Dab-D-Phe-L-Leu-L-Dab-L-Dab-L-Leu]

| ID | Formula | Exact Mass | [M + nH]^{n+} found | [M + nH]^{n+} calc'd | calc'd for |
|---|---|---|---|---|---|
| 5002 | C51H89N13O10 | 1043.6855 | 522.8497 | 522.85 | [C51H91N13O10]2+ |

3(R)OH-nC9CO-D-Dab-cyc[L-Dab-L-Dab-L-Phe-L-Leu-L-Dab-L-Dab-L-Leu]

| ID | Formula | Exact Mass | [M + nH]$^{n+}$ found | [M + nH]$^{n+}$ calc'd | [M + nH]$^{n+}$ calc'd for |
|---|---|---|---|---|---|
| 5003 | C54H87N13O10 | 1077.6699 | 539.8418 | 539.8422 | [C54H89N13O10]2+ |

3(R)OH-nC9CO-D-Dab-cyc[L-Dab-L-Dab-D-Phe-L-Phe-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 5004 | C54H87N13O10 | 1077.6699 | 539.8422 | 539.8422 | [C54H89N13O10]2+ |

3(R)OH-nC9CO-D-Dab-cyc[L-Dab-L-Dab-D-Phe-L-Leu-L-Dab-L-Dab-L-Phe]

-continued

| ID | Formula | Exact Mass | [M + nH]$^{n+}$ found | [M + nH]$^{n+}$ calc'd | calc'd for |
|---|---|---|---|---|---|
| 5005 | C57H85N13O10 | 1111.6542 | 556.8367 | 556.8344 | [C57H87N13O10]2+ |

Structure: 3(R)OH-nC9CO-D-Dab-cyc[L-Dab-L-Dab-D-Phe-L-Phe-L-Dab-L-Dab-L-Phe]

-continued
| ID | Formula | Exact Mass | [M + nH]^n+ found | [M + nH]^n+ calc'd | calc'd for |
|---|---|---|---|---|---|
| 5006 | C45H85N13O10 | 967.6542 | 484.8363 | 484.8344 | [C45H87N13O10]2+ |
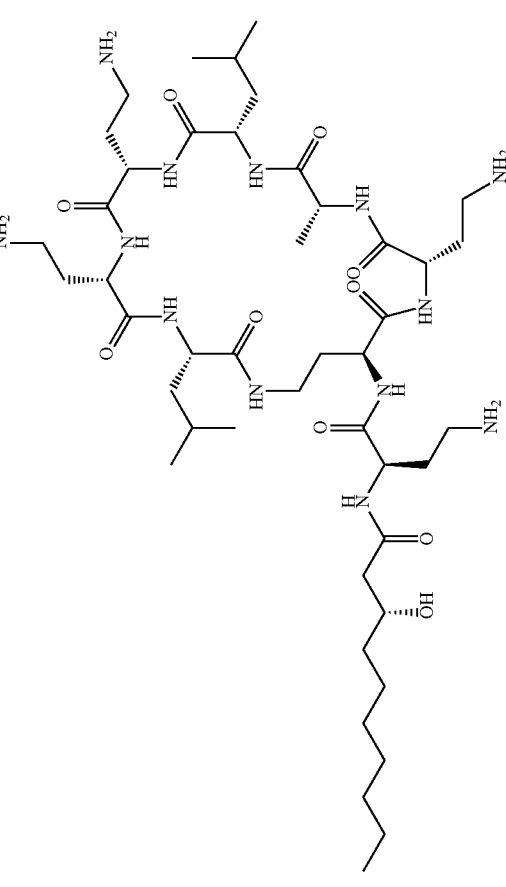
3(R)OH-nC9CO-D-Dab-cyc[L-Dab-L-Dab-D-Ala-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 5008 | C51H89N13O11 | 1059.6805 | 530.8496 | 530.8475 | [C51H91N13O11]2+ |

Structure: 3(R)OH-nC9CO-D-Dab-cyc[L-Dab-L-Dab-D-Tyr-L-Leu-L-Dab-L-Dab-L-Leu]

-continued

| Structure | ID | Formula | Exact Mass | [M + nH]ⁿ⁺ found | [M + nH]ⁿ⁺ calc'd | calc'd for |
|---|---|---|---|---|---|---|
| 3(R)OH-nC9CO-D-Dab-cyc[L-Dab-L-Dab-L-Dab-D-Bip-L-Leu-L-Dab-L-Dab-L-Leu] | 5010 | C57H93N13O10 | 1119.7168 | 560.9 | 560.8657 | [C57H95N13O10]2+ |

-continued

| ID | Formula | Exact Mass | [M + nH]ⁿ⁺ found | [M + nH]ⁿ⁺ calc'd | calc'd for |
|---|---|---|---|---|---|
| 5012 | C49H85N13O10 | 1015.6542 | 508.8342 | 508.8344 | [C49H87N13O10]2+ |

3OH-nC7CO-D-Dab-cyc[L-Dab-L-Dab-D-Phe-L-Leu-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 5013 | C51H89N13O10 | 1043.6855 | 522.8509 | 522.85 | [C51H91N13O10]2+ |
| 5014 | C53H93N13O10 | 1071.7168 | 536.8656 | 536.8657 | [C53H95N13O10]2+ |

5013: 3OH-nC9CO-D-Dab-cyc[L-Dab-L-Dab-D-Phe-L-Leu-L-Dab-L-Dab-L-Leu]

5014: 3OH-nC11CO-D-Dab-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 5015 | C55H97N13O10 | 1099.7481 | 550.8812 | 550.8813 | [C55H99N13O10]2+ |
| 5016 | C65H109N13O12 | 1263.8319 | 632.9243 | 632.9232 | [C65H129N13O1]2+ |

Structure

3OH-nC13CO-D-Dab-cyc[L-Dab-L-Dab-D-Phe-L-Leu-L-Dab-L-Dab-L-Leu]

cholic acid-D-Dab-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 5017 | C51H89N13O9 | 1027.6906 | 514.8531 | 514.8526 | [C51H91N13O9]2+ |

Structure: nC9CO-D-Dab-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 5381 | C53H93N13O10 | 1071.7168 | 536.867 | 536.8657 | [C53H95N13O10]2+ |

Structure: 3(R)OH-nC9CO-D-Lys-cyc[L-Dab-L-Dab-D-Phe-L-Leu-L-Dab-L-Dab-L-Leu]

-continued

| ID | Formula | Exact Mass | [M + nH]^{n+} found | [M + nH]^{n+} calc'd | calc'd for |
|---|---|---|---|---|---|
| 5382 | C53H93N13O10 | 1071.7168 | 536.8666 | 536.8657 | [C53H95N13O10]2+ |

3(R)OH-nC9CO-D-Dab-cyc[L-Lys-L-Dab-D-Phe-L-Leu-L-Dab-L-Dab-L-Leu]

| ID | Formula | Exact Mass | [M + nH]ⁿ⁺ found | [M + nH]ⁿ⁺ calc'd | calc'd for |
|---|---|---|---|---|---|
| 5383 | C56H91N13O10 | 1105.7012 | 553.8592 | 553.8579 | [C56H93N13O10]2+ |
| 5384 | C59H89N13O10 | 1139.6855 | 570.8 | 570.8501 | [C59H91N13O10]2+ |

5383: 3(R)OH-nC9CO-D-Dab-cyc[L-Dab-L-Dab-D-Bip-L-Leu-L-Dab-L-Dap-L-Leu]

5384: 3(R)OH-nC9CO-D-Dab-cyc[L-Dab-L-Dab-D-Bip-L-Leu-L-Dab-L-Dap-L-Phe]

| ID | Formula | Exact Mass | [M + nH]$^{n+}$ found | [M + nH]$^{n+}$ calc'd | [M + nH]$^{n+}$ calc'd for |
|---|---|---|---|---|---|
| 5385 | C53H85N13O10 | 1063.6542 | 532.8 | 532.8344 | [C53H87N13O10]2+ |

3(R)OH-nC9CO-D-Dab-cyc[L-Dab-L-Dab-D-Phe-L-Leu-L-Dab-L-Dap-L-Phe]

-continued

| ID | Formula | Exact Mass | [M + nH]^n+ found | [M + nH]^n+ calc'd | calc'd for |
|---|---|---|---|---|---|
| 5386 | C48H83N13O11 | 1017.6335 | 509.9 | 509.8241 | [C48H85N13O11]2+ |

Structure: 3(R)OH-nC9CO-D-Dab-cyc[L-Dab-L-Dab-D-Phe-L-Leu-L-Dab-L-Dap-L-Thr]

-continued
| ID | Formula | Exact Mass | [M + nH]ⁿ⁺ found | [M + nH]ⁿ⁺ calc'd | calc'd for |
|---|---|---|---|---|---|
| 5387 | C49H85N13O11 | 1031.6492 | 516.7 | 516.8319 | [C49H87N13O11]2+ |
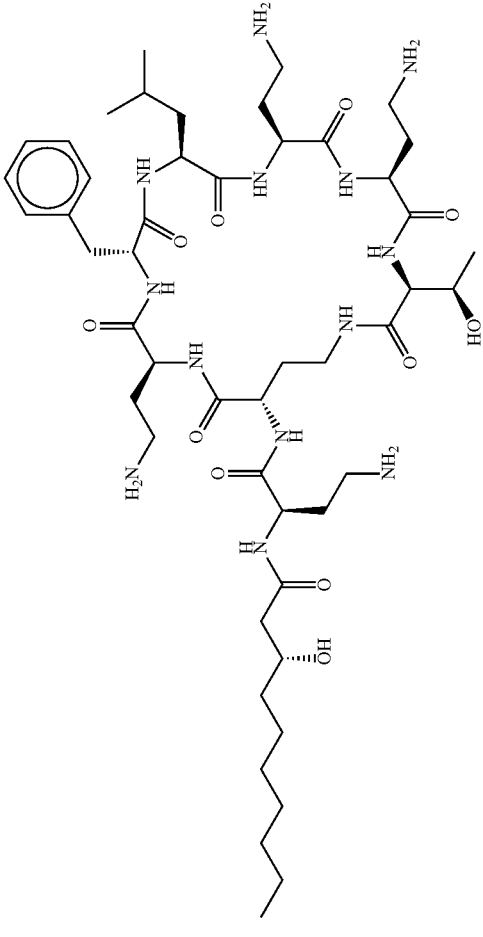
3(R)OH-nC9CO-D-Dab-cyc[L-Dab-L-Dab-D-Phe-L-Leu-L-Dab-L-Dab-L-Thr]

-continued

| ID | Formula | Exact Mass | [M + nH]ⁿ⁺ found | [M + nH]ⁿ⁺ calc'd | calc'd for |
|---|---|---|---|---|---|
| 5561 | C50H87N13O10 | 1029.6699 | 515.8428 | 515.8422 | [C50H89N13O10]2+ |

3(R)OH-nC9CO-L-Dap-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | [M + nH]$^{n+}$ calc'd for |
|---|---|---|---|---|---|
| 5562 | C53H93N13O10 | 1071.7168 | 536.8663 | 536.8657 | [C53H95N13O10]2+ |

Structure: 3(R)OH-nC9CO-L-Lys-cyc[L-Dab-L-Dab-L-Dab-D-Phe-L-Leu-L-Dab-L-Dab-L-Leu]

-continued
| ID | Formula | Exact Mass | [M + nH]$^{n+}$ found | [M + nH]$^{n+}$ calc'd | calc'd for |
|---|---|---|---|---|---|
| 5563 | C48H83N13O10 | 1001.6386 | 501.8268 | 501.8266 | [C48H85N13O10]2+ |
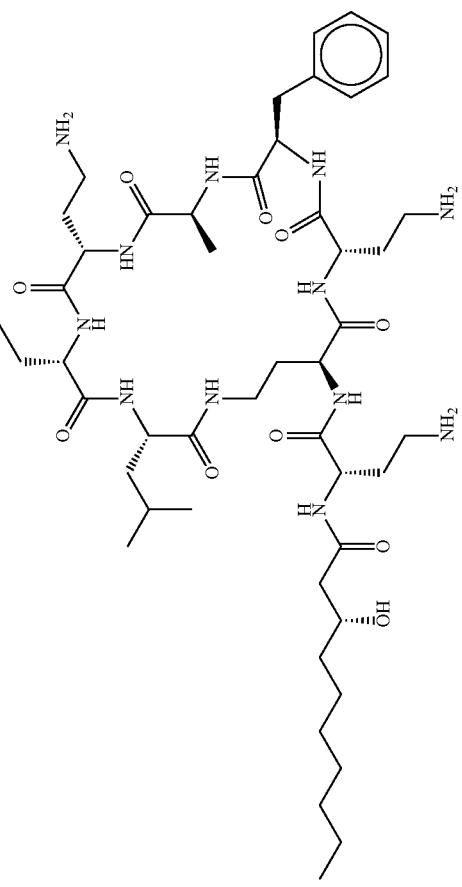
3(R)OH-nC9CO-L-Dab-cyc[L-Dab-L-Dab-D-Phe-L-Ala-L-Dab-L-Dab-L-Leu]

-continued

| ID | Formula | Exact Mass | [M + nH]^n+ found | [M + nH]^n+ calc'd | calc'd for |
|---|---|---|---|---|---|
| 5564 | C50H87N13O10 | 1029.6699 | 515.8417 | 515.8422 | [C50H89N13O10]2+ |

3(R)OH-nC9CO-L-Dab-cyc[L-Dab-L-Dab-D-Phe-L-Leu-L-Dab-L-Dap-L-Leu]

-continued
| ID | Formula | Exact Mass | [M + nH]^n+ found | [M + nH]^n+ calc'd | calc'd for |
|---|---|---|---|---|---|
| 5565 | C56H91N13O10 | 1105.7012 | 553.8588 | 553.8579 | [C56H93N13O10]2+ |
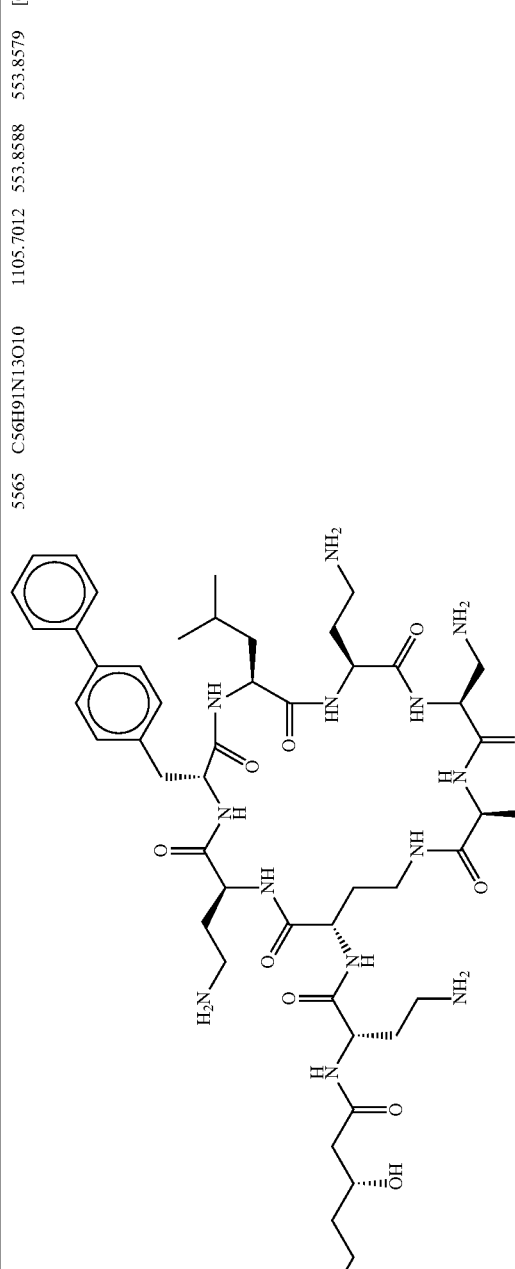
3(R)OH-nC9CO-L-Dab-cyc[L-Dab-L-Dab-D-Dab-D-Bip-L-Leu-L-Dab-L-Dap-L-Leu]

-continued

| ID | Formula | Exact Mass | [M + nH]$^{n+}$ found | [M + nH]$^{n+}$ calc'd | calc'd for |
|---|---|---|---|---|---|
| 5566 | C50H87N13O10 | 1029.6699 | 515.8445 | 515.8422 | [C50H89N13O10]2+ |

Structure:

nC5(7-Me)CH(OH)CH2CO-L-Dab-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 5567 | C52H91N13O10 | 1057.7012 | 529.8582 | 529.8579 | [C52H93N13O10]2+ | nC7(8-Me)CH(OH)CH2CO-L-Dab-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 5568 | C51H89N13O9 | 1027.6906 | 514.854 | 514.8526 | [C51H91N13O9]2+ |
| 5603 | C55H97N17O12 | 1187.7503 | 594.7 | 594.8825 | [C55H99N17O12]2+ |

Structure nC9CO-L-Dab-cyc[L-Dab-L-Dab-D-Phe-L-Leu-L-Dab-L-Dab-L-Leu]

3(R)OH-nC9CO-D-Dab-cyc[L-Dab-L-Dab-D-Phe-L-Leu-L-Dab-L-Dab(L-Arg)-L-Thr]

-continued

| ID | Formula | Exact Mass | [M + nH]ⁿ⁺ found | [M + nH]ⁿ⁺ calc'd | calc'd for |
|---|---|---|---|---|---|
| 5605 | C54H87N13O11 | 1093.6648 | 547.6 | 547.8397 | [C54H89N13O11]2+ |

Structure: 3(R)OH-nC9CO-D-Dab-cyc[L-Dab-L-Dab-L-Dab-D-Phe-L-Leu-L-Dab-L-4NH2Phe-L-Thr]

-continued
| ID | Formula | Exact Mass | [M + nH]^n+ found | [M + nH]^n+ calc'd | calc'd for |
|---|---|---|---|---|---|
| 5606 | C51H89N15O11 | 1087.6866 | 544.7 | 544.8506 | [C51H91N15O11]2+ |
| 5607 | C58H87N13O11 | 1141.6648 | 571.7 | 571.8397 | [C58H89N13O11]2+ |
Structure
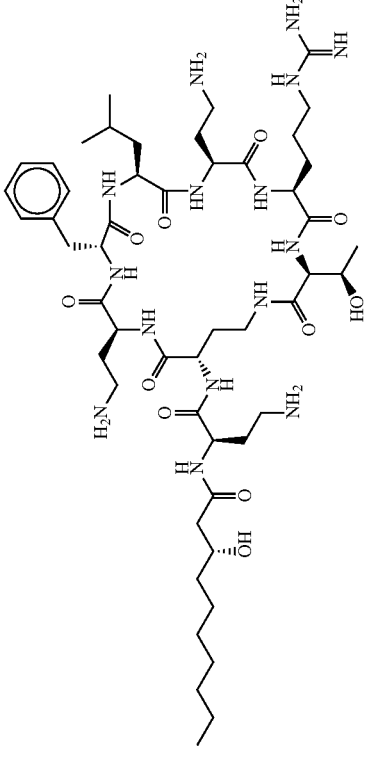
3(R)OH-nC9CO-D-Dab-cyc[L-Dab-L-Dab-D-Phe-L-Leu-L-Dab-L-Arg-L-Thr]
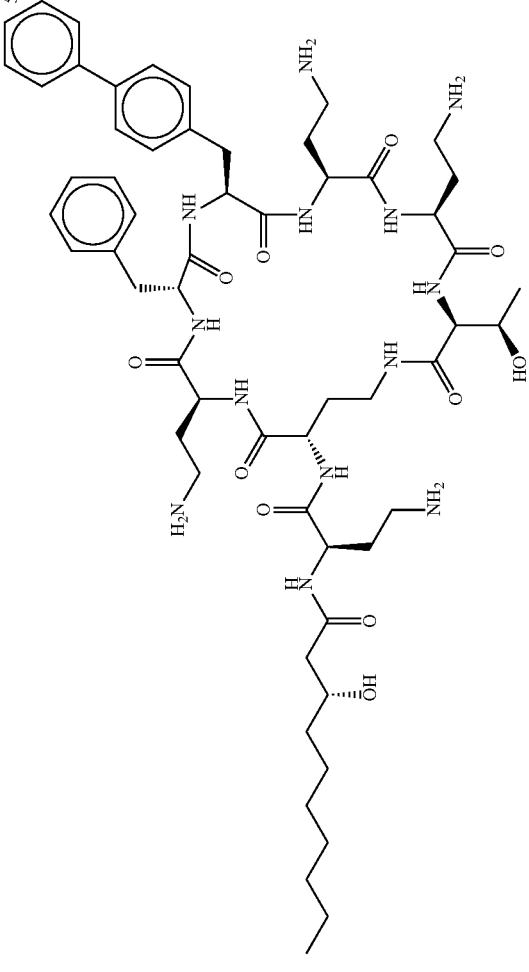
3(R)OH-nC9CO-D-Dab-cyc[L-Dab-L-Dab-D-Phe-L-Bip-L-Dab-L-Dab-L-Thr]

-continued

| ID | Formula | Exact Mass | [M + nH]$^{n+}$ found | [M + nH]$^{n+}$ calc'd | [M + nH]$^{n+}$ calc'd for |
|---|---|---|---|---|---|
| 5608 | C55H89N13O11 | 1107.6805 | 554.8 | 554.8476 | [C55H91N13O11]2+ |

Structure: 3(R)OH-nC9CO-D-Dab-cyc[L-Dab-L-Dab-L-Dab-D-Bip-L-Leu-L-Dab-L-Dab-L-Thr]

-continued

| ID | Formula | Exact Mass | [M + nH]^n+ found | [M + nH]^n+ calc'd | calc'd for |
|---|---|---|---|---|---|
| 6371 | C50H87N13O10 | 1029.6699 | 515.8423 | 515.8422 | [C50H89N13O10]2+ |

Structure: nC5(6-Me)CH(OH)CH2CO-D-Dab-cyc[L-Dab-L-Dab-L-Leu-L-Phe-L-Dab-L-Dab-L-Leu]

-continued
| ID | Formula | Exact Mass | [M + nH]$^{n+}$ found | [M + nH]$^{n+}$ calc'd | calc'd for |
|---|---|---|---|---|---|
| 6394 | C56H87N13O11 | 1116.657 | 559.2 | 559.3358 | [C56H89N13O11]2+ |
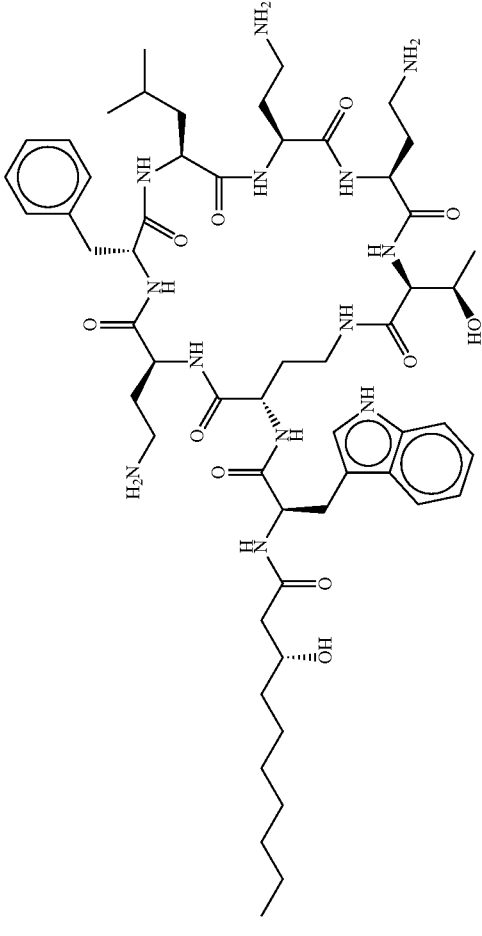
3(R)OH-nC9CO-D-Trp-cyc[L-Dab-L-Dab-D-Phe-L-Leu-L-Dab-L-Dab-L-Thr]

-continued
| ID | Formula | Exact Mass | [M + nH]ⁿ⁺ found | [M + nH]ⁿ⁺ calc'd | calc'd for |
|---|---|---|---|---|---|
| 6395 | C48H83N13O11 | 1017.6335 | 509.7 | 509.8241 | [C48H85N13O11]2+ |
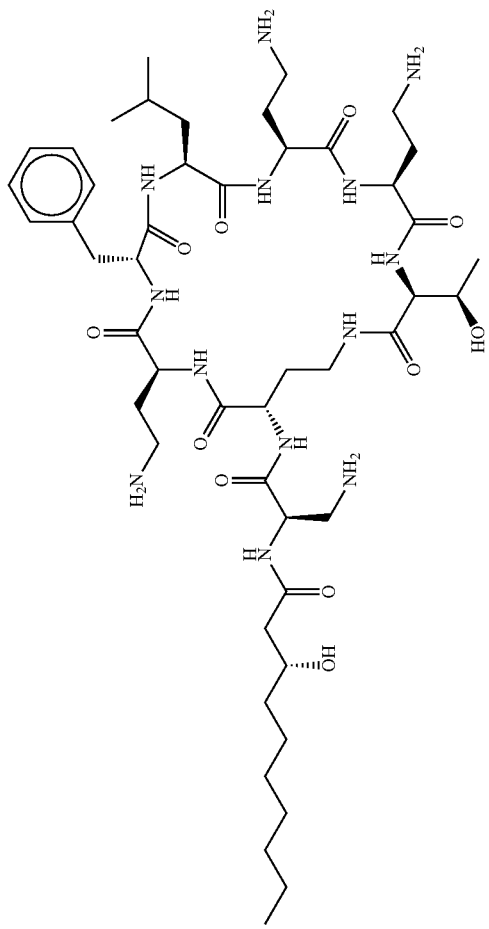
3(R)OH-nC9CO-D-Dap-cyc[L-Dab-L-Dab-D-Phe-L-Leu-L-Dab-L-Dab-L-Thr]

-continued

| ID | Formula | Exact Mass | [M + nH]^n+ found | [M + nH]^n+ calc'd | calc'd for |
|---|---|---|---|---|---|
| 6396 | C50H87N13O11 | 1045.6648 | 523.7 | 523.8397 | [C50H89N13O11]2+ |

Structure: 3(R)OH-nC9CO-D-Orn-cyc[L-Dab-L-Dab-D-Phe-L-Leu-L-Dab-L-Dab-L-Thr]

-continued

| ID | Formula | Structure | Exact Mass | [M + nH]$^{n+}$ found | [M + nH]$^{n+}$ calc'd | calc'd for |
|---|---|---|---|---|---|---|
| 6397 | C54H87N13O11 | 3(R)OH-nC9CO-D-4NH2Phe-cyc[L-Dab-L-Dab-D-Phe-L-Leu-L-Dab-L-Dab-L-Dab-L-Thr] | 1093.6648 | 547.8 | 547.8397 | [C54H89N13O11]2+ |

-continued

| ID | Formula | Exact Mass | [M + nH]ⁿ⁺ found | [M + nH]ⁿ⁺ calc'd | calc'd for |
|---|---|---|---|---|---|
| 6398 | C53H85N13O11 | 1079.6492 | 540.6 | 540.8319 | [C53H87N13O11]2+ |
| 6399 | C47H81N13O10 | 987.6229 | 494.8181 | 494.8187 | [C47H83N13O10]2+ |

3(R)OH-nC9CO-D-3PyPhe-cyc[L-Dab-L-Dab-D-Phe-L-Leu-L-Dab-L-Dab-L-Thr]

nC7CO-D-Dab-cyc[L-Dab-L-Dab-D-Phe-L-Leu-L-Dab-L-Dab-L-Thr]

-continued

| ID | Formula | Exact Mass | [M + nH]ⁿ⁺ found | [M + nH]ⁿ⁺ calc'd | calc'd for |
|---|---|---|---|---|---|
| 6403 | C53H86N14O10 | 1078.6651 | 540.4 | 540.3340 | [C53H88N14O10]2+ |
| 6404 | C51H87N13O10 | 1041.6699 | 521.7 | 521.8423 | [C51H89N13O10]2+ |

Structure:

4(C7H15NH)PheCO-D-Dab-cyc[L-Dab-L-Dab-D-Phe-L-Leu-L-Dab-L-Dab-L-Thr]

C11H21CO-D-Dab-cyc[L-Dab-L-Dab-D-Phe-L-Leu-L-Dab-L-Dab-L-Thr]

-continued
| ID | Formula | Exact Mass | [M + nH]ⁿ⁺ found | [M + nH]ⁿ⁺ calc'd | calc'd for |
|---|---|---|---|---|---|
| 6405 | C51H74N14O10 | 1042.5712 | 522.3 | 522.2929 | [C51H76N14O10]2+ |
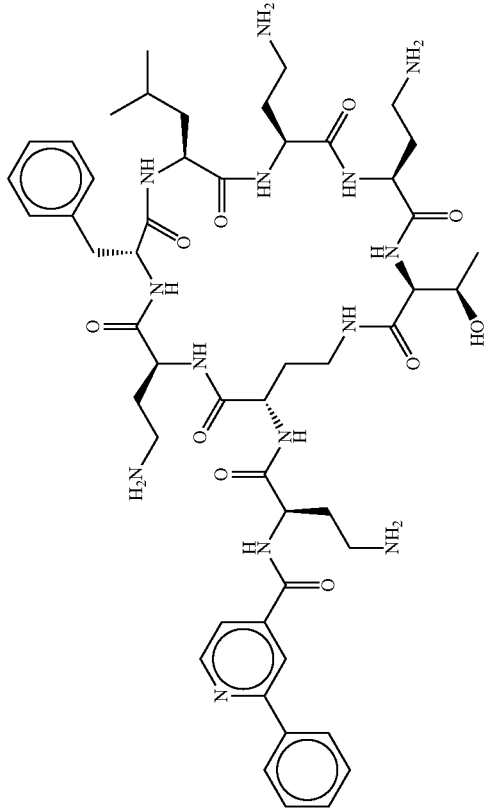
3Phe4-PyCO-D-Dab-cyc[L-Dab-L-Dab-D-Phe-L-Leu-L-Dab-L-Dab-L-Thr]

-continued
| ID | Formula | Exact Mass | [M + nH]ⁿ⁺ found | [M + nH]ⁿ⁺ calc'd | calc'd for |
|---|---|---|---|---|---|
| 6426 | C58H91N13O10 | 1128.6934 | 565.8595 | 565.8579 | [C58H93N13O10]2+ |
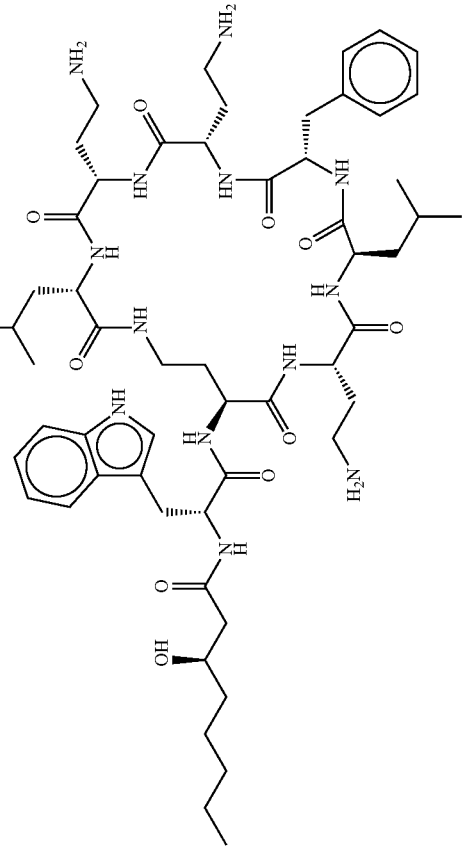
3(R)OH-nC9CO-D-Trp-cyc[L-Dab-L-Dab-L-Dab-D-Leu-L-Phe-L-Dab-L-Dab-L-Leu]

| ID | Formula | Exact Mass | [M + nH]ⁿ⁺ found | [M + nH]ⁿ⁺ calc'd | calc'd for |
|---|---|---|---|---|---|
| 6427 | C50H87N13O10 | 1029.6699 | 515.8423 | 515.8422 | [C50H89N13O10]2+ |

3(R)OH-nC9CO-D-Dap-cyc[L-Dab-L-Dab-D-Leu-L-Phe-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 6428 | C52H91N13O10 | 1057.7012 | 529.8578 | 529.8579 | [C52H93N13O10]2+ |

3(R)OH-nC9CO-D-Orn-cyc[L-Dab-L-Dab-D-Leu-L-Phe-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6429 | C56H91N13O10 | 1105.7012 | 553.8595 | 553.8579 | [C56H93N13O10]2+ |

Structure: 3(R)OH-nC9CO-D-4NH2Phe-cyc[L-Dab-L-Dab-D-Leu-L-Phe-L-Dab-L-Dab-L-Leu]

| ID | Formula | Exact Mass | [M + nH]^n+ found | [M + nH]^n+ calc'd | calc'd for |
|---|---|---|---|---|---|
| 6430 | C55H89N13O10 | 1091.6855 | 546.8496 | 546.85 | [C55H91N13O10]2+ |

3(R)OH-nC9CO-D-3PyPhe-cyc[L-Dab-L-Dab-D-Leu-L-Phe-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6431 | C49H84N12O10 | 1000.6433 | 501.33 | 501.3289 | [C49H86N12O10]2+ |

3(R)OH-nC9CO-Gly-cyc[L-Dab-L-Dab-D-Leu-L-Phe-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6432 | C51H87N13O11 | 1057.6648 | 529.8401 | 529.8397 | [C51H89N13O11]2+ |

Structure: 3(R)OH-nC9CO-D-Asn-cyc[L-Dab-L-Dab-D-Leu-L-Phe-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6433 | C56H89N13O12 | 1135.6754 | 568.8457 | 568.845 | [C56H91N13O12]2+ |

Structure: 3(R)OH-nC9CO-D-4NO2Phe-cyc[L-Dab-L-Dab-D-Leu-L-Phe-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 6441 | C58H91N13O10 | 1128.6934 | 565.8587 | 565.8579 | [C58H93N13O10]2+ |

3(R)OH-nC9CO-D-Trp-cyc[L-Dab-L-Dab-D-Phe-L-Leu-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 6442 | C50H87N13O10 | 1029.6699 | 515.8426 | 515.8422 | [C50H89N13O10]2+ |

3(R)OH-nC9CO-D-Dap-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6443 | C52H91N13O10 | 1057.7012 | 529.8581 | 529.8579 | [C52H93N13O10]2+ |

3(R)OH-nC9CO-D-Orn-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6444 | C56H91N13O10 | 1105.7012 | 553.859 | 553.8579 | [C56H93N13O10]2+ |

Structure: 3(R)OH-nC9CO-D-4NH2Phe-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | [M + nH]$^{n+}$ calc'd for |
|---|---|---|---|---|---|
| 6445 | C55H89N13O10 | 1091.6855 | 546.8498 | 546.85 | [C55H91N13O10]2+ |

Structure: 3(R)OH-nC9CO-D-3PyPhe-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6446 | C49H84N12O10 | 1000.6433 | 501.3301 | 501.3289 | [C49H86N12O10]2+ |

Structure: 3(R)OH-nC9CO-Gly-cyc[L-Dab-L-Dab-L-Dab-D-Phe-L-Leu-L-Dab-L-Dab-L-Leu]

-continued

| ID | Formula | Exact Mass | [M + nH]^n+ found | [M + nH]^n+ calc'd | [M + nH]^n+ calc'd for |
|---|---|---|---|---|---|
| 6447 | C51H87N13O11 | 1057.6648 | 529.8393 | 529.8397 | [C51H89N13O11]2+ |

3(R)OH-nC9CO-D-Asn-cyc[L-Dab-L-Dab-D-Phe-L-Leu-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 6448 | C56H89N13O12 | 1135.6754 | 568.847 | 568.845 | [C56H91N13O12]2+ |

3(R)OH-nC9CO-D-4NO2Phe-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6508 | C51H90N16O10 | 1086.7026 | 544.4 | 544.3586 | [C51H92N16O10]2+ |

Structure: 3(R)OH-nC9CO-D-Dab-cyc[L-Dab-L-Dab-L-Dab-D-Phe-L-Leu-L-Dab-L-Dab-L-Arg]

-continued

| ID | Formula | Exact Mass | [M + nH]$^{n+}$ found | [M + nH]$^{n+}$ calc'd | calc'd for |
|---|---|---|---|---|---|
| 6509 | C56H88N14O10 | 1115.673 | 373.2355 | 373.2342 | [C56H91N14O10]3+ |

3(R)OH-nC9CO-D-Dab-cyc[L-Dab-L-Dab-D-Phe-L-Leu-L-Dab-L-Dab-L-Trp]

-continued

| ID | Formula | Exact Mass | [M + nH]^n+ found | [M + nH]^n+ calc'd | calc'd for |
|---|---|---|---|---|---|
| 6510 | C48H83N13O11 | 1017.6335 | 509.7 | 509.8241 | [C48H85N13O11]2+ |

Structure: 3(R)OH-nC9CO-D-Dab-cyc[L-Dab-L-Dab-D-Phe-L-Leu-L-Dab-L-Dab-L-Ser]

-continued

| ID | Formula | Exact Mass | [M + nH]^{n+} found | [M + nH]^{n+} calc'd | calc'd for |
|---|---|---|---|---|---|
| 6511 | C54H87N13O11 | 1093.6648 | 547.6 | 547.8397 | [C54H89N13O11]2+ |

Structure: 3(R)OH-nC9CO-D-Dab-cyc[L-Dab-L-Dab-D-Phe-L-Leu-L-Dab-L-Dab-L-Tyr]

-continued

| ID | Formula | Exact Mass | [M + nH]$^{n+}$ found | [M + nH]$^{n+}$ calc'd | calc'd for |
|---|---|---|---|---|---|
| 6512 | C50H85N13O12 | 1059.6441 | 530.7 | 530.8294 | [C50H87N13O12]2+ |

Structure: 3(R)OH-nC9CO-D-Dab-cyc[L-Dab-L-Dab-D-Phe-L-Leu-L-Dab-L-Dab-L-Glu]

-continued

| ID | Formula | Exact Mass | [M + nH]ⁿ⁺ found | [M + nH]ⁿ⁺ calc'd | calc'd for |
|---|---|---|---|---|---|
| 6513 | C49H83N13O12 | 1045.6248 | 523.8 | 523.8215 | [C49H85N13O12]2+ |

3(R)OH-nC9CO-D-Dab-cyc[L-Dab-L-Dab-L-Dab-D-Phe-L-Leu-L-Dab-L-Dab-L-Asp]

-continued

| ID | Formula | Exact Mass | [M + nH]^n+ found | [M + nH]^n+ calc'd | calc'd for |
|---|---|---|---|---|---|
| 6514 | C49H85N13O10 | 1015.6542 | 508.8324 | 508.8344 | [C49H87N13O10]2+ |

Structure:

8OH-nC7CO-D-Dab-cyc[L-Dab-L-Dab-D-Leu-L-Phe-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6515 | C51H89N13O9 | 1027.6906 | 514.8535 | 514.8526 | [C51H91N13O9]2+ |

3,7-dimethyloctanoic acid-D-Dab-cyc[L-Dab-L-Dab-D-Leu-L-Phe-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6516 | C54H94N14O9 | 1082.7328 | 542.374 | 542.3737 | [C54H96N14O9]2+ |

Structure:

1-heptylpiperidine-4-carboxylic acid-D-Dab-cyc[L-Dab-L-Dab-D-Leu-L-Phe-L-Dab-L-Dab-L-Leu]

-continued

| ID | Formula | Exact Mass | [M + nH]^n+ found | [M + nH]^n+ calc'd | [M + nH]^n+ calc'd for |
|---|---|---|---|---|---|
| 6517 | C53H78N14O9 | 1054.6076 | 528.3117 | 528.3111 | [C53H80N14O9]2+ |

Structure: 3Phe4-PyCO-D-Dab-cyc[L-Dab-L-Dab-D-Leu-L-Phe-L-Dab-L-Dab-L-Leu]

-continued

| ID | Formula | Exact Mass | [M + nH]$^{n+}$ found | [M + nH]$^{n+}$ calc'd | [M + nH]$^{n+}$ calc'd for |
|---|---|---|---|---|---|
| 6518 | C54H79N13O9 | 1053.6124 | 527.8129 | 527.8135 | [C54H81N13O9]2+ |

Structure: Ph-4-PhCO-D-Dab-cyc[L-Dab-L-Dab-D-Leu-L-Phe-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 6519 | C54H79N13O10 | 1069.6073 | 535.8107 | 535.8109 | [C54H81N13O10]2+ |

Ph-4-OPhCO-D-Dab-cyc[L-Dab-L-Dab-D-Leu-L-Phe-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6520 | C53H85N13O10 | 1063.6542 | 532.8341 | 532.8344 | [C53H87N13O10]2+ |

4-(pentyloxy)benzoic acid-D-Dab-cyc[L-Dab-L-Dab-D-Leu-L-Phe-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6521 | C51H81N13O10 | 1035.6229 | 518.819 | 518.8187 | [C51H83N13O10]2+ |

4-phenoxybutanoic acid-D-Dab-cyc[L-Dab-L-Dab-D-Leu-L-Phe-L-Dab-L-Dab-L-Leu]

-continued

| ID | Formula | Exact Mass | [M + nH]^{n+} found | [M + nH]^{n+} calc'd | calc'd for |
|---|---|---|---|---|---|
| 6522 | C49H85N13O10 | 1015.6542 | 508.8332 | 508.8344 | [C49H87N13O10]2+ |

8OH-nC7CO-D-Dab-cyc[L-Dab-L-Dab-D-Phe-L-Leu-L-Dab-L-Dab-L-Leu]

-continued
| ID | Formula | Exact Mass | [M + nH]^n+ found | [M + nH]^n+ calc'd | calc'd for |
|---|---|---|---|---|---|
| 6523 | C51H89N13O9 | 1027.6906 | 514.8525 | 514.8526 | [C51H91N13O9]2+ |
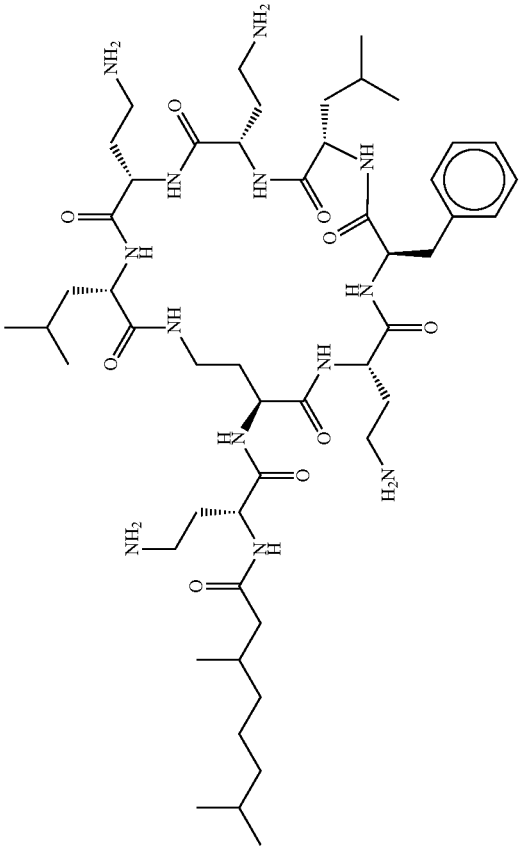
3,7-dimethyloctanoic acid-D-Dab-cyc[L-Dab-L-Dab-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6524 | C54H94N14O9 | 1082.7328 | 542.3743 | 542.3737 | [C54H96N14O9]$^{2+}$ |

Structure: 1-heptylpiperidine-4-carboxylic acid-D-Dab-cyc[L-Dab-L-Dab-D-Phe-L-Leu-L-Dab-L-Dab-L-Leu]

-continued
| ID | Formula | Exact Mass | [M + nH]$^{n+}$ found | [M + nH]$^{n+}$ calc'd | [M + nH]$^{n+}$ calc'd for |
|---|---|---|---|---|---|
| 6525 | C53H78N14O9 | 1054.6076 | 528.3111 | 528.3111 | [C53H80N14O9]2+ |
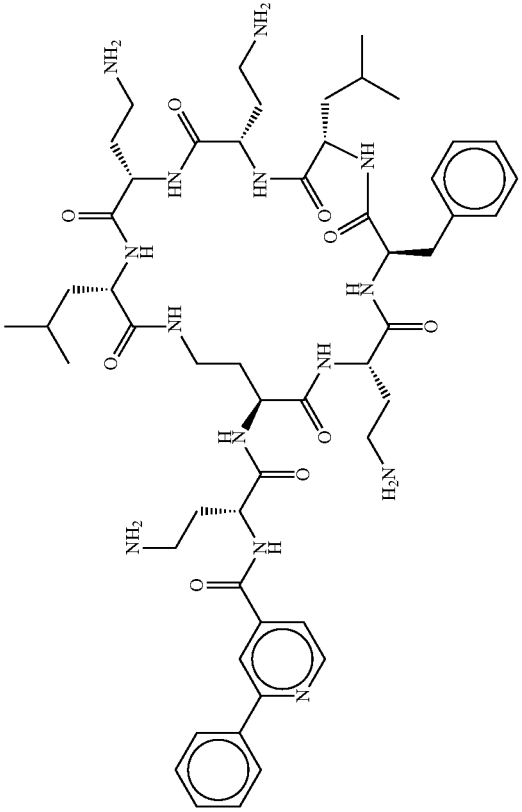
3Phe4-PyCO-D-Dab-cyc[L-Dab-L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6526 | C54H79N13O9 | 1053.6124 | 527.814 | 527.8135 | [C54H81N13O9]2+ |

Ph-4-PhCO-D-Dab-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6527 | C54H79N13O10 | 1069.6073 | 535.8126 | 535.8109 | [C54H81N13O10]2+ |

Structure: Ph-4-OPhCO-D-Dab-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6528 | C53H85N13O10 | 1063.6542 | 532.8363 | 532.8344 | [C53H87N13O10]2+ |

Structure: 4-(pentyloxy)benzoic acid-D-Dab-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 6529 | C51H81N13O10 | 1035.6229 | 518.8199 | 518.8187 | [C51H83N13O10]2+ |
| 6653 | C57H101N17O11 | 1199.7866 | 600.9035 | 600.9006 | [C57H121N17O1]2+ |

Structure:

4-phenoxybutanoic acid-D-Dab-cyc[L-Dab-L-Dab-D-Phe-L-Leu-L-Dab-L-Dab-L-Leu]

3(R)OH-nC9CO-D-Dab-cyc[L-Dab-L-Dab-D-Phe-L-Leu-L-Dab-L-Dab(L-Arg)-L-Leu]

| ID | Formula | Exact Mass | [M + nH]$^{n+}$ found | [M + nH]$^{n+}$ calc'd | calc'd for |
|---|---|---|---|---|---|
| 6654 | C57H101N17O11 | 1199.7866 | 600.9035 | 600.9006 | [C57H121N17O11]2+ |
| 6655 | C57H101N17O11 | 1199.7866 | 600.9033 | 600.9006 | [C57H121N17O11]2+ |
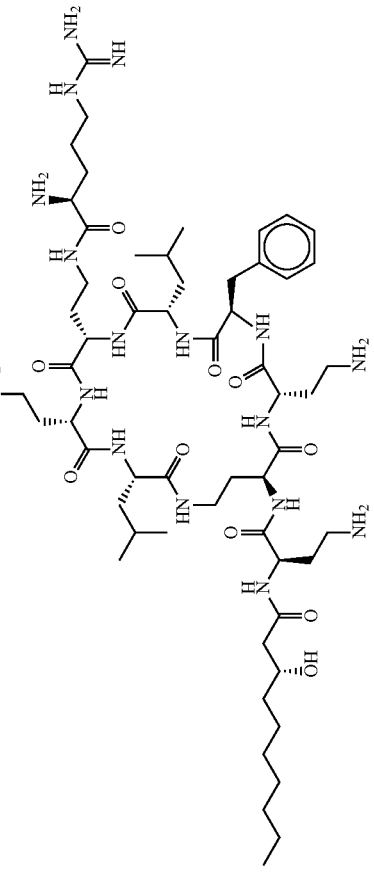
3(R)OH-nC9CO-D-Dab-cyc[L-Dab-L-Dab-L-Dab-D-Phe-L-Leu-L-Dab(L-Arg)-L-Dab-L-Leu]
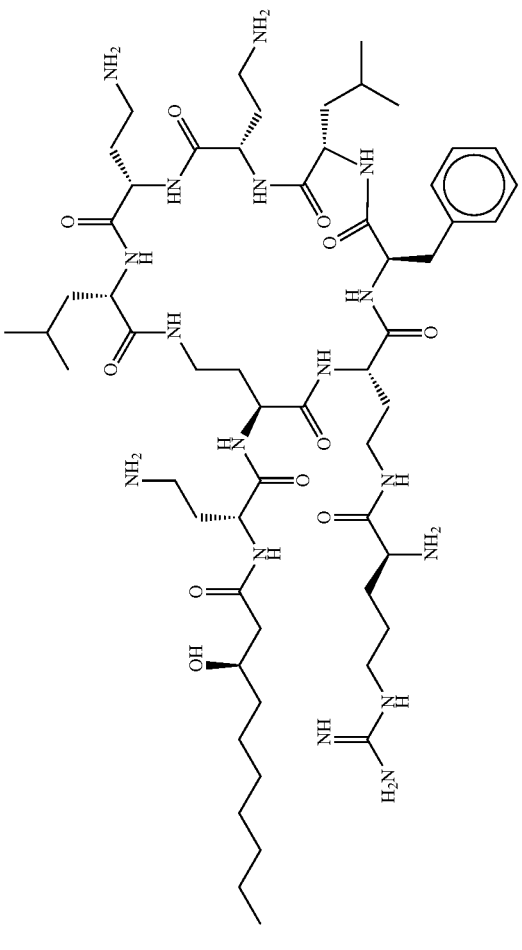
3(R)OH-nC9CO-D-Dab-cyc[L-Dab-L-Dab(L-Arg)-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6656 | C55H97N17O12 | 1187.7503 | 595.1 | 594.8825 | [C55H97N17O12]+ |
| 6657 | C55H97N17O12 | 1187.7503 | 594.6 | 594.8825 | [C55H97N17O12]+ |

3(R)OH-nC9CO-D-Dab-cyc[L-Dab-L-Dab-L-Dab-D-Phe-L-Leu-L-Dab(L-Arg)-L-Dab-L-Thr]

3(R)OH-nC9CO-D-Dab-cyc[L-Dab-L-Dab(L-Arg)-D-Phe-L-Leu-L-Dab-L-Dab-L-Thr]

| ID | Formula | Exact Mass | [M + nH]^{n+} found | [M + nH]^{n+} calc'd | calc'd for |
|---|---|---|---|---|---|
| 6658 | C51H89N13O10 | 1043.6855 | 522.8503 | 522.85 | [C51H91N13O10]2+ |

3(R)OH-nC9CO-L-Dab-cyc[D-Dab-L-Dab-D-Phe-L-Leu-L-Dab-L-Dab-L-Leu]

-continued
| ID | Formula | Exact Mass | [M + nH]^{n+} found | [M + nH]^{n+} calc'd | calc'd for |
|---|---|---|---|---|---|
| 6660 | C48H83N13O10 | 1001.6386 | 501.826 | 501.8266 | [C48H85N13O10]2+ |
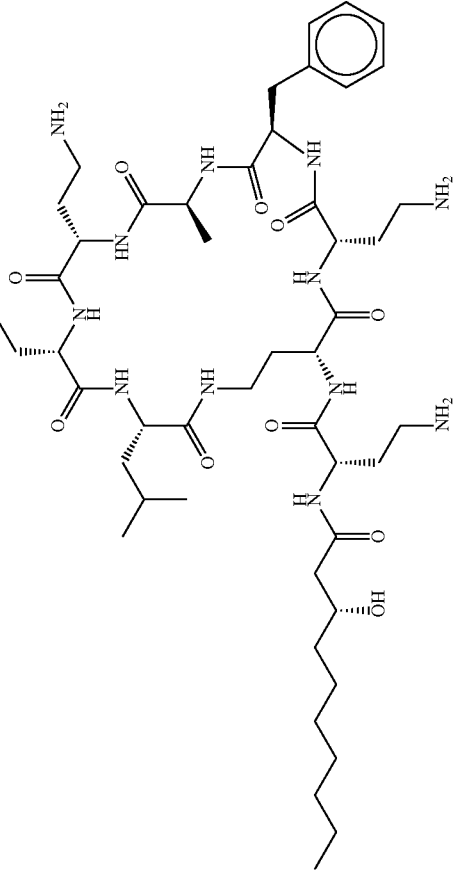
3(R)OH-nC9CO-L-Dab-cyc[D-Dab-L-Dab-L-Dab-D-Phe-L-Ala-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 6661 | C57H93N13O10 | 1119.7168 | 560.8656 | 560.8657 | [C57H95N13O10]2+ |

Structure: 3(R)OH-nC9CO-L-Dab-cyc[D-Dab-L-Dab-D-Bip-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 7037 | C52H99N15O11 | 1109.7648 | 555.8919 | 555.8897 | [C52H101N15O11]2+ |

Structure: 3(R)OH-nC9CO-D-Dab-cyc[L-Dab-D-Dab-D-Dab-L-Dab-D-Leu-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 7038 | C55H97N15O11 | 1143.7492 | 572.8833 | 572.8819 | [C55H99N15O11]2+ |

Structure: 3(R)OH-nC9CO-D-Dab-cyc[L-Dab-D-Dab-L-Dab-D-Leu-L-Phe-L-Dab-L-Dab-L-Leu]

-continued

| ID | Formula | Exact Mass | [M + nH]^n+ found | [M + nH]^n+ calc'd | calc'd for |
|---|---|---|---|---|---|
| 7039 | C55H97N15O11 | 1143.7492 | 572.8828 | 572.8819 | [C55H99N15O11]2+ |

Structure: 3(R)OH-nC9CO-D-Dab-cyc[L-Dab-D-Dab-D-Dab-L-Dab-L-Leu-D-Phe-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 7040 | C55H97N15O11 | 1143.7492 | 572.8831 | 572.8819 | [C55H99N15O11]2+ |

Structure:

3(R)OH-nC9CO-D-Dab-cyc[L-Dab-D-Dab-D-Dab-L-Dab-D-Phe-L-Leu-L-Dab-L-Dab-L-Leu]

| Structure | ID | Formula | Exact Mass | [M + nH]^n+ found | [M + nH]^n+ calc'd | [M + nH]^n+ calc'd for |
|---|---|---|---|---|---|---|
| 3(R)OH-nC9CO-D-Dab-cyc[L-Dab-L-Dab-D-Phe-L-Ala(cycloprop)-L-Dab-L-Dab-L-Trp] | 8099 | C56H86N14O10 | 1114.6651 | 558.3 | 558.3399 | [C56H86N14O10]+ |

-continued

| ID | Formula | Exact Mass | [M + nH]$^{n+}$ found | [M + nH]$^{n+}$ calc'd | calc'd for |
|---|---|---|---|---|---|
| 8101 | C59H92N14O10 | 1156.7121 | 579.3 | 579.3634 | [C59H92N14O10]+ |

Structure:

3(R)OH-nC9CO-D-Dab-cyc[L-Dab-L-Dab-L-Dab-D-Phe-L-Ala(cyclohexyl)-L-Dab-L-Dab-L-Trp]

-continued

| Structure | ID | Formula | Exact Mass | [M + nH]^n+ found | [M + nH]^n+ calc'd | calc'd for |
|---|---|---|---|---|---|---|
| (structure shown below) | 8103 | C61H88N14O10 | 1176.6808 | 589.3478 | 589.3477 | [C61H90N14O10]2+ |

3(R)OH-nC9CO-D-Dab-cyc[L-Dab-L-Dab-L-Dab-D-Phe-L-indanylgly-L-Dab-L-Dab-L-Trp]

-continued

| ID | Formula | Exact Mass | [M + nH]^n+ found | [M + nH]^n+ calc'd | calc'd for |
|---|---|---|---|---|---|
| 8105 | C57H87N15O10 | 1141.676 | 571.6 | 571.8453 | [C57H87N15O10]+ |

3(R)OH-nC9CO-D-Dab-cyc[L-Dab-L-Dab-L-Dab-D-Phe(4-CN)-L-Leu-L-Dab-L-Dab-L-Trp]

-continued

| ID | Formula | Exact Mass | [M + nH]^n+ found | [M + nH]^n+ calc'd | calc'd for |
|---|---|---|---|---|---|
| 8109 | C62H92N14O10 | 1192.7121 | 597.4 | 597.3634 | [C62H92N14O10]+ |

Structure:

3(R)OH-nC9CO-D-Dab-cyc[L-Dab-L-Dab-L-Dab-D-Ala(3,3'-diphenyl)-L-Leu-L-Dab-L-Dab-L-Trp]

| ID | Formula | Exact Mass | [M + nH]$^{n+}$ found | [M + nH]$^{n+}$ calc'd | calc'd for |
|---|---|---|---|---|---|
| 8113 | C60H90N14O10 | 1166.6964 | 584.6 | 584.3555 | [C60H92N14O10]2+ |

3(R)OH-nC9CO-D-Dab-cyc[L-Dab-L-Dab-L-Dab-D-Ala(2-Na)-L-Leu-L-Dab-L-Dab-L-Trp]

-continued

| ID | Formula | Exact Mass | [M + nH]^n+ found | [M + nH]^n+ calc'd | calc'd for |
|---|---|---|---|---|---|
| 8119 | C56H87FN14O10 | 1134.6714 | 568.2 | 568.343 | [C56H87N14O10]+ |

Structure:

3(R)OH-nC9CO-D-Dab-cyc[L-Dab-L-Dab-L-Dab-D-Phe(4-F)-L-Leu-L-Dab-L-Dab-L-Trp]

| ID | Formula | Exact Mass | [M + nH]^n+ found | [M + nH]^n+ calc'd | calc'd for |
|---|---|---|---|---|---|
| 8127 | C58H89N15O10 | 1155.6917 | 578.8549 | 578.8532 | [C58H91N15O10]2+ |

3(R)OH-nC9CO-D-Dab-cyc[L-Dab-L-Dab-L-Dab-D-Trp-L-Leu-L-Dab-L-Dab-L-Trp]

| ID | Formula | Exact Mass | [M + nH]^n+ found | [M + nH]^n+ calc'd | calc'd for |
|---|---|---|---|---|---|
| 8129 | C57H90N14O10 | 1130.6964 | 566.3562 | 566.3555 | [C57H92N14O10]2+ |

3(R)OH-nC9CO-D-Dab-cyc[L-Dab-L-Dab-L-Dab-D-hPhe-L-Leu-L-Dab-L-Dab-L-Trp]

-continued

| ID | Formula | Exact Mass | [M + nH]^n+ found | [M + nH]^n+ calc'd | calc'd for |
|---|---|---|---|---|---|
| 8634 | C53H93N15O10 | 1099.723 | 550.8679 | 550.8688 | [C53H95N15O10]2+ |

Structure: 3(R)OH-nC9CO-D-Dab-cyc[L-Dab-L-Arg-D-Phe-L-Leu-L-Dab-L-Dab-L-Leu]

-continued
| ID | Formula | Exact Mass | [M + nH]$^{n+}$ found | [M + nH]$^{n+}$ calc'd | calc'd for |
|---|---|---|---|---|---|
| 8635 | C56H91N13O10 | 1105.7012 | 553.8606 | 553.8579 | [C56H93N13O10]2+ |
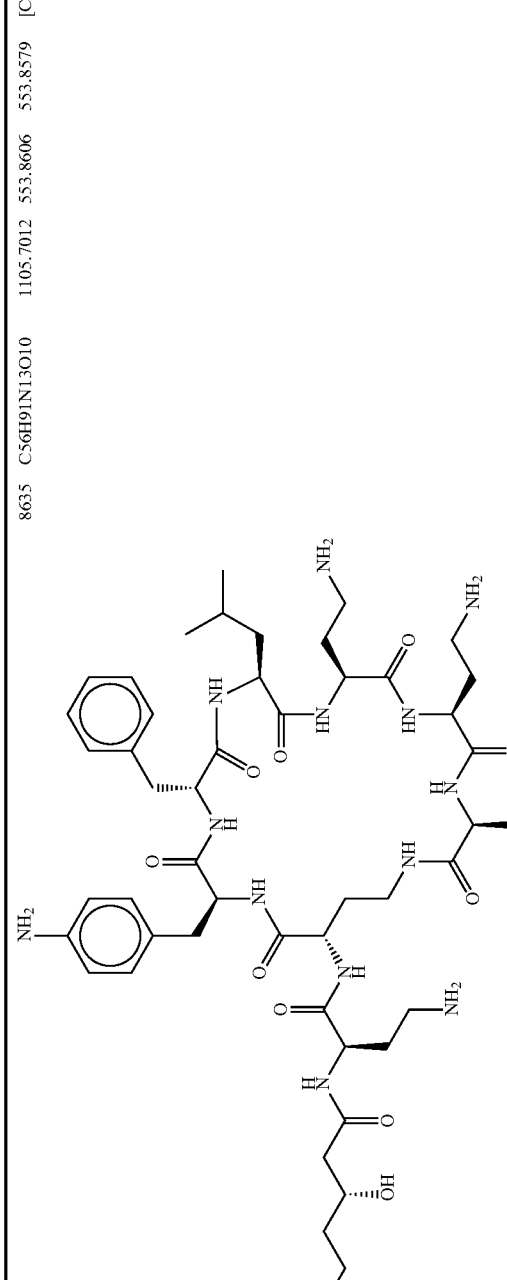
3(R)OH-nC9CO-D-Dab-cyc[L-Dab-L-4NH2Phe-D-Phe-L-Leu-L-Dab-L-Dab-L-Leu]

-continued
| ID | Formula | Exact Mass | [M + nH]^n+ found | [M + nH]^n+ calc'd | calc'd for |
|---|---|---|---|---|---|
| 8636 | C50H88N14O10 | 1044.6808 | 523.3488 | 523.3477 | [C50H90N14O10]2+ |
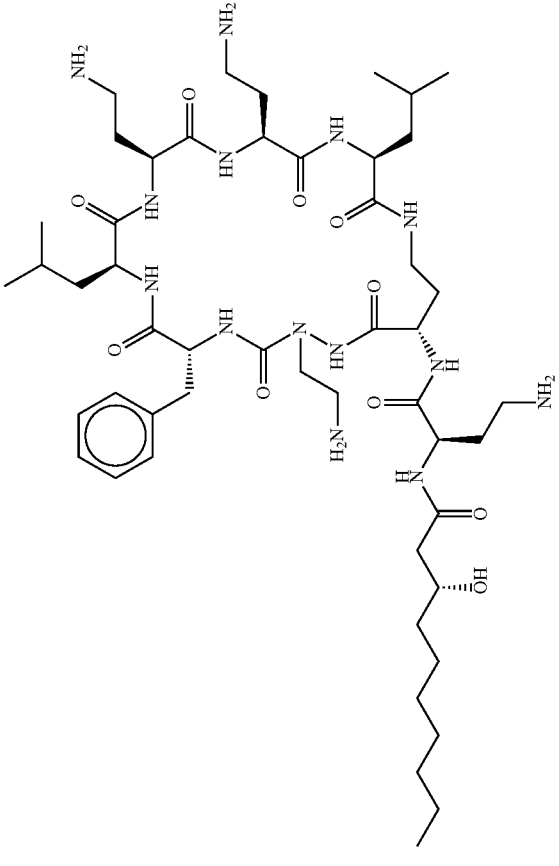
3(R)OH-nC9CO-D-Dab-cyc[L-Dab-azaDAB-D-Phe-L-Leu-L-Dab-L-Dab-L-Leu]

-continued

| ID | Formula | Exact Mass | [M + nH]$^{n+}$ found | [M + nH]$^{n+}$ calc'd | [M + nH]$^{n+}$ calc'd for |
|---|---|---|---|---|---|
| 8638 | C51H89N13O10 | 1043.6855 | 522.8495 | 522.85 | [C51H91N13O10]2+ |

3(R)OH-nC9CO-L-Dab-L-Dab-cyc[L-Dab-L-DAB-D-Phe-L-Leu-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 8639 | C50H88N14O10 | 1044.6808 | 523.3497 | 523.3477 | [C50H90N14O10]2+ |

3(R)OH-nC9CO-azaDab-cyc[L-Dab-L-DAB-D-Phe-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 8640 | C51H89N13O10 | 1043.6855 | 522.8497 | 522.85 | [C51H91N13O10]2+ |

3(R)OH-nC9CO-D-Dab-cyc[L-Dab-L-DAB-L-Phe-D-Leu-L-Dab-L-Dab-L-Leu]

-continued

| Structure | ID | Formula | Exact Mass | [M + nH]^n+ found | [M + nH]^n+ calc'd | calc'd for |
|---|---|---|---|---|---|---|
| 3(R)OH-nC9CO-D-Dab-cyc[L-Dab-L-DAB-D-Phe-L-Leu-azaDab-L-Dab-L-Leu] | 8641 | C50H88N14O10 | 1044.6808 | 523.3499 | 523.3477 | [C50H90N14O10]2+ |
| 3(R)OH-nC9CO-D-Dab-cyc[L-Dab-L-DAB-D-Phe-L-Leu-L-4NH2Phe-L-Dab-L-Leu] | 8642 | C56H91N13O10 | 1105.7012 | 553.8603 | 553.8579 | [C56H93N13O10]2+ |

-continued

| ID | Formula | Exact Mass | [M + nH]^n+ found | [M + nH]^n+ calc'd | calc'd for |
|---|---|---|---|---|---|
| 8643 | C53H93N15O10 | 1099.723 | 367.583 | 367.5816 | [C53H96N15O10]3+ |
| 8644 | C56H91N13O10 | 1105.7012 | 553.8606 | 553.8579 | [C56H93N13O10]2+ |

Structure for 8643: 3(R)OH-nC9CO-D-Dab-cyc[L-Dab-L-DAB-D-Phe-L-Leu-L-Dab-L-Arg-L-Leu]

Structure for 8644: 3(R)OH-nC9CO-D-Dab-cyc[L-Dab-L-DAB-D-Phe-L-Leu-L-Dab-L-4NH2Phe-L-Leu]

-continued

| ID | Formula | Exact Mass | [M + nH]$^{n+}$ found | [M + nH]$^{n+}$ calc'd | calc'd for |
|---|---|---|---|---|---|
| 8733 | C53H93N15O10 | 1099.723 | 367.5824 | 367.5816 | [C53H96N15O10]3+ |
| 8782 | C50H88N14O10 | 1044.6808 | 523.349 | 523.3477 | [C50H90N14O10]2+ |

Structure: 3(R)OH-nC9CO-D-Dab-cyc[L-Dab-L-DAB-D-Phe-L-Leu-L-Arg-L-Dab-L-Leu]

Structure: 3(R)OH-nC9CO-D-Dab-cyc[L-Dab-L-DAB-D-Phe-L-Leu-L-Dab-azaDab-L-Leu]

-continued

| ID | Formula | Exact Mass | [M + nH]^n+ found | [M + nH]^n+ calc'd | calc'd for |
|---|---|---|---|---|---|
| 8803 | C50H88N14O10 | 1044.6808 | 523.3489 | 523.3477 | [C50H90N14O10]2+ |

Structure: 3(R)OH-nC9CO-D-Dab-cyc[L-Dab-L-DAB-D-Phe-azaLeu-L-Dab-L-Dab-L-Leu]

-continued

| ID | Formula | Exact Mass | [M + nH]ⁿ⁺ found | [M + nH]ⁿ⁺ calc'd | calc'd for |
|---|---|---|---|---|---|
| 8826 | C58H90N14O10 | 1141.6886 | 572.3547 | 572.3555 | [C58H92N14O10]2+ | nC10-3(R)OH-D-Dab-cyc[L-Dab-L-Dab-D-indanylgyl-L-Leu-L-Dab-L-Dab-L-Trp]

-continued

| ID | Formula | Exact Mass | [M + nH]$^{n+}$ found | [M + nH]$^{n+}$ calc'd | calc'd for |
|---|---|---|---|---|---|
| 8832 | C63H88N14O10 | 1199.673 | 600.6 | 600.8438 | [C63H90N14O10]2+ |

Structure: nC10-3(R)OH-D-Dab-cyc[L-Dab-L-Dab-D-Phe-L-2-NaphthylAla-L-Dab-L-Dab-L-Trp]

-continued

| ID | Formula | Exact Mass | [M + nH]ⁿ⁺ found | [M + nH]ⁿ⁺ calc'd | calc'd for |
|---|---|---|---|---|---|
| 8834 | C60H88N14O10 | 1163.673 | 582.6 | 582.8438 | [C60H90N14O10]2+ |

Structure: nC10-3(R)OH-D-Dab-cyc[L-Dab-L-Dab-L-Dab-D-Phe-L-hPhe-L-Dab-L-Dab-L-Trp]

-continued

| ID | Formula | Exact Mass | [M + nH]^n+ found | [M + nH]^n+ calc'd | [M + nH]^n+ calc'd for |
|---|---|---|---|---|---|
| 8884 | C58H92N16O10 | 1171.7104 | 587.3682 | 587.3664 | [C58H94N16O10]2+ |

Structure: nC10-3(R)OH-D-Arg-cyc[L-Dab-L-Dab-D-Phe-L-Leu-L-Dab-L-Dab-L-Trp]

-continued

| ID | Formula | Exact Mass | [M + nH]$^{n+}$ found | [M + nH]$^{n+}$ calc'd | calc'd for |
|---|---|---|---|---|---|
| 8886 | C55H86N14O10 | 1101.6573 | 552.3403 | 552.3398 | [C55H88N14O10]2+ |

Structure: 3(R)OH-nC9CO-D-Dap-cyc[L-Dab-L-Dab-D-Phe-L-Leu-L-Dab-L-Dab-L-Trp]

-continued

| ID | Formula | Exact Mass | [M + nH]^n+ found | [M + nH]^n+ calc'd | calc'd for |
|---|---|---|---|---|---|
| 8887 | C53H82N14O9 | 1057.6311 | 530.3268 | 530.3267 | [C53H84N14O9]2+ |

Structure: nC7CO-D-Dap-cyc[L-Dab-L-Dab-D-Phe-L-Leu-L-Dab-L-Dab-L-Trp]

-continued

| ID | Formula | Exact Mass | [M + nH]ⁿ⁺ found | [M + nH]ⁿ⁺ calc'd | calc'd for |
|---|---|---|---|---|---|
| 8888 | C64H94N16O10 | 1245.7261 | 624.3736 | 624.3742 | [C64H96N16O10]2+ |
| 8890 | C64H94N16O10 | 1245.7261 | 624.374 | 624.3742 | [C64H96N16O10]2+ |

3(R)OH-nC9CO-D-Dap-cyc[L-Dab-L-Dab-D-Phe-L-indanylgly-L-Lys-L-Arg-L-Trp]

3(R)OH-nC9CO-D-Dap-cyc[L-Dab-L-Dab-D-Phe-L-indanylgly-L-Arg-L-Lys-L-Trp]

-continued

| Structure | ID | Formula | Exact Mass | [M + nH]$^{n+}$ found | [M + nH]$^{n+}$ calc'd | [M + nH]$^{n+}$ calc'd for |
|---|---|---|---|---|---|---|
| 3(R)OH-nC9CO-D-Dap-cyc[L-Dab-L-Dab-D-Bip-L-tert-Leu-L-Lys-L-Arg-L-Trp] | 8892 | C65H98N16O10 | 1261.7574 | 632.3925 | 632.3899 | [C65H100N16O10]2+ |

-continued

| ID | Formula | Exact Mass | [M + nH]$^{n+}$ found | [M + nH]$^{n+}$ calc'd | [M + nH]$^{n+}$ calc'd for |
|---|---|---|---|---|---|
| 8896 | C61H96N16O10 | 1211.7417 | 607.3828 | 607.382 | [C61H98N16O10]2+ |

Structure: 3(R)OH-nC9CO-D-Dap-cyc[L-Dab-L-Dab-D-indanylgly-L-Leu-L-Lys-L-Arg-L-Trp]

-continued

| ID | Formula | Exact Mass | [M + nH]ⁿ⁺ found | [M + nH]ⁿ⁺ calc'd | calc'd for |
|---|---|---|---|---|---|
| 8897 | C62H88N14O10 | 1187.673 | 595.3496 | 595.3477 | [C62H90N14O10]2+ |

3(R)OH-nC9CO-D-Dap-cyc[L-Dab-L-Dab-D-indanylgly-L-indanylgly-L-Dab-L-Dab-L-Trp]

-continued

| ID | Formula | Exact Mass | [M + nH]$^{n+}$ found | [M + nH]$^{n+}$ calc'd | calc'd for |
|---|---|---|---|---|---|
| 8898 | C59H84N14O9 | 1131.6467 | 378.5605 | 378.5588 | [C59H87N14O9]3+ |

Structure: nC7CO-D-Dab-cyc[L-Dab-L-Dab-D-Phe-L-indanylgly-L-Dab-L-Dab-L-Trp]

-continued

| ID | Formula | Exact Mass | [M + nH]^{n+} found | [M + nH]^{n+} calc'd | calc'd for |
|---|---|---|---|---|---|
| 8899 | C55H92N14O10 | 1107.7043 | 555.3636 | 555.3633 | [C55H94N14O10]2+ |

3(R)OH-nC9CO-D-Dab-cyc[L-Dab-L-Dab-D-Chg-L-Leu-L-Dab-L-Dab-L-Trp]

-continued
| ID | Formula | Exact Mass | [M + nH]^n+ found | [M + nH]^n+ calc'd | calc'd for |
|---|---|---|---|---|---|
| 8900 | C56H86N14O9 | 1097.6624 | 550.3432 | 550.3424 | [C56H88N14O9]2+ |
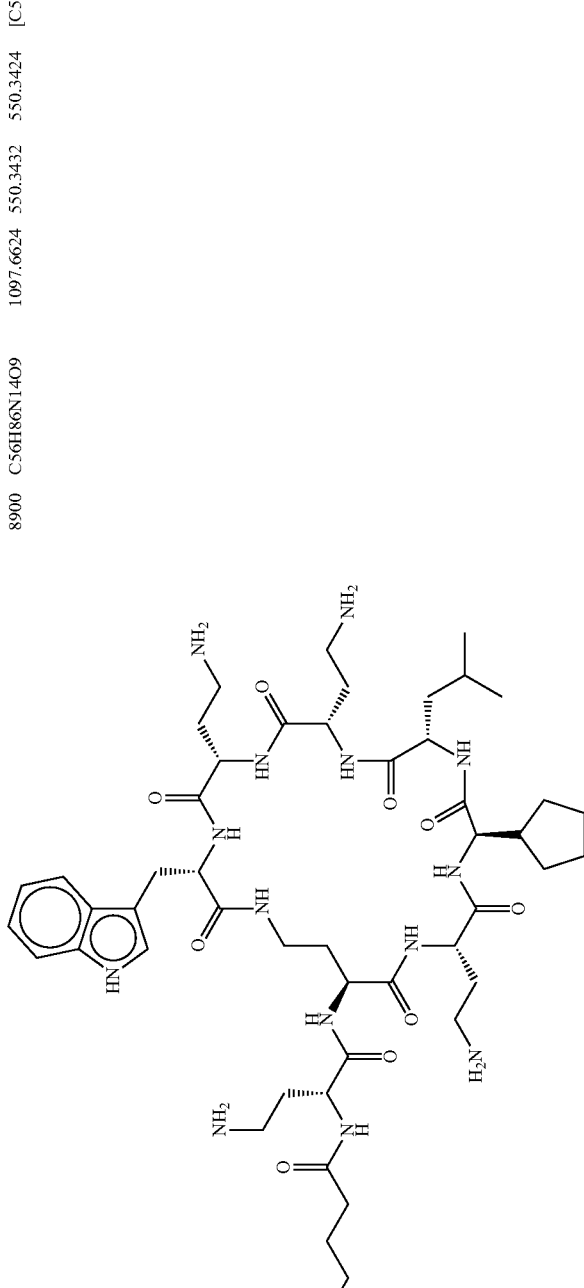
nC7CO-D-Dab-cyc[L-Dab-L-Dab-D-indanyl-gly-L-Leu-L-Dab-L-Dab-L-Trp]

-continued
| ID | Formula | Exact Mass | [M + nH]^n+ found | [M + nH]^n+ calc'd | calc'd for |
|---|---|---|---|---|---|
| 8901 | C54H84N14O9 | 1071.6467 | 537.3551 | 537.3346 | [C54H86N14O9]2+ |
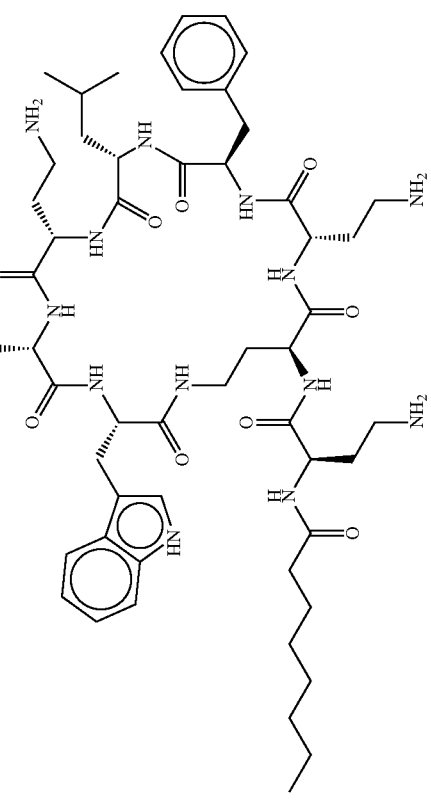
nC7CO-D-Dab-cyc[L-Dab-L-Dab-D-Phe-L-Leu-L-Dab-L-Dab-L-Trp]

-continued

| ID | Formula | Exact Mass | [M + nH]^n+ found | [M + nH]^n+ calc'd | calc'd for |
|---|---|---|---|---|---|
| 8906 | C53H86N14O10 | 1078.6651 | 540.3409 | 540.3398 | [C53H88N14O10]2+ |

Structure: 3(R)OH-nC9CO-D-Dab-cyc[L-Dab-L-Dab-L-Dab-D-Phe-L-Leu-L-Dab-L-Dab-L-Ala(4py)]

-continued

| ID | Formula | Exact Mass | [M + nH]$^{n+}$ found | [M + nH]$^{n+}$ calc'd | calc'd for |
|---|---|---|---|---|---|
| 8907 | C53H86N14O10 | 1078.6651 | 540.3409 | 540.3398 | [C53H88N14O10]2+ |

Structure: 3(R)OH-nC9CO-D-Dab-cyc[L-Dab-L-Dab-L-Dab-D-Phe-L-Leu-L-Dab-L-Dab-L-Ala(3py)]

-continued

| ID | Formula | Exact Mass | [M + nH]$^{n+}$ found | [M + nH]$^{n+}$ calc'd | calc'd for |
|---|---|---|---|---|---|
| 8908 | C58H89N13O10 | 1127.6855 | 564.8513 | 564.85 | [C58H91N13O10]2+ |

Structure: 3(R)OH-nC9CO-D-Dab-cyc[L-Dab-L-Dab-D-Phe-L-Leu-L-Dab-L-Dab-L-Ala(2Naphthyl)]

-continued

| ID | Formula | Exact Mass | [M + nH]ⁿ⁺ found | [M + nH]ⁿ⁺ calc'd | calc'd for |
|---|---|---|---|---|---|
| 8909 | C58H89N13O10 | 1127.6855 | 564.8514 | 564.85 | [C58H91N13O10]2+ |

Structure: 3(R)OH-nC9CO-D-Dab-cyc[L-Dab-L-Dab-L-Dab-D-Phe-L-Leu-L-Dab-L-Dab-L-Ala(1Naphthyl)]

| ID | Formula | Exact Mass | [M + nH]^n+ found | [M + nH]^n+ calc'd | calc'd for |
|---|---|---|---|---|---|
| 8910 | C55H86N14O10S | 1134.6372 | 568.3271 | 568.3259 | [C55H88N14O10]2+ |

3(R)OH-nC9CO-D-Dab-cyc[L-Dab-L-Dab-D-Phe-L-Leu-L-Dab-L-Dab-L-Ala(Bth)]

| ID | Formula | Exact Mass | [M + nH]^n+ found | [M + nH]^n+ calc'd | calc'd for |
|---|---|---|---|---|---|
| 8911 | C51H85N15O10 | 1066.6526 | 534.8378 | 534.8375 | [C51H87N15O10]2+ |

3(R)OH-nC9CO-D-Dab-cyc[L-Dab-L-Dab-D-Phe-L-Leu-L-Dab-L-His]

-continued

| ID | Formula | Exact Mass | [M + nH]^n+ found | [M + nH]^n+ calc'd | calc'd for |
|---|---|---|---|---|---|
| 8912 | C56H89N13O10 | 1103.6855 | 552.8506 | 552.85 | [C56H91N13O10]2+ |

Structure:

3(R)OH-nC9CO-D-Dab-cyc[L-Dab-L-Dab-D-Phe-L-Leu-L-Dab-L-Dab-L-indanylgly]

-continued

| ID | Formula | Exact Mass | [M + nH]^n+ found | [M + nH]^n+ calc'd | [M + nH]^n+ calc'd for |
|---|---|---|---|---|---|
| 8913 | C55H89N13O10 | 1091.6855 | 546.85 | 546.85 | [C55H91N13O10]2+ |

Structure: 3(R)OH-nC9CO-D-Dab-cyc[L-Dab-L-Dab-D-Phe-L-Leu-L-Dab-L-Dab-L-hPhe]

-continued

| ID | Formula | Exact Mass | [M + nH]ⁿ⁺ found | [M + nH]ⁿ⁺ calc'd | calc'd for |
|---|---|---|---|---|---|
| 8914 | C56H87ClN14O10 | 1149.634 | 576.3294 | 576.3282 | [C56H89ClN14O]2+ |

Structure: 3(R)OH-nC9CO-D-Dab-cyc[L-Dab-L-Dab-D-Phe(3-Cl)-L-Leu-L-Dab-L-Dab-L-Trp]

-continued

| ID | Formula | Exact Mass | [M + nH]ⁿ⁺ found | [M + nH]ⁿ⁺ calc'd | calc'd for |
|---|---|---|---|---|---|
| 8942 | C50H88N14O10 | 1044.6808 | 523.3 | 523.3477 | [C50H90N14O10]2+ |

3(R)OH-nC9CO-D-Dab-cyc[L-Dab-L-Dab-azaPhe-L-Leu-L-Dab-L-Dab-L-Trp]

-continued
| ID | Formula | Exact Mass | $[M + nH]^{n+}$ found | $[M + nH]^{n+}$ calc'd | calc'd for |
|---|---|---|---|---|---|
| 8976 | C48H83N13O9 | 985.6437 | 329.5561 | 329.5552 | [C48H86N13O9]3+ |
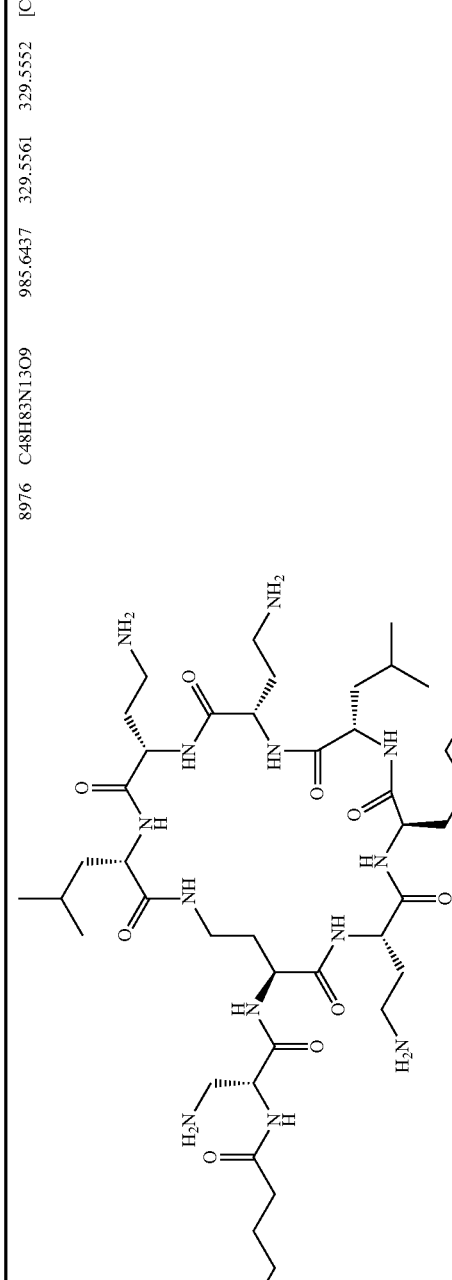
nC7CO-D-Dap-cyc[L-Dab-L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 8977 | C47H89N13O10 | 995.6855 | 332.9023 | 332.9025 | [C47H92N13O10]3+ |

Structure: nC10-3(R)OH-D-Dap-(L-Dab-L-Dab-D-Leu-L-Leu-L-Dab-L-Dab-L-Leu)

-continued

| ID | Formula | Exact Mass | [M + nH]$^{n+}$ found | [M + nH]$^{n+}$ calc'd | calc'd for |
|---|---|---|---|---|---|
| 8978 | C45H85N13O9 | 951.6593 | 318.2276 | 318.2271 | [C45H88N13O9]3+ |

Structure: nC7CO-D-Dap-cyc[L-Dab-L-Dab-D-Leu-L-Leu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 8980 | C42H71N13O9 | 901.5498 | 451.7838 | 451.7822 | [C42H73N13O9]2+ |

Ac-D-Dap-cyc[L-Dab-L-Dab-D-Phe-L-Leu-L-Dab-L-Dab-L-Leu]

-continued
| ID | Formula | Exact Mass | [M + nH]^n+ found | [M + nH]^n+ calc'd | calc'd for |
|---|---|---|---|---|---|
| 8981 | C48H72N14O9 | 987.5528 | 495.2898 | 495.2876 | [C48H74N14O9]2+ |
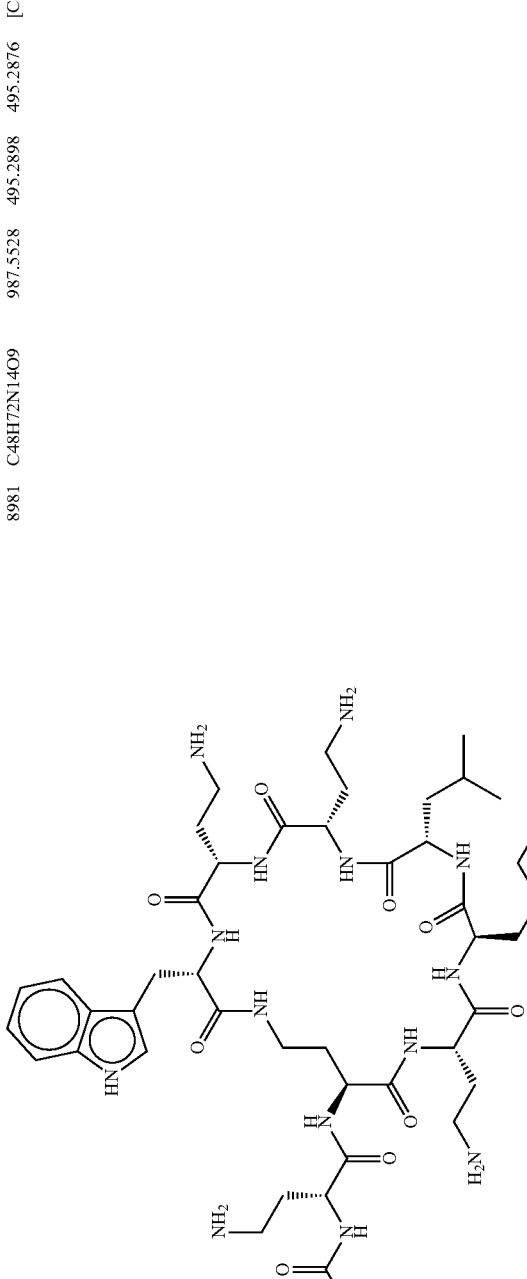
Ac-D-Dab-cyc[L-Dab-L-Dab-D-Phe-L-Leu-L-Dab-L-Dab-L-Trp]

-continued
| ID | Formula | Exact Mass | [M + nH]^n+ found | [M + nH]^n+ calc'd | calc'd for |
|---|---|---|---|---|---|
| 9032 | C63H101N17O12 | 1286.7737 | 644.8996 | 644.8981 | [C63H103N17O12]2+ |
| 9188 | C47H73ClN14O9 | 1012.5373 | 507.2 | 507.2760 | [C47H75ClN14O9]2+ |
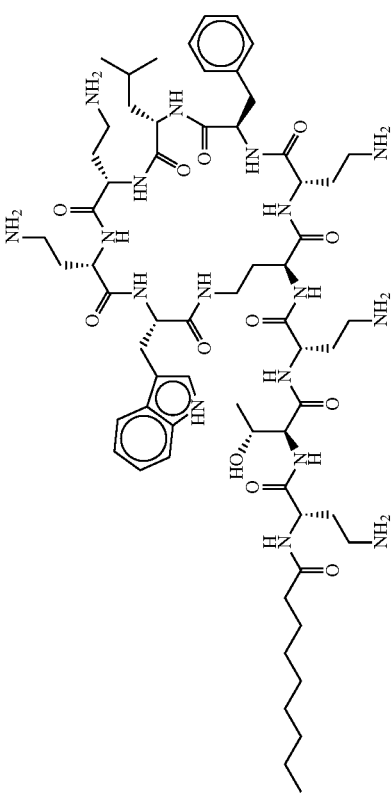
nC8CO-L-Dab-L-Thr-L-Dab-cyc[L-Dab-L-Dab-D-Phe-L-Leu-L-Dab-L-Trp]
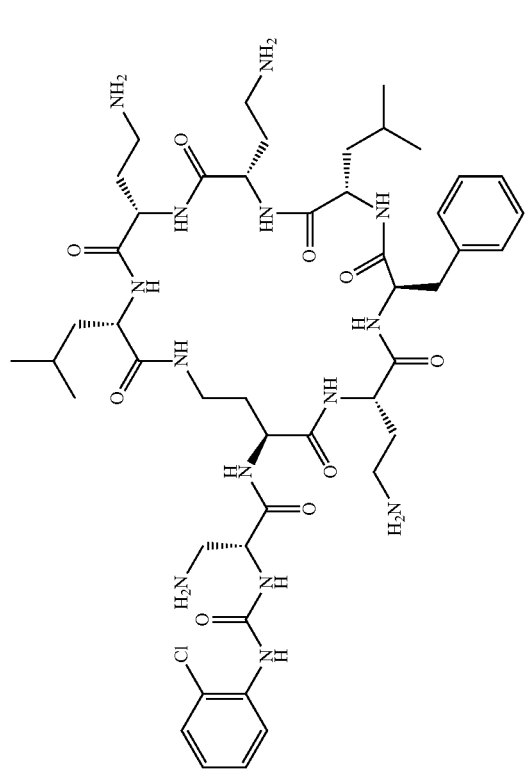
2-ClPh-NHCO-D-Dap-cyc[L-Dab-L-Dab-D-Phe-L-Leu-L-Dab-L-Leu]

-continued
| ID | Formula | Exact Mass | [M + nH]^{n+} found | [M + nH]^{n+} calc'd | [M + nH]^{n+} calc'd for |
|---|---|---|---|---|---|
| 9189 | C52H76N14O10 | 1056.5868 | 529.1 | 529.3007 | [C52H78N14O10]2+ |
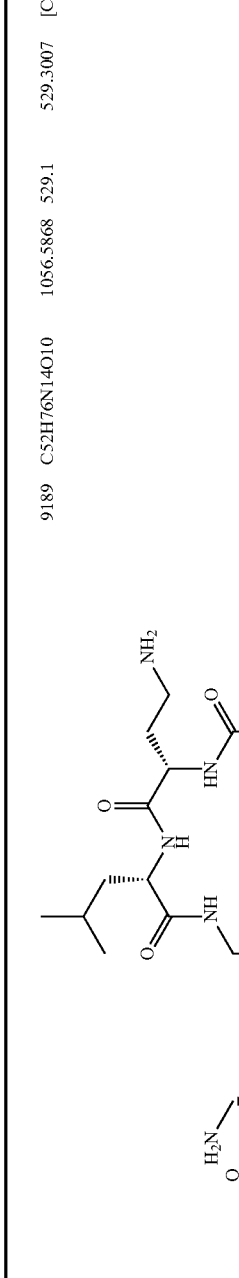
4-(1-Ph-pyridinone)-D-Dap-cyc[L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 9190 | C47H81N13O9 | 971.6280 | 486.7 | 486.8213 | [C47H83N13O9]2+ | nC6CO-D-Dap-cyc[L-Dab-L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 9191 | C47H81N13O9 | 999.6593 | 500.9 | 500.8370 | [C49H87N13O9]2+ | nC8CO-D-Dap-cyc[L-Dab-L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 9192 | C50H87N13O9 | 1013.6749 | 507.5 | 507.8448 | [C50H89N13O9]2+ |

Structure: nC9CO-D-Dap-cyc[L-Dab-L-Dab-L-Dab-D-Phe-L-Leu-L-Dab-L-Dab-L-Leu]

-continued

| ID | Formula | Exact Mass | [M + nH]^n+ found | [M + nH]^n+ calc'd | calc'd for |
|---|---|---|---|---|---|
| 9193 | C49H84N12O11 | 1016.6382 | 509.5 | 509.3264 | [C49H86N12O11]2+ |

Structure: 3(R)-OH-nC9CO-D-Dab-cyc[L-Dab-L-Dab-L-Dab-L-Leu-D-Phe-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 9194 | C51H89N13O10 | 1043.6855 | 522.9 | 522.8501 | [C51H91N13O10]2+ |

Structure:

3(R)-OH-nC9CO-D-Dab-cyc[L-Dab-L-Dab-L-Leu-D-Phe-L-Dab-L-Dab-L-Leu]

-continued
| ID | Formula | Exact Mass | [M + nH]^n+ found | [M + nH]^n+ calc'd | calc'd for |
|---|---|---|---|---|---|
| 9289 | C49H85N13O11 | 1031.6491 | 516.7 | 516.8319 | [C49H87N13O11]2+ |
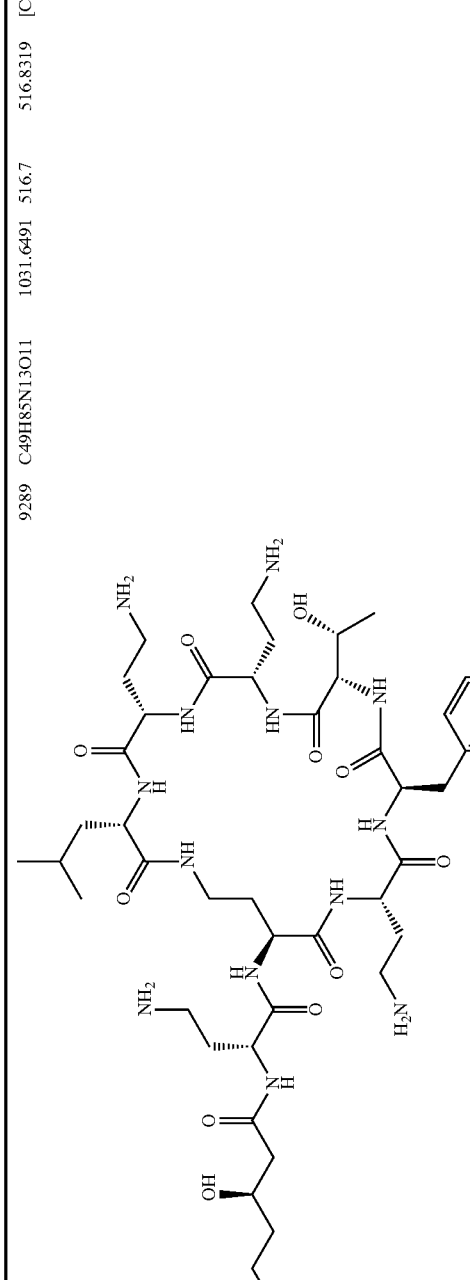
3(R)OH-nC9CO-D-Dab-cyc[L-Dab-L-Dab-D-Phe-L-Thr-L-Dab-L-Dab-L-Leu]

-continued

| ID | Formula | Exact Mass | [M + nH]^n+ found | [M + nH]^n+ calc'd | calc'd for |
|---|---|---|---|---|---|
| 9290 | C49H85N13O9 | 999.6593 | 500.7 | 500.8370 | [C49H87N13O9]2+ |

6Me-nC6CO-D-Dab-cyc[L-Dab-L-Dab-L-Dab-D-Phe-L-Leu-L-Dab-L-Dab-L-Leu]

| ID | Formula | Exact Mass | [M + nH]^n+ found | [M + nH]^n+ calc'd | calc'd for |
|---|---|---|---|---|---|
| 9291 | C49H85N13O10 | 1015.6542 | 508.7 | 508.8344 | [C49H87N13O10]2+ |

3(R)OH-nC9CO-D-Dap-cyc[L-Dab-L-Dab-D-Phe-L-Val-L-Dab-L-Dab-L-Leu]

-continued

| ID | Formula | Exact Mass | [M + nH]^n+ found | [M + nH]^n+ calc'd | calc'd for |
|---|---|---|---|---|---|
| 9292 | C48H83N13O10 | 1001.6385 | 501.8 | 501.8266 | [C48H85N13O10]2+ |

Structure: 3(R)OH-nC9CO-D-Dap-cyc[L-Dab-L-Dab-D-Phe-L-Abu-L-Dab-L-Dab-L-Leu]

-continued

| ID | Formula | Exact Mass | [M + nH]$^{n+}$ found | [M + nH]$^{n+}$ calc'd | calc'd for |
|---|---|---|---|---|---|
| 9293 | C49H85N13O10 | 1015.6542 | 508.7 | 508.8344 | [C49H87N13O10]2+ |

3(R)OH-nC9CO-D-Dap-cyc[L-Dab-L-Dab-D-Phe-L-NorVal-L-Dab-L-Dab-L-Leu]

| ID | Formula | Exact Mass | [M + nH]$^{n+}$ found | [M + nH]$^{n+}$ calc'd | [M + nH]$^{n+}$ calc'd for |
|---|---|---|---|---|---|
| 9294 | C50H87N13O10 | 1029.6698 | 515.7 | 515.8422 | [C50H89N13O10]2+ |

3(R)OH-nC9CO-D-Dap-cyc[L-Dab-L-Dab-D-Phe-L-NorLeu-L-Dab-L-Dab-L-Leu]

| ID | Formula | Exact Mass | [M + nH]^n+ found | [M + nH]^n+ calc'd | calc'd for |
|---|---|---|---|---|---|
| 9295 | C48H83N13O11 | 1017.6335 | 509.8 | 509.8241 | [C48H85N13O11]2+ |

3(R)OH-nC9CO-D-Dap-cyc[L-Dab-L-Dab-D-Phe-L-Thr-L-Dab-L-Dab-L-Leu]

| ID | Formula | Exact Mass | [M + nH]^{n+} found | [M + nH]^{n+} calc'd | calc'd for |
|---|---|---|---|---|---|
| 9296 | C51H89N13O9 | 1027.6906 | 515.1 | 514.8526 | [C51H91N13O9]2+ |
| 9297 | C52H91N13O9 | 1041.7062 | 521.9 | 521.8604 | [C52H93N13O9]2+ |
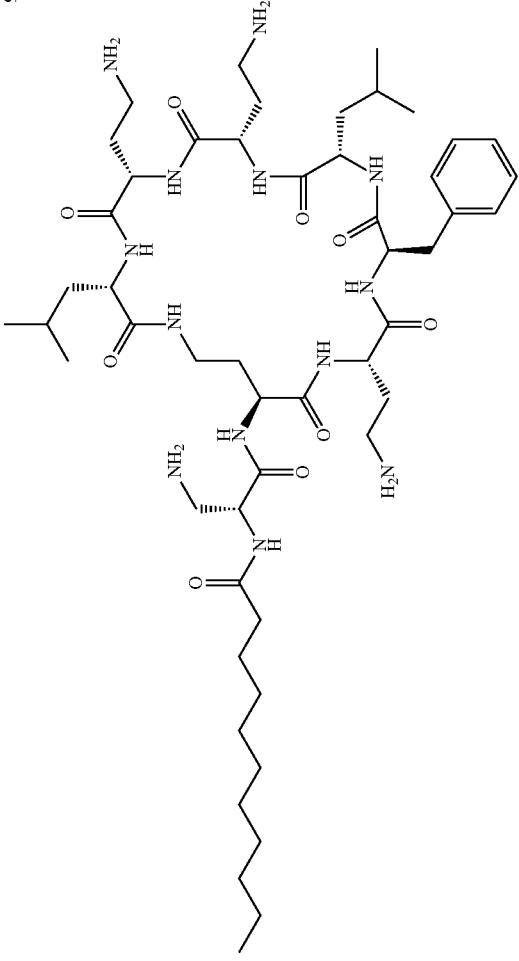
nC10CO-D-Dap-cyc[L-Dab-L-Dab-D-Phe-L-Leu-L-Dab-L-Dab-L-Leu]
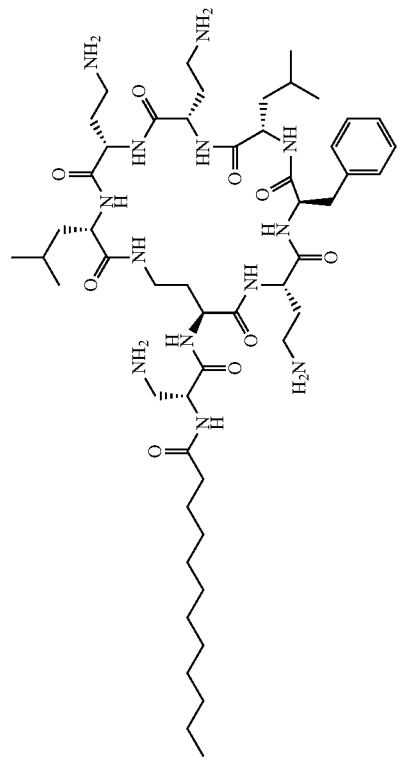
nC11CO-D-Dap-cyc[L-Dab-L-Dab-D-Phe-L-Leu-L-Dab-L-Dab-L-Leu]

| ID | Formula | Exact Mass | [M + nH]^n+ found | [M + nH]^n+ calc'd | calc'd for |
|---|---|---|---|---|---|
| 9416 | C50H88N14O10 | 1044.6807 | 523.4 | 523.3477 | [C50H90N14O10]2+ |

3(R)OH-nC9CO-D-Dab-cyc[L-Dab-L-Dab-L-Dab-D-Phe-L-Leu-L-Dab-L-Dab-(aza-Leu)]

| ID | Formula | Exact Mass | [M + nH]$^{n+}$ found | [M + nH]$^{n+}$ calc'd | calc'd for |
|---|---|---|---|---|---|
| 9417 | C50H88N14O10 | 1044.6807 | 523.3 | 523.3477 | [C50H90N14O10]2+ |
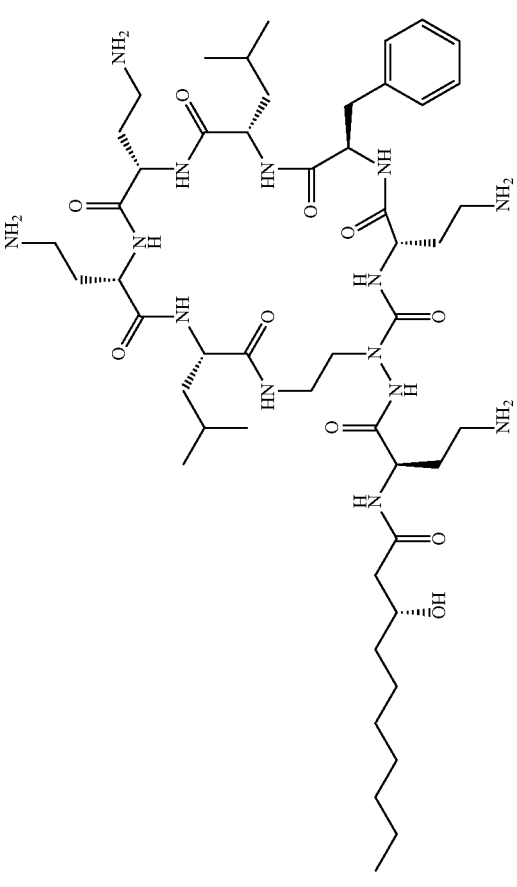
3(R)OH-nC9CO-D-Dab-cycl(aza-Dab)-L-Dab-D-Phe-L-Leu-L-Dab-L-Leu]

Minimum Inhibitory Concentration (MIC) Determination

Bacteria were either obtained from American Type Culture Collection (ATCC; Manassas, Va., USA) or independent academic clinical isolate collections, as listed in Table 18 below. Bacteria were cultured in Nutrient broth (NB; Bacto Laboratories, catalogue No. 234000) or Mueller Hinton broth (MHB; Bacto Laboratories, catalogue No. 211443) at 37° C. overnight with shaking (~180 RPM). A sample of each culture was then diluted 50-fold in fresh MHB and incubated at 37° C. for 2-3 h with shaking (~180 RPM). Compound stock solutions were prepared as 0.64 mg/mL or 2.56 mg/mL in water. The compounds, at twice the final desired concentration, were serially diluted 2-fold across the wells of 96-well plates (Polystyrene, Corning, catalogue No. 3370). Mid-log phase bacterial cultures (after 2-3 h incubation) were diluted to a final concentration of $1\times10^6$ colony forming units (CFU)/mL, and 50 µL was added to each well giving a final cell density of $5\times10^5$ and a compound concentration range of 32 µg/mL to 0.015 µg/mL (128-0.06 µg/mL against P. aeruginosa PA9704). MICs were determined visually after 20-24 hours of incubation at 37° C., with the MIC defined as the lowest compound concentration at which no bacterial growth was visible.

Potentiation/synergy antimicrobial assays were conducted in the same manner as the standard MICs described above, with the following modifications. Assays were performed in 384-well non-binding surface plates (NBS; Corning 3460) and in Cation-adjusted Mueller Hinton Broth (CA-MHB; BD, Cat. No. 212322) with a final assay volume of 50 µL once bacteria was added at $5\times10^5$ CFU/mL. Antibiotics and octapeptin compounds were plated in duplicate as a 2-fold concentration series, in a matrix checkerboard format. The bacterial cell density of the resultant assay plates after 18-20 h incubation at 37° C. was read by optical density 600 nm (OD600) using a Tecan M1000 Pro Spectrophotometer, and analysed for ≥90% growth inhibition compared to the growth control to determine active concentrations. Synergistic effect was calculated based on the fractional inhibitory concentration index (FICI) by the following equation, where synergy is deemed FICI 0.5:

$$FICI = \frac{MIC\ cpdA\ \text{in combination}}{MIC\ cpdA\ \text{alone}} + \frac{MIC\ cpdB\ \text{in combination}}{MIC\ cpdB\ \text{alone}}$$

TABLE 18

Bacterial strains used for Minimum Inhibitory Concentration (MIC) determinations.

| Organism | Strain | Strain description | Strain Source |
|---|---|---|---|
| Escherichia coli | ATCC 25922 | FDA strain Seattle 1946 | ATCC |
| Escherichia coli | GN_007 | ESBL | Clinical pathology laboratory |
| Escherichia coli | GN_181 | mcr-1, ESBL/CTX-M | Clinical pathology laboratory |
| Klebsiella pneumoniae | ATCC 13883 | Type strain | ATCC |
| Klebsiella pneumoniae | ATCC 700603 | K6, ESBL (SHV-18) | ATCC |
| Klebsiella pneumoniae | BAA-2146 | NDM-1 (New Delhi Metallo-beta-lactamase-1) positive | ATCC |
| Acinetobacter baumannii | ATCC 19606 | Type strain | ATCC |
| Acinetobacter baumannii | GN_019 | Clinical isolate, Carbapenem resistant | Clinical pathology laboratory |
| Acinetobacter baumannii | GN_093 | Clinical isolate, Carbapenem, & polymyxin resistant | Clinical pathology laboratory |
| Pseudomonas aeruginosa | ATCC 27853 | Control strain | ATCC |
| Pseudomonas aeruginosa | GN_043 | Clinical isolate, polymyxin resistant | Clinical pathology laboratory |
| Pseudomonas aeruginosa | PA9704 | Clinical isolate, polymyxin resistant | Clinical pathology laboratory |
| Acinetobacter baumannii | GN_093 | Clinical isolate, Carbapenem & polymyxin resistant | Clinical pathology laboratory |
| Klebsiella pneumoniae | GN_102 | Clinical isolate, Carbapenem, & polymyxin resistant | Clinical pathology laboratory |
| Klebsiella pneumoniae | GN_106 | Clinical isolate, Carbapenem, & polymyxin resistant | Clinical pathology laboratory |
| Staphylococcus aureus | ATCC 25923 | MSSA (methicillin Susceptible S. aureus) | ATCC |

Cytotoxicity Methodology: HK2 LDH Assay

Cytotoxicity of the synthesised peptides was evaluated by comparison with commercially available colistin (polymyxin E), polymyxin B (Sigma chemical Co., St. Louis, Mo., U.S.A.) and synthetic octapeptin C4 by conducting lactate dehydrogenase (LDH) assay. $CC_{50}$ values calculated based on curve fitting of dose dependent inhibition of cell growth represented the cytotoxicity of the peptide. Human kidney 2 (HK2) cells were seeded as 2000 cells per well in a 384 well cell culture plate in a final volume of 20 µL in DMEM/F12 medium (Invitrogen #11330057), in which 10% of FBS was added. Cells were incubated for 24 hours at 37° C., 5% CO2 to allow cells to attach to the plates. Similar conditions were employed for HEK293 and HepG2 cytotoxicity assays.

Colistin and polymyxin B were tested from a range of 2 mM to 0.9 µM. 120 µL of the 1 mM stock solutions in water of each synthesised peptide were freeze-dried and processed for LDH assay. After freeze-dry procedure, the compounds were reconstituted into 600 µM solutions using culture media. All tested compounds were diluted from 600 µM to 0.27 µM in 3-fold dilutions. Then 20 µL of each dilution was added into 20 uL of culture medium in quadruplicate to reach the final concentrations. The cells were incubated with the compounds for 24 h at 37° C., 5% $CO_2$. After the incubation, 5 µL of culture medium was added to 50 µL of LDH assay buffer and incubated for 1 h at room temperature. The absorbance was read at 450 nm using Polarstar. The data was then analysed by Prism software. Results are presented as the average percentage of control×SD for each set of quadruplicated wells using the following equation: cytotoxicity %=(ABSsamples−ABSuntreated/ABS 1% Triton X-100−ABSuntreated)*100. Nephrotoxicity Assessment in Human Proximal Tubule Cells.

Cytotoxicity Methodology: Resazurin Assay

Cytotoxicity to HEK293 and HepG2 cells was determined using the resazurin assay (McMillian, M. K.; Li, L.; Parker, J. B.; Patel, L.; Zhong, Z.; Gunnett, J. W.; Powers, W. J.; Johnson, M. D. An improved resazurin-based cytotoxicity assay for hepatic cells; *Cell Biol. Toxicol.* 2002, 18, 157-173; O'Brien, J.; Wilson, I.; Orton, T.; Pognan, F. Investigation of the Alamar Blue (resazurin) fluorescent dye for the assessment of mammalian cell cytotoxicity. *Eur. J. Biochem.* 2000, 267, 5421-5426). In brief, HEK293 and HepG2 cells were seeded at 4000 cells/well in black-wall, clear-bottom 384-well plates (Corning, Australia) and incubated for 24 h at 37° C., 5% $CO_2$. Compounds were then added into each well. After 24 h incubation, 5 µM resazurin was added per well and incubated at 37° C. for 2 h. Fluorescence intensity was then read using a Polarstar Omega with excitation/emission 560/590. The data was then analyzed using GraphPad Prism 6 software. CC50 values were determined using GraphPad Prism 6 software (Inc. La Jolla, Calif.).

Isolation and Culture of hPT Cells hPT cells were derived from whole human kidneys procured by the International Institute for the Advancement of Medicine (Edison, N.J., USA). All tissue was scored by a pathologist as normal (i.e., derived from non-cancerous, non-diseased tissue). Cell isolation procedures were based on those originally described by Todd et al. (1996) and modified (Cummings and Lash, 2000; Cummings et al., 2000) with use of sterile conditions (i.e., all instruments and glassware were autoclaved and all buffers were filtered through a 0.2-µm pore-size filter). Renal cortex and outer stripe were cut into slices, washed with sterile PBS, minced, and the pieces were placed in a trypsinization flask filled with 300 ml of sterile, filtered Hanks' buffer, containing 25 mM $NaHCO_3$, 25 mM HEPES, pH 7.4, 0.5 mM EGTA, 0.2% (w/v) bovine serum albumin, 50 µg/ml gentamicin, 1.3 mg/mL collagenase, and 0.59 mg/ml $CaCl_2$), which was filtered prior to use. Whole kidneys were perfused with Wisconsin medium and kept on ice until they arrived at the laboratory, which was usually within 24 h of removal from the donor.

All buffers were continuously bubbled with 95% $O_2$/5% $CO_2$ and were maintained at 37° C. Minced cortical pieces from whole kidneys were subjected to collagenase digestion for 60 min, after which the supernatant was filtered through a 70-µm mesh filter to remove tissue fragments, centrifuged at 150×g for 7 min, and the pellet resuspended in Dulbecco's Modified Eagle's Medium: Ham's F12 Medium (DMEM/F12; 1/1). Approximately 5 to 7×10$^6$ cells were obtained per 1 g of human kidney cortical tissue.

hPT cells were resuspended in 2 mL of DMEM/F12 and diluted to 500 mL with cell culture medium, which was serum-free and hormonally-defined. Composition of this supplemented medium was based on earlier work establishing optimal conditions for primary culture of rat PT cells (Lash et al., 1995). Basal medium was a 1:1 mixture of DMEM/F12. Standard supplements included 15 mM HEPES, pH 7.4, 20 mM $NaHCO_3$, antibiotics for day 0 through day 3 only (192 IU penicillin G/mL+200 µg streptomycin sulfate/ml or 50 µg gentamicin/ml) to inhibit bacterial growth, 2.5 µg amphotericin B/mL to inhibit fungal growth, 5 µg bovine insulin/mL (=0.87 µM), 5 µg human transferrin/ml (=66 nM), 30 nM sodium selenite, 100 ng hydrocortisone/ml (=0.28 µM), 100 ng epidermal growth factor/mL (=17 nM), and 7.5 pg 3,3',5-triiodo-DL-thyronine/ml (=111 nM). Cells were seeded in a volume of 0.5 ml at a density of 50-100 µg protein per cm$^2$ (0.5-1.0×10$^6$ cells/ml) on 24-well plates. Cultures were grown at 37° C. in a humidified incubator under an atmosphere of 95% air/5% CO2 at pH 7.4. Cultures were grown to approximately 80%-90% confluence (generally 5-6 days) prior to experiments. Cells were harvested by either scraping the flasks with a Teflon scraper or by brief incubation with Cellstripper (Cellgro, Herndon, Va., USA) (in $Ca^{2+}$- and $Mg^{2+}$-free Hanks' buffer).

KIM-1 and NGAL: ELISA Assay

KIM-1 (DY1750), and NGAL (DY1757)) Duo-Set® ELISA kits were purchased from R&D systems (Minneapolis, Minn., USA). Sandwich-ELISA experiments were conducted following the manufacturer's instructions with slight modifications. A 96-well microplate (MaxiSorp®, Nunc) was coated with 100 µL of capture antibodies (diluted 1:200 in PBS) and incubated overnight. The plate was then washed twice with washing buffer (0.05% Tween 20 in PBS, pH 7.4) and blocked by adding 300 µL of blocking buffer (1% BSA in PBS) for 1 h at room temperature. After washing two times with PBS, 100 µl of samples (cell culture media or cell lysates) or standards were then added to each well and incubated for 2 h at room temperature. The biotinylated detection antibodies were then diluted in blocking buffer, added to each well and incubated for 2 h. Horseradish peroxidase (HRP)-labeled streptavidin (100 µL) was then added to bind to detection antibodies. To each well, 100 µL of substrate solution (1:1 mixture of $H_2O_2$ and tetramethylbenzidine) was added and incubated for 20 min before reaction termination with 50 µL of stop solution (2N $H_2SO_4$). The optical density of each well was measured at 450 nm using a POLARstar Omega plate reader (BMG Labtech; Mornington VIC, Australia). All assays were performed at least three times.

Assay of Gamma-Glutamyltransferase:

Release of gamm-glutanyltransferase was assessed according to Orlowski, M., Meister, A. 1963. γ-Glutamyl-p-nitroanilide: A new convenient substrate for determination and study of L- and D-γ-glutamyltranspeptidase activities (Biochim. Biophys. Acta 73: 679-681.)

A 2.5 mM substrate Solution was prepared from 67 mg γ-glutamyl-p-nitroanilide+264 mg glycylglycine in 100 mL of 0.05 M Tris, pH 8.2 (50 mM Tris, pH 8.2: 605 mg Tris/HCl per 100 mL).

For the assay in 96-well plates, 6-µL of sample and 0.3 mL substrate solution were added to each well. The absorbance was measured at 410 nm for the appearance of product, p-nitroanilide (molar extinction=8800 $M^{-1}$ $cm^{-1}$).

Mouse Pharmacokinetic Study

Male 6-9 week old CD-1 mice (3 per test group) were acclimated at the test facility for at least 3 days prior to the study. Animals were group housed during acclimation and individually housed during the study. The animal room environment was controlled (target conditions: temperature 20 to 26° C., relative humidity 30 to 70%, 12 hours artificial light and 12 hours dark). Temperature and relative humidity were monitored daily.

Animals were fasted at least 12 hours prior to the administration. All animals have access to Certified Rodent Diet. Water was autoclaved before provided to the animals ad libitum. Body weights were determined before selection to the study and on the day of dose administration. Cage-side observations for general health and appearance were done on the dosing day. The animals were observed at each sample collection time point and at each dosing time point. Any unusual observations noted throughout the duration of the study were recorded.

Appropriate amount of test article was accurately weighed and mixed with appropriate volume of vehicle to get a clear solution or a uniform suspension, with vortexing or sonication in water bath if needed. Solutions for IV dosing were sterile filtered through a 0.45 µM filter before dosing. Animals were dosed within four hours after the formulation was prepared, with formulation samples removed from each of the formulation solutions or suspensions, transferred into 1.5 mL of polypropylene microcentrifuge tubes and run dose validation by LC/UV or LC-MS/MS.

For SC dosing, the dose formulation was administered via subcutaneous following facility SOPs. For IV dosing, the dose formulation was administered via tail vein. The dose volume was determined by the animals' body weight collected on the morning of dosing day.

Blood Collection: Each blood collection (about 0.03 mL per time point) was performed from tail vein or saphenous vein of each animal into polypropylene tubes at each timepoint. Each PP tube contained 2 µL of EDTA-K2 as anticoagulant. Collected blood was stored in wet ice before centrifugation.

Plasma Processing: Each collected blood sample was centrifuged for 15 minutes at 4° C. and 3000 g for plasma collection. Plasma was collected and transferred into a pre-labeled PP tube in wet ice. After terminal collection, all plasma samples were stored at approximately −80° C. Freezer until delivered for bioanalysis.

Bioanalytical Method and Sample Analysis: LC-MS/MS methods for the quantitative determination of test compound in corresponded biological matrix were developed under non-GLP compliance. A benchtop stability of the test article in animal plasma was determined at mid QC concentrations in triplicate at 0, 2 hours at room temperature. The stability was determined using mean peak area ratio of T2/T0 sample. If the mean peak area ratio was within 80%-120%, the test article in the plasma was considered stable for 2 hours at room temperature. A calibration curve with 8 non-zero calibration standards was applied for the method development including determination of the LLOQ. A set of QC samples consisting of low, middle, and high concentrations was used for the method development. The study sample analysis was performed concurrently with a set of calibration standards and two sets of QC samples using the LC-MS/MS method.

For plasma samples: An aliquot of 8 µL sample was added to 16 µL water with 0.1% FA water, vortex-mixed well, and then protein precipitated with 64 µL IS Solution, the mixture was vortex-mixed well and centrifuged at 13000 rpm for 10 min. 70 µL supernatant was then mixed with 70 µL ACN/water (v:v, 20:80) with 0.1% FA, then vortex-mixed well for 10 min. 10 µL supernatant was injected for LC-MS/MS analysis. Samples were run on an AB Sciex Triple Quad 5500 LC/MS/MS.

Data Analysis: Plasma concentration versus time data was analyzed by non-compartmental approaches using the Phoenix WinNonlin 6.3 software program. CI, Vdss, C0, Cmax, Tmax, T½, AUC(0-t), AUC(0-inf), MRT(0-t), MRT(0-inf), % F and graphs of plasma concentration versus time profile were determined.

Mouse Thigh Infection Model.

Polymyxin B (MCC_000636:003), MCC_006442:003, and MCC_000631:008 were tested in the *Escherichia coli* ATCC 25922 thigh infection model with neutropenic mice. Test animals were intramuscularly infected with *E. coli* ATCC 25922, 8.1×104 CFU/mouse (0.1 mL/thigh).

Groups of 5 male ICR mice weighing 22+/−2 g were used. Immune suppression was induced by two intraperitoneal injections of cyclophosphamide, the first dose at 150 mg/kg 4 days before infection (Day −4) and the second one at 100 mg/kg 1 day before infection (Day −1). On Day 0, animals were intramuscularly inoculated (0.1 mL/thigh) with the targeted inoculum size at 1.0×105 CFU/mouse (the actual inoculum sizes were 8.1×104 CFU/mouse) of *E. coli* (ATCC 25922) into the right thigh. Three dosing regimens of MCC_006442:003 were evaluated. MCC_006442:003 at 25 and 40 mg/kg were administrated subcutaneously (SC) once daily (QD) 2 hour post infection, and MCC_006442:003 at 25 mg/kg was administrated SC twice daily (BID) 2 and 8 hours post infection. Polymyxin B (MCC_000636:003) and MCC_000631:008 were administrated SC at 25 mg/kg once daily (QD) 2 hour post infection. The reference compound gentamicin at 10 mg/kg was administered SC twice (BID) 2 and 8 hr post-infection. An additional study compared intravenous dosing, with polymyxin B, octapeptin $C_4$ and MCC_006442 dosed at 5 mg/kg QD, with an additional test of MCC_006442 dosed at 10 mg/kg QD, and control gentamicin at 10 mg/kg was administered SC twice (BID) 2 and 8 hr post-infection.

The tested animals were humanely euthanized by $CO_2$ asphyxiation 26 hr post-inoculation and thigh tissues were harvested and weighed. The thigh tissue was homogenized in 3 mL sterile PBS (pH 7.4) and then 10-fold serial dilutions were generated. Aliquots of the dilutions (100 µL) were separately plated onto nutrient broth medium with 1.5% Bacto agar. The bacterial counts (CFU/g) in thigh tissues were calculated and the percentage decrease in counts compared to the corresponding vehicle control was calculated with the following formula:

$$\text{Decrease (\%)} = [(\text{CFU/g of vehicle} - \text{CFU/g of treatment})/(\text{CFU/g of vehicle})] \times 100\%$$

A two-log reduction in bacterial count (≥99% reduction) indicates significant activity according to our in-house significance criterion. Statistical significance ($p<0.05$) was also assessed with one-way ANOVA followed by Dunnett's method Subcutaneous administrations of polymyxin B (MCC_000636:003) at 25 mg/kg QD, MCC_006442:003 at 25 mg/kg QD, 25 mg/kg BID and 40 mg/kg QD, and MCC_000631:008 at 25 mg/kg QD resulted in significant antimicrobial effects (2-log reduction and $p<0.05$) in bacterial counts relative to the 26 hr vehicle control group (See Table and Figure). Significant antimicrobial activity was also observed with the subcutaneous administration of gentamicin, consistent with historical data. Compounds were also efficacious when dosed at 5 mg/kg intravenously.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:
1. A compound of formula (I), or a salt or stereoisomer thereof:

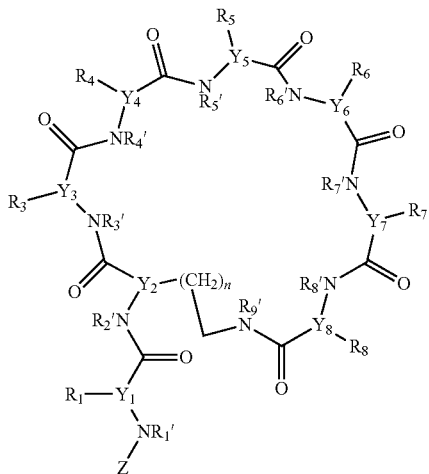

Formula (I)

wherein, $Y_1$, $Y_2$, $Y_3$, $Y_4$, $Y_5$, $Y_6$, $Y_7$ and $Y_8$ are independently selected from the group consisting of CH and N;

$R_1$, $R_3$, $R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; wherein $R_8$ is not

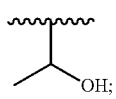

wherein $R_4$ is selected from the group consisting of:

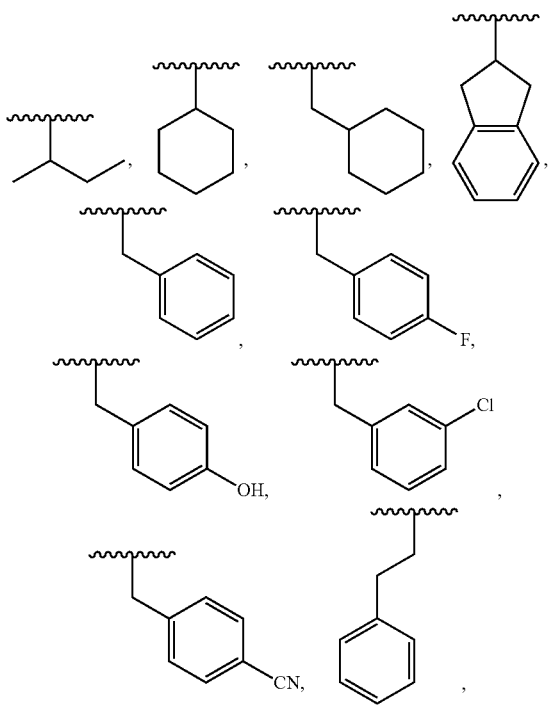

-continued

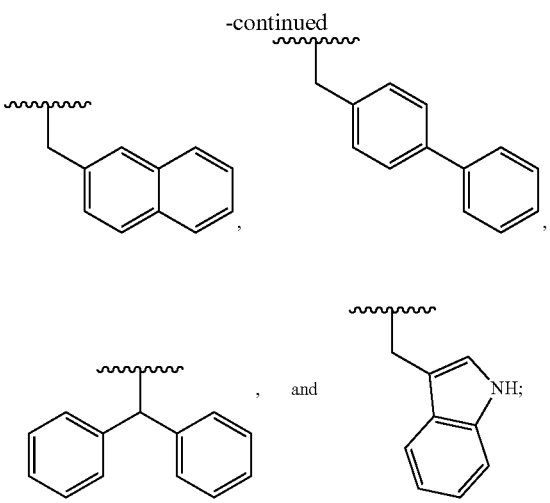

$R_1'$, $R_2'$, $R_3'$, $R_4'$, $R_5'$, $R_6'$, $R_7'$, $R_8'$ and $R_9'$ are independently selected from the group consisting of hydrogen and substituted or unsubstituted alkyl, or each pair of $R_1'$ and $R_1$, $R_3'$ and $R_3$, $R_5'$ and $R_5$, $R_6'$ and $R_6$, $R_7'$ and $R_7$, and $R_8'$ and $R_8$ may be linked via an alkylene;

n is an integer selected from 0 or 1; and

Z is selected from

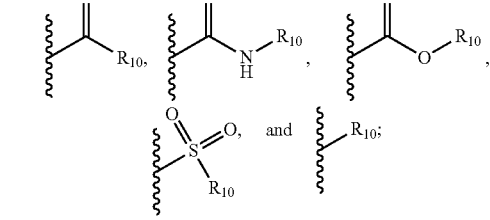

wherein $R_{10}$ is selected from the group consisting of hydrogen, alkyl, alkenyl, cycloalkyl, cycloalkenyl, heterocyclyl, aryl and heteroaryl, each of which groups may be substituted or unsubstituted; wherein Z does not comprise more than one (1) peptide linkage or bond, and wherein Z does not have the structure

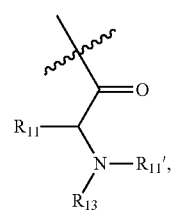

wherein $R_{11}$, $R_{11}'$, and $R_{13}$ are independently selected from the group consisting of hydrogen, alkyl, alkenyl, cycloalkyl, cycloalkenyl, heterocyclyl, aryl and heteroaryl, each of which groups may be substituted or unsubstituted;

wherein, when $R_4$ is

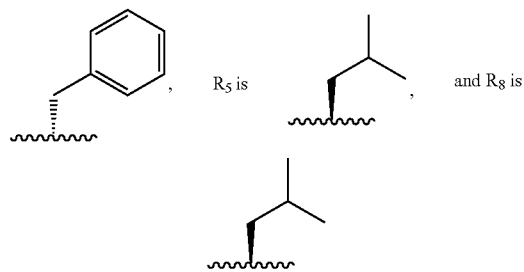

then Z is not selected from the group consisting of

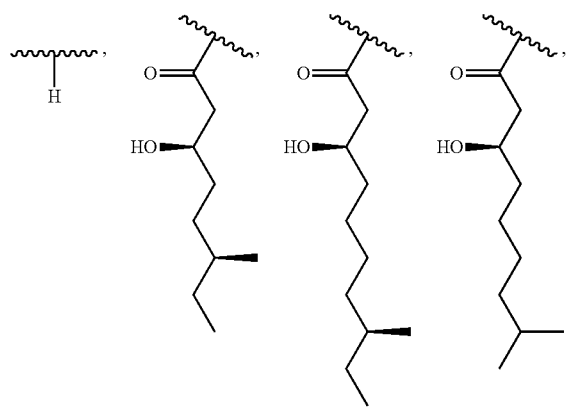

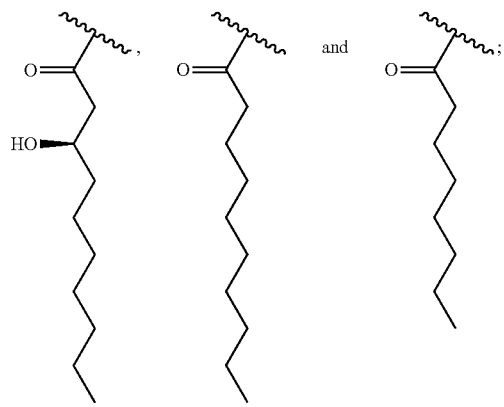

and when $R_4$ is

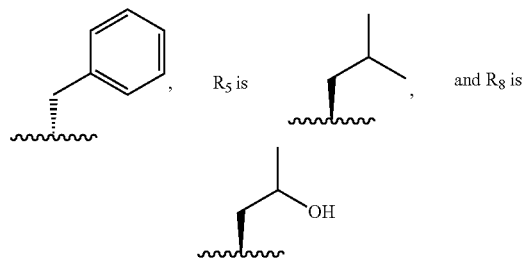

then Z is not selected from the group consisting

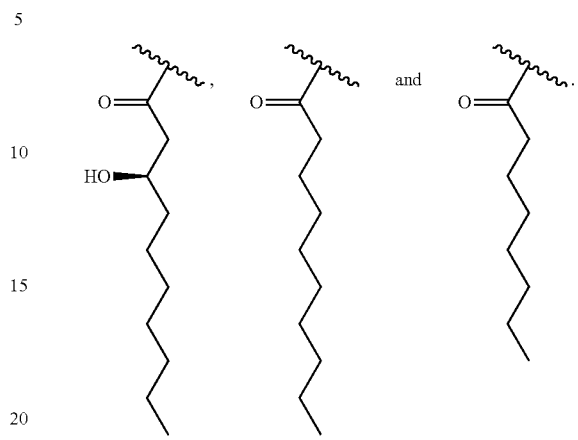

2. The compound of claim 1, wherein the compound is a compound of formula (Ib):

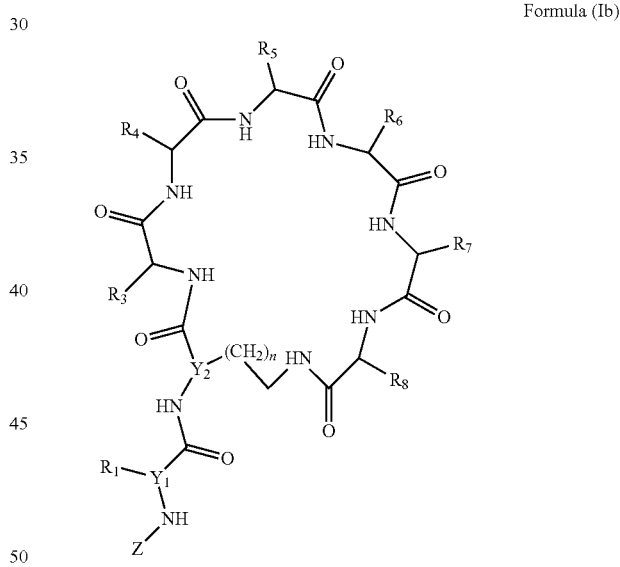

Formula (Ib)

wherein, $Y_1$ and $Y_2$ are independently selected from the group consisting of CH and N;

$R_5$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; wherein $R_8$ is not

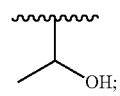 [SMILES: *C(C)O]

$R_1$ is selected from the group consisting of:

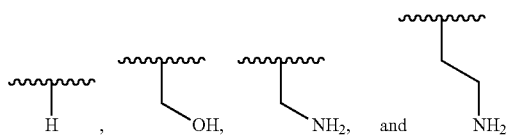

$R_3$ is

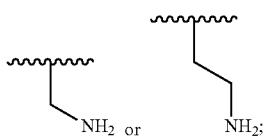

$R_6$ is selected from the group consisting of:

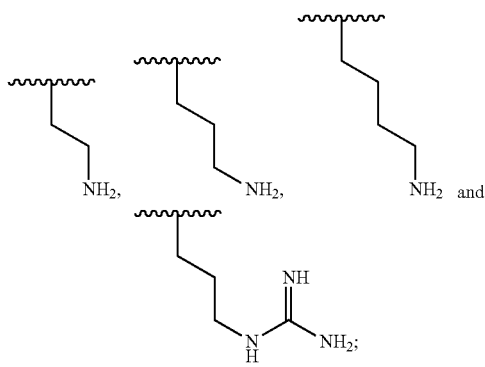

$R_7$ is selected from the group consisting of:

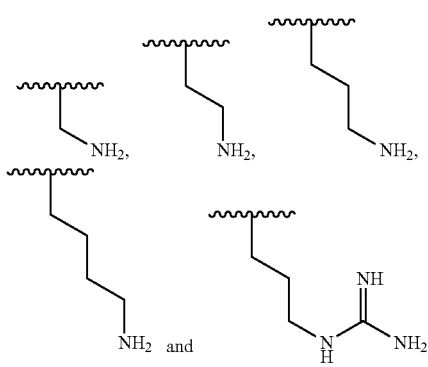

n is 1; and
Z is selected from

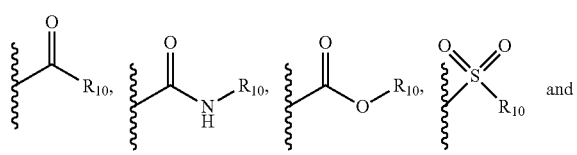

-continued

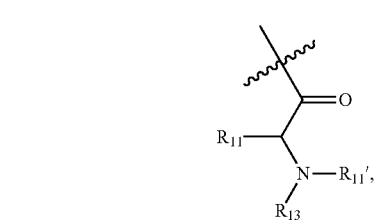

wherein
$R_{10}$ is selected from the group consisting of alkyl, alkenyl, cycloalkyl, cycloalkenyl, heterocyclyl, aryl and heteroaryl, each of which groups may be substituted or unsubstituted; wherein Z does not comprise more than one (1) peptide linkage or bond, and
wherein Z does not have the structure

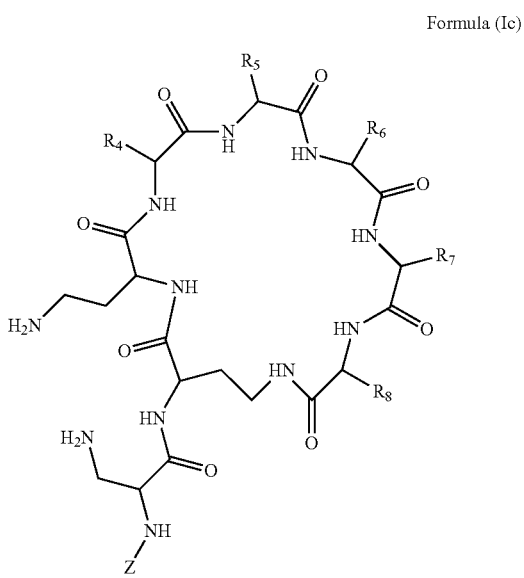

wherein $R_{11}$, $R_{11}'$, and $R_{13}$ are independently selected from the group consisting of hydrogen, alkyl, alkenyl, cycloalkyl, cycloalkenyl, heterocyclyl, aryl and heteroaryl, each of which groups may be substituted or unsubstituted.

3. The compound of claim 1, wherein the compound is a compound of formula (Ic):

Formula (Ic)

wherein,
$R_5$, $R_6$, $R_7$ and $R_8$ are independently selected from the group consisting of hydrogen, alkyl, alkenyl, cycloalkyl, cycloalkenyl, heterocyclyl, aryl and heteroaryl, each of which groups may be substituted or unsubstituted; wherein $R_8$ is not

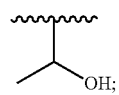 [SMILES: *C(C)O]

and

Z is selected from

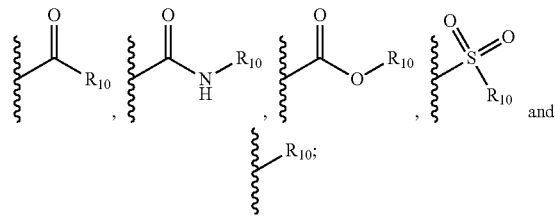

wherein

R$_{10}$ is selected from the group consisting of hydrogen, alkyl, alkenyl, cycloalkyl, cycloalkenyl, heterocyclyl, aryl and heteroaryl, each of which groups may be substituted or unsubstituted; wherein Z does not comprise more than one (1) peptide linkage or bond, and wherein Z does not have the structure

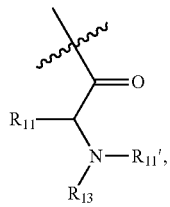

wherein R$_{11}$, R$_{11}$', and R$_{13}$ are independently selected from the group consisting of hydrogen, alkyl, alkenyl, cycloalkyl, cycloalkenyl, heterocyclyl, aryl and heteroaryl, each of which groups may be substituted or unsubstituted.

4. The compound of claim 3, wherein the compound is a compound of formula (Id):

Formula (Id)

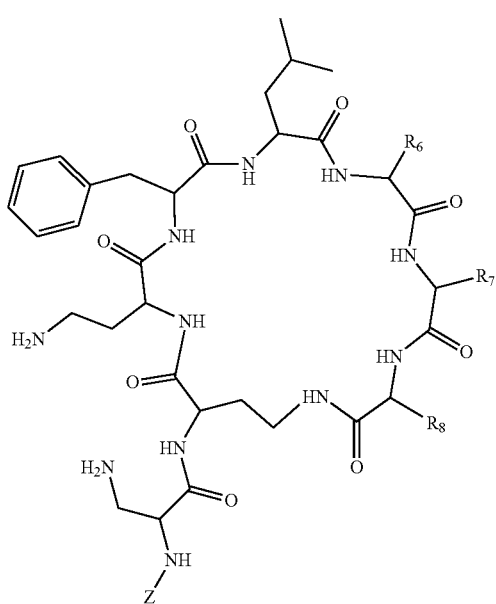

wherein

R$_6$, R$_7$, and R$_8$ are independently selected from the group consisting of hydrogen, alkyl, alkenyl, cycloalkyl, cycloalkenyl, heterocyclyl, aryl and heteroaryl, each of which groups may be substituted or unsubstituted; wherein R$_8$ is not

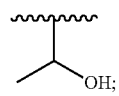

and

Z is selected from

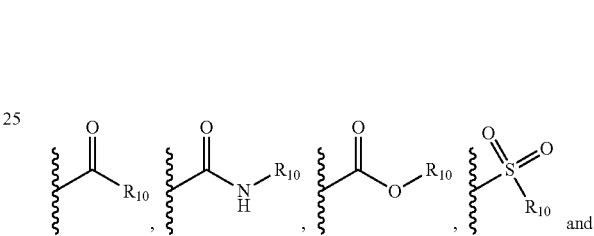

wherein

R$_{10}$ is selected from the group consisting of hydrogen, alkyl, alkenyl, cycloalkyl, cycloalkenyl, heterocyclyl, aryl and heteroaryl, each of which groups may be substituted or unsubstituted; wherein Z does not comprise more than one (1) peptide linkage or bond, and wherein Z does not have the structure

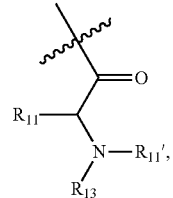

wherein R$_{11}$, R$_{11}$', and R$_{13}$ are independently selected from the group consisting of hydrogen, alkyl, alkenyl, cycloalkyl, cycloalkenyl, heterocyclyl, aryl and heteroaryl, each of which groups may be substituted or unsubstituted.

5. The compound of claim 1, wherein the compound is a compound of formula (Ig):

515

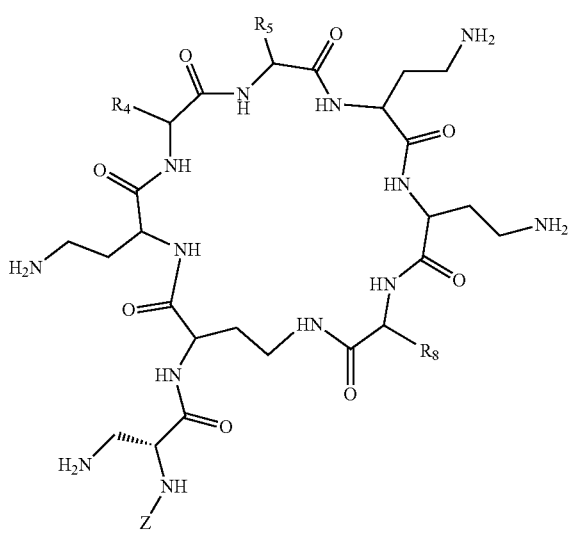

Formula (Ig)

wherein,
R₅ and R₈ are independently selected from the group consisting of hydrogen, alkyl, alkenyl, cycloalkyl, cycloalkenyl, heterocyclyl, aryl and heteroaryl, each of which groups may be substituted or unsubstituted; wherein R₈ is not

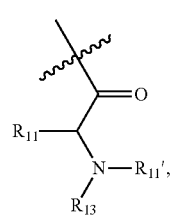

and
Z is selected from

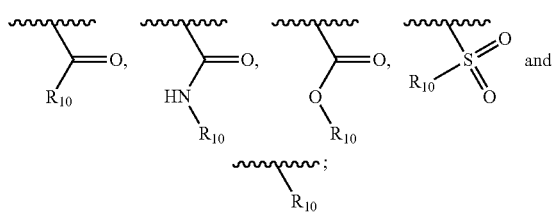

wherein
R₁₀ is selected from the group consisting of hydrogen, alkyl, alkenyl, cycloalkyl, cycloalkenyl, heterocyclyl, aryl and heteroaryl, each of which groups may be substituted or unsubstituted; wherein Z does not comprise more than one (1) peptide linkage or bond, and wherein Z does not have the structure

516 wherein $R_{11}$, $R_{11}'$, and $R_{13}$ are independently selected from the group consisting of hydrogen, alkyl, alkenyl, cycloalkyl, cycloalkenyl, heterocyclyl, aryl and heteroaryl, each of which groups may be substituted or unsubstituted.

6. The compound of claim 2, wherein R₄ is selected from the group consisting of

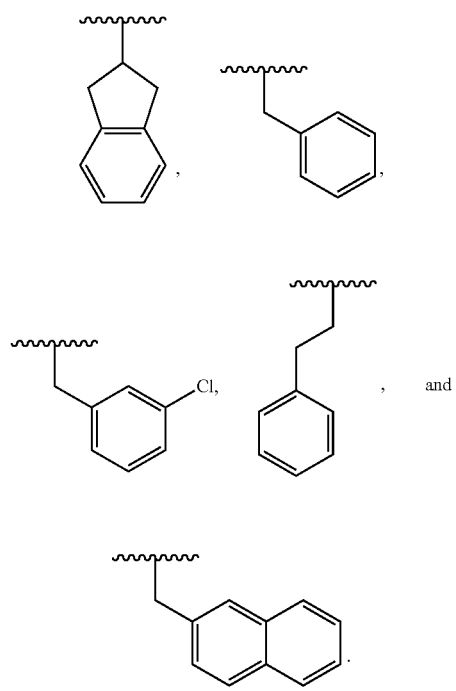

7. The compound of claim 2, wherein R₅ is selected from the group consisting of hydrogen, C1-C6 alkyl, C1-C6 amine, C1-C6 amide, C3-C10 cycloalkyl, heterocyclic, aryl and heteroaryl, each of which groups may be substituted or unsubstituted.

8. The compound of claim 7, wherein R₅ is selected from the group consisting of:

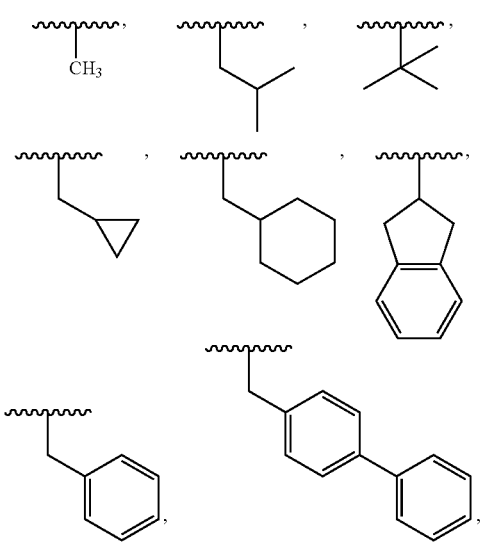

517
-continued

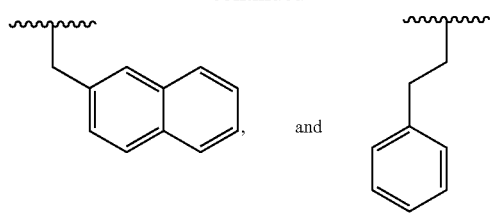

9. The compound of claim 2, wherein $R_8$ is C1-C6 alkyl.

10. The compound of claim 2, wherein $R_8$ is selected from the group consisting of:

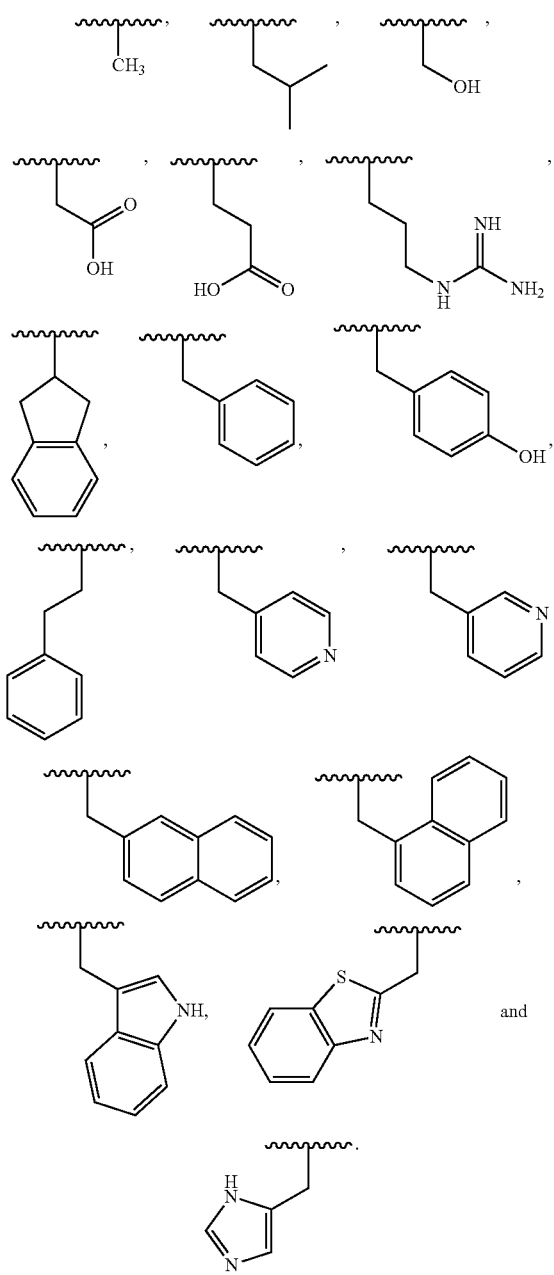

518

11. The compound of claim 3, wherein Z is

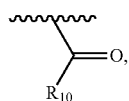

wherein $R_{10}$ is selected from C1-C18 alkyl, C2-C18 alkenyl, C1-C6 cycloalkyl, heterocyclyl, aryl and heteroaryl, each of which groups may be substituted or unsubstituted; wherein Z does not comprise more than one (1) peptide linkage or bond, and wherein $R_{10}$ does not have the structure

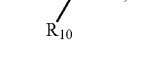

wherein $R_{11}$, $R_{11}'$, and $R_{13}$ are independently selected from the group consisting of hydrogen, alkyl, alkenyl, cycloalkyl, cycloalkenyl, heterocyclyl, aryl and heteroaryl, each of which groups may be substituted or unsubstituted.

12. The compound of claim 11, wherein $R_{10}$ is a substituted or unsubstituted C1-C13 alkyl group: wherein Z does not comprise more than one (1) peptide linkage or bond, and wherein $R_{10}$ does not have the structure

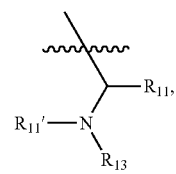

wherein $R_{11}$, $R_{11}'$, and $R_{13}$ are independently selected from the group consisting of hydrogen, alkyl, alkenyl, cycloalkyl, cycloalkenyl, heterocyclyl, aryl and heteroaryl, each of which groups may be substituted or unsubstituted.

13. A pharmaceutical composition comprising a compound of claim 1, or a salt or stereoisomer thereof, and a pharmaceutically acceptable carrier, diluent and/or excipient.

14. The pharmaceutical composition of claim 13 further comprising at least one other pharmaceutically-active agent.

15. The pharmaceutical composition of claim 14, wherein the at least one other pharmaceutically-active agent is selected from the group consisting of antibiotic agents, antivirulence agents, biofilm-disrupting agents, anti-inflammatory agents, agents potentiating antibiotic efficacy, and antifungal agents.

16. The pharmaceutical composition of claim 15, wherein the at least one other pharmaceutically-active agent is selected from the group consisting of rifampicin (rifampin), minocycline, clarithromycin, azithromycin, fusidic acid, mupirocin, retapamulin, meropenem, aztreonam, clarithromycin, erythromycin, novobiocin, telithromycin, colistin, polymyxin B, fosfomycin, ciprofloxacin, tetracycline, gentamycin, vancomycin, quinupristin-dalfopristin, ramoplanin, teicoplanin, levofloxacin, arenicin-3, linezolid and antimicrobial peptides.

17. A method of treatment or prevention of a disease, disorder or condition in a subject including the step of administering an effective amount of a compound of claim 1, or a salt or stereoisomer thereof, to the subject to thereby treat or prevent the disease, disorder or condition, wherein the disease, disorder or condition is associated with a bacterial or fungal infection.

18. The compound of claim 3, wherein $R_{10}$ is not hydrogen.

19. The compound of claim 1, wherein the compound is a compound of formula (Ib):

Formula (Ib)

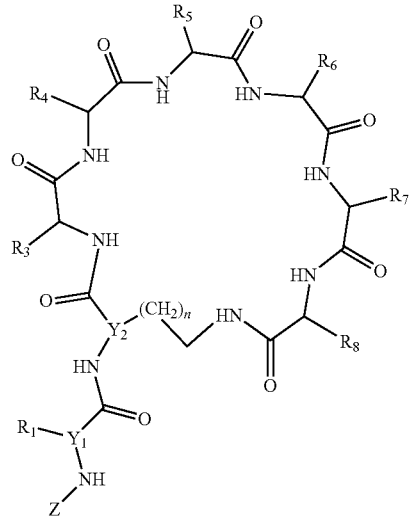

wherein,
$Y_1$ and $Y_2$ are independently selected from the group consisting of CH and N;
$R_1$ is selected from the group consisting of:

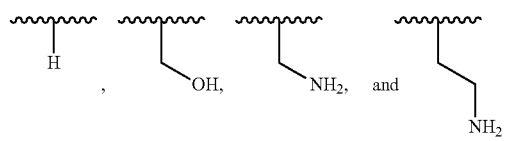

$R_3$ is

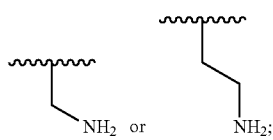

$R_4$ is selected from the group consisting of:

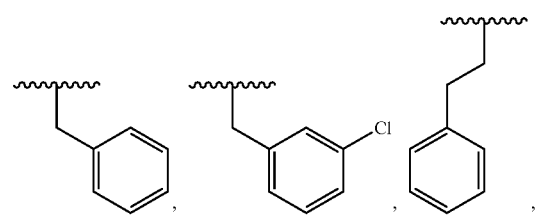

-continued

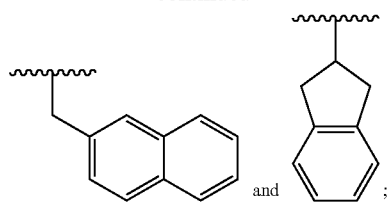

$R_5$ is

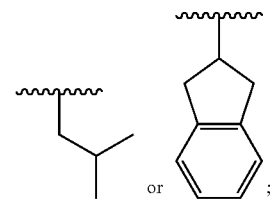

$R_6$ is selected from the group consisting of:

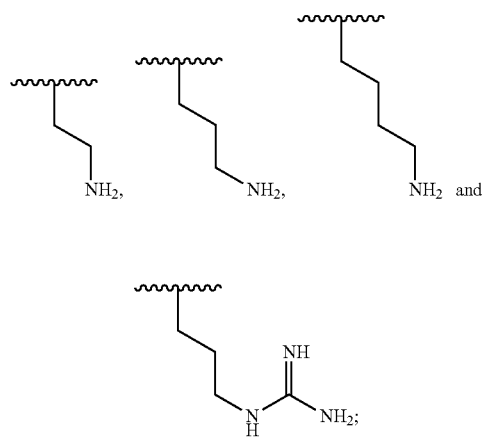

$R_7$ is selected from the group consisting of:

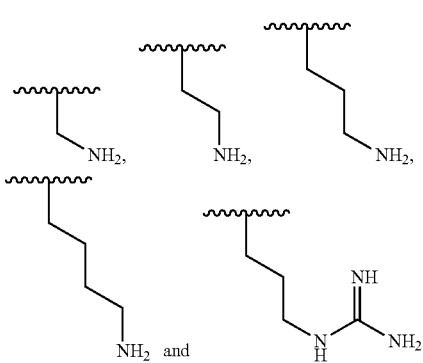

$R_8$ is selected from the group consisting of:
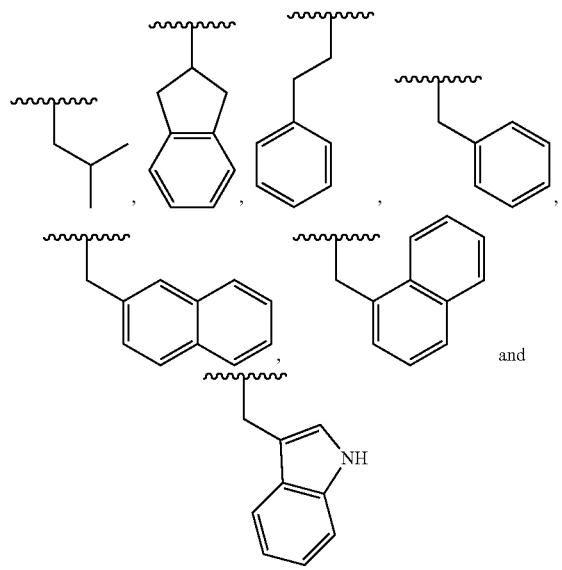
and
n is 1; and
Z is 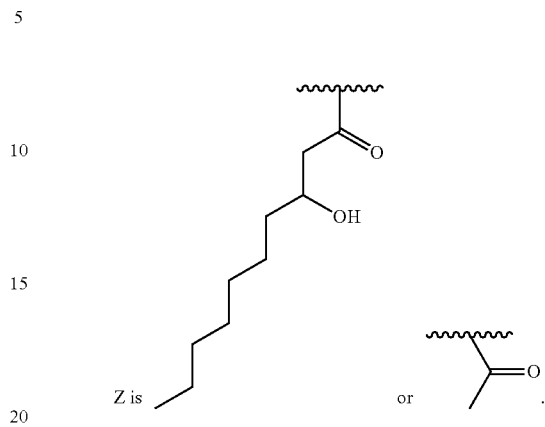.
20. The compound of claim 1, wherein Z does not contain any amino acids or any peptide linkage or bond.
* * * * *